(12) United States Patent
Henkes et al.

US008273952B2

(10) Patent No.: US 8,273,952 B2
(45) Date of Patent: Sep. 25, 2012

(54) PLANTS HAVING IMPROVED GROWTH CHARACTERISTICS AND METHOD FOR MAKING THE SAME

(75) Inventors: Stefan Henkes, Potsdam (DE); Christian Dammann, Durham, NC (US)

(73) Assignee: BASF Plant Science GmbH (DE)

( * ) Notice: Subject to any disclaimer, the term of this patent is extended or adjusted under 35 U.S.C. 154(b) by 551 days.

(21) Appl. No.: 12/303,570

(22) PCT Filed: May 31, 2007

(86) PCT No.: PCT/EP2007/055336

§ 371 (c)(1), (2), (4) Date: Dec. 5, 2008

(87) PCT Pub. No.: WO2007/141189

PCT Pub. Date: Dec. 13, 2007

(65) Prior Publication Data

US 2010/0229259 A1 Sep. 9, 2010

(30) Foreign Application Priority Data

Jun. 8, 2006 (EP) .................................... 06115168

(51) Int. Cl.
*C12N 15/82* (2006.01)
*A01H 5/00* (2006.01)

(52) U.S. Cl. ........ 800/290; 800/298; 800/306; 800/312; 800/314; 800/317.2; 800/320; 800/320.1; 800/320.2; 800/320.3; 800/322; 435/419; 435/320.1

(58) Field of Classification Search ........................ None
See application file for complete search history.

(56) References Cited

FOREIGN PATENT DOCUMENTS

| | | | |
|---|---|---|---|
| WO | WO-96/25494 | A1 | 8/1996 |
| WO | WO 99/54489 | * | 10/1999 |
| WO | WO-99/54489 | A1 | 10/1999 |
| WO | WO-00/52171 | A1 | 9/2000 |
| WO | WO 00/52172 | * | 9/2000 |
| WO | WO-00/52172 | A1 | 9/2000 |
| WO | WO 00/56905 | * | 9/2000 |
| WO | WO 00/56905 | A2 | 9/2000 |
| WO | WO-03/027299 | A2 | 4/2003 |
| WO | WO-2005/024029 | A2 | 3/2005 |
| WO | WO-2005/083094 | A2 | 9/2005 |
| WO | WO-2006/058897 | A2 | 6/2006 |
| WO | WO-2008/129060 | A2 | 10/2008 |

OTHER PUBLICATIONS

Hiei et al. Efficient transformation of rice (*Oryza sativa* L.) mediated by *Agrobacterium* and sequence analysis of the boundaries of the T-DNA. Plant J. Aug. 1994;6(2):271-82.*

Wen,J.Q. et al. Two novel mitogen-activated protein signaling components, OsMEK1 and OsMAP1, are involved in a moderate low-temperature signaling pathway in rice. Plant Physiol. 129 (4), 1880-1891 (2002).*

Morello et al. Overexpression of the calcium-dependent protein kinase OsCDPK2 in transgenic rice is repressed by light in leaves and disrupts seed development. Transgenic Res. Dec. 2000;9(6):453-62.*

Wen, J.-Q., et al., "Two Novel Mitogen-Activated Protein Signaling Components, OsMEK1 and OsMAP1, Are Involved in a Moderate Low-Temperature Signaling Pathway in Rice", Plant Physiology, vol. 129, (2002), pp. 1880-1891.

"*Oryza sativa* MAP kinase 3 mRNA, complete cds.", Database EMBL, Accession No. AF216317, Dec. 18, 2000.

"RecName: Full=Mitogen-activated protein kinase 3; Short=MAP kinase 3; EC=2.7.11.24"; Database UniProt, Accession No. Q6Z437, Jul. 5, 2004.

Fowler, M.R., et al., "The Plant Cell Cycle in Context", Molecular Biotechnology, vol. 10, No. 2, (1998), pp. 123-153.

Müller, H., et al., "E2Fs Regulate the Expression of Genes Involved in Differentiation, Development, Proliferation, and Apoptosis", Genes & Development, vol. 15, (2001), pp. 267-285.

De Veylder, L., et al., "Control of Proliferation, Endoreduplication and Differentiation by the *Arabidopsis* E2Fa-DPa Transcription Factor", The Embo Journal, vol. 21, No. 6, (2002), pp. 1360-1368.

Mironov, V., et al., "Cyclin-Dependent Kinases and Cell Division in Plants—The Nexus", The Plant Cell, vol. 11, (1999), pp. 509-521.

Reed, S.I., "G1/S Regulatory Mechanisms from Yeast to Man", Progress in Cell Cycle Research, vol. 2, (1996), pp. 15-27.

Hemerly, A., et al., "Dominant Negative Mutants of the Cdc2 Kinase Uncouple Cell Division from Iterative Plant Development", The EMBO Journal, vol. 14, No. 16, (1995), pp. 3925-3936.

Magyar, Z., et al., "Cell Cycle Phase Specificity of Putative Cyclin-Dependent Kinase Variants in Synchronized Alfalfa Cells", The Plant Cell, vol. 9, (1997), pp. 223-235.

Porceddu, A., et al., "A Plant-Specific Cyclin-Dependent Kinase is Involved in the Control of ($G_2$/M Progression in Plants", The Journal of Biological Chemistry, vol. 276, No. 39, (2001), pp. 36354-36360.

Umeda, M., et al., "A Distinct Cyclin-Dependent Kinase-Activating Kinase of *Arabidopsis thaliana*", Proc. Nat'l Acad. Sci. USA, vol. 95, (1998), pp. 5021-5026.

Joubès, J., et al., "A New C-Type Cyclin-Dependent Kinase from Tomato Expressed in Dividing Tissues Does Not Interact with Mitotic and G1 Cyclins", Plant Physiology, vol. 126, (2001), pp. 1403-1415.

(Continued)

*Primary Examiner* — Cynthia Collins
(74) *Attorney, Agent, or Firm* — Connolly Bove Lodge & Hutz LLP

(57) ABSTRACT

The present invention relates generally to the field of molecular biology and concerns a method for improving plant growth characteristics. More specifically, the present invention concerns a method for improving plant growth characteristics by modulating expression in a plant of a plant nucleic acid encoding a cyclin dependent kinase (CDK) and/or by modulating activity in a plant of a plant CDK protein, which CDK protein comprises different motifs or which CDK nucleic acid encodes such protein. The present invention also concerns plants having modulated expression of a plant CDK nucleic acid and/or modulated activity of a plant CDK protein, which CDK protein comprises different sequence motifs or which nucleic acid encodes such protein and which plants have improved growth characteristics relative to corresponding wild type plants. The invention additionally relates to specific nucleic acid sequences encoding for the aforementioned proteins having the aforementioned plant growth improving activity, nucleic acid constructs, vectors and plants containing said nucleic acid sequences.

34 Claims, 9 Drawing Sheets

OTHER PUBLICATIONS

Vandepoele, K., et al., "Genome-Wide Analysis of Core Cell Cycle Genes in *Arabidopsis*", The Plant Cell, vol. 14, (2002), pp. 903-916.
Goldsmith, E.J., et al., "Protein Kinases", Current Opinion in Structural Biology, vol. 4, (1994), pp. 833-840.
Gu, Y., et al., "Cell Cycle Regulation of CDK2 Activity by Phosphorylation of Thr160 and Tyr15", The EMBO Journal, vol. 11, No. 11, (1992), pp. 3995-4005.
Ducommun, B., et al., "cdc2 Phosphorylation is Required for its Interaction with Cyclin", The EMBO Journal, Vol, 10, No. 11, (1991), pp. 3311-3319.
Gould, K.L., et al., "Phosphorylation at Thr167 is Required for *Schizosaccharomyces pombe* $p34^{cdc2}$ Function", The EMBO Journal, vol. 10, No. 11, (1991), pp. 3297-3309.
Marcote, M.J., et al., "A Three-Dimensional Model of the Cdc2 Protein Kinase: Localization of Cyclin- and Suc1-Binding Regions and Phosphorylation Sites", Molecular and Cellular Biology, vol. 13, No. 8, (1993), pp. 5122-5131.
Ducommun, B., et al., "Mutations at Sites Involved in Suc1 Binding Inactivate Cdc2", Molecular and Cellular Biology, vol. 11, No. 12, (1991) pp. 6177-6184.
Coleman, K.G., et al., "Identification of CDK4 Sequences Involved in Cyclin D1 and p16 Binding", The Journal of Biological Chemistry, vol. 272, No. 30, (1997), pp. 18869-18874.
Martinez, A.-M., et al., "Dual Phosphorylation of the T-loop in cdk7: Its Role in Controlling Cyclin H Binding and CAK Activity", The EMBO Journal, vol. 16, No. 2, (1997), pp. 343-354.
Gould, K.L., et al., "A Phosphorylation Site Mutant of *Schizosaccharomyces pombe* cdc2p Fails to Promote the Metaphase to Anaphase Transition", Mol. Gen. Genet., vol. 259, (1998), pp. 437-448.
Booher, R., et al., "Site-Specific Mutagenesis of *cdc2*$^{+}$, a Cell Cycle Control Gene of the Fission Yeast *Schizosaccharomyces pombe*", Molecular and Cellular Biology, vol. 6, No. 10, (1986), pp. 3523-3530.
Solomon, M.J., et al., "Role of Phosphorylation in $p34^{cdc2}$ Activation: Identification of an Activating Kinase", Molecular Biology of the Cell, vol. 3, (1992), pp. 13-27.
Lim, H.H., et al., "Dephosphorylation of Threonine 169 of Cdc28 Is Not Required for Exit from Mitosis but May Be Necessary for Start in *Saccharomyces cerevisiae*", Molecular and Cellular Biology, vol. 16, No. 8, (1996), pp. 4573-4583.
De Bondt, H.L., et al., "Crystal Structure of Cyclin-Dependent Kinase 2". Nature, vol. 363, No. 17, (1993), pp. 595-602.
"SubName: Full=cyclin dependent kinase;" EBI Database Accession No. Q8W2D3, Mar. 1, 2002.
"Rice B-type cyclin dependent kinase", EBI Database Accession No. ADY69032, Jun. 2, 2005.
European Search Report EP 11 19 2293 dated Feb. 23, 2012.
"SubName: Full=CDC2 homolog" EBI Database Accession No. Q9AUH4, Jun. 1, 2001.
"SubName: Full=Cdc2 kinase", EBI Database Accession No. 022292, Jan. 1, 1998.
"Oil-associated gene related protein #1175", EBI Database Accession No. ADJ49675, May 6, 2004.
European Search Report EP 11 19 2291 dated Feb. 23, 2012.

* cited by examiner

EG073qcz (SeqID NO: 57)

gtttacccgccaatatatcctgtcaaacactgatagtttgtggaattcgagctcggtacccggggatcctctagagtcgacctgcaggcatgcaag
ctttgcagtgcagcgtgacccggtcgtgcccctctctagagataatgagcattgcatgtctaagttataaaaaattaccacatattttttttgtcacact
tgtttgaagtgcagtttatctatctttatacatatatttaaactttactctacgaataatataatctatagtactacaataatatcagtgttttagagaatcat
ataaatgaacagttagacatggtctaaaggacaattgagtattttgacaacaggactctacagttttatctttttagtgtgcatgtgttctcctttttttttgc
aaatagcttcacctatataatacttcatccattttattagtacatccatttagggtttagggttaatggtttttatagactaattttttttagtacatctattttattc
tattttagcctctaaattaagaaaactaaaactctattttagtttttttatttaatagtttagatataaaatagaataaaataaagtgactaaaaattaaa
caaataccctttaagaaattaaaaaaactaaggaaacatttttcttgtttcgagtagataatgccagcctgttaaacgccgtcgacgagtctaacg
gacaccaaccagcgaaccagcagcgtcgcgtcgggccaagcgaagcagacggcacggcatctctgtcgctgcctctggacccctctcgag
agttccgctccaccgttggacttgctccgctgtcggcatccagaaattgcgtggcggagcggcagacgtgagccggcacggcaggcggcctc
ctcctcctctcacggcaccggcagctacgggggattcctttcccaccgctccttcgctttcccttcctcgcccgccgtaataaatagacacccctc
cacaccctctttccccaacctcgtgttgttcggagcgcacacacacacaaccagatctcccccaaatccacccgtcggcacctccgcttcaagg
tacgccgctcgtcctcccccccccccccctctctaccttctctagatcggcgttccggtccatggttagggcccggtagttctacttctgttcatgtttg
tgttagatccgtgtttgtgttagatccgtgctgctagcgttcgtacacggatgcgacctgtacgtcagacacgttctgattgctaacttgccagtgtttct
ctttggggaatcctgggatggctctagccgttccgcagacgggatcgatttcatgattttttttgtttcgttgcatagggtttggtttgcccttttcctttatttc
aatatatgccgtgcacttgtttgtcgggtcatcttttcatgcttttttttgtcttggttgtgatgatgtggtctggttgggcggtcgttctagatcggagtagaa
ttctgtttcaaactacctggtggatttattaattttggatctgtatgtgtgtgccatacatattcatagttacgaattgaagatgatggatggaaatatcga
tctaggataggtatacatgttgatgcgggttttactgatgcatatacagagatgctttttgttcgcttggttgtgatgatgtggtgtggttgggcggtcgtt
cattcgttctagatcggagtagaatactgtttcaaactacctggtgtatttattaattttggaactgtatgtgtgtgtcatacatcttcatagttacgagttta
agatggatggaaatatcgatctaggataggtatacatgttgatgtgggttttactgatgcatatacatgatggcatatgcagcatctattcatatgctc
taaccttgagtacctatctattataataaacaagtatgttttataattatttcgatcttgatatacttggatgatggcatatgcagcagctatatgtggattt
ttttagccctgccttcatacgctatttatttgcttggtactgtttcttttgtcgatgctcaccctgttgtttggtgttacttctgcagggtacccccggggatcc
actagttctagaaaccatggccaccgccgccgccgcgtctaccgcgctcactggcgccactaccgctgcgcccaaggcgaggcgccgggc
gcacctcctggccacccgccgcgccctcgccgcgcccatcaggtgctcagcggcgtcacccgccatgccgatggctcccccggccaccccg
ctccggccgtggggccccaccgatccccgcaagggcgccgacatcctcgtcgagtccctcgagcgctgcggcgtccgcgacgtcttcgccta
ccccggcggcgcgtccatggagatccaccaggcactcacccgctcccccgtcatcgccaaccacctcttccgccacgagcaaggggaggc
ctttgcggcctccggctacgcgcgctcctcgggccgcgtcggcgtctgcatcgccacctccggccccggcgccaccaaccttgtctccgcgctc
gccgacgcgctgctcgattccgtccccatggtcgccatcacgggacaggtgccgcgacgcatgattggcaccgacgccttccaggagacgcc
catcgtcgaggtcacccgctccatcaccaagcacaactacctggtcctcgacgtcgacgacatcccccgcgtcgtgcaggaggctttcttcctc
gcctcctctggtcgaccggggccggtgcttgtcgacatccccaaggacatccagcagcagatggcggtgcctgtctgggacaagcccatgagt
ctgcctgggtacattgcgcgccttcccaagccccctgcgactgagttgcttgagcaggtgctgcgtcttgttggtgaatcccggcgccctgttctttat
gttggcggtggctgcgcagcatctggtgaggagttgcgacgctttgtggagctgactggaatcccggtcacaactactcttatgggcctcggcaa
cttccccagcgacgacccactgtctctgcgcatgctaggtatgcatggcacggtgtatgcaaattatgcagtggataaggccgatctgttgcttgc
acttggtgtgcggtttgatgatcgtgtgacagggaagattgaggcttttgcaagcagggctaagattgtgcacgttgatattgatccggctgagatt
ggcaagaacaagcagccacatgtgtccatctgtgcagatgttaagcttgctttgcagggcatgaatgctcttcttgaaggaagcacatcaaaga
agagctttgactttggctcatggaacgatgagttggatcagcagaagagggaattccccccttgggtataaaacatctaatgaggagatccagcc
acaatatgctattcaggttcttgatgagctgacgaaaggcgaggccatcatcggcacaggtgttgggcagcaccagatgtgggcggcacagta
ctacacttacaagcggccaaggcagtggttgtcttcagctggtcttggggctatgggatttggtttgccggctgctgctggtgcttctgtggccaacc
caggtgttactgttgttgacatcgatggagatggtagctttctcatgaacgttcaggagctagctatgatccgaattgagaacctcccggtgaaggt
ctttgtgctaaacaaccagcacctggggatggtggtgcagtgggaggacaggttctataaggccaacagagcgcacacatacttgggaaacc
cagagaatgaaagtgagatatatccagatttcgtgacgatcgccaaagggttcaacattccagcggtccgtgtgacaaagaagaacgaagtc
cgcgcagcgataaagaagatgctcgagactccagggccgtacctcttggatataatcgtcccacaccaggagcatgtgttgcctatgatccta
atggtggggctttcaaggatatgatcctggatggtgatggcaggactgtgtactgatctaaaatccagcaagcaactgatctaaaatccagcaa
gcaccgcctccctgctagtacaagggtgatatgtttttatctgtgtgatgttctcctgtattctatcttttttttgtaggccgtcagctatctgttatggtaatcc
tatgtagcttccgaccttgtaattgtgtagtctgttgttttccttctggcatgtgtcataagagatcatttaagtgccttttgctacatataaataagataata
agcactgctatgcagtggttctgaattggcttctgttgccaaatttaagtgtccaactggtccttgcttttgttttcgctatttttttcctttttagttattattatat
tggtaatttcaactcaacatatgatgtatggaataatgctagggctgcaatttcaaactattttacaaaccagaatggcatttcgtggtttgagggg
agtgaaaaaaaatgaggcatttgactgaattagttacctgatccattttcgtggtttggatcattggaattaaattccattctaataatagtaattttggc
atatatcaattaagttaattcggttttatgcaaaatatatttgtatactattattatcaagatgtcggagatatttatatgctacatttttactatacaggagt
gagatgaagagtgtcatgtaagttacacagtagaaacaaattctattaatgcataaaatcatttccatcatccaccctatgaatttgagatagacct
atatctaaactttgaaaagtggttgaatatcaaattccaaattaaataagttattttattgagtgaattctaatttctctaaaacgaagggatctaaacg
ccctctaaagctaatttggaaactcaaactttcttagcattggaggggattgagaaaaaatattaattcattttcatctcaatcattcaatctccaaag
agatttgagttccttattagtctgttccatgcatcaaatcggctcaatgtgtcattatttgccatgacgattgacgagttgttctggggcctagcgctttcc
acgccgatgtgctggggcctggtcctggagaagacagcttgatatttaaagctatcaattgtttcaattgattcccacttcattttctaaatgtagaa

FIG. 4A aacggtgacgtataagaaaaagaatgaattaggacttttattccgtacactaatctagagcggccccttaaggcgctgcgatcgcgttaacagct
tgctgaggaggcctcggaccgttaattaacacgtgggcgcgccactagtcaattcagtacattaaaaacgtccgcaatgtgttattaagttgtcta
agcgtcaatttgtttacaccacaatatatcctgccaccagccagccaacagctccccgaccggcagctcggcacaaaatcaccactcgataca
ggcagcccatcagtccgggacggcgtcagcgggagagccgttgtaaggcggcagactttgctcatgttaccgatgctattcggaagaacggc
aactaagctgccgggtttgaaacacggatgatctcgcggagggtagcatgttgattgtaacgatgacagagcgttgctgcctgtgatcaaatatc
atctccctcgcagagatccgaattatcagccttcttattcatttctcgcttaaccgtgacaggctgtcgatcttgagaactatgccgacataatagga
aatcgctggataaagccgctgaggaagctgagtggcgctatttctttagaagtgaacgttgacgatcgtcgaccgtaccccgatgaattaattcg
gacgtacgttctgaacacagctggatacttacttgggcgattgtcatacatgacatcaacaatgtacccgtttgtgtaaccgtctcttggaggttcgt
atgacactagtggttcccctcagcttgcgactagatgttgaggcctaacattttattagagagcaggctagttgcttagatacatgatcttcaggccg
ttatctgtcagggcaagcgaaaattggccatttatgacgaccaatgccccgcagaagctcccatctttgccgccatagacgccgcgccccccttt
tggggtgtagaacatccttttgccagatgtggaaaagaagttcgttgtcccattgttggcaatgacgtagtagccggcgaaagtgcgagacccat
ttgcgctatatataagcctacgatttccgttgcgactattgtcgtaattggatgaactattatcgtagttgctctcagagttgtcgtaatttgatggactatt
gtcgtaattgcttatggagttgtcgtagttgcttggagaaatgtcgtagttggatggggagtagtcatagggaagacgagcttcatccactaaaac
aattggcaggtcagcaagtgcctgccccgatgccatcgcaagtacgaggcttagaaccaccttcaacagatcgcgcatagtcttccccagctct
ctaacgcttgagttaagccgcgccgcgaagcggcgtcggcttgaacgaattgttagacattatttgccgactaccttggtgatctcgcctttcacgt
agtgaacaaattcttccaactgatctgcgcgcgaggccaagcgatcttcttgtccaagataagcctgcctagcttcaagtatgacgggctgatact
gggccggcaggcgctccattgcccagtcggcagcgacatccttcggcgcgattttgccggttactgcgctgtaccaaatgcgggacaacgtaa
gcactacatttcgctcatcgccagcccagtcgggcggcgagttccatagcgttaaggtttcatttagcgcctcaaatagatcctgttcaggaaccg
gatcaaagagttcctccgccgctggacctaccaaggcaacgctatgttctcttgcttttgtcagcaagatagccagatcaatgtcgatcgtggctg
gctcgaagatacctgcaagaatgtcattgcgctgccattctccaaattgcagttcgcgcttagctggataacgccacggaatgatgtcgtcgtgca
caacaatggtgacttctacagcgcggagaatctcgctctctccaggggaagccgaagtttccaaaaggtcgttgatcaaagctcgccgcgttgtt
tcatcaagccttacggtcaccgtaaccagcaaatcaatatcactgtgtggcttcaggccgccatccactgcggagccgtacaaatgtacggcca
gcaacgtcggttcgagatggcgctcgatgacgccaactacctctgatagttgagtcgatacttcggcgatcaccgcttccctcatgatgtttaactc
ctgaattaagccgcgccgcgaagcggtgtcggcttgaatgaattgttaggcgtcatcctgtgctcccgagaaccagtaccagtacatcgctgtttc
gttcgagacttgaggtctagttttatacgtgaacaggtcaatgccgccgagagtaaagccacattttgcgtacaaattgcaggcaggtacattgtt
cgtttgtgtctctaatcgtatgccaaggagctgtctgcttagtgcccactttttcgcaaattcgatgagactgtgcgcgactcctttgcctcggtgcgtgt
gcgacacaacaatgtgttcgatagaggctagatcgttccatgttgagttgagttcaatcttcccgacaagctcttggtcgatgaatgcgccatagc
aagcagagtcttcatcagagtcatcatccgagatgtaatccttccggtaggggctcacacttctggtagatagttcaaagccttggtcggataggt
gcacatcgaacacttcacgaacaatgaaatggttctcagcatccaatgtttccgccacctgctcagggatcaccgaaatcttcatatgacgccta
acgcctggcacagcggatcgcaaacctggcgcggcttttggcacaaaaggcgtgacaggtttgcgaatccgttgctgccacttgttaaccctttt
gccagatttggtaactataatttatgttagaggcgaagtcttgggtaaaaactggcctaaaattgctggggatttcaggaaagtaaacatcaccttc
cggctcgatgtctattgtagatatatgtagtgtatctacttgatcgggggatctgctgcctcgcgcgtttcggtgatgacggtgaaaacctctgacac
atgcagctcccggagacggtcacagcttgtctgtaagcggatgccgggagcagacaagcccgtcagggcgcgtcagcgggtgttggcgggt
gtcggggcgcagccatgacccagtcacgtagcgatagcggagtgtatactggcttaactatgcggcatcagagcagattgtactgagagtgca
ccatatgcggtgtgaaataccgcacagatgcgtaaggagaaaataccgcatcaggcgctcttccgcttcctcgctcactgactcgctgcgctcg
gtcgttcggctgcggcgagcggtatcagctcactcaaaggcggtaatacggttatccacagaatcaggggataacgcaggaaagaacatgtg
agcaaaaggccagcaaaaggccaggaaccgtaaaaaggccgcgttgctggcgtttttccataggctccgcccccctgacgagcatcacaa
aaatcgacgctcaagtcagaggtggcgaaacccgacaggactataaagataccaggcgtttccccctggaagctccctcgtgcgctctcctgt
tccgaccctgccgcttaccggatacctgtccgcctttctcccttcgggaagcgtggcgctttctcatagctcacgctgtaggtatctcagttcggtgta
ggtcgttcgctccaagctgggctgtgtgcacgaaccccccgttcagcccgaccgctgcgccttatccggtaactatcgtcttgagtccaacccggt
aagacacgacttatcgccactggcagcagccactggtaacaggattagcagagcgaggtatgtaggcggtgctacagagttcttgaagtggt
ggcctaactacggctacactagaaggacagtatttggtatctgcgctctgctgaagccagttaccttcggaaaaagagttggtagctcttgatccg
gcaaacaaaccaccgctggtagcggtggtttttttgtttgcaagcagcagattacgcgcagaaaaaaaggatctcaagaagatcctttgatcttt
ctacggggtctgacgctcagtggaacgaaaactcacgttaagggattttggtcatgagattatcaaaaaggatcttcacctagatccttttaaatta
aaaatgaagttttaaatcaatctaaagtatatatgagtaaacttggtctgacagttaccaatgcttaatcagtgaggcacctatctcagcgatctgtc
tatttcgttcatccatagttgcctgactccccgtcgtgtagataactacgatacgggagggcttaccatctggccccagtgctgcaatgataccgcg
agacccacgctcaccggctccagatttatcagcaataaaccagccagccggaagggccgagcgcagaagtggtcctgcaactttatccgcct
ccatccagtctattaattgttgccgggaagctagagtaagtagttcgccagttaatagtttgcgcaacgttgttgccattgctgcaggggggggg
ggggggggacttccattgttcattccacggacaaaaacagagaaaggaaacgacagaggccaaaaagcctcgctttcagcacctgtcgttt
cctttcttttcagagggtattttaaataaaaacattaagttatgacgaagaagaacggaaacgccttaaaccggaaaattttcataaatagcgaa
aacccgcgaggtcgccgccccgtaacctgtcggatcaccggaaaggacccgtaaagtgataatgattatcatctacatatcacaacgtgcgtg
gaggccatcaaaccacgtcaaataatcaattatgacgcaggtatcgtattaattgatctgcatcaacttaacgtaaaaacaacttcagacaatac
aaatcagcgacactgaatacggggcaacctcatgtccccccccccccccccctgcaggcatcgtggtgtcacgctcgtcgtttggtatggcttc
attcagctccggttcccaacgatcaaggcgagttacatgatcccccatgttgtgcaaaaaagcggttagctccttcggtcctccgatcgttgtcag
aagtaagttggccgcagtgttatcactcatggttatggcagcactgcataattctcttactgtcatgccatccgtaagatgcttttctgtgactggtgag
tactcaaccaagtcattctgagaatagtgtatgcggcgaccgagttgctcttgcccggcgtcaacacgggataataccgcgccacatagcaga
actttaaaagtgctcatcattggaaaacgttcttcggggcgaaaactctcaaggatcttaccgctgttgagatccagttcgatgtaacccactcgtg
cacccaactgatcttcagcatcttttactttcaccagcgtttctgggtgagcaaaaacaggaaggcaaaatgccgcaaaaaagggaataaggg

FIG. 4B cgacacggaaatgttgaatactcatactcttcctttttcaatattattgaagcatttatcagggttattgtctcatgagcggatacatatttgaatgtattta
gaaaaataaacaaataggggttccgcgcacatttccccgaaaagtgccacctgacgtctaagaaaccattattatcatgacattaacctataaa
aataggcgtatcacgaggccctttcgtcttcaagaattggtcgacgatcttgctgcgttcggatattttcgtggagttcccgccacagacccggattg
aaggcgagatccagcaactcgcgccagatcatcctgtgacggaactttggcgcgtgatgactggccaggacgtcggccgaaagagcgaca
agcagatcacgcttttcgacagcgtcggatttgcgatcgaggatttttcggcgctgcgctacgtccgcgaccgcgttgagggatcaagccacag
cagcccactcgaccttctagccgacccagacgagccaagggatctttttggaatgctgctccgtcgtcaggctttccgacgtttgggtggttgaac
agaagtcattatcgtacggaatgccaagcactcccgaggggaaccctgtggttggcatgcacatacaaatggacgaacggataaacctttca
cgcccttttaaatatccgttattctaataaacgctcttttctcttag

>EG065qcz (SeqID NO: 58)

acacaggaaacagctatgaccatgattacgccaagctatcgtttaaaccttaaggcgatcgcgctgaggcggaccgcacgtggaattagcttg
gcgcgccaattcccgatctagtaacatagatgacaccgcgcgcgataatttatcctagtttgcgcgctatattttgttttctatcgcgtattaaatgtat
aattgcgggactctaatcataaaaacccatctcataaataacgtcatgcattacatgttaattattacatgcttaacgtaattcaacagaaattatat
gataatcatcgcaagaccggcaacaggattcaatcttaagaaactttattgccaaatgtttgaacgatcggggaaattcgagctccaccgcggt
ggcggccgctctagaactagtggatcccccgggctgcaggaattcgatatcaagcttatcgataccgtcgacctcgagggggggcccggtac
cttggtgaactaccgatgatcgtaagagcttacagacggtgccttatataggcagagcgtcggaagggggtggtgtcacacacgcactgcga
tccttgcttacaagctaagcaaaggcatcgtggcagacaaggaataaagtggcacaggtgccaaaagaaagtggacagcacacttgtccga
aaagcacacaataatacaactcagtggagcatccactgaatgggcccagtactctccgctgcggtcatccctgacgtcaatgcctcctcaatcg
tcattgcttacgtcttggagatctagcacatcttctgcggctactggcgacatagcccttggtgtggcctggtattcctcgaactcctgctcttctatcttc
agcttggtgacttccttcataagttcctcctccattgtttgcacgccaccggtcttcagaacttcaagattcttgagaaattcatcaattctgtcttgaatg
tgttcttcaatgagatctgcccagtaccagcaatggcatttgttcattgcgcacttgaagaatttccttcctgggttggcagatgttctggacactaact
gaattgcaggcttcctgcatgcacagagtagaactggttcctctgttagcataaaagcttgctctgttctttcgaacatgtccttcttgaatgtgggga
atggatccagaattttgtttccccattctctgagttgctcagtgtatggatgatctggataaggaattacttcccttatggcttgtgtaagcaggatcatc
tcttccgttggttcattctgagctaatttggctttgagcctggacaagatgtcagctaaaccattgctcttccctttatgtgttcaatgactatctctggtcc
tgcaccagtgatgtagtccatgaacctgatccatctgatctcagaaggcttgtgttcagcactcttgttgtagaacctttcgattgcactactgtcagtt
ctgactgtgatctctcttttgtccaagtagaacaatctcatcttttctaagccattcataaccccatagatttctgcatcacaggttccttttggcttatcaa
attttccactggcatacctacagatttgctctgtatttcttgggtctgccttgtttttcttccacttgcatactgctccccatccagttgcacatgcatctgtttc
aatgataatgtatgcatcttctggtggaatagtgagatttggaagcgttctcaccattgtcttgatcctattgatcagcttccaatcttctgaattgagcc
ttcgctcacctttctctgaggtctttggatataatgggccaagaagcttgcccatatctttgatgtggtttctggcatagttcagtgttgctagccaggatt
aattaaaggcctgttaacagcgctgggcccgataattcactggccgtcgttttacaacgtcgtgactgggaaaaccctggcgttacccaacttaat
cgccttgcagcacatccccctttcgccagctggcgtaatagcgaagaggcccgcaccgatcgcccttcccaacagttgcgcagcctgaatggc
gaatggcgcctgatgcggtattttctccttacgcatctgtgcggtatttcacaccgcatatggtgcactctcagtacaatctgctctgatgccgcatag
ttaagccagccccgacacccgccaacacccgctgacgcgccctgacgggcttgtctgctcccggcatccgcttacagacaagctgtgaccgtc
tccgggagctgcatgtgtcagaggttttcaccgtcatcaccgaaacgcgcgagacgaaagggcctcgtgatacgcctatttttataggttaatgtc
atgataataatggtttcttagacgtcaggtggcacttttcggggaaatgtgcgcggaacccctatttgtttatttttctaaatacattcaaatatgtatcc
gctcatgagacaataaccctgataaatgcttcaataatattgaaaaaggaagagtatgagtattcaacatttccgtgtcgcccttattcccttttttgc
ggcattttgccttcctgtttttgctcacccagaaacgctggtgaaagtaaaagatgctgaagatcagttgggtgcacgagtgggttacatcgaact
ggatctcaacagcggtaagatccttgagagttttcgccccgaagaacgttttccaatgatgagcacttttaaagttctgctatgtggcgcggtattat
cccgtattgacgccgggcaagagcaactcggtcgccgcatacactattctcagaatgacttggttgagtactcaccagtcacagaaaagcatct
tacggatggcatgacagtaagagaattatgcagtgctgccataaccatgagtgataacactgcggccaacttacttctgacaacgatcggagg
accgaaggagctaaccgcttttttgcacaacatgggggatcatgtaactcgccttgatcgttgggaaccggagctgaatgaagccataccaaa
cgacgagcgtgacaccacgatgcctgtagcaatggcaacaacgttgcgcaaactattaactggcgaactacttactctagcttcccggcaaca
attaatagactggatggaggcggataaagttgcaggaccacttctgcgctcggcccttccggctggctggtttattgctgataaatctggagccgg
tgagcgtgggtctcgcggtatcattgcagcactggggccagatggtaagccctcccgtatcgtagttatctacacgacggggagtcaggcaact
atggatgaacgaaatagacagatcgctgagataggtgcctcactgattaagcattggtaactgtcagaccaagtttactcatatatactttagattg
atttaaaacttcatttttaatttaaaaggatctaggtgaagatcctttttgataatctcatgaccaaaatcccttaacgtgagttttcgttccactgagcgt
cagaccccgtagaaaagatcaaaggatcttcttgagatcctttttttctgcgcgtaatctgctgcttgcaaacaaaaaaaccaccgctaccagcg
gtggtttgtttgccggatcaagagctaccaactctttttccgaaggtaactggcttcagcagagcgcagataccaaatactgttcttctagtgtagcc
gtagttaggccaccacttcaagaactctgtagcaccgcctacatacctcgctctgctaatcctgttaccagtggctgctgccagtggcgataagtc
gtgtcttaccgggttggactcaagacgatagttaccggataaggcgcagcggtcgggctgaacggggggttcgtgcacacagcccagcttgg
agcgaacgacctacaccgaactgagatacctacagcgtgagctatgagaaagcgccacgcttcccgaagggagaaaggcggacaggtat
ccggtaagcggcagggtcggaacaggagagcgcacgagggagcttccagggggaaacgcctggtatctttatagtcctgtcgggtttcgcca
cctctgacttgagcgtcgatttttgtgatgctcgtcaggggggcggagcctatggaaaaacgccagcaacgcggcctttttacggttcctggcctttt
gctggccttttgctcacatgttctttcctgcgttatcccctgattctgtggataaccgtattaccgcctttgagtgagctgataccgctcgccgcagccg
aacgaccgagcgcagcgagtcagtgagcgaggaagcggaagagcgcccaatacgcaaaccgcctctccccgcgcgttggccgattcatt
aatgcagctggcacgacaggtttcccgactggaaagcgggcagtgagcgcaacgcaattaatgtgagttagctcactcattaggcaccccag
gctttacactttatgcttccggctcgtatgttgtgtggaattgtgagcggataacaatttc

FIG. 4C

>pMME0607 (SeqID NO: 59)
gtttacccgccaatatatcctgtcaaacactgatagtttgtggaattcgagctcggtacccggggatcctctagagtcgacctgcaggcatgcaag
cttccggctgcagtgcagcgtgacccggtcgtgcccctctctagagataatgagcattgcatgtctaagttataaaaaattaccacatttttttgt
cacacttgtttgaagtgcagtttatctatctttatacatatatttaaactttactctacgaataatataatctatagtactacaataatatcagtgttttagag
aatcatataaatgaacagttagacatggtctaaaggacaattgagtattttgacaacaggactctacagttttatctttttagtgtgcatgtgttctccttt
ttttttgcaaatagcttcacctatataatacttcatccattttattagtacatccatttagggtttagggttaatggtttttatagactaatttttttagtacatcta
ttttattctattttagcctctaaattaagaaaactaaaactctatttagtttttttatttaatagtttagatataaaatagaataaaataaagtgactaaaa
attaaacaaatacccttttaagaaattaaaaaaactaaggaaacatttttcttgtttcgagtagataatgccagcctgttaaacgccgtcgacgagt
ctaacggacaccaaccagcgaaccagcagcgtcgcgtcgggccaagcgaagcagacggcacggcatctctgtcgctgcctctggacccct
ctcgagagttccgctccaccgttggacttgctccgctgtcggcatccagaaattgcgtggcggagcggcagacgtgagccggcacggcaggc
ggcctcctcctcctctcacggcaccggcagctacgggggattcctttcccaccgctccttcgctttcccttcctcgcccgccgtaataaatagacac
cccctccacaccctctttccccaacctcgtgttgttcggagcgcacacacacacaaccagatctcccccaaatccacccgtcggcacctccgctt
caaggtacgccgctcgtcctcccccccccccccctctctaccttctctagatcggcgttccggtccatggttagggcccggtagttctacttctgttc
atgtttgtgttagatccgtgtttgtgttagatccgtgctgctagcgttcgtacacggatgcgacctgtacgtcagacacgttctgattgctaacttgcca
gtgtttctctttggggaatcctgggatggctctagccgttccgcagacgggatcgatttcatgattttttttgtttcgttgcatagggtttggtttgcccttttc
ctttatttcaatatatgccgtgcacttgtttgtcgggtcatcttttcatgcttttttttgtcttggttgtgatgatgtggtctggttgggcggtcgttctagatcgg
agtagaattctgtttcaaactacctggtggatttattaattttggatctgtatgtgtgtgccatacatattcatagttacgaattgaagatgatggatgga
aatatcgatctaggataggtatacatgttgatgcgggttttactgatgcatatacagagatgctttttgttcgcttggttgtgatgatgtggtgtggttggg
cggtcgttcattcgttctagatcggagtagaatactgtttcaaactacctggtgtatttattaattttggaactgtatgtgtgtgtcatacatcttcatagtta
cgagtttaagatggatggaaatatcgatctaggataggtatacatgttgatgtgggttttactgatgcatatacatgatggcatatgcagcatctattc
atatgctctaaccttgagtacctatctattataataaacaagtatgttttataattatttcgatcttgatatacttggatgatggcatatgcagcagctatat
gtggatttttttagccctgccttcatacgctatttatttgcttggtactgtttcttttgtcgatgctcaccctgttgtttggtgttacttctgcagggtacccccgg
ggatccactagttctagaaaccatggccaccgccgccgccgcgtctaccgcgctcactggcgccactaccgctgcgcccaaggcgaggcgc
cgggcgcacctcctggccacccgccgcgccctcgccgcgcccatcaggtgctcagcggcgtcacccgccatgccgatggctcccccggcca
ccccgctccggccgtggggccccaccgatccccgcaagggcgccgacatcctcgtcgagtccctcgagcgctgcggcgtccgcgacgtcttc
gcctaccccggcggcgcgtccatggagatccaccaggcactcacccgctcccccgtcatcgccaaccacctcttccgccacgagcaagggg
aggcctttgcggcctccggctacgcgcgctcctcgggccgcgtcggcgtctgcatcgccacctccggccccggcgccaccaaccttgtctccgc
gctcgccgacgcgctgctcgattccgtccccatggtcgccatcacgggacaggtgccgcgacgcatgattggcaccgacgccttccaggaga
cgcccatcgtcgaggtcacccgctccatcaccaagcacaactacctggtcctcgacgtcgacgacatcccccgcgtcgtgcaggaggctttctt
cctcgcctcctctggtcgaccggggccggtgcttgtcgacatccccaaggacatccagcagcagatggcggtgcctgtctgggacaagcccat
gagtctgcctgggtacattgcgcgccttcccaagccccctgcgactgagttgcttgagcaggtgctgcgtcttgttggtgaatcccggcgccctgtt
ctttatgttggcggtggctgcgcagcatctggtgaggagttgcgacgctttgtggagctgactggaatcccggtcacaactactcttatgggcctcg
gcaacttccccagcgacgacccactgtctctgcgcatgctaggtatgcatggcacggtgtatgcaaattatgcagtggataaggccgatctgttg
cttgcacttggtgtgcggtttgatgatcgtgtgacagggaagattgaggcttttgcaagcagggctaagattgtgcacgttgatattgatccggctga
gattggcaagaacaagcagccacatgtgtccatctgtgcagatgttaagcttgctttgcagggcatgaatgctcttcttgaaggaagcacatcaa
agaagagctttgactttggctcatggaacgatgagttggatcagcagaagagggaattccccttgggtataaaacatctaatgaggagatcca
gccacaatatgctattcaggttcttgatgagctgacgaaaggcgaggccatcatcggcacaggtgttgggcagcaccagatgtggcggcac
agtactacacttacaagcggccaaggcagtggttgtcttcagctggtcttggggctatgggatttggtttgccggctgctgctggtgcttctgtggcc
aacccaggtgttactgttgttgacatcgatggagatggtagctttctcatgaacgttcaggagctagctatgatccgaattgagaacctcccggtga
aggtctttgtgctaaacaaccagcacctggggatggtggtgcagtgggaggacaggttctataaggccaacagagcgcacacatacttggga
aacccagagaatgaaagtgagatatatccagatttcgtgacgatcgccaaagggttcaacattccagcggtccgtgtgacaaagaagaacg
aagtccgcgcagcgataaagaagatgctcgagactccagggccgtacctcttggatataatcgtcccacaccaggagcatgtgttgcctatgat
ccctaatggtggggctttcaaggatatgatcctggatggtgatggcaggactgtgtactgatctaaaatccagcaagcaactgatctaaaatcca
gcaagcaccgcctccctgctagtacaagggtgatatgtttttatctgtgtgatgttctcctgtattctatctttttttgtaggccgtcagctatctgttatggt
aatcctatgtagcttccgaccttgtaattgtgtagtctgttgttttccttctggcatgtgtcataagagatcatttaagtgccttttgctacatataaataag
ataataagcactgctatgcagtggttctgaattggcttctgttgccaaatttaagtgtccaactggtccttgcttttgttttcgctattttttttcctttttttagttatt
attatattggtaatttcaactcaacatatgatgtatggaataatgctagggctgcaatttcaaactattttacaaaccagaatggcattttcgtggtttg
aggggagtgaaaaaaaatgaggcatttgactgaattagttacctgatccattttcgtggtttggatcattggaattaaattccattctaataatagtaa
ttttggcatatatcaattaagttaattcggttttatgcaaaatatatttgtatactattattatcaagatgtcggagatatttatatgctacatttttactataca
ggagtgagatgaagagtgtcatgtaagttacacagtagaaacaaattctattaatgcataaaatcatttccatcatccaccctatgaatttgagata
gacctatatctaaactttgaaaagtggttgaatatcaaattccaaattaaataagttattttattgagtgaattctaatttctctaaaacgaagggatct
aaacgccctctaaagctaatttggaaactcaaactttcttagcattggaggggattgagaaaaaatattaattcattttcatctcaatcattcaatctc
caaagagatttgagttccttattagtctgttccatgcatcaaatcggctcaatgtgtcattatttgccatgacgattgacgagttgttctggggcctagc
gctttccacgccgatgtgctggggcctggtcctggagaagacagcttgatatttaaagctatcaattgtttcaattgattcccacttcattttctaaatg
tagaaaacggtgacgtataagaaaaagaatgaattaggactttttattccgtacactaatctagagcggccccttaaggcgctgcgatcgcgtta
acagcttgctgaggaggcctcggaccgttaattaatcctggctagcaacactgaactatgccagaaaccacatcaaagatatgggcaagcttc
ttggcccattatatccaaagacctcagagaaaggtgagcgaaggctcaattcagaagattggaagctgatcaataggatcaagacaatggtg
agaacgcttccaaatctcactattccaccagaagatgcatacattatcattgaaacagatgcatgtgcaactggatggggagcagtatgcaagt

FIG. 4D ggaagaaaaacaaggcagacccaagaaatacagagcaaatctgtaggtatgccagtggaaaatttgataagccaaaaggaacctgtgat
gcagaaatctatggggttatgaatggcttagaaaagatgagattgttctacttggacaaaagagagatcacagtcagaactgacagtagtgca
atcgaaaggttctacaacaagagtgctgaacacaagccttctgagatcagatggatcaggttcatggactacatcactggtgcaggaccagag
atagtcattgaacacataaaagggaagagcaatggtttagctgacatcttgtccaggctcaaagccaaattagctcagaatgaaccaacgga
agagatgatcctgcttacacaagccataagggaagtaattccttatccagatcatccatacactgagcaactcagagaatggggaaacaaaat
tctggatccattccccacattcaagaaggacatgttcgaaagaacagagcaagcttttatgctaacagaggaaccagttctactctgtgcatgca
ggaagcctgcaattcagttagtgtccagaacatctgccaacccaggaaggaaattcttcaagtgcgcaatgaacaaatgccattgctggtactg
ggcagatctcattgaagaacacattcaagacagaattgatgaatttctcaagaatcttgaagttctgaagaccggtggcgtgcaaacaatggag
gaggaacttatgaaggaagtcaccaagctgaagatagaagagcaggagttcgaggaataccaggccacaccaagggctatgtcgccagt
agccgcagaagatgtgctagatctccaagacgtaagcaatgacgattgaggaggcattgacgtcagggatgaccgcagcggagagtactg
ggcccattcagtggatgctccactgagttgtattattgtgtgcttttcggacaagtgtgctgtccactttcttttggcacctgtgccactttattccttgtctg
ccacgatgcctttgcttagcttgtaagcaaggatcgcagtgcgtgtgtgacaccaccccccttccgacgctctgcctatataaggcaccgtctgta
agctcttacgatcatcggtagttcaccaaggtacgcccgggtcgctcctacgcgtcaatgatccgcggacgccgagcccgagctcgaatttccc
cgatcgttcaaacatttggcaataaagtttcttaagattgaatcctgttgccggtcttgcgatgattatcatataatttctgttgaattacgttaagcatgt
aataattaacatgtaatgcatgacgttatttatgagatgggtttttatgattagagtcccgcaattatacatttaatacgcgatagaaaacaaaatata
gcgcgcaaactaggataaattatcgcgcgcggtgtcatctatgttactagatcgggaattggcgcgccactagtcaattcagtacattaaaaacg
tccgcaatgtgttattaagttgtctaagcgtcaatttgtttacaccacaatatatcctgccaccagccagccaacagctccccgaccggcagctcg
gcacaaaatcaccactcgatacaggcagcccatcagtccgggacggcgtcagcgggagagccgttgtaaggcggcagactttgctcatgtta
ccgatgctattcggaagaacggcaactaagctgccgggtttgaaacacggatgatctcgcggagggtagcatgttgattgtaacgatgacaga
gcgttgctgcctgtgatcaaatatcatctccctcgcagagatccgaattatcagccttcttattcatttctcgcttaaccgtgacaggctgtcgatcttg
agaactatgccgacataataggaaatcgctggataaagccgctgaggaagctgagtggcgctatttctttagaagtgaacgttgacgatcgtcg
accgtaccccgatgaattaattcggacgtacgttctgaacacagctggatacttacttgggcgattgtcatacatgacatcaacaatgtacccgttt
gtgtaaccgtctcttggaggttcgtatgacactagtggttcccctcagcttgcgactagatgttgaggcctaacattttattagagagcaggctagttg
cttagatacatgatcttcaggccgttatctgtcagggcaagcgaaaattggccatttatgacgaccaatgccccgcagaagctcccatctttgccg
ccatagacgccgcgcccccctttggggtgtagaacatccttttgccagatgtggaaaagaagttcgttgtcccattgttggcaatgacgtagtag
ccggcgaaagtgcgagacccatttgcgctatatataagcctacgatttccgttgcgactattgtcgtaattggatgaactattatcgtagttgctctca
gagttgtcgtaatttgatggactattgtcgtaattgcttatggagttgtcgtagttgcttggagaaatgtcgtagttggatggggagtagtcatággga
agacgagcttcatccactaaaacaattggcaggtcagcaagtgcctgccccgatgccatcgcaagtacgaggcttagaaccaccttcaacag
atcgcgcatagtcttccccagctctctaacgcttgagttaagccgcgccgcgaagcggcgtcggcttgaacgaattgttagacattatttgccgac
taccttggtgatctcgcctttcacgtagtgaacaaattcttccaactgatctgcgcgcgaggccaagcgatcttcttgtccaagataagcctgccta
gcttcaagtatgacgggctgatactgggccggcaggcgctccattgcccagtcggcagcgacatccttcggcgcgattttgccggttactgcgct
gtaccaaatgcgggacaacgtaagcactacatttcgctcatcgccagcccagtcgggcggcgagttccatagcgttaaggtttcatttagcgcct
caaatagatcctgttcaggaaccggatcaaagagttcctccgccgctggacctaccaaggcaacgctatgttctcttgcttttgtcagcaagatag
ccagatcaatgtcgatcgtggctggctcgaagatacctgcaagaatgtcattgcgctgccattctccaaattgcagttcgcgcttagctggataac
gccacggaatgatgtcgtcgtgcacaacaatggtgacttctacagcgcggagaatctcgctctctccaggggaagccgaagtttccaaaaggt
cgttgatcaaagctcgccgcgttgtttcatcaagccttacggtcaccgtaaccagcaaatcaatatcactgtgtggcttcaggccgccatccactg
cggagccgtacaaatgtacggccagcaacgtcggttcgagatggcgctcgatgacgccaactacctctgatagttgagtcgatacttcggcgat
caccgcttccctcatgatgtttaactcctgaattaagccgcgccgcgaagcggtgtcggcttgaatgaattgttaggcgtcatcctgtgctcccgag
aaccagtaccagtacatcgctgtttcgttcgagacttgaggtctagttttatacgtgaacaggtcaatgccgccgagagtaaagccacattttgcgt
acaaattgcaggcaggtacattgttcgtttgtgtctctaatcgtatgccaaggagctgtctgcttagtgcccactttttcgcaaattcgatgagactgtg
cgcgactcctttgcctcggtgcgtgtgcgacacaacaatgtgttcgatagaggctagatcgttccatgttgagttgagttcaatcttcccgacaagct
cttggtcgatgaatgcgccatagcaagcagagtcttcatcagagtcatcatccgagatgtaatccttccggtaggggctcacacttctggtagata
gttcaaagccttggtcggataggtgcacatcgaacacttcacgaacaatgaaatggttctcagcatccaatgtttccgccacctgctcagggatc
accgaaatcttcatatgacgcctaacgcctggcacagcggatcgcaaacctggcgcggcttttggcacaaaaggcgtgacaggtttgcgaatc
cgttgctgccacttgttaacccttttgccagatttggtaactataatttatgttagaggcgaagtcttgggtaaaaactggcctaaaattgctggggatt
tcaggaaagtaaacatcaccttccggctcgatgtctattgtagatatatgtagtgtatctacttgatcgggggatctgctgcctcgcgcgtttcggtga
tgacggtgaaaacctctgacacatgcagctcccggagacggtcacagcttgtctgtaagcggatgccgggagcagacaagcccgtcagggc
gcgtcagcgggtgttggcgggtgtcggggcgcagccatgacccagtcacgtagcgatagcggagtgtatactggcttaactatgcggcatcag
agcagattgtactgagagtgcaccatatgcggtgtgaaataccgcacagatgcgtaaggagaaaataccgcatcaggcgctcttccgcttcct
cgctcactgactcgctgcgctcggtcgttcggctgcggcgagcggtatcagctcactcaaaggcggtaatacggttatccacagaatcagggg
ataacgcaggaaagaacatgtgagcaaaaggccagcaaaaggccaggaaccgtaaaaaggccgcgttgctggcgtttttccataggctcc
gcccccctgacgagcatcacaaaaatcgacgctcaagtcagaggtggcgaaacccgacaggactataaagataccaggcgtttccccctg
gaagctccctcgtgcgctctcctgttccgaccctgccgcttaccggatacctgtccgcctttctcccttcgggaagcgtggcgctttctcatagctcac
gctgtaggtatctcagttcggtgtaggtcgttcgctccaagctgggctgtgtgcacgaaccccccgttcagcccgaccgctgcgccttatccggta
actatcgtcttgagtccaacccggtaagacacgacttatcgccactggcagcagccactggtaacaggattagcagagcgaggtatgtaggc
ggtgctacagagttcttgaagtggtggcctaactacggctacactagaaggacagtatttggtatctgcgctctgctgaagccagttaccttcgga
aaaagagttggtagctcttgatccggcaaacaaaccaccgctggtagcggtggtttttttgtttgcaagcagcagattacgcgcagaaaaaaag
gatctcaagaagatcctttgatcttttctacggggtctgacgctcagtggaacgaaaactcacgttaagggatttggtcatgagattatcaaaaag

FIG. 4E gatcttcacctagatccttttaaattaaaaatgaagttttaaatcaatctaaagtatatatgagtaaacttggtctgacagttaccaatgcttaatcagt
gaggcacctatctcagcgatctgtctatttcgttcatccatagttgcctgactccccgtcgtgtagataactacgatacgggagggcttaccatctgg
ccccagtgctgcaatgataccgcgagacccacgctcaccggctccagatttatcagcaataaaccagccagccggaagggccgagcgcag
aagtggtcctgcaactttatccgcctccatccagtctattaattgttgccgggaagctagagtaagtagttcgccagttaatagtttgcgcaacgttgt
tgccattgctgcagggggggggggggggggggggggacttccattgttcattccacggacaaaaacagagaaaggaaacgacagaggccaaaa
agcctcgctttcagcacctgtcgtttcctttcttttcagagggtattttaaataaaaacattaagttatgacgaagaagaacggaaacgccttaaacc
ggaaaattttcataaatagcgaaaacccgcgaggtcgccgccccgtaacctgtcggatcaccggaaaggacccgtaaagtgataatgattat
catctacatatcacaacgtgcgtggaggccatcaaaccacgtcaaataatcaattatgacgcaggtatcgtattaattgatctgcatcaacttaac
gtaaaaacaacttcagacaatacaaatcagcgacactgaatacggggcaacctcatgtcccccccccccccccccctgcaggcatcgtggtg
tcacgctcgtcgtttggtatggcttcattcagctccggttcccaacgatcaaggcgagttacatgatcccccatgttgtgcaaaaaagcggttagct
ccttcggtcctccgatcgttgtcagaagtaagttggccgcagtgttatcactcatggttatggcagcactgcataattctcttactgtcatgccatccgt
aagatgcttttctgtgactggtgagtactcaaccaagtcattctgagaatagtgtatgcggcgaccgagttgctcttgcccggcgtcaacacggga
taataccgcgccacatagcagaactttaaaagtgctcatcattggaaaacgttcttcggggcgaaaactctcaaggatcttaccgctgttgagat
ccagttcgatgtaacccactcgtgcacccaactgatcttcagcatcttttactttcaccagcgtttctgggtgagcaaaaacaggaaggcaaaatg
ccgcaaaaaagggaataagggcgacacggaaatgttgaatactcatactcttcctttttcaatattattgaagcatttatcagggttattgtctcatg
agcggatacatatttgaatgtatttagaaaaataaacaaataggggttccgcgcacatttccccgaaaagtgccacctgacgtctaagaaacca
ttattatcatgacattaacctataaaaataggcgtatcacgaggccctttcgtcttcaagaattggtcgacgatcttgctgcgttcggatattttcgtgg
agttcccgccacagacccggattgaaggcgagatccagcaactcgcgccagatcatcctgtgacggaactttggcgcgtgatgactggccag
gacgtcggccgaaagagcgacaagcagatcacgcttttcgacagcgtcggatttgcgatcgaggatttttcggcgctgcgctacgtccgcgac
cgcgttgagggatcaagccacagcagcccactcgaccttctagccgacccagacgagccaagggatctttttggaatgctgctccgtcgtcag
gctttccgacgtttgggtggttgaacagaagtcattatcgtacggaatgccaagcactcccgaggggaaccctgtggttggcatgcacatacaa
atggacgaacggataaacctttcacgccctttaaatatccgattattctaataaacgctcttttctcttag

FIG. 4F

SEQUENCE LISTING

```
<160> NUMBER OF SEQ ID NOS: 68

<210> SEQ ID NO 1
<211> LENGTH: 885
<212> TYPE: DNA
<213> ORGANISM: Oryza sativa
<220> FEATURE:
<221> NAME/KEY: CDS
<222> LOCATION: (1)..(885)
<223> OTHER INFORMATION: cdc2 kinase

<400> SEQUENCE: 1

atg gag cag tac gag aag gag gag aag att ggg gag ggc acg tac ggg       48
Met Glu Gln Tyr Glu Lys Glu Glu Lys Ile Gly Glu Gly Thr Tyr Gly
1               5                   10                  15
```

-continued

```
gtg gtg tac agg gcg cgg gac aag gtc acc aac gag acg atc gcg ctc        96
Val Val Tyr Arg Ala Arg Asp Lys Val Thr Asn Glu Thr Ile Ala Leu
            20                  25                  30

aag aag atc cgg ctt gag cag gag gat gag ggc gtc ccc tcc acc gca       144
Lys Lys Ile Arg Leu Glu Gln Glu Asp Glu Gly Val Pro Ser Thr Ala
        35                  40                  45

atc cgc gag atc tcg ctc ctc aag gag atg cat cac ggc aac atc gtc       192
Ile Arg Glu Ile Ser Leu Leu Lys Glu Met His His Gly Asn Ile Val
    50                  55                  60

agg tta cac gat gtt atc cac agt gag aag cgc ata tat ctt gtc ttt       240
Arg Leu His Asp Val Ile His Ser Glu Lys Arg Ile Tyr Leu Val Phe
65                  70                  75                  80

gag tat ctg gat ctg gac cta aag aag ttc atg gac tct tgt cca gag       288
Glu Tyr Leu Asp Leu Asp Leu Lys Lys Phe Met Asp Ser Cys Pro Glu
                85                  90                  95

ttt gcg aaa aac ccc act tta att aag tca tat ctc tat cag ata ctc       336
Phe Ala Lys Asn Pro Thr Leu Ile Lys Ser Tyr Leu Tyr Gln Ile Leu
            100                 105                 110

cgc ggc gtt gct tac tgt cat tct cat aga gtt ctt cat cga gat ttg       384
Arg Gly Val Ala Tyr Cys His Ser His Arg Val Leu His Arg Asp Leu
        115                 120                 125

aaa cct cag aat tta ttg ata gat cgg cgt act aat gca ctg aag ctt       432
Lys Pro Gln Asn Leu Leu Ile Asp Arg Arg Thr Asn Ala Leu Lys Leu
    130                 135                 140

gca gac ttt ggt tta gcc agg gca ttt gga att cct gtc cgc acg ttt       480
Ala Asp Phe Gly Leu Ala Arg Ala Phe Gly Ile Pro Val Arg Thr Phe
145                 150                 155                 160

gat cac gag gtt gta acc ttg tgg tat aga gct cca gag atc ctt ctt       528
Asp His Glu Val Val Thr Leu Trp Tyr Arg Ala Pro Glu Ile Leu Leu
                165                 170                 175

gga tca agg cag tat tct aca cca gtt gat atg tgg tca gtt ggt tgt       576
Gly Ser Arg Gln Tyr Ser Thr Pro Val Asp Met Trp Ser Val Gly Cys
            180                 185                 190

atc ttt gca gaa atg gtg aac cag aaa cca ctg ttc cct ggt gat tct       624
Ile Phe Ala Glu Met Val Asn Gln Lys Pro Leu Phe Pro Gly Asp Ser
        195                 200                 205

gag att gat gaa tta ttt aag ata ttc agg gta cta gga act cca aat       672
Glu Ile Asp Glu Leu Phe Lys Ile Phe Arg Val Leu Gly Thr Pro Asn
    210                 215                 220

gaa caa agt tgg cca gga gtt agc tca tta cct gac tac aag tct gct       720
Glu Gln Ser Trp Pro Gly Val Ser Ser Leu Pro Asp Tyr Lys Ser Ala
225                 230                 235                 240

ttc ccc aag tgg cag gca cag gat ctt gca act att gtc cct act ctt       768
Phe Pro Lys Trp Gln Ala Gln Asp Leu Ala Thr Ile Val Pro Thr Leu
                245                 250                 255

gac cct gct ggt ttg gac ctt ctc tct aaa atg ctt cgg tac gag cca       816
Asp Pro Ala Gly Leu Asp Leu Leu Ser Lys Met Leu Arg Tyr Glu Pro
            260                 265                 270

aac aaa agg atc aca gct aga cag gct ctt gag cat gaa tac ttc aag       864
Asn Lys Arg Ile Thr Ala Arg Gln Ala Leu Glu His Glu Tyr Phe Lys
        275                 280                 285

gac ctt gag atg gta caa tga                                           885
Asp Leu Glu Met Val Gln
    290             294
```

<210> SEQ ID NO 2
<211> LENGTH: 294
<212> TYPE: PRT
<213> ORGANISM: Oryza sativa

<400> SEQUENCE: 2

```
Met Glu Gln Tyr Glu Lys Glu Glu Lys Ile Gly Glu Gly Thr Tyr Gly
1               5                   10                  15

Val Val Tyr Arg Ala Arg Asp Lys Val Thr Asn Glu Thr Ile Ala Leu
            20                  25                  30

Lys Lys Ile Arg Leu Glu Gln Glu Asp Glu Gly Val Pro Ser Thr Ala
        35                  40                  45

Ile Arg Glu Ile Ser Leu Leu Lys Glu Met His His Gly Asn Ile Val
    50                  55                  60

Arg Leu His Asp Val Ile His Ser Glu Lys Arg Ile Tyr Leu Val Phe
65                  70                  75                  80

Glu Tyr Leu Asp Leu Asp Leu Lys Lys Phe Met Asp Ser Cys Pro Glu
                85                  90                  95

Phe Ala Lys Asn Pro Thr Leu Ile Lys Ser Tyr Leu Tyr Gln Ile Leu
            100                 105                 110

Arg Gly Val Ala Tyr Cys His Ser His Arg Val Leu His Arg Asp Leu
        115                 120                 125

Lys Pro Gln Asn Leu Leu Ile Asp Arg Arg Thr Asn Ala Leu Lys Leu
    130                 135                 140

Ala Asp Phe Gly Leu Ala Arg Ala Phe Gly Ile Pro Val Arg Thr Phe
145                 150                 155                 160

Asp His Glu Val Val Thr Leu Trp Tyr Arg Ala Pro Glu Ile Leu Leu
                165                 170                 175

Gly Ser Arg Gln Tyr Ser Thr Pro Val Asp Met Trp Ser Val Gly Cys
            180                 185                 190

Ile Phe Ala Glu Met Val Asn Gln Lys Pro Leu Phe Pro Gly Asp Ser
        195                 200                 205

Glu Ile Asp Glu Leu Phe Lys Ile Phe Arg Val Leu Gly Thr Pro Asn
    210                 215                 220

Glu Gln Ser Trp Pro Gly Val Ser Ser Leu Pro Asp Tyr Lys Ser Ala
225                 230                 235                 240

Phe Pro Lys Trp Gln Ala Gln Asp Leu Ala Thr Ile Val Pro Thr Leu
                245                 250                 255

Asp Pro Ala Gly Leu Asp Leu Leu Ser Lys Met Leu Arg Tyr Glu Pro
            260                 265                 270

Asn Lys Arg Ile Thr Ala Arg Gln Ala Leu Glu His Glu Tyr Phe Lys
        275                 280                 285

Asp Leu Glu Met Val Gln
    290
```

<210> SEQ ID NO 3
<211> LENGTH: 882
<212> TYPE: DNA
<213> ORGANISM: Oryza sativa (japonica cultivar-group)
<220> FEATURE:
<221> NAME/KEY: CDS
<222> LOCATION: (1)..(882)

<400> SEQUENCE: 3

```
atg gag cag tac gag gag gag aag att gga gag ggc acg tac ggg gta      48
Met Glu Gln Tyr Glu Glu Glu Lys Ile Gly Glu Gly Thr Tyr Gly Val
1               5                   10                  15

gtg tac aag gcg cgg gac aag gtc acc aac gag acg atc gcg ctc aag      96
Val Tyr Lys Ala Arg Asp Lys Val Thr Asn Glu Thr Ile Ala Leu Lys
            20                  25                  30

aag atc cgg ctt gag cag gag gat gag ggt gtc ccc tcc acc gcc atc     144
Lys Ile Arg Leu Glu Gln Glu Asp Glu Gly Val Pro Ser Thr Ala Ile
        35                  40                  45
```

```
cgc gag atc tcg ctc ctc aag gag atg cat cac cgc aac atc gtc agg      192
Arg Glu Ile Ser Leu Leu Lys Glu Met His His Arg Asn Ile Val Arg
    50                  55                  60

tta cac gat gtt atc cac agt gag aag cgc ata ggt ctt gtc ttt gag      240
Leu His Asp Val Ile His Ser Glu Lys Arg Ile Gly Leu Val Phe Glu
65                  70                  75                  80

tat ctg gat ctg gac ctg aag aag ttc atg gac tct tgt cca gag ttt      288
Tyr Leu Asp Leu Asp Leu Lys Lys Phe Met Asp Ser Cys Pro Glu Phe
                85                  90                  95

gca aaa aac ccc act tta att aag tca tat ctc tat cag ata ctc cgc      336
Ala Lys Asn Pro Thr Leu Ile Lys Ser Tyr Leu Tyr Gln Ile Leu Arg
            100                 105                 110

ggc gtt gct tac tgt cat tct cat aga gtt ctt cat cga gat ttg aaa      384
Gly Val Ala Tyr Cys His Ser His Arg Val Leu His Arg Asp Leu Lys
        115                 120                 125

cct cag aat tta ttg ata gat cgg cgt act aat aca ctg aag ctt gca      432
Pro Gln Asn Leu Leu Ile Asp Arg Arg Thr Asn Thr Leu Lys Leu Ala
    130                 135                 140

gac ttt ggt tta gcc agg gca ttt gga att cct gtc cgc aca ttt act      480
Asp Phe Gly Leu Ala Arg Ala Phe Gly Ile Pro Val Arg Thr Phe Thr
145                 150                 155                 160

cat gag gtt gta acc ttg tgg tat aga gct cca gag atc ctt ctt gga      528
His Glu Val Val Thr Leu Trp Tyr Arg Ala Pro Glu Ile Leu Leu Gly
                165                 170                 175

tca agg cag tat tct aca cca gtt gat atg tgg tca gtt ggt tgt atc      576
Ser Arg Gln Tyr Ser Thr Pro Val Asp Met Trp Ser Val Gly Cys Ile
            180                 185                 190

ttt gca gaa atg gtg aac cag aaa cca ctg ttc cct ggt gat tct gag      624
Phe Ala Glu Met Val Asn Gln Lys Pro Leu Phe Pro Gly Asp Ser Glu
        195                 200                 205

att gat gaa tta ttt aag ata ttc agg gta cta gga act cca aat gaa      672
Ile Asp Glu Leu Phe Lys Ile Phe Arg Val Leu Gly Thr Pro Asn Glu
    210                 215                 220

caa agt tgg cca gga gtt agc tca tta cct gac tac aag tct gct ttc      720
Gln Ser Trp Pro Gly Val Ser Ser Leu Pro Asp Tyr Lys Ser Ala Phe
225                 230                 235                 240

ccc aag tgg cag gca cag gct ctt gca act att gtc cct act ctt gac      768
Pro Lys Trp Gln Ala Gln Ala Leu Ala Thr Ile Val Pro Thr Leu Asp
                245                 250                 255

cct gct ggt ttg gac ctt ctc tct aaa atg ctt cgg tac gag cca aac      816
Pro Ala Gly Leu Asp Leu Leu Ser Lys Met Leu Arg Tyr Glu Pro Asn
            260                 265                 270

aaa agg atc aca gct aga cag gct ctt gag cat gag tac ttc aag gac      864
Lys Arg Ile Thr Ala Arg Gln Ala Leu Glu His Glu Tyr Phe Lys Asp
        275                 280                 285

ctt gag atg gaa cgc taa                                              882
Leu Glu Met Glu Arg
    290


<210> SEQ ID NO 4
<211> LENGTH: 293
<212> TYPE: PRT
<213> ORGANISM: Oryza sativa (japonica cultivar-group)

<400> SEQUENCE: 4

Met Glu Gln Tyr Glu Glu Glu Lys Ile Gly Glu Gly Thr Tyr Gly Val
1               5                   10                  15

Val Tyr Lys Ala Arg Asp Lys Val Thr Asn Glu Thr Ile Ala Leu Lys
            20                  25                  30

Lys Ile Arg Leu Glu Gln Glu Asp Glu Gly Val Pro Ser Thr Ala Ile
        35                  40                  45
```

```
Arg Glu Ile Ser Leu Leu Lys Glu Met His His Arg Asn Ile Val Arg
    50                  55                  60

Leu His Asp Val Ile His Ser Glu Lys Arg Ile Gly Leu Val Phe Glu
65                  70                  75                  80

Tyr Leu Asp Leu Asp Leu Lys Lys Phe Met Asp Ser Cys Pro Glu Phe
                85                  90                  95

Ala Lys Asn Pro Thr Leu Ile Lys Ser Tyr Leu Tyr Gln Ile Leu Arg
            100                 105                 110

Gly Val Ala Tyr Cys His Ser His Arg Val Leu His Arg Asp Leu Lys
        115                 120                 125

Pro Gln Asn Leu Leu Ile Asp Arg Arg Thr Asn Thr Leu Lys Leu Ala
    130                 135                 140

Asp Phe Gly Leu Ala Arg Ala Phe Gly Ile Pro Val Arg Thr Phe Thr
145                 150                 155                 160

His Glu Val Val Thr Leu Trp Tyr Arg Ala Pro Glu Ile Leu Leu Gly
                165                 170                 175

Ser Arg Gln Tyr Ser Thr Pro Val Asp Met Trp Ser Val Gly Cys Ile
            180                 185                 190

Phe Ala Glu Met Val Asn Gln Lys Pro Leu Phe Pro Gly Asp Ser Glu
        195                 200                 205

Ile Asp Glu Leu Phe Lys Ile Phe Arg Val Leu Gly Thr Pro Asn Glu
    210                 215                 220

Gln Ser Trp Pro Gly Val Ser Ser Leu Pro Asp Tyr Lys Ser Ala Phe
225                 230                 235                 240

Pro Lys Trp Gln Ala Gln Ala Leu Ala Thr Ile Val Pro Thr Leu Asp
                245                 250                 255

Pro Ala Gly Leu Asp Leu Leu Ser Lys Met Leu Arg Tyr Glu Pro Asn
            260                 265                 270

Lys Arg Ile Thr Ala Arg Gln Ala Leu Glu His Glu Tyr Phe Lys Asp
        275                 280                 285

Leu Glu Met Glu Arg
    290


<210> SEQ ID NO 5
<211> LENGTH: 885
<212> TYPE: DNA
<213> ORGANISM: Allium cepa
<220> FEATURE:
<221> NAME/KEY: CDS
<222> LOCATION: (1)..(885)

<400> SEQUENCE: 5

atg gat cag tat gag aaa gtg gag aag att gga gaa gga act tat gga       48
Met Asp Gln Tyr Glu Lys Val Glu Lys Ile Gly Glu Gly Thr Tyr Gly
1               5                   10                  15

gtt gtt tac aaa gca cgt gat cgg ctg act aat gaa acg att gct ttg       96
Val Val Tyr Lys Ala Arg Asp Arg Leu Thr Asn Glu Thr Ile Ala Leu
            20                  25                  30

aag aag att agg ttg gag cag gaa gat gag gga gtt cct agt act gcc      144
Lys Lys Ile Arg Leu Glu Gln Glu Asp Glu Gly Val Pro Ser Thr Ala
        35                  40                  45

att aga gaa ata tca ctg ttg aag gaa atg cag cat gct aac att gtc      192
Ile Arg Glu Ile Ser Leu Leu Lys Glu Met Gln His Ala Asn Ile Val
    50                  55                  60

agg ctg caa gac gta gtt cat agt gag aag cga ata tat ctt gtg ttc      240
Arg Leu Gln Asp Val Val His Ser Glu Lys Arg Ile Tyr Leu Val Phe
65                  70                  75                  80
```

```
gag tat cta gat ctg gac ctt aag aag cat atg gat tca tgc cca gat       288
Glu Tyr Leu Asp Leu Asp Leu Lys Lys His Met Asp Ser Cys Pro Asp
                85                  90                  95

ttt gct aaa gat tct cgt ttg gct aaa aca ttt ctc tat cag ctt ctc       336
Phe Ala Lys Asp Ser Arg Leu Ala Lys Thr Phe Leu Tyr Gln Leu Leu
            100                 105                 110

cga gga att gct tat tgt cac tca cac cga gtt ctt cat cgt gac tta       384
Arg Gly Ile Ala Tyr Cys His Ser His Arg Val Leu His Arg Asp Leu
        115                 120                 125

aag cct caa aat tta ttg atc gac aga cgt acc aat tca tta aag ctt       432
Lys Pro Gln Asn Leu Leu Ile Asp Arg Arg Thr Asn Ser Leu Lys Leu
    130                 135                 140

gct gac ttt gga ctt gca agg gca ttt ggt atc cca gtc cga acc ttc       480
Ala Asp Phe Gly Leu Ala Arg Ala Phe Gly Ile Pro Val Arg Thr Phe
145                 150                 155                 160

aca cac gag gtt gtg aca ctg tgg tat agg gca cct gaa atc ctc tta       528
Thr His Glu Val Val Thr Leu Trp Tyr Arg Ala Pro Glu Ile Leu Leu
                165                 170                 175

ggt gct cgt cag tat tct act cct gta gac ata tgg tct gtg gga tgt       576
Gly Ala Arg Gln Tyr Ser Thr Pro Val Asp Ile Trp Ser Val Gly Cys
            180                 185                 190

atc ttt gct gaa atg gtg aac caa cga cct cta ttc cct ggg gac tct       624
Ile Phe Ala Glu Met Val Asn Gln Arg Pro Leu Phe Pro Gly Asp Ser
        195                 200                 205

gag atc gac gag ctg ttc aaa ata ttt aga att atg ggt acc cca aac       672
Glu Ile Asp Glu Leu Phe Lys Ile Phe Arg Ile Met Gly Thr Pro Asn
    210                 215                 220

gaa gac aca tgg cca ggt gtt act tcc ttg ccc gac ttc aag tct gct       720
Glu Asp Thr Trp Pro Gly Val Thr Ser Leu Pro Asp Phe Lys Ser Ala
225                 230                 235                 240

ttt cca aag tgg ccg gca aag gac ttg gca act ata gtt cca aag ctt       768
Phe Pro Lys Trp Pro Ala Lys Asp Leu Ala Thr Ile Val Pro Lys Leu
                245                 250                 255

gat tca gct gga att gat ctt ctt tat aaa atg ctg cac ctt gaa ccg       816
Asp Ser Ala Gly Ile Asp Leu Leu Tyr Lys Met Leu His Leu Glu Pro
            260                 265                 270

agc aaa aga atc act gct cgg aag gct ctt gag cat gaa tac ttc agg       864
Ser Lys Arg Ile Thr Ala Arg Lys Ala Leu Glu His Glu Tyr Phe Arg
        275                 280                 285

gat ctt ggg aca att cca tga                                           885
Asp Leu Gly Thr Ile Pro
    290


<210> SEQ ID NO 6
<211> LENGTH: 294
<212> TYPE: PRT
<213> ORGANISM: Allium cepa

<400> SEQUENCE: 6

Met Asp Gln Tyr Glu Lys Val Glu Lys Ile Gly Glu Gly Thr Tyr Gly
1               5                   10                  15

Val Val Tyr Lys Ala Arg Asp Arg Leu Thr Asn Glu Thr Ile Ala Leu
            20                  25                  30

Lys Lys Ile Arg Leu Glu Gln Glu Asp Glu Gly Val Pro Ser Thr Ala
        35                  40                  45

Ile Arg Glu Ile Ser Leu Leu Lys Glu Met Gln His Ala Asn Ile Val
    50                  55                  60

Arg Leu Gln Asp Val Val His Ser Glu Lys Arg Ile Tyr Leu Val Phe
65                  70                  75                  80

Glu Tyr Leu Asp Leu Asp Leu Lys Lys His Met Asp Ser Cys Pro Asp
```

```
                85                  90                  95

Phe Ala Lys Asp Ser Arg Leu Ala Lys Thr Phe Leu Tyr Gln Leu Leu
            100                 105                 110

Arg Gly Ile Ala Tyr Cys His Ser His Arg Val Leu His Arg Asp Leu
        115                 120                 125

Lys Pro Gln Asn Leu Leu Ile Asp Arg Arg Thr Asn Ser Leu Lys Leu
    130                 135                 140

Ala Asp Phe Gly Leu Ala Arg Ala Phe Gly Ile Pro Val Arg Thr Phe
145                 150                 155                 160

Thr His Glu Val Val Thr Leu Trp Tyr Arg Ala Pro Glu Ile Leu Leu
                165                 170                 175

Gly Ala Arg Gln Tyr Ser Thr Pro Val Asp Ile Trp Ser Val Gly Cys
            180                 185                 190

Ile Phe Ala Glu Met Val Asn Gln Arg Pro Leu Phe Pro Gly Asp Ser
        195                 200                 205

Glu Ile Asp Glu Leu Phe Lys Ile Phe Arg Ile Met Gly Thr Pro Asn
    210                 215                 220

Glu Asp Thr Trp Pro Gly Val Thr Ser Leu Pro Asp Phe Lys Ser Ala
225                 230                 235                 240

Phe Pro Lys Trp Pro Ala Lys Asp Leu Ala Thr Ile Val Pro Lys Leu
                245                 250                 255

Asp Ser Ala Gly Ile Asp Leu Leu Tyr Lys Met Leu His Leu Glu Pro
            260                 265                 270

Ser Lys Arg Ile Thr Ala Arg Lys Ala Leu Glu His Glu Tyr Phe Arg
        275                 280                 285

Asp Leu Gly Thr Ile Pro
    290


<210> SEQ ID NO 7
<211> LENGTH: 885
<212> TYPE: DNA
<213> ORGANISM: Lycopersicon esculentum
<220> FEATURE:
<221> NAME/KEY: CDS
<222> LOCATION: (1)..(885)

<400> SEQUENCE: 7

atg gac cag tat gaa aaa gtt gag aag att ggg gaa gga aca tat ggt       48
Met Asp Gln Tyr Glu Lys Val Glu Lys Ile Gly Glu Gly Thr Tyr Gly
1               5                   10                  15

gta gtg tac aag gct cgt gat cgt gta act aat gaa act att gca ctg       96
Val Val Tyr Lys Ala Arg Asp Arg Val Thr Asn Glu Thr Ile Ala Leu
            20                  25                  30

aag aaa ata agg ttg gag cag gaa gac gag ggg gta cca agc aca gct      144
Lys Lys Ile Arg Leu Glu Gln Glu Asp Glu Gly Val Pro Ser Thr Ala
        35                  40                  45

att aga gaa ata tct ctc ttg aaa gag atg caa cat gct aat att gtg      192
Ile Arg Glu Ile Ser Leu Leu Lys Glu Met Gln His Ala Asn Ile Val
    50                  55                  60

agg ttg cag gat gtg gtg cac agt gaa aag cga ttg tat cta gtg ttt      240
Arg Leu Gln Asp Val Val His Ser Glu Lys Arg Leu Tyr Leu Val Phe
65                  70                  75                  80

gaa tat ctt gac ttg gac ttg aag aag cac atg gat tcg tgt cct gaa      288
Glu Tyr Leu Asp Leu Asp Leu Lys Lys His Met Asp Ser Cys Pro Glu
                85                  90                  95

ttc tct aag gat cca cgt ctg gtt aaa atg ttc ttg tat caa ata ctc      336
Phe Ser Lys Asp Pro Arg Leu Val Lys Met Phe Leu Tyr Gln Ile Leu
            100                 105                 110
```

-continued

```
cgt ggt att gct tat tgt cat tct cat aga gtt ctt cat aga gat ttg      384
Arg Gly Ile Ala Tyr Cys His Ser His Arg Val Leu His Arg Asp Leu
        115                 120                 125

aag cct cag aac tta cta ata gat cga cgt aca aat gct tta aag ctg      432
Lys Pro Gln Asn Leu Leu Ile Asp Arg Arg Thr Asn Ala Leu Lys Leu
    130                 135                 140

gca gac ttt ggt ttg gct aga gca ttt ggt att cct gtc aga act ttc      480
Ala Asp Phe Gly Leu Ala Arg Ala Phe Gly Ile Pro Val Arg Thr Phe
145                 150                 155                 160

act cat gag gtg gtg aca ttg tgg tac agg gca cca gaa ata ctg ctt      528
Thr His Glu Val Val Thr Leu Trp Tyr Arg Ala Pro Glu Ile Leu Leu
                165                 170                 175

gga tca cgc cat tac tct act cct gtt gat gtg tgg tca gtt ggt tgc      576
Gly Ser Arg His Tyr Ser Thr Pro Val Asp Val Trp Ser Val Gly Cys
            180                 185                 190

ata ttt gct gag atg gtg aat cag ccg cct ctg ttt cct ggt gac tct      624
Ile Phe Ala Glu Met Val Asn Gln Pro Pro Leu Phe Pro Gly Asp Ser
        195                 200                 205

gag att gat gaa ctt ttc aag att ttc aga gta ttg ggt act cca aat      672
Glu Ile Asp Glu Leu Phe Lys Ile Phe Arg Val Leu Gly Thr Pro Asn
    210                 215                 220

gag gat aca tgg cct gga gtg act tct ctg cct gat tac aaa tct gcc      720
Glu Asp Thr Trp Pro Gly Val Thr Ser Leu Pro Asp Tyr Lys Ser Ala
225                 230                 235                 240

ttc cca aaa tgg cct cct aag gac ctg gca att att gta cca aat gtt      768
Phe Pro Lys Trp Pro Pro Lys Asp Leu Ala Ile Ile Val Pro Asn Val
                245                 250                 255

gat gga gca ggc ctt gat ctt ctt ggt aaa atg ctc tcc ttg gat ccc      816
Asp Gly Ala Gly Leu Asp Leu Leu Gly Lys Met Leu Ser Leu Asp Pro
            260                 265                 270

agt aag aga atc acc gcg agg aat gcc ctt gag cat gag tac ttc aag      864
Ser Lys Arg Ile Thr Ala Arg Asn Ala Leu Glu His Glu Tyr Phe Lys
        275                 280                 285

gat att ggg tat gtg ccg tga                                          885
Asp Ile Gly Tyr Val Pro
    290


<210> SEQ ID NO 8
<211> LENGTH: 294
<212> TYPE: PRT
<213> ORGANISM: Lycopersicon esculentum

<400> SEQUENCE: 8

Met Asp Gln Tyr Glu Lys Val Glu Lys Ile Gly Glu Gly Thr Tyr Gly
1               5                   10                  15

Val Val Tyr Lys Ala Arg Asp Arg Val Thr Asn Glu Thr Ile Ala Leu
            20                  25                  30

Lys Lys Ile Arg Leu Glu Gln Glu Asp Glu Gly Val Pro Ser Thr Ala
        35                  40                  45

Ile Arg Glu Ile Ser Leu Leu Lys Glu Met Gln His Ala Asn Ile Val
    50                  55                  60

Arg Leu Gln Asp Val Val His Ser Glu Lys Arg Leu Tyr Leu Val Phe
65                  70                  75                  80

Glu Tyr Leu Asp Leu Asp Leu Lys Lys His Met Asp Ser Cys Pro Glu
                85                  90                  95

Phe Ser Lys Asp Pro Arg Leu Val Lys Met Phe Leu Tyr Gln Ile Leu
            100                 105                 110

Arg Gly Ile Ala Tyr Cys His Ser His Arg Val Leu His Arg Asp Leu
        115                 120                 125
```

```
Lys Pro Gln Asn Leu Leu Ile Asp Arg Arg Thr Asn Ala Leu Lys Leu
    130                 135                 140

Ala Asp Phe Gly Leu Ala Arg Ala Phe Gly Ile Pro Val Arg Thr Phe
145                 150                 155                 160

Thr His Glu Val Val Thr Leu Trp Tyr Arg Ala Pro Glu Ile Leu Leu
                165                 170                 175

Gly Ser Arg His Tyr Ser Thr Pro Val Asp Val Trp Ser Val Gly Cys
            180                 185                 190

Ile Phe Ala Glu Met Val Asn Gln Pro Pro Leu Phe Pro Gly Asp Ser
        195                 200                 205

Glu Ile Asp Glu Leu Phe Lys Ile Phe Arg Val Leu Gly Thr Pro Asn
    210                 215                 220

Glu Asp Thr Trp Pro Gly Val Thr Ser Leu Pro Asp Tyr Lys Ser Ala
225                 230                 235                 240

Phe Pro Lys Trp Pro Pro Lys Asp Leu Ala Ile Ile Val Pro Asn Val
                245                 250                 255

Asp Gly Ala Gly Leu Asp Leu Leu Gly Lys Met Leu Ser Leu Asp Pro
            260                 265                 270

Ser Lys Arg Ile Thr Ala Arg Asn Ala Leu Glu His Glu Tyr Phe Lys
        275                 280                 285

Asp Ile Gly Tyr Val Pro
    290


<210> SEQ ID NO 9
<211> LENGTH: 885
<212> TYPE: DNA
<213> ORGANISM: Pisum sativum
<220> FEATURE:
<221> NAME/KEY: CDS
<222> LOCATION: (1)..(885)

<400> SEQUENCE: 9

atg gaa cag tat gag aag gtt gag aaa ata gga gaa ggt aca tac ggt       48
Met Glu Gln Tyr Glu Lys Val Glu Lys Ile Gly Glu Gly Thr Tyr Gly
1               5                   10                  15

gtg gtg tac aag gct agg gac cgt gtt acc aat gag acc att gct ttg       96
Val Val Tyr Lys Ala Arg Asp Arg Val Thr Asn Glu Thr Ile Ala Leu
            20                  25                  30

aag aag att cga ctc gaa cag gaa gat gag ggg gtt cct agc act gcc      144
Lys Lys Ile Arg Leu Glu Gln Glu Asp Glu Gly Val Pro Ser Thr Ala
        35                  40                  45

ata aga gag att tct ctt ttg aaa gaa atg cag cat cgg aac att gtt      192
Ile Arg Glu Ile Ser Leu Leu Lys Glu Met Gln His Arg Asn Ile Val
    50                  55                  60

agg ttg cag gat gtt gtg cat agt gag aag cga ttg tat ctt gtt ttt      240
Arg Leu Gln Asp Val Val His Ser Glu Lys Arg Leu Tyr Leu Val Phe
65                  70                  75                  80

gag tac ctt gac tta gat cta aag aag cat atg gat tca tct ccg gaa      288
Glu Tyr Leu Asp Leu Asp Leu Lys Lys His Met Asp Ser Ser Pro Glu
                85                  90                  95

ttt tcc aaa gat caa cgt caa gta aaa atg ttc ctc tat caa att ctc      336
Phe Ser Lys Asp Gln Arg Gln Val Lys Met Phe Leu Tyr Gln Ile Leu
            100                 105                 110

tgt ggc att gct tac tgt cat tct cat aga gtt ctt cac cga gac ctg      384
Cys Gly Ile Ala Tyr Cys His Ser His Arg Val Leu His Arg Asp Leu
        115                 120                 125

aaa cca caa aat ctg ttg ata gat cgc agc tct aat gcg cta aag ctt      432
Lys Pro Gln Asn Leu Leu Ile Asp Arg Ser Ser Asn Ala Leu Lys Leu
    130                 135                 140
```

-continued

```
gca gat ttt ggg ttg gct aga gca ttt gga att cct gtt agg aca ttt      480
Ala Asp Phe Gly Leu Ala Arg Ala Phe Gly Ile Pro Val Arg Thr Phe
145                 150                 155                 160

aca cat gag gtg gtg aca cta tgg tac aga gct cca gaa ata ttg ctt      528
Thr His Glu Val Val Thr Leu Trp Tyr Arg Ala Pro Glu Ile Leu Leu
                165                 170                 175

ggg tcc cgt cat tat tct acc cca gtt gat gtt tgg tca gtg gga tgc      576
Gly Ser Arg His Tyr Ser Thr Pro Val Asp Val Trp Ser Val Gly Cys
            180                 185                 190

ata ttt gca gag atg ata aac cag cga cca ctt ttc cct ggg gat tct      624
Ile Phe Ala Glu Met Ile Asn Gln Arg Pro Leu Phe Pro Gly Asp Ser
        195                 200                 205

gag att gat gaa ttg ttt aaa ata ttc aga atc acg ggt aca cca aat      672
Glu Ile Asp Glu Leu Phe Lys Ile Phe Arg Ile Thr Gly Thr Pro Asn
    210                 215                 220

gaa gat aca tgg cct gga gtg act tca ttg cct gat ttt aaa tcc gcc      720
Glu Asp Thr Trp Pro Gly Val Thr Ser Leu Pro Asp Phe Lys Ser Ala
225                 230                 235                 240

ttt ccc aag tgg cca tct aag gac ctg gca act ctg gtc cca agt ctt      768
Phe Pro Lys Trp Pro Ser Lys Asp Leu Ala Thr Leu Val Pro Ser Leu
                245                 250                 255

gag cca tct ggt ctt gat ctg tta tct agt atg ctt cgc ttg gat ccc      816
Glu Pro Ser Gly Leu Asp Leu Leu Ser Ser Met Leu Arg Leu Asp Pro
            260                 265                 270

agc aga aga att act gcc agg ggc gct ctt gag cac gaa tac ttc aaa      864
Ser Arg Arg Ile Thr Ala Arg Gly Ala Leu Glu His Glu Tyr Phe Lys
        275                 280                 285

gac att aaa ttt gtc ccc tga                                          885
Asp Ile Lys Phe Val Pro
    290
```

<210> SEQ ID NO 10
<211> LENGTH: 294
<212> TYPE: PRT
<213> ORGANISM: Pisum sativum

<400> SEQUENCE: 10

```
Met Glu Gln Tyr Glu Lys Val Glu Lys Ile Gly Glu Gly Thr Tyr Gly
1               5                   10                  15

Val Val Tyr Lys Ala Arg Asp Arg Val Thr Asn Glu Thr Ile Ala Leu
            20                  25                  30

Lys Lys Ile Arg Leu Glu Gln Glu Asp Glu Gly Val Pro Ser Thr Ala
        35                  40                  45

Ile Arg Glu Ile Ser Leu Leu Lys Glu Met Gln His Arg Asn Ile Val
    50                  55                  60

Arg Leu Gln Asp Val Val His Ser Glu Lys Arg Leu Tyr Leu Val Phe
65                  70                  75                  80

Glu Tyr Leu Asp Leu Asp Leu Lys Lys His Met Asp Ser Ser Pro Glu
                85                  90                  95

Phe Ser Lys Asp Gln Arg Gln Val Lys Met Phe Leu Tyr Gln Ile Leu
            100                 105                 110

Cys Gly Ile Ala Tyr Cys His Ser His Arg Val Leu His Arg Asp Leu
        115                 120                 125

Lys Pro Gln Asn Leu Leu Ile Asp Arg Ser Ser Asn Ala Leu Lys Leu
    130                 135                 140

Ala Asp Phe Gly Leu Ala Arg Ala Phe Gly Ile Pro Val Arg Thr Phe
145                 150                 155                 160

Thr His Glu Val Val Thr Leu Trp Tyr Arg Ala Pro Glu Ile Leu Leu
                165                 170                 175
```

```
Gly Ser Arg His Tyr Ser Thr Pro Val Asp Val Trp Ser Val Gly Cys
            180                 185                 190

Ile Phe Ala Glu Met Ile Asn Gln Arg Pro Leu Phe Pro Gly Asp Ser
        195                 200                 205

Glu Ile Asp Glu Leu Phe Lys Ile Phe Arg Ile Thr Gly Thr Pro Asn
    210                 215                 220

Glu Asp Thr Trp Pro Gly Val Thr Ser Leu Pro Asp Phe Lys Ser Ala
225                 230                 235                 240

Phe Pro Lys Trp Pro Ser Lys Asp Leu Ala Thr Leu Val Pro Ser Leu
                245                 250                 255

Glu Pro Ser Gly Leu Asp Leu Leu Ser Ser Met Leu Arg Leu Asp Pro
            260                 265                 270

Ser Arg Arg Ile Thr Ala Arg Gly Ala Leu Glu His Glu Tyr Phe Lys
        275                 280                 285

Asp Ile Lys Phe Val Pro
    290


<210> SEQ ID NO 11
<211> LENGTH: 885
<212> TYPE: DNA
<213> ORGANISM: Camellia sinensis
<220> FEATURE:
<221> NAME/KEY: CDS
<222> LOCATION: (1)..(885)

<400> SEQUENCE: 11

atg gag cag tac gaa aaa gtt gag aag att ggt gaa gga acc tat ggt       48
Met Glu Gln Tyr Glu Lys Val Glu Lys Ile Gly Glu Gly Thr Tyr Gly
1               5                   10                  15

gtg gtc tat aag gct cgg gac cga gtg acc aat gaa act ata gct tta       96
Val Val Tyr Lys Ala Arg Asp Arg Val Thr Asn Glu Thr Ile Ala Leu
            20                  25                  30

aag aag att cgt ttg gag cag gaa gat gag ggt gta cca agc acg gca      144
Lys Lys Ile Arg Leu Glu Gln Glu Asp Glu Gly Val Pro Ser Thr Ala
        35                  40                  45

att aga gaa att tct cta ttg aaa gag atg aag cat gga aat gtt gtc      192
Ile Arg Glu Ile Ser Leu Leu Lys Glu Met Lys His Gly Asn Val Val
    50                  55                  60

agg tta cag gat gta gtg cac agt gag aag cgt ttg tat ctg gtt ttt      240
Arg Leu Gln Asp Val Val His Ser Glu Lys Arg Leu Tyr Leu Val Phe
65                  70                  75                  80

gag tat ctg gac ttg gat ttg aag aaa cac atg gat tca tgt ccg gag      288
Glu Tyr Leu Asp Leu Asp Leu Lys Lys His Met Asp Ser Cys Pro Glu
                85                  90                  95

ttc tct aag gat cca cgt ctg ata aaa atg ttc ctg tat caa att ctt      336
Phe Ser Lys Asp Pro Arg Leu Ile Lys Met Phe Leu Tyr Gln Ile Leu
            100                 105                 110

cgt ggt att gct tat tgt cac tcc cat aga gtt ctg cat cga gat ctg      384
Arg Gly Ile Ala Tyr Cys His Ser His Arg Val Leu His Arg Asp Leu
        115                 120                 125

aaa cct cag aat ctg ctg ata gat cgc cgt aca aat gct tta aag ctt      432
Lys Pro Gln Asn Leu Leu Ile Asp Arg Arg Thr Asn Ala Leu Lys Leu
    130                 135                 140

gca gat ttt gga ttg gcc aga gca ttt ggt att ccc gtc agg aca ttt      480
Ala Asp Phe Gly Leu Ala Arg Ala Phe Gly Ile Pro Val Arg Thr Phe
145                 150                 155                 160

aca cat gag gtg gtg act cta tgg tac agg gca cca gaa ata ctc ctt      528
Thr His Glu Val Val Thr Leu Trp Tyr Arg Ala Pro Glu Ile Leu Leu
                165                 170                 175
```

-continued

```
gga tcc cgc cac tat tcg act cct gtg gat gtg tgg tca gtg ggt tgt       576
Gly Ser Arg His Tyr Ser Thr Pro Val Asp Val Trp Ser Val Gly Cys
            180                 185                 190

ata ttt gct gaa atg gtg aat cag cgg cca ttg ttt cct ggg gac tct       624
Ile Phe Ala Glu Met Val Asn Gln Arg Pro Leu Phe Pro Gly Asp Ser
        195                 200                 205

gag att gat gaa cta ttc aaa atc ttc aga atc ttg ggt act cca aat       672
Glu Ile Asp Glu Leu Phe Lys Ile Phe Arg Ile Leu Gly Thr Pro Asn
    210                 215                 220

gag gat acg tgg cct gga gtg act tct ttg gct gat ttt aaa tct gcc       720
Glu Asp Thr Trp Pro Gly Val Thr Ser Leu Ala Asp Phe Lys Ser Ala
225                 230                 235                 240

ttt cca aaa tgg cct tct aag gac ctg gcc act gtg gtc cca aat ctt       768
Phe Pro Lys Trp Pro Ser Lys Asp Leu Ala Thr Val Val Pro Asn Leu
                245                 250                 255

gac tca gct ggc att gat ctt ctt agt aaa atg ctc tgt ctg gat cca       816
Asp Ser Ala Gly Ile Asp Leu Leu Ser Lys Met Leu Cys Leu Asp Pro
            260                 265                 270

agc aga aga att aca gct aga agt gcc ctt gaa cat gaa tac ttc aag       864
Ser Arg Arg Ile Thr Ala Arg Ser Ala Leu Glu His Glu Tyr Phe Lys
        275                 280                 285

gat att ggg ttt gta cct tga                                           885
Asp Ile Gly Phe Val Pro
    290


<210> SEQ ID NO 12
<211> LENGTH: 294
<212> TYPE: PRT
<213> ORGANISM: Camellia sinensis

<400> SEQUENCE: 12

Met Glu Gln Tyr Glu Lys Val Glu Lys Ile Gly Glu Gly Thr Tyr Gly
1               5                   10                  15

Val Val Tyr Lys Ala Arg Asp Arg Val Thr Asn Glu Thr Ile Ala Leu
            20                  25                  30

Lys Lys Ile Arg Leu Glu Gln Glu Asp Glu Gly Val Pro Ser Thr Ala
        35                  40                  45

Ile Arg Glu Ile Ser Leu Leu Lys Glu Met Lys His Gly Asn Val Val
    50                  55                  60

Arg Leu Gln Asp Val Val His Ser Glu Lys Arg Leu Tyr Leu Val Phe
65                  70                  75                  80

Glu Tyr Leu Asp Leu Asp Leu Lys Lys His Met Asp Ser Cys Pro Glu
                85                  90                  95

Phe Ser Lys Asp Pro Arg Leu Ile Lys Met Phe Leu Tyr Gln Ile Leu
            100                 105                 110

Arg Gly Ile Ala Tyr Cys His Ser His Arg Val Leu His Arg Asp Leu
        115                 120                 125

Lys Pro Gln Asn Leu Leu Ile Asp Arg Arg Thr Asn Ala Leu Lys Leu
    130                 135                 140

Ala Asp Phe Gly Leu Ala Arg Ala Phe Gly Ile Pro Val Arg Thr Phe
145                 150                 155                 160

Thr His Glu Val Val Thr Leu Trp Tyr Arg Ala Pro Glu Ile Leu Leu
                165                 170                 175

Gly Ser Arg His Tyr Ser Thr Pro Val Asp Val Trp Ser Val Gly Cys
            180                 185                 190

Ile Phe Ala Glu Met Val Asn Gln Arg Pro Leu Phe Pro Gly Asp Ser
        195                 200                 205

Glu Ile Asp Glu Leu Phe Lys Ile Phe Arg Ile Leu Gly Thr Pro Asn
```

-continued

```
    210                 215                 220

Glu Asp Thr Trp Pro Gly Val Thr Ser Leu Ala Asp Phe Lys Ser Ala
225                 230                 235                 240

Phe Pro Lys Trp Pro Ser Lys Asp Leu Ala Thr Val Val Pro Asn Leu
                245                 250                 255

Asp Ser Ala Gly Ile Asp Leu Leu Ser Lys Met Leu Cys Leu Asp Pro
            260                 265                 270

Ser Arg Arg Ile Thr Ala Arg Ser Ala Leu Glu His Glu Tyr Phe Lys
        275                 280                 285

Asp Ile Gly Phe Val Pro
    290


<210> SEQ ID NO 13
<211> LENGTH: 885
<212> TYPE: DNA
<213> ORGANISM: Pinus contorta
<220> FEATURE:
<221> NAME/KEY: CDS
<222> LOCATION: (1)..(885)

<400> SEQUENCE: 13

atg gaa cag tat gag aaa gtt gag aag ata gga gaa gga aca tat ggt       48
Met Glu Gln Tyr Glu Lys Val Glu Lys Ile Gly Glu Gly Thr Tyr Gly
1               5                   10                  15

gtg gtt tac aag gcc cgt gat cgc ttg aca aat gag acc ata gct ctc       96
Val Val Tyr Lys Ala Arg Asp Arg Leu Thr Asn Glu Thr Ile Ala Leu
            20                  25                  30

aag aaa att cgt ttg gag caa gaa gat gag ggt gta cca agc act gcg      144
Lys Lys Ile Arg Leu Glu Gln Glu Asp Glu Gly Val Pro Ser Thr Ala
        35                  40                  45

att aga gaa att tct ctt ctt aaa gaa atg caa cat ggg aac atc gta      192
Ile Arg Glu Ile Ser Leu Leu Lys Glu Met Gln His Gly Asn Ile Val
    50                  55                  60

agg ttg caa gat gtt gtc cat agt gaa aag cgg ctc tat ttg gtt ttc      240
Arg Leu Gln Asp Val Val His Ser Glu Lys Arg Leu Tyr Leu Val Phe
65                  70                  75                  80

gag tat ttg gat ttg gac ctc aag aag cat atg gat tct tgc cct gag      288
Glu Tyr Leu Asp Leu Asp Leu Lys Lys His Met Asp Ser Cys Pro Glu
                85                  90                  95

cta gca aag gat cct cgt cta atc aaa aca ttt ctg tat cag att ctg      336
Leu Ala Lys Asp Pro Arg Leu Ile Lys Thr Phe Leu Tyr Gln Ile Leu
            100                 105                 110

cgt ggc att gcc tat tgt cat tct cat cgg gtt ctt cat cgt gat ctg      384
Arg Gly Ile Ala Tyr Cys His Ser His Arg Val Leu His Arg Asp Leu
        115                 120                 125

aag ccg caa aat ttg ctt att gac cgc aaa acc aat gcg ttg aaa ctt      432
Lys Pro Gln Asn Leu Leu Ile Asp Arg Lys Thr Asn Ala Leu Lys Leu
    130                 135                 140

gcc gac ttt gga ctt gcc agg gca ttt gga att cca gtg agg acc ttt      480
Ala Asp Phe Gly Leu Ala Arg Ala Phe Gly Ile Pro Val Arg Thr Phe
145                 150                 155                 160

act cat gag gtg gtt aca ttg tgg tat cgt gca ccc gag atc tta ctt      528
Thr His Glu Val Val Thr Leu Trp Tyr Arg Ala Pro Glu Ile Leu Leu
                165                 170                 175

ggt tcc cgg cat tat tcg act cct gtt gat gtt tgg tct gtt gga tgt      576
Gly Ser Arg His Tyr Ser Thr Pro Val Asp Val Trp Ser Val Gly Cys
            180                 185                 190

atc ttt gct gaa atg gtc aat cag cga cca ctt ttc cca gga gac tca      624
Ile Phe Ala Glu Met Val Asn Gln Arg Pro Leu Phe Pro Gly Asp Ser
        195                 200                 205
```

```
gag att gat gag ctc ttt aag ata ttt aga gtg ctg ggg acg cca aat      672
Glu Ile Asp Glu Leu Phe Lys Ile Phe Arg Val Leu Gly Thr Pro Asn
    210                 215                 220

gaa gaa aca tgg cca gga gtc acc tct ctg cct gac ttc aag tca gcc      720
Glu Glu Thr Trp Pro Gly Val Thr Ser Leu Pro Asp Phe Lys Ser Ala
225                 230                 235                 240

ttc cca aag tgg cca gcc aag gat ttg gca act gtg gtt tca ggt ctt      768
Phe Pro Lys Trp Pro Ala Lys Asp Leu Ala Thr Val Val Ser Gly Leu
                245                 250                 255

gag cca gca gga att gat att ctc tcg aaa atg ctg tgc ctg gag ccc      816
Glu Pro Ala Gly Ile Asp Ile Leu Ser Lys Met Leu Cys Leu Glu Pro
            260                 265                 270

agt aga cgc atc act gct cgt agt gct ctg gag cac gag tat ttc aaa      864
Ser Arg Arg Ile Thr Ala Arg Ser Ala Leu Glu His Glu Tyr Phe Lys
        275                 280                 285

gat cta ggt ttt gta ccc tga                                          885
Asp Leu Gly Phe Val Pro
    290


<210> SEQ ID NO 14
<211> LENGTH: 294
<212> TYPE: PRT
<213> ORGANISM: Pinus contorta

<400> SEQUENCE: 14

Met Glu Gln Tyr Glu Lys Val Glu Lys Ile Gly Glu Gly Thr Tyr Gly
1               5                   10                  15

Val Val Tyr Lys Ala Arg Asp Arg Leu Thr Asn Glu Thr Ile Ala Leu
            20                  25                  30

Lys Lys Ile Arg Leu Glu Gln Glu Asp Glu Gly Val Pro Ser Thr Ala
        35                  40                  45

Ile Arg Glu Ile Ser Leu Leu Lys Glu Met Gln His Gly Asn Ile Val
    50                  55                  60

Arg Leu Gln Asp Val Val His Ser Glu Lys Arg Leu Tyr Leu Val Phe
65                  70                  75                  80

Glu Tyr Leu Asp Leu Asp Leu Lys Lys His Met Asp Ser Cys Pro Glu
                85                  90                  95

Leu Ala Lys Asp Pro Arg Leu Ile Lys Thr Phe Leu Tyr Gln Ile Leu
            100                 105                 110

Arg Gly Ile Ala Tyr Cys His Ser His Arg Val Leu His Arg Asp Leu
        115                 120                 125

Lys Pro Gln Asn Leu Leu Ile Asp Arg Lys Thr Asn Ala Leu Lys Leu
    130                 135                 140

Ala Asp Phe Gly Leu Ala Arg Ala Phe Gly Ile Pro Val Arg Thr Phe
145                 150                 155                 160

Thr His Glu Val Val Thr Leu Trp Tyr Arg Ala Pro Glu Ile Leu Leu
                165                 170                 175

Gly Ser Arg His Tyr Ser Thr Pro Val Asp Val Trp Ser Val Gly Cys
            180                 185                 190

Ile Phe Ala Glu Met Val Asn Gln Arg Pro Leu Phe Pro Gly Asp Ser
        195                 200                 205

Glu Ile Asp Glu Leu Phe Lys Ile Phe Arg Val Leu Gly Thr Pro Asn
    210                 215                 220

Glu Glu Thr Trp Pro Gly Val Thr Ser Leu Pro Asp Phe Lys Ser Ala
225                 230                 235                 240

Phe Pro Lys Trp Pro Ala Lys Asp Leu Ala Thr Val Val Ser Gly Leu
                245                 250                 255
```

```
Glu Pro Ala Gly Ile Asp Ile Leu Ser Lys Met Leu Cys Leu Glu Pro
            260                 265                 270

Ser Arg Arg Ile Thr Ala Arg Ser Ala Leu Glu His Glu Tyr Phe Lys
        275                 280                 285

Asp Leu Gly Phe Val Pro
    290


<210> SEQ ID NO 15
<211> LENGTH: 885
<212> TYPE: DNA
<213> ORGANISM: Picea abies
<220> FEATURE:
<221> NAME/KEY: CDS
<222> LOCATION: (1)..(885)

<400> SEQUENCE: 15

atg gag cag tat gag aaa gtt gag aag ata gga gaa gga aca tat ggt       48
Met Glu Gln Tyr Glu Lys Val Glu Lys Ile Gly Glu Gly Thr Tyr Gly
1               5                   10                  15

gtg gtc tac aag gcc cgt gat cgc ttg aca aat gag acc ata gct ctc       96
Val Val Tyr Lys Ala Arg Asp Arg Leu Thr Asn Glu Thr Ile Ala Leu
            20                  25                  30

aag aaa att cgt ttg gag caa gaa gat gag ggt gta cca agc act gca      144
Lys Lys Ile Arg Leu Glu Gln Glu Asp Glu Gly Val Pro Ser Thr Ala
        35                  40                  45

att aga gaa att tct ctt ctc aaa gaa atg caa cat ggg aac atc gta      192
Ile Arg Glu Ile Ser Leu Leu Lys Glu Met Gln His Gly Asn Ile Val
    50                  55                  60

agg ttg cag gat gtt gtc cac agt gaa aag cgt ctc tat tta gtt ttt      240
Arg Leu Gln Asp Val Val His Ser Glu Lys Arg Leu Tyr Leu Val Phe
65                  70                  75                  80

gag tat ttg gac ttg gac ctc aag aag cat atg gat tct tgc ccc gag      288
Glu Tyr Leu Asp Leu Asp Leu Lys Lys His Met Asp Ser Cys Pro Glu
                85                  90                  95

cta gca aag gat cct cgt cta atc aaa aca ttt ctg tat cag att ctg      336
Leu Ala Lys Asp Pro Arg Leu Ile Lys Thr Phe Leu Tyr Gln Ile Leu
            100                 105                 110

cgt ggc att gcc tat tgt cat tct cat cga gtt ctt cat cgt gat ttg      384
Arg Gly Ile Ala Tyr Cys His Ser His Arg Val Leu His Arg Asp Leu
        115                 120                 125

aaa cca caa aat ttg ctt att gac cgc aaa acc aat gcg ttg aaa ctt      432
Lys Pro Gln Asn Leu Leu Ile Asp Arg Lys Thr Asn Ala Leu Lys Leu
    130                 135                 140

gcc gac ttt gga ctt gca agg gca ttt gga att cca gtg agg acc ttt      480
Ala Asp Phe Gly Leu Ala Arg Ala Phe Gly Ile Pro Val Arg Thr Phe
145                 150                 155                 160

act cat gag gtg gtt aca ttg tgg tac cgt gca cca gag atc ttg ctt      528
Thr His Glu Val Val Thr Leu Trp Tyr Arg Ala Pro Glu Ile Leu Leu
                165                 170                 175

ggg tcc cga cat tat tcg act cct gtt gat gtt tgg tct gtg ggg tgt      576
Gly Ser Arg His Tyr Ser Thr Pro Val Asp Val Trp Ser Val Gly Cys
            180                 185                 190

atc ttt gct gaa atg gtg aat cag cga cca ctt ttc cca gga gac tca      624
Ile Phe Ala Glu Met Val Asn Gln Arg Pro Leu Phe Pro Gly Asp Ser
        195                 200                 205

gag att gat gaa ctc ttt aag ata ttt aga gtg ctg ggg aca cca aat      672
Glu Ile Asp Glu Leu Phe Lys Ile Phe Arg Val Leu Gly Thr Pro Asn
    210                 215                 220

gaa gaa aca tgg cca gga gtc acc tct ctg cca gac ttc aag tca gcc      720
Glu Glu Thr Trp Pro Gly Val Thr Ser Leu Pro Asp Phe Lys Ser Ala
225                 230                 235                 240
```

-continued

```
ttc cca aag tgg cca gcc aag gat ttg gca act gtg gtt cca ggt ctt      768
Phe Pro Lys Trp Pro Ala Lys Asp Leu Ala Thr Val Val Pro Gly Leu
                245                 250                 255

gag cca gca gga att gat ctt ctc tcg aaa atg ttg tgc ctg gag ccc      816
Glu Pro Ala Gly Ile Asp Leu Leu Ser Lys Met Leu Cys Leu Glu Pro
            260                 265                 270

agt aaa cgc atc act gct cgt agt gct ctg gag cat gag tat ttc aaa      864
Ser Lys Arg Ile Thr Ala Arg Ser Ala Leu Glu His Glu Tyr Phe Lys
        275                 280                 285

gat cta ggt ttt gta ccc tga                                          885
Asp Leu Gly Phe Val Pro
    290


<210> SEQ ID NO 16
<211> LENGTH: 294
<212> TYPE: PRT
<213> ORGANISM: Picea abies

<400> SEQUENCE: 16

Met Glu Gln Tyr Glu Lys Val Glu Lys Ile Gly Glu Gly Thr Tyr Gly
1               5                   10                  15

Val Val Tyr Lys Ala Arg Asp Arg Leu Thr Asn Glu Thr Ile Ala Leu
            20                  25                  30

Lys Lys Ile Arg Leu Glu Gln Glu Asp Glu Gly Val Pro Ser Thr Ala
        35                  40                  45

Ile Arg Glu Ile Ser Leu Leu Lys Glu Met Gln His Gly Asn Ile Val
    50                  55                  60

Arg Leu Gln Asp Val Val His Ser Glu Lys Arg Leu Tyr Leu Val Phe
65                  70                  75                  80

Glu Tyr Leu Asp Leu Asp Leu Lys Lys His Met Asp Ser Cys Pro Glu
                85                  90                  95

Leu Ala Lys Asp Pro Arg Leu Ile Lys Thr Phe Leu Tyr Gln Ile Leu
            100                 105                 110

Arg Gly Ile Ala Tyr Cys His Ser His Arg Val Leu His Arg Asp Leu
        115                 120                 125

Lys Pro Gln Asn Leu Leu Ile Asp Arg Lys Thr Asn Ala Leu Lys Leu
    130                 135                 140

Ala Asp Phe Gly Leu Ala Arg Ala Phe Gly Ile Pro Val Arg Thr Phe
145                 150                 155                 160

Thr His Glu Val Val Thr Leu Trp Tyr Arg Ala Pro Glu Ile Leu Leu
                165                 170                 175

Gly Ser Arg His Tyr Ser Thr Pro Val Asp Val Trp Ser Val Gly Cys
            180                 185                 190

Ile Phe Ala Glu Met Val Asn Gln Arg Pro Leu Phe Pro Gly Asp Ser
        195                 200                 205

Glu Ile Asp Glu Leu Phe Lys Ile Phe Arg Val Leu Gly Thr Pro Asn
    210                 215                 220

Glu Glu Thr Trp Pro Gly Val Thr Ser Leu Pro Asp Phe Lys Ser Ala
225                 230                 235                 240

Phe Pro Lys Trp Pro Ala Lys Asp Leu Ala Thr Val Val Pro Gly Leu
                245                 250                 255

Glu Pro Ala Gly Ile Asp Leu Leu Ser Lys Met Leu Cys Leu Glu Pro
            260                 265                 270

Ser Lys Arg Ile Thr Ala Arg Ser Ala Leu Glu His Glu Tyr Phe Lys
        275                 280                 285

Asp Leu Gly Phe Val Pro
    290
```

<210> SEQ ID NO 17
<211> LENGTH: 885
<212> TYPE: DNA
<213> ORGANISM: Saccharum officinarum
<220> FEATURE:
<221> NAME/KEY: CDS
<222> LOCATION: (1)..(885)

<400> SEQUENCE: 17

```
atg gag cag tac gag aag gtg gag aag atc ggg gag ggc acg tac ggg       48
Met Glu Gln Tyr Glu Lys Val Glu Lys Ile Gly Glu Gly Thr Tyr Gly
1               5                   10                  15

gtg gtg tac aag ggg ctg gac aag gcc acc aac gag acg atc gcg ctc       96
Val Val Tyr Lys Gly Leu Asp Lys Ala Thr Asn Glu Thr Ile Ala Leu
            20                  25                  30

aag aag atc cgc ctc gag cag gag gac gag ggc gtc ccg tcc acc gcc      144
Lys Lys Ile Arg Leu Glu Gln Glu Asp Glu Gly Val Pro Ser Thr Ala
        35                  40                  45

atc cgc gag atc tct ctc ctc aag gag atg aac cac gac aac atc gtc      192
Ile Arg Glu Ile Ser Leu Leu Lys Glu Met Asn His Asp Asn Ile Val
    50                  55                  60

agg tta cat gat gtt atc cac agc gag aag cgc ata tat ctt gtc ttc      240
Arg Leu His Asp Val Ile His Ser Glu Lys Arg Ile Tyr Leu Val Phe
65                  70                  75                  80

gag ttc ctg gat ctg gac ctg aag aag ttc atg gac tct tgc ccg gag      288
Glu Phe Leu Asp Leu Asp Leu Lys Lys Phe Met Asp Ser Cys Pro Glu
                85                  90                  95

ttt gct aag aat ccc act ttg att aag tca tac ctc tac cag ata ctc      336
Phe Ala Lys Asn Pro Thr Leu Ile Lys Ser Tyr Leu Tyr Gln Ile Leu
            100                 105                 110

cgt ggt gtt gct tac tgc cat tct cat aga ttt ctt cat cga gat ttg      384
Arg Gly Val Ala Tyr Cys His Ser His Arg Phe Leu His Arg Asp Leu
        115                 120                 125

aaa cct cag aac tta ttg ata gat cgg cgt act aat aca ctg aag ctt      432
Lys Pro Gln Asn Leu Leu Ile Asp Arg Arg Thr Asn Thr Leu Lys Leu
    130                 135                 140

gca gac ttt ggt tta tcc agg gca ttt gga att cct gtc cgt aca ttc      480
Ala Asp Phe Gly Leu Ser Arg Ala Phe Gly Ile Pro Val Arg Thr Phe
145                 150                 155                 160

act cat gag gta gtg aca tta tgg tac aga gct cca gaa att ctg ctt      528
Thr His Glu Val Val Thr Leu Trp Tyr Arg Ala Pro Glu Ile Leu Leu
                165                 170                 175

gga gcg aaa cag tat tcc aca cca gtc gat gta tgg tct gtg ggc tgt      576
Gly Ala Lys Gln Tyr Ser Thr Pro Val Asp Val Trp Ser Val Gly Cys
            180                 185                 190

atc ttt gcg gaa atg gtg aac caa aag cca cta ttc cct ggt gat tct      624
Ile Phe Ala Glu Met Val Asn Gln Lys Pro Leu Phe Pro Gly Asp Ser
        195                 200                 205

gag atc gac gaa ctg ttt aag ata ttc agg gta cta ggt aca cca aat      672
Glu Ile Asp Glu Leu Phe Lys Ile Phe Arg Val Leu Gly Thr Pro Asn
    210                 215                 220

gaa caa agt tgg cca gga gtc agt tgt ttg cct gac ttc aag act gct      720
Glu Gln Ser Trp Pro Gly Val Ser Cys Leu Pro Asp Phe Lys Thr Ala
225                 230                 235                 240

ttc ccc agg tgg cag gct cag gac ctg gca aca att gtc cca aat ctt      768
Phe Pro Arg Trp Gln Ala Gln Asp Leu Ala Thr Ile Val Pro Asn Leu
                245                 250                 255

gaa cct gct ggt ttg gac ctt ctc tcg aaa atg ctt cga tac gag cca      816
Glu Pro Ala Gly Leu Asp Leu Leu Ser Lys Met Leu Arg Tyr Glu Pro
            260                 265                 270
```

```
agc aaa aga atc aca gct agg caa gca ctt gag cat gag tac ttc aag      864
Ser Lys Arg Ile Thr Ala Arg Gln Ala Leu Glu His Glu Tyr Phe Lys
        275                 280                 285

gac ctt gaa atg gta cag tga                                          885
Asp Leu Glu Met Val Gln
    290


<210> SEQ ID NO 18
<211> LENGTH: 294
<212> TYPE: PRT
<213> ORGANISM: Saccharum officinarum

<400> SEQUENCE: 18

Met Glu Gln Tyr Glu Lys Val Glu Lys Ile Gly Glu Gly Thr Tyr Gly
1               5                   10                  15

Val Val Tyr Lys Gly Leu Asp Lys Ala Thr Asn Glu Thr Ile Ala Leu
            20                  25                  30

Lys Lys Ile Arg Leu Glu Gln Glu Asp Glu Gly Val Pro Ser Thr Ala
        35                  40                  45

Ile Arg Glu Ile Ser Leu Leu Lys Glu Met Asn His Asp Asn Ile Val
    50                  55                  60

Arg Leu His Asp Val Ile His Ser Glu Lys Arg Ile Tyr Leu Val Phe
65                  70                  75                  80

Glu Phe Leu Asp Leu Asp Leu Lys Lys Phe Met Asp Ser Cys Pro Glu
                85                  90                  95

Phe Ala Lys Asn Pro Thr Leu Ile Lys Ser Tyr Leu Tyr Gln Ile Leu
            100                 105                 110

Arg Gly Val Ala Tyr Cys His Ser His Arg Phe Leu His Arg Asp Leu
        115                 120                 125

Lys Pro Gln Asn Leu Leu Ile Asp Arg Arg Thr Asn Thr Leu Lys Leu
    130                 135                 140

Ala Asp Phe Gly Leu Ser Arg Ala Phe Gly Ile Pro Val Arg Thr Phe
145                 150                 155                 160

Thr His Glu Val Val Thr Leu Trp Tyr Arg Ala Pro Glu Ile Leu Leu
                165                 170                 175

Gly Ala Lys Gln Tyr Ser Thr Pro Val Asp Val Trp Ser Val Gly Cys
            180                 185                 190

Ile Phe Ala Glu Met Val Asn Gln Lys Pro Leu Phe Pro Gly Asp Ser
        195                 200                 205

Glu Ile Asp Glu Leu Phe Lys Ile Phe Arg Val Leu Gly Thr Pro Asn
    210                 215                 220

Glu Gln Ser Trp Pro Gly Val Ser Cys Leu Pro Asp Phe Lys Thr Ala
225                 230                 235                 240

Phe Pro Arg Trp Gln Ala Gln Asp Leu Ala Thr Ile Val Pro Asn Leu
                245                 250                 255

Glu Pro Ala Gly Leu Asp Leu Leu Ser Lys Met Leu Arg Tyr Glu Pro
            260                 265                 270

Ser Lys Arg Ile Thr Ala Arg Gln Ala Leu Glu His Glu Tyr Phe Lys
        275                 280                 285

Asp Leu Glu Met Val Gln
    290


<210> SEQ ID NO 19
<211> LENGTH: 885
<212> TYPE: DNA
<213> ORGANISM: Helianthus tuberosus
<220> FEATURE:
<221> NAME/KEY: CDS
```

<222> LOCATION: (1)..(885)

<400> SEQUENCE: 19

```
atg gag cag tac gag aag gtt gag aag att ggt gaa gga aca tac ggt       48
Met Glu Gln Tyr Glu Lys Val Glu Lys Ile Gly Glu Gly Thr Tyr Gly
1               5                   10                  15

gtg gtc tac aag gct cgt gac aaa gtg acc aat gaa aca att gct ttg       96
Val Val Tyr Lys Ala Arg Asp Lys Val Thr Asn Glu Thr Ile Ala Leu
            20                  25                  30

aaa aag atc cgt ctg gaa caa gaa gat gag ggt gtc ccg agc acg gct      144
Lys Lys Ile Arg Leu Glu Gln Glu Asp Glu Gly Val Pro Ser Thr Ala
        35                  40                  45

atc aga gag att tca ctg ttg aag gag atg caa cat gga aac att gtc      192
Ile Arg Glu Ile Ser Leu Leu Lys Glu Met Gln His Gly Asn Ile Val
    50                  55                  60

agg tta cag gat gtt gtg cac agt gac aaa cga ttg tat cta gtt ttt      240
Arg Leu Gln Asp Val Val His Ser Asp Lys Arg Leu Tyr Leu Val Phe
65                  70                  75                  80

gag tat ctg gac ctt gat ttg aag aag cac atg gac tcg tgt cca gag      288
Glu Tyr Leu Asp Leu Asp Leu Lys Lys His Met Asp Ser Cys Pro Glu
                85                  90                  95

ttt tca aag gat cca cgc ctt gta aaa acg ttt ctt tat caa atc cta      336
Phe Ser Lys Asp Pro Arg Leu Val Lys Thr Phe Leu Tyr Gln Ile Leu
            100                 105                 110

cgt ggc att gct tat tgt cat tcc cat aga gtt ctc cac aga gat cta      384
Arg Gly Ile Ala Tyr Cys His Ser His Arg Val Leu His Arg Asp Leu
        115                 120                 125

aaa cct caa aac ttg tta att gat cgc cgt acc aat gca cta aaa ctt      432
Lys Pro Gln Asn Leu Leu Ile Asp Arg Arg Thr Asn Ala Leu Lys Leu
    130                 135                 140

gcc gat ttt gga ttg gcc agg gcc ttt ggt atc cct gtc agg acg ttc      480
Ala Asp Phe Gly Leu Ala Arg Ala Phe Gly Ile Pro Val Arg Thr Phe
145                 150                 155                 160

aca cat gag gtg gtg aca ctg tgg tat aga gcc ccc gaa att ctt ctt      528
Thr His Glu Val Val Thr Leu Trp Tyr Arg Ala Pro Glu Ile Leu Leu
                165                 170                 175

ggg tcc cgt cac tat tct act cct gtt gat gtg tgg tcc gtt ggt tgt      576
Gly Ser Arg His Tyr Ser Thr Pro Val Asp Val Trp Ser Val Gly Cys
            180                 185                 190

ata ttt gct gag atg gtg aac cag cga cca ctc ttt cct gga gac tca      624
Ile Phe Ala Glu Met Val Asn Gln Arg Pro Leu Phe Pro Gly Asp Ser
        195                 200                 205

gag att gat gaa ctt ttc aag att ttc agg atc atg gga act cca aat      672
Glu Ile Asp Glu Leu Phe Lys Ile Phe Arg Ile Met Gly Thr Pro Asn
    210                 215                 220

gaa gag aca tgg cct ggt gtc act tct ctg cct gac ttt aag tcc gcc      720
Glu Glu Thr Trp Pro Gly Val Thr Ser Leu Pro Asp Phe Lys Ser Ala
225                 230                 235                 240

ttt cca aag tgg tca tca aag gat ctg gca acc gtg gtc ccg aat ctt      768
Phe Pro Lys Trp Ser Ser Lys Asp Leu Ala Thr Val Val Pro Asn Leu
                245                 250                 255

gaa aaa gcc ggt ctc gat ctc tta tgt aaa atg ctg tgg ctt gat ccc      816
Glu Lys Ala Gly Leu Asp Leu Leu Cys Lys Met Leu Trp Leu Asp Pro
            260                 265                 270

agt aaa agg att aca gcc cgg acc gca ctg gag cat gaa tac ttc aaa      864
Ser Lys Arg Ile Thr Ala Arg Thr Ala Leu Glu His Glu Tyr Phe Lys
        275                 280                 285

gat atc gga ttc gtg cca taa                                          885
Asp Ile Gly Phe Val Pro
    290
```

-continued

<210> SEQ ID NO 20
<211> LENGTH: 294
<212> TYPE: PRT
<213> ORGANISM: Helianthus tuberosus

<400> SEQUENCE: 20

```
Met Glu Gln Tyr Glu Lys Val Glu Lys Ile Gly Glu Gly Thr Tyr Gly
1               5                   10                  15

Val Val Tyr Lys Ala Arg Asp Lys Val Thr Asn Glu Thr Ile Ala Leu
            20                  25                  30

Lys Lys Ile Arg Leu Glu Gln Glu Asp Glu Gly Val Pro Ser Thr Ala
        35                  40                  45

Ile Arg Glu Ile Ser Leu Leu Lys Glu Met Gln His Gly Asn Ile Val
    50                  55                  60

Arg Leu Gln Asp Val Val His Ser Asp Lys Arg Leu Tyr Leu Val Phe
65                  70                  75                  80

Glu Tyr Leu Asp Leu Asp Leu Lys Lys His Met Asp Ser Cys Pro Glu
                85                  90                  95

Phe Ser Lys Asp Pro Arg Leu Val Lys Thr Phe Leu Tyr Gln Ile Leu
            100                 105                 110

Arg Gly Ile Ala Tyr Cys His Ser His Arg Val Leu His Arg Asp Leu
        115                 120                 125

Lys Pro Gln Asn Leu Leu Ile Asp Arg Arg Thr Asn Ala Leu Lys Leu
    130                 135                 140

Ala Asp Phe Gly Leu Ala Arg Ala Phe Gly Ile Pro Val Arg Thr Phe
145                 150                 155                 160

Thr His Glu Val Val Thr Leu Trp Tyr Arg Ala Pro Glu Ile Leu Leu
                165                 170                 175

Gly Ser Arg His Tyr Ser Thr Pro Val Asp Val Trp Ser Val Gly Cys
            180                 185                 190

Ile Phe Ala Glu Met Val Asn Gln Arg Pro Leu Phe Pro Gly Asp Ser
        195                 200                 205

Glu Ile Asp Glu Leu Phe Lys Ile Phe Arg Ile Met Gly Thr Pro Asn
    210                 215                 220

Glu Glu Thr Trp Pro Gly Val Thr Ser Leu Pro Asp Phe Lys Ser Ala
225                 230                 235                 240

Phe Pro Lys Trp Ser Ser Lys Asp Leu Ala Thr Val Val Pro Asn Leu
                245                 250                 255

Glu Lys Ala Gly Leu Asp Leu Leu Cys Lys Met Leu Trp Leu Asp Pro
            260                 265                 270

Ser Lys Arg Ile Thr Ala Arg Thr Ala Leu Glu His Glu Tyr Phe Lys
        275                 280                 285

Asp Ile Gly Phe Val Pro
    290
```

<210> SEQ ID NO 21
<211> LENGTH: 885
<212> TYPE: DNA
<213> ORGANISM: Daucus carota
<220> FEATURE:
<221> NAME/KEY: CDS
<222> LOCATION: (1)..(885)

<400> SEQUENCE: 21

```
atg gac cag tat gaa aag gtt gag aag att ggg gag ggg acg tat ggg       48
Met Asp Gln Tyr Glu Lys Val Glu Lys Ile Gly Glu Gly Thr Tyr Gly
1               5                   10                  15
```

```
gta gtt tat aag gct cgt gac cgc gtt aca aat gaa act att gct tta        96
Val Val Tyr Lys Ala Arg Asp Arg Val Thr Asn Glu Thr Ile Ala Leu
            20                  25                  30

aag aaa att cgt tta gag cag gaa gat gag gga gtg cca agc act gct       144
Lys Lys Ile Arg Leu Glu Gln Glu Asp Glu Gly Val Pro Ser Thr Ala
        35                  40                  45

att aga gaa att tct tta ctg aag gag atg cag cat gaa aat att gtc       192
Ile Arg Glu Ile Ser Leu Leu Lys Glu Met Gln His Glu Asn Ile Val
    50                  55                  60

agg cta caa gat gtt gtg cat agc gag aaa cgg ctg tat ctg gta ttt       240
Arg Leu Gln Asp Val Val His Ser Glu Lys Arg Leu Tyr Leu Val Phe
65                  70                  75                  80

gaa tat ctg gac ctg gat ctg aag aaa cat atg gat tca tgt cca gag       288
Glu Tyr Leu Asp Leu Asp Leu Lys Lys His Met Asp Ser Cys Pro Glu
                85                  90                  95

ttt gca aag gat cca cgt ctg att aaa atg ttt ctg tat caa ata ctg       336
Phe Ala Lys Asp Pro Arg Leu Ile Lys Met Phe Leu Tyr Gln Ile Leu
            100                 105                 110

cgt ggt att gct tat tgt cat tcc cat aga gtt ctg cat cgc gat ctc       384
Arg Gly Ile Ala Tyr Cys His Ser His Arg Val Leu His Arg Asp Leu
        115                 120                 125

aaa ccc caa aac ctg ctc ata gat cgc cgt acc aat gct cta aag ctt       432
Lys Pro Gln Asn Leu Leu Ile Asp Arg Arg Thr Asn Ala Leu Lys Leu
    130                 135                 140

gca gat ttt gga ctt gcc agg gca ttt gga att cca gtc agg aca ttt       480
Ala Asp Phe Gly Leu Ala Arg Ala Phe Gly Ile Pro Val Arg Thr Phe
145                 150                 155                 160

acc cac gag gtg gtg aca ctt tgg tac agg gcc cca gag ata ctc ctt       528
Thr His Glu Val Val Thr Leu Trp Tyr Arg Ala Pro Glu Ile Leu Leu
                165                 170                 175

gga tcc cgc cac tac tcc aca cca gtt gat gtg tgg tca gtt ggt tgt       576
Gly Ser Arg His Tyr Ser Thr Pro Val Asp Val Trp Ser Val Gly Cys
            180                 185                 190

att ttt gct gag atg gtg aac caa cag cca ttg ttt ccg ggc gat tct       624
Ile Phe Ala Glu Met Val Asn Gln Gln Pro Leu Phe Pro Gly Asp Ser
        195                 200                 205

gag att gat gaa tta ttt aag att ttc aga att gtg ggt acc cca aat       672
Glu Ile Asp Glu Leu Phe Lys Ile Phe Arg Ile Val Gly Thr Pro Asn
    210                 215                 220

gag gat acc tgg cct gga gta aca gct ctt cct gat ttt aag tct gcc       720
Glu Asp Thr Trp Pro Gly Val Thr Ala Leu Pro Asp Phe Lys Ser Ala
225                 230                 235                 240

ttc cca aaa tgg cca tct aag gaa ctg gga aac gta gtc cca aat ctc       768
Phe Pro Lys Trp Pro Ser Lys Glu Leu Gly Asn Val Val Pro Asn Leu
                245                 250                 255

gat gtg gcc ggt ctc aat ctc ctc aaa aaa atg ctt tgc ttg gat ccc       816
Asp Val Ala Gly Leu Asn Leu Leu Lys Lys Met Leu Cys Leu Asp Pro
            260                 265                 270

agc aga aga att act gcc agg agt gca ctt gag cat gaa tac ttc aag       864
Ser Arg Arg Ile Thr Ala Arg Ser Ala Leu Glu His Glu Tyr Phe Lys
        275                 280                 285

gat atc ggg att gtt cct taa                                            885
Asp Ile Gly Ile Val Pro
    290
```

<210> SEQ ID NO 22
<211> LENGTH: 294
<212> TYPE: PRT
<213> ORGANISM: Daucus carota

<400> SEQUENCE: 22

-continued

```
Met Asp Gln Tyr Glu Lys Val Glu Lys Ile Gly Glu Gly Thr Tyr Gly
1               5                   10                  15

Val Val Tyr Lys Ala Arg Asp Arg Val Thr Asn Glu Thr Ile Ala Leu
            20                  25                  30

Lys Lys Ile Arg Leu Glu Gln Glu Asp Glu Gly Val Pro Ser Thr Ala
        35                  40                  45

Ile Arg Glu Ile Ser Leu Leu Lys Glu Met Gln His Glu Asn Ile Val
    50                  55                  60

Arg Leu Gln Asp Val Val His Ser Glu Lys Arg Leu Tyr Leu Val Phe
65                  70                  75                  80

Glu Tyr Leu Asp Leu Asp Leu Lys Lys His Met Asp Ser Cys Pro Glu
                85                  90                  95

Phe Ala Lys Asp Pro Arg Leu Ile Lys Met Phe Leu Tyr Gln Ile Leu
            100                 105                 110

Arg Gly Ile Ala Tyr Cys His Ser His Arg Val Leu His Arg Asp Leu
        115                 120                 125

Lys Pro Gln Asn Leu Leu Ile Asp Arg Arg Thr Asn Ala Leu Lys Leu
    130                 135                 140

Ala Asp Phe Gly Leu Ala Arg Ala Phe Gly Ile Pro Val Arg Thr Phe
145                 150                 155                 160

Thr His Glu Val Val Thr Leu Trp Tyr Arg Ala Pro Glu Ile Leu Leu
                165                 170                 175

Gly Ser Arg His Tyr Ser Thr Pro Val Asp Val Trp Ser Val Gly Cys
            180                 185                 190

Ile Phe Ala Glu Met Val Asn Gln Gln Pro Leu Phe Pro Gly Asp Ser
        195                 200                 205

Glu Ile Asp Glu Leu Phe Lys Ile Phe Arg Ile Val Gly Thr Pro Asn
    210                 215                 220

Glu Asp Thr Trp Pro Gly Val Thr Ala Leu Pro Asp Phe Lys Ser Ala
225                 230                 235                 240

Phe Pro Lys Trp Pro Ser Lys Glu Leu Gly Asn Val Val Pro Asn Leu
                245                 250                 255

Asp Val Ala Gly Leu Asn Leu Leu Lys Lys Met Leu Cys Leu Asp Pro
            260                 265                 270

Ser Arg Arg Ile Thr Ala Arg Ser Ala Leu Glu His Glu Tyr Phe Lys
        275                 280                 285

Asp Ile Gly Ile Val Pro
    290


<210> SEQ ID NO 23
<211> LENGTH: 885
<212> TYPE: DNA
<213> ORGANISM: Coffea arabica
<220> FEATURE:
<221> NAME/KEY: CDS
<222> LOCATION: (1)..(885)

<400> SEQUENCE: 23

atg gat cag tat gag aag gtg gag aag ata ggg gaa gga acg tat gga       48
Met Asp Gln Tyr Glu Lys Val Glu Lys Ile Gly Glu Gly Thr Tyr Gly
1               5                   10                  15

gtg gtg tac aag gca cgt gac aag tcg act aat gaa act att gct ttg       96
Val Val Tyr Lys Ala Arg Asp Lys Ser Thr Asn Glu Thr Ile Ala Leu
            20                  25                  30

aag aag att cgt ctg gag cag gaa gat gaa ggt gtg ccg agc act gct      144
Lys Lys Ile Arg Leu Glu Gln Glu Asp Glu Gly Val Pro Ser Thr Ala
        35                  40                  45
```

-continued

```
att aga gaa att tct ctc ttg aaa gag atg cag cat gga aac att gtc      192
Ile Arg Glu Ile Ser Leu Leu Lys Glu Met Gln His Gly Asn Ile Val
    50                  55                  60

agg ttg cag gat gtg gtg cac agc gag aag cgc tta tat ctt gta ttt      240
Arg Leu Gln Asp Val Val His Ser Glu Lys Arg Leu Tyr Leu Val Phe
65                  70                  75                  80

gag tat ctg gac ttg gat ctg aag aag cac atg gat tcc tgt cca gaa      288
Glu Tyr Leu Asp Leu Asp Leu Lys Lys His Met Asp Ser Cys Pro Glu
                85                  90                  95

ttc tct aag gac cca cgc ctt gta aaa atg ttt ctg tat caa atc ctt      336
Phe Ser Lys Asp Pro Arg Leu Val Lys Met Phe Leu Tyr Gln Ile Leu
            100                 105                 110

cgt ggt atc gca tat tgc cat tct cac aga gtt ctt cat aga gac ttg      384
Arg Gly Ile Ala Tyr Cys His Ser His Arg Val Leu His Arg Asp Leu
        115                 120                 125

aaa cca caa aac ttg ctc ata gat cgc cgt act aat gca ctg aag ctt      432
Lys Pro Gln Asn Leu Leu Ile Asp Arg Arg Thr Asn Ala Leu Lys Leu
    130                 135                 140

gca gat ttt gga ttg gcc cgt gcc ttt ggt att cct gtc agg aca ttt      480
Ala Asp Phe Gly Leu Ala Arg Ala Phe Gly Ile Pro Val Arg Thr Phe
145                 150                 155                 160

act cat gag gtt gtt acg ctg tgg tac agg gca cca gaa ata cta ctt      528
Thr His Glu Val Val Thr Leu Trp Tyr Arg Ala Pro Glu Ile Leu Leu
                165                 170                 175

gga tca cgc cac tat tct act cct gtt gac gtg tgg tca gtt ggc tgc      576
Gly Ser Arg His Tyr Ser Thr Pro Val Asp Val Trp Ser Val Gly Cys
            180                 185                 190

ata ttt gct gag atg gtg aac cag cgg cct ttg ttc cct ggg gat tct      624
Ile Phe Ala Glu Met Val Asn Gln Arg Pro Leu Phe Pro Gly Asp Ser
        195                 200                 205

gag ata gat gaa ctc ttc aaa att ttc aga gtt atg ggc act cca aat      672
Glu Ile Asp Glu Leu Phe Lys Ile Phe Arg Val Met Gly Thr Pro Asn
    210                 215                 220

gag gat act tgg cct gga gta acc tct ctg cct gat ttc aag tct gca      720
Glu Asp Thr Trp Pro Gly Val Thr Ser Leu Pro Asp Phe Lys Ser Ala
225                 230                 235                 240

ttt cca agg tgg ctt tca cag gat ctg gca act gtg gtt ccc aat ctt      768
Phe Pro Arg Trp Leu Ser Gln Asp Leu Ala Thr Val Val Pro Asn Leu
                245                 250                 255

gat gct gct ggt ctt gat ctc ctg cgt aaa atg ctg tgc ctg gat ccc      816
Asp Ala Ala Gly Leu Asp Leu Leu Arg Lys Met Leu Cys Leu Asp Pro
            260                 265                 270

agc aag aga atc aca gct agg aat gca ctt gag cat gag tac ttc aaa      864
Ser Lys Arg Ile Thr Ala Arg Asn Ala Leu Glu His Glu Tyr Phe Lys
        275                 280                 285

gat atc ggt ttt gtc cct taa                                          885
Asp Ile Gly Phe Val Pro
    290


<210> SEQ ID NO 24
<211> LENGTH: 294
<212> TYPE: PRT
<213> ORGANISM: Coffea arabica

<400> SEQUENCE: 24

Met Asp Gln Tyr Glu Lys Val Glu Lys Ile Gly Glu Gly Thr Tyr Gly
1               5                   10                  15

Val Val Tyr Lys Ala Arg Asp Lys Ser Thr Asn Glu Thr Ile Ala Leu
            20                  25                  30

Lys Lys Ile Arg Leu Glu Gln Glu Asp Glu Gly Val Pro Ser Thr Ala
        35                  40                  45
```

-continued

```
Ile Arg Glu Ile Ser Leu Leu Lys Glu Met Gln His Gly Asn Ile Val
    50                  55                  60

Arg Leu Gln Asp Val Val His Ser Glu Lys Arg Leu Tyr Leu Val Phe
65                  70                  75                  80

Glu Tyr Leu Asp Leu Asp Leu Lys Lys His Met Asp Ser Cys Pro Glu
                85                  90                  95

Phe Ser Lys Asp Pro Arg Leu Val Lys Met Phe Leu Tyr Gln Ile Leu
            100                 105                 110

Arg Gly Ile Ala Tyr Cys His Ser His Arg Val Leu His Arg Asp Leu
        115                 120                 125

Lys Pro Gln Asn Leu Leu Ile Asp Arg Arg Thr Asn Ala Leu Lys Leu
    130                 135                 140

Ala Asp Phe Gly Leu Ala Arg Ala Phe Gly Ile Pro Val Arg Thr Phe
145                 150                 155                 160

Thr His Glu Val Val Thr Leu Trp Tyr Arg Ala Pro Glu Ile Leu Leu
                165                 170                 175

Gly Ser Arg His Tyr Ser Thr Pro Val Asp Val Trp Ser Val Gly Cys
            180                 185                 190

Ile Phe Ala Glu Met Val Asn Gln Arg Pro Leu Phe Pro Gly Asp Ser
        195                 200                 205

Glu Ile Asp Glu Leu Phe Lys Ile Phe Arg Val Met Gly Thr Pro Asn
    210                 215                 220

Glu Asp Thr Trp Pro Gly Val Thr Ser Leu Pro Asp Phe Lys Ser Ala
225                 230                 235                 240

Phe Pro Arg Trp Leu Ser Gln Asp Leu Ala Thr Val Val Pro Asn Leu
                245                 250                 255

Asp Ala Ala Gly Leu Asp Leu Leu Arg Lys Met Leu Cys Leu Asp Pro
            260                 265                 270

Ser Lys Arg Ile Thr Ala Arg Asn Ala Leu Glu His Glu Tyr Phe Lys
        275                 280                 285

Asp Ile Gly Phe Val Pro
    290
```

<210> SEQ ID NO 25
<211> LENGTH: 885
<212> TYPE: DNA
<213> ORGANISM: Helianthus annuus
<220> FEATURE:
<221> NAME/KEY: CDS
<222> LOCATION: (1)..(885)

<400> SEQUENCE: 25

```
atg gag cag tac gag aag gtt gag aag att ggt gaa gga aca tat ggt       48
Met Glu Gln Tyr Glu Lys Val Glu Lys Ile Gly Glu Gly Thr Tyr Gly
1               5                   10                  15

gtg gtc tac aag gct cgt gac aaa gtg acc aat gaa aca att gct ttg       96
Val Val Tyr Lys Ala Arg Asp Lys Val Thr Asn Glu Thr Ile Ala Leu
            20                  25                  30

aaa aag atc cgt ttg gag caa gaa gat gag ggt gtc ccg agc acg gct      144
Lys Lys Ile Arg Leu Glu Gln Glu Asp Glu Gly Val Pro Ser Thr Ala
        35                  40                  45

atc aga gag att tca ctg ttg aag gag atg caa cat gga aac att gtc      192
Ile Arg Glu Ile Ser Leu Leu Lys Glu Met Gln His Gly Asn Ile Val
    50                  55                  60

agg tta cag gat gtt gtg cac agt gac aaa cga ttg tat cta gtt ttt      240
Arg Leu Gln Asp Val Val His Ser Asp Lys Arg Leu Tyr Leu Val Phe
65                  70                  75                  80
```

-continued

```
gag tat ctg gac ctt gat ttg aag aag cac atg gac tcg tgt cca gag      288
Glu Tyr Leu Asp Leu Asp Leu Lys Lys His Met Asp Ser Cys Pro Glu
                85                  90                  95

ttt tca aag gat cca cgc ctt gta aaa acg ttt ctt tat caa atc cta      336
Phe Ser Lys Asp Pro Arg Leu Val Lys Thr Phe Leu Tyr Gln Ile Leu
            100                 105                 110

cgt ggc att gct tat tgt cat tcc cat aga gtt ctc cac aga gat cta      384
Arg Gly Ile Ala Tyr Cys His Ser His Arg Val Leu His Arg Asp Leu
        115                 120                 125

aaa cct caa aac ttg tta att gat cgc cgt acc aat gca cta aaa ctt      432
Lys Pro Gln Asn Leu Leu Ile Asp Arg Arg Thr Asn Ala Leu Lys Leu
    130                 135                 140

gcc gat ttt gga ttg gcc agg gcc ttt ggt atc cct gtc agg aca ttc      480
Ala Asp Phe Gly Leu Ala Arg Ala Phe Gly Ile Pro Val Arg Thr Phe
145                 150                 155                 160

aca cat gag gtg gtg aca ctg tgg tat aga gcc ccc gaa att ctt ctt      528
Thr His Glu Val Val Thr Leu Trp Tyr Arg Ala Pro Glu Ile Leu Leu
                165                 170                 175

ggg tcc cgt cac tat tct act cct gtt gat gtg tgg tcc gtt ggt tgt      576
Gly Ser Arg His Tyr Ser Thr Pro Val Asp Val Trp Ser Val Gly Cys
            180                 185                 190

ata ttt gct gag atg gtg aac cag cga cca ctc ttt cct gga gac tca      624
Ile Phe Ala Glu Met Val Asn Gln Arg Pro Leu Phe Pro Gly Asp Ser
        195                 200                 205

gag att gat gaa ctt ttc aag att ttc agg atc atg gga act cca aat      672
Glu Ile Asp Glu Leu Phe Lys Ile Phe Arg Ile Met Gly Thr Pro Asn
    210                 215                 220

gaa gag aca tgg cct ggc gtc act tct ctg cct gac ttt aag tcc gcc      720
Glu Glu Thr Trp Pro Gly Val Thr Ser Leu Pro Asp Phe Lys Ser Ala
225                 230                 235                 240

ttt cca aag tgg tca tca aag gat ctg gca acc gtg gtc ccg aat ctt      768
Phe Pro Lys Trp Ser Ser Lys Asp Leu Ala Thr Val Val Pro Asn Leu
                245                 250                 255

gaa aaa acc ggt ctc gat ctc tta cgt aaa atg ctg tgc ttg gat ccc      816
Glu Lys Thr Gly Leu Asp Leu Leu Arg Lys Met Leu Cys Leu Asp Pro
            260                 265                 270

agt aaa aga att aca gcc cgg acc gca ctg gag cat gaa tac ttc aaa      864
Ser Lys Arg Ile Thr Ala Arg Thr Ala Leu Glu His Glu Tyr Phe Lys
        275                 280                 285

gat atc gga ttc gtg cca taa                                          885
Asp Ile Gly Phe Val Pro
    290


<210> SEQ ID NO 26
<211> LENGTH: 294
<212> TYPE: PRT
<213> ORGANISM: Helianthus annuus

<400> SEQUENCE: 26

Met Glu Gln Tyr Glu Lys Val Glu Lys Ile Gly Glu Gly Thr Tyr Gly
1               5                   10                  15

Val Val Tyr Lys Ala Arg Asp Lys Val Thr Asn Glu Thr Ile Ala Leu
            20                  25                  30

Lys Lys Ile Arg Leu Glu Gln Glu Asp Glu Gly Val Pro Ser Thr Ala
        35                  40                  45

Ile Arg Glu Ile Ser Leu Leu Lys Glu Met Gln His Gly Asn Ile Val
    50                  55                  60

Arg Leu Gln Asp Val Val His Ser Asp Lys Arg Leu Tyr Leu Val Phe
65                  70                  75                  80

Glu Tyr Leu Asp Leu Asp Leu Lys Lys His Met Asp Ser Cys Pro Glu
```

```
                85                  90                  95

Phe Ser Lys Asp Pro Arg Leu Val Lys Thr Phe Leu Tyr Gln Ile Leu
            100                 105                 110

Arg Gly Ile Ala Tyr Cys His Ser His Arg Val Leu His Arg Asp Leu
        115                 120                 125

Lys Pro Gln Asn Leu Leu Ile Asp Arg Arg Thr Asn Ala Leu Lys Leu
    130                 135                 140

Ala Asp Phe Gly Leu Ala Arg Ala Phe Gly Ile Pro Val Arg Thr Phe
145                 150                 155                 160

Thr His Glu Val Val Thr Leu Trp Tyr Arg Ala Pro Glu Ile Leu Leu
                165                 170                 175

Gly Ser Arg His Tyr Ser Thr Pro Val Asp Val Trp Ser Val Gly Cys
            180                 185                 190

Ile Phe Ala Glu Met Val Asn Gln Arg Pro Leu Phe Pro Gly Asp Ser
        195                 200                 205

Glu Ile Asp Glu Leu Phe Lys Ile Phe Arg Ile Met Gly Thr Pro Asn
    210                 215                 220

Glu Glu Thr Trp Pro Gly Val Thr Ser Leu Pro Asp Phe Lys Ser Ala
225                 230                 235                 240

Phe Pro Lys Trp Ser Ser Lys Asp Leu Ala Thr Val Val Pro Asn Leu
                245                 250                 255

Glu Lys Thr Gly Leu Asp Leu Leu Arg Lys Met Leu Cys Leu Asp Pro
            260                 265                 270

Ser Lys Arg Ile Thr Ala Arg Thr Ala Leu Glu His Glu Tyr Phe Lys
        275                 280                 285

Asp Ile Gly Phe Val Pro
    290


<210> SEQ ID NO 27
<211> LENGTH: 885
<212> TYPE: DNA
<213> ORGANISM: Populus tremula x Populus tremuloides
<220> FEATURE:
<221> NAME/KEY: CDS
<222> LOCATION: (1)..(885)

<400> SEQUENCE: 27

atg gat cag tat gag aaa gtg gaa aaa att ggt gaa gga acc tac gga       48
Met Asp Gln Tyr Glu Lys Val Glu Lys Ile Gly Glu Gly Thr Tyr Gly
1               5                   10                  15

gtg gtc tac aaa gct cgt gat cgt gtc acc aat gag acc att gct ttg       96
Val Val Tyr Lys Ala Arg Asp Arg Val Thr Asn Glu Thr Ile Ala Leu
            20                  25                  30

aag aag atc cgt ttg gag cag gaa gac gag ggc gta ccc agc act gct      144
Lys Lys Ile Arg Leu Glu Gln Glu Asp Glu Gly Val Pro Ser Thr Ala
        35                  40                  45

atc cga gaa att tct ctc ttg aaa gag atg cag cat ggt aac att gtc      192
Ile Arg Glu Ile Ser Leu Leu Lys Glu Met Gln His Gly Asn Ile Val
    50                  55                  60

aga ctg cag gat gtg gtg cac agt gag aag cgc ctt tac ttg gtt ttt      240
Arg Leu Gln Asp Val Val His Ser Glu Lys Arg Leu Tyr Leu Val Phe
65                  70                  75                  80

gag tat cta gac ttg gat ttg aag aag cac atg gat tct tct cct gaa      288
Glu Tyr Leu Asp Leu Asp Leu Lys Lys His Met Asp Ser Ser Pro Glu
                85                  90                  95

ttt gct aag gat cca cgc ctt gtg aaa aca ttt ctt tat caa att ctc      336
Phe Ala Lys Asp Pro Arg Leu Val Lys Thr Phe Leu Tyr Gln Ile Leu
            100                 105                 110
```

```
cgt ggc att gct tac tgc cat tct cat aga gtt ctg cat cga gat ttg      384
Arg Gly Ile Ala Tyr Cys His Ser His Arg Val Leu His Arg Asp Leu
        115                 120                 125

aaa cct cag aat ttg ctt att gat cgc cgt acc aac gct ctg aag ctt      432
Lys Pro Gln Asn Leu Leu Ile Asp Arg Arg Thr Asn Ala Leu Lys Leu
    130                 135                 140

gca gat ttt ggt ctg gct aga gca ttt ggt ata cct gtt agg aca ttt      480
Ala Asp Phe Gly Leu Ala Arg Ala Phe Gly Ile Pro Val Arg Thr Phe
145                 150                 155                 160

aca cat gag gtt gtt acc ctg tgg tat aga gcc cct gaa att ctg ctt      528
Thr His Glu Val Val Thr Leu Trp Tyr Arg Ala Pro Glu Ile Leu Leu
                165                 170                 175

gga tct cgc cat tac tca act cca gtt gat gtg tgg tcg gtg gga tgt      576
Gly Ser Arg His Tyr Ser Thr Pro Val Asp Val Trp Ser Val Gly Cys
            180                 185                 190

ata ttt gct gag atg gtg aac cag aag cca tta ttc cca ggg gat tcc      624
Ile Phe Ala Glu Met Val Asn Gln Lys Pro Leu Phe Pro Gly Asp Ser
        195                 200                 205

gag att gat gaa cta ttc aaa att ttc aga atc ttg ggt act cca aat      672
Glu Ile Asp Glu Leu Phe Lys Ile Phe Arg Ile Leu Gly Thr Pro Asn
    210                 215                 220

gag gac acg tgg cct gga gtt act tct ttg ccc gac ttc aag agt gca      720
Glu Asp Thr Trp Pro Gly Val Thr Ser Leu Pro Asp Phe Lys Ser Ala
225                 230                 235                 240

ttc cct aag tgg cct tct aag gat ttg gca act gta gtt cca acc ctt      768
Phe Pro Lys Trp Pro Ser Lys Asp Leu Ala Thr Val Val Pro Thr Leu
                245                 250                 255

gaa aaa gct ggt gtg gat ctt ctc tct aaa atg ctt ttc ttg gat ccc      816
Glu Lys Ala Gly Val Asp Leu Leu Ser Lys Met Leu Phe Leu Asp Pro
            260                 265                 270

act aaa aga att act gcc agg agt gct ttg gag cat gaa tac ttc aag      864
Thr Lys Arg Ile Thr Ala Arg Ser Ala Leu Glu His Glu Tyr Phe Lys
        275                 280                 285

gat att ggt ttt gta cca taa                                          885
Asp Ile Gly Phe Val Pro
    290


<210> SEQ ID NO 28
<211> LENGTH: 294
<212> TYPE: PRT
<213> ORGANISM: Populus tremula x Populus tremuloides

<400> SEQUENCE: 28

Met Asp Gln Tyr Glu Lys Val Glu Lys Ile Gly Glu Gly Thr Tyr Gly
1               5                   10                  15

Val Val Tyr Lys Ala Arg Asp Arg Val Thr Asn Glu Thr Ile Ala Leu
            20                  25                  30

Lys Lys Ile Arg Leu Glu Gln Glu Asp Glu Gly Val Pro Ser Thr Ala
        35                  40                  45

Ile Arg Glu Ile Ser Leu Leu Lys Glu Met Gln His Gly Asn Ile Val
    50                  55                  60

Arg Leu Gln Asp Val Val His Ser Glu Lys Arg Leu Tyr Leu Val Phe
65                  70                  75                  80

Glu Tyr Leu Asp Leu Asp Leu Lys Lys His Met Asp Ser Ser Pro Glu
                85                  90                  95

Phe Ala Lys Asp Pro Arg Leu Val Lys Thr Phe Leu Tyr Gln Ile Leu
            100                 105                 110

Arg Gly Ile Ala Tyr Cys His Ser His Arg Val Leu His Arg Asp Leu
        115                 120                 125
```

```
Lys Pro Gln Asn Leu Leu Ile Asp Arg Arg Thr Asn Ala Leu Lys Leu
    130                 135                 140

Ala Asp Phe Gly Leu Ala Arg Ala Phe Gly Ile Pro Val Arg Thr Phe
145                 150                 155                 160

Thr His Glu Val Val Thr Leu Trp Tyr Arg Ala Pro Glu Ile Leu Leu
                165                 170                 175

Gly Ser Arg His Tyr Ser Thr Pro Val Asp Val Trp Ser Val Gly Cys
            180                 185                 190

Ile Phe Ala Glu Met Val Asn Gln Lys Pro Leu Phe Pro Gly Asp Ser
        195                 200                 205

Glu Ile Asp Glu Leu Phe Lys Ile Phe Arg Ile Leu Gly Thr Pro Asn
    210                 215                 220

Glu Asp Thr Trp Pro Gly Val Thr Ser Leu Pro Asp Phe Lys Ser Ala
225                 230                 235                 240

Phe Pro Lys Trp Pro Ser Lys Asp Leu Ala Thr Val Val Pro Thr Leu
                245                 250                 255

Glu Lys Ala Gly Val Asp Leu Leu Ser Lys Met Leu Phe Leu Asp Pro
            260                 265                 270

Thr Lys Arg Ile Thr Ala Arg Ser Ala Leu Glu His Glu Tyr Phe Lys
        275                 280                 285

Asp Ile Gly Phe Val Pro
    290


<210> SEQ ID NO 29
<211> LENGTH: 882
<212> TYPE: DNA
<213> ORGANISM: Nicotiana tabacum
<220> FEATURE:
<221> NAME/KEY: CDS
<222> LOCATION: (1)..(882)

<400> SEQUENCE: 29

atg gac cag tat gaa aaa gtt gag aag att ggg gaa gga aca tac ggt       48
Met Asp Gln Tyr Glu Lys Val Glu Lys Ile Gly Glu Gly Thr Tyr Gly
1               5                   10                  15

gta gtg tac aag gct cgt gat cgt gta act aat gaa aca att gcg ctg       96
Val Val Tyr Lys Ala Arg Asp Arg Val Thr Asn Glu Thr Ile Ala Leu
            20                  25                  30

aag aaa ata agg ctg gag cag gaa gat gag gga gta cca agc aca gct      144
Lys Lys Ile Arg Leu Glu Gln Glu Asp Glu Gly Val Pro Ser Thr Ala
        35                  40                  45

att aga gaa atc tct ctt ttg aaa gag atg cag cat gct aat att gtg      192
Ile Arg Glu Ile Ser Leu Leu Lys Glu Met Gln His Ala Asn Ile Val
    50                  55                  60

agg ttg cag gat gtt gtg cac agt gaa aag cga ttg tat cta gtt ttt      240
Arg Leu Gln Asp Val Val His Ser Glu Lys Arg Leu Tyr Leu Val Phe
65                  70                  75                  80

gaa tat ctt gac ttg gac ttg aag aag cac atg gat tca tct cct gaa      288
Glu Tyr Leu Asp Leu Asp Leu Lys Lys His Met Asp Ser Ser Pro Glu
                85                  90                  95

ttc tct aag gat cca cgt ctg gtt aaa atg ttt ttg tat caa ata ctc      336
Phe Ser Lys Asp Pro Arg Leu Val Lys Met Phe Leu Tyr Gln Ile Leu
            100                 105                 110

cgt ggt att gct tat tgt cat tct cat aga gtt ctt cat cga gat ttg      384
Arg Gly Ile Ala Tyr Cys His Ser His Arg Val Leu His Arg Asp Leu
        115                 120                 125

aag cct caa aac ttg ctg ata gat cga cgt aca aat gct tta aag ctt      432
Lys Pro Gln Asn Leu Leu Ile Asp Arg Arg Thr Asn Ala Leu Lys Leu
    130                 135                 140
```

```
gca gac ttt gga ttg gct aga gca ttt ggt att cct gtc aga act ttc      480
Ala Asp Phe Gly Leu Ala Arg Ala Phe Gly Ile Pro Val Arg Thr Phe
145                 150                 155                 160

act cat gag gtg gtg aca ttg tgg tac agg gca cca gaa ata ctg ctg      528
Thr His Glu Val Val Thr Leu Trp Tyr Arg Ala Pro Glu Ile Leu Leu
                165                 170                 175

gga tca cgc cat tat tct act cct gtt gat gtg tgg tca gtt ggt tgc      576
Gly Ser Arg His Tyr Ser Thr Pro Val Asp Val Trp Ser Val Gly Cys
            180                 185                 190

ata ttt gct gag atg gtg act cag cgc cct ctg ttt cct ggt gac tcc      624
Ile Phe Ala Glu Met Val Thr Gln Arg Pro Leu Phe Pro Gly Asp Ser
        195                 200                 205

gag att gat gaa ctt ttc aag att ttc aga gtg atg ggt act cca aat      672
Glu Ile Asp Glu Leu Phe Lys Ile Phe Arg Val Met Gly Thr Pro Asn
    210                 215                 220

gag gat aca tgg cct gga gtg act act ctg cct gat ttt aaa tct gcc      720
Glu Asp Thr Trp Pro Gly Val Thr Thr Leu Pro Asp Phe Lys Ser Ala
225                 230                 235                 240

ttc cca aaa tgg cct tct aag gac ctg gca act att gtc cca aat ctt      768
Phe Pro Lys Trp Pro Ser Lys Asp Leu Ala Thr Ile Val Pro Asn Leu
                245                 250                 255

gat gga gca ggc ctt gat ctt ctt gat aaa atg ctc cgc ttg gat ccc      816
Asp Gly Ala Gly Leu Asp Leu Leu Asp Lys Met Leu Arg Leu Asp Pro
            260                 265                 270

agc aag aga atc act gcc agg aat gcc ctt gag cat gag tac ttc aag      864
Ser Lys Arg Ile Thr Ala Arg Asn Ala Leu Glu His Glu Tyr Phe Lys
        275                 280                 285

gat att ggg tat gtt ccg                                              882
Asp Ile Gly Tyr Val Pro
    290


<210> SEQ ID NO 30
<211> LENGTH: 294
<212> TYPE: PRT
<213> ORGANISM: Nicotiana tabacum

<400> SEQUENCE: 30

Met Asp Gln Tyr Glu Lys Val Glu Lys Ile Gly Glu Gly Thr Tyr Gly
1               5                   10                  15

Val Val Tyr Lys Ala Arg Asp Arg Val Thr Asn Glu Thr Ile Ala Leu
            20                  25                  30

Lys Lys Ile Arg Leu Glu Gln Glu Asp Glu Gly Val Pro Ser Thr Ala
        35                  40                  45

Ile Arg Glu Ile Ser Leu Leu Lys Glu Met Gln His Ala Asn Ile Val
    50                  55                  60

Arg Leu Gln Asp Val Val His Ser Glu Lys Arg Leu Tyr Leu Val Phe
65                  70                  75                  80

Glu Tyr Leu Asp Leu Asp Leu Lys Lys His Met Asp Ser Ser Pro Glu
                85                  90                  95

Phe Ser Lys Asp Pro Arg Leu Val Lys Met Phe Leu Tyr Gln Ile Leu
            100                 105                 110

Arg Gly Ile Ala Tyr Cys His Ser His Arg Val Leu His Arg Asp Leu
        115                 120                 125

Lys Pro Gln Asn Leu Leu Ile Asp Arg Arg Thr Asn Ala Leu Lys Leu
    130                 135                 140

Ala Asp Phe Gly Leu Ala Arg Ala Phe Gly Ile Pro Val Arg Thr Phe
145                 150                 155                 160

Thr His Glu Val Val Thr Leu Trp Tyr Arg Ala Pro Glu Ile Leu Leu
                165                 170                 175
```

```
Gly Ser Arg His Tyr Ser Thr Pro Val Asp Val Trp Ser Val Gly Cys
            180                 185                 190

Ile Phe Ala Glu Met Val Thr Gln Arg Pro Leu Phe Pro Gly Asp Ser
        195                 200                 205

Glu Ile Asp Glu Leu Phe Lys Ile Phe Arg Val Met Gly Thr Pro Asn
    210                 215                 220

Glu Asp Thr Trp Pro Gly Val Thr Thr Leu Pro Asp Phe Lys Ser Ala
225                 230                 235                 240

Phe Pro Lys Trp Pro Ser Lys Asp Leu Ala Thr Ile Val Pro Asn Leu
                245                 250                 255

Asp Gly Ala Gly Leu Asp Leu Leu Asp Lys Met Leu Arg Leu Asp Pro
            260                 265                 270

Ser Lys Arg Ile Thr Ala Arg Asn Ala Leu Glu His Glu Tyr Phe Lys
        275                 280                 285

Asp Ile Gly Tyr Val Pro
    290


<210> SEQ ID NO 31
<211> LENGTH: 885
<212> TYPE: DNA
<213> ORGANISM: Triticum aestivum
<220> FEATURE:
<221> NAME/KEY: CDS
<222> LOCATION: (1)..(885)

<400> SEQUENCE: 31

atg gag cag tac gag aag gtg gag aag atc ggg gag ggc acg tac ggg       48
Met Glu Gln Tyr Glu Lys Val Glu Lys Ile Gly Glu Gly Thr Tyr Gly
1               5                   10                  15

gtg gtg tac aag gcc cgg gac agg acc acc aac gag acc atc gcg ctc       96
Val Val Tyr Lys Ala Arg Asp Arg Thr Thr Asn Glu Thr Ile Ala Leu
            20                  25                  30

aag aag atc cgc ctg gag cag gag gac gag ggc gtc ccc tcc acc gcc      144
Lys Lys Ile Arg Leu Glu Gln Glu Asp Glu Gly Val Pro Ser Thr Ala
        35                  40                  45

atc cgc gag atc tcg ctc ctc aag gag atg cag cac ggc aac atc gtc      192
Ile Arg Glu Ile Ser Leu Leu Lys Glu Met Gln His Gly Asn Ile Val
    50                  55                  60

aag ctg cac gat gtt gtc cac agc gag aag cgc ata tgg ctc gtc ttt      240
Lys Leu His Asp Val Val His Ser Glu Lys Arg Ile Trp Leu Val Phe
65                  70                  75                  80

gag tac ctg gat ctg gac ctg aag aag ttc atg gac tcc tgt cca gag      288
Glu Tyr Leu Asp Leu Asp Leu Lys Lys Phe Met Asp Ser Cys Pro Glu
                85                  90                  95

ttt gcc aag agc ccc gcc ttg atc aag tca tat ctc tat cag ata ctc      336
Phe Ala Lys Ser Pro Ala Leu Ile Lys Ser Tyr Leu Tyr Gln Ile Leu
            100                 105                 110

cgc ggc gtt gct tac tgt cat tct cat aga gtt ctt cat cga gat ttg      384
Arg Gly Val Ala Tyr Cys His Ser His Arg Val Leu His Arg Asp Leu
        115                 120                 125

aaa cct cag aat tta ttg ata gac cgg cgt act aat gca ctg aag ctt      432
Lys Pro Gln Asn Leu Leu Ile Asp Arg Arg Thr Asn Ala Leu Lys Leu
    130                 135                 140

gca gac ttt ggt tta gca agg gca ttt gga att cct gtc cgt aca ttt      480
Ala Asp Phe Gly Leu Ala Arg Ala Phe Gly Ile Pro Val Arg Thr Phe
145                 150                 155                 160

act cat gag gta gta aca tta tgg tac aga gct cct gaa atc ctt ctt      528
Thr His Glu Val Val Thr Leu Trp Tyr Arg Ala Pro Glu Ile Leu Leu
                165                 170                 175
```

```
gga gca agg cag tat tcc aca cca gtt gac gtg tgg tca gtg ggc tgt      576
Gly Ala Arg Gln Tyr Ser Thr Pro Val Asp Val Trp Ser Val Gly Cys
            180                 185                 190

atc ttt gca gaa atg gtg aac cag aaa cca ctg ttc cct ggc gat tct      624
Ile Phe Ala Glu Met Val Asn Gln Lys Pro Leu Phe Pro Gly Asp Ser
        195                 200                 205

gag att gat gag cta ttt aag ata ttc agg gta ctc ggc act cca aat      672
Glu Ile Asp Glu Leu Phe Lys Ile Phe Arg Val Leu Gly Thr Pro Asn
    210                 215                 220

gaa caa act tgg cca ggc gtg agt tcc ttg cct gac tac aag tcc gcc      720
Glu Gln Thr Trp Pro Gly Val Ser Ser Leu Pro Asp Tyr Lys Ser Ala
225                 230                 235                 240

ttc ccc agg tgg cag gca gag gac ctt gca acc gtt gtc ccc aat ctt      768
Phe Pro Arg Trp Gln Ala Glu Asp Leu Ala Thr Val Val Pro Asn Leu
                245                 250                 255

gaa cct gtt ggc ctg gac ctt ctc tcg aaa atg ctt cgg ttc gag cca      816
Glu Pro Val Gly Leu Asp Leu Leu Ser Lys Met Leu Arg Phe Glu Pro
            260                 265                 270

aac aag agg atc acg gct agg cag gct ctt gag cat gag tac ttc aag      864
Asn Lys Arg Ile Thr Ala Arg Gln Ala Leu Glu His Glu Tyr Phe Lys
        275                 280                 285

gac atg gag atg gta cag tga                                          885
Asp Met Glu Met Val Gln
    290


<210> SEQ ID NO 32
<211> LENGTH: 294
<212> TYPE: PRT
<213> ORGANISM: Triticum aestivum

<400> SEQUENCE: 32

Met Glu Gln Tyr Glu Lys Val Glu Lys Ile Gly Glu Gly Thr Tyr Gly
1               5                   10                  15

Val Val Tyr Lys Ala Arg Asp Arg Thr Thr Asn Glu Thr Ile Ala Leu
            20                  25                  30

Lys Lys Ile Arg Leu Glu Gln Glu Asp Glu Gly Val Pro Ser Thr Ala
        35                  40                  45

Ile Arg Glu Ile Ser Leu Leu Lys Glu Met Gln His Gly Asn Ile Val
    50                  55                  60

Lys Leu His Asp Val Val His Ser Glu Lys Arg Ile Trp Leu Val Phe
65                  70                  75                  80

Glu Tyr Leu Asp Leu Asp Leu Lys Lys Phe Met Asp Ser Cys Pro Glu
                85                  90                  95

Phe Ala Lys Ser Pro Ala Leu Ile Lys Ser Tyr Leu Tyr Gln Ile Leu
            100                 105                 110

Arg Gly Val Ala Tyr Cys His Ser His Arg Val Leu His Arg Asp Leu
        115                 120                 125

Lys Pro Gln Asn Leu Leu Ile Asp Arg Arg Thr Asn Ala Leu Lys Leu
    130                 135                 140

Ala Asp Phe Gly Leu Ala Arg Ala Phe Gly Ile Pro Val Arg Thr Phe
145                 150                 155                 160

Thr His Glu Val Val Thr Leu Trp Tyr Arg Ala Pro Glu Ile Leu Leu
                165                 170                 175

Gly Ala Arg Gln Tyr Ser Thr Pro Val Asp Val Trp Ser Val Gly Cys
            180                 185                 190

Ile Phe Ala Glu Met Val Asn Gln Lys Pro Leu Phe Pro Gly Asp Ser
        195                 200                 205

Glu Ile Asp Glu Leu Phe Lys Ile Phe Arg Val Leu Gly Thr Pro Asn
```

```
    210                 215                 220

Glu Gln Thr Trp Pro Gly Val Ser Ser Leu Pro Asp Tyr Lys Ser Ala
225                 230                 235                 240

Phe Pro Arg Trp Gln Ala Glu Asp Leu Ala Thr Val Val Pro Asn Leu
                245                 250                 255

Glu Pro Val Gly Leu Asp Leu Leu Ser Lys Met Leu Arg Phe Glu Pro
            260                 265                 270

Asn Lys Arg Ile Thr Ala Arg Gln Ala Leu Glu His Glu Tyr Phe Lys
        275                 280                 285

Asp Met Glu Met Val Gln
    290


<210> SEQ ID NO 33
<211> LENGTH: 885
<212> TYPE: DNA
<213> ORGANISM: Medicago sativa
<220> FEATURE:
<221> NAME/KEY: CDS
<222> LOCATION: (1)..(885)

<400> SEQUENCE: 33

atg gaa cag tac gag aaa gtt gag aag ata gga gaa ggt act tac ggt       48
Met Glu Gln Tyr Glu Lys Val Glu Lys Ile Gly Glu Gly Thr Tyr Gly
1               5                   10                  15

gtg gtt tac aag gct cgt gac cgt gct acc aat gag acg ata gct ttg       96
Val Val Tyr Lys Ala Arg Asp Arg Ala Thr Asn Glu Thr Ile Ala Leu
            20                  25                  30

aag aag att cgt ctt gag cag gaa gat gag gga gtt ccg agt acc gct      144
Lys Lys Ile Arg Leu Glu Gln Glu Asp Glu Gly Val Pro Ser Thr Ala
        35                  40                  45

att cga gag att tct ctc ttg aag gaa atg cag cac agg aac att gtt      192
Ile Arg Glu Ile Ser Leu Leu Lys Glu Met Gln His Arg Asn Ile Val
    50                  55                  60

agg ttg cag gat gtg gtg cac agt gag aag cga ttg tat ctg gtt ttt      240
Arg Leu Gln Asp Val Val His Ser Glu Lys Arg Leu Tyr Leu Val Phe
65                  70                  75                  80

gag tac ctt gac ttg gat cta aag aag ttt atg gat tca tct cca gaa      288
Glu Tyr Leu Asp Leu Asp Leu Lys Lys Phe Met Asp Ser Ser Pro Glu
                85                  90                  95

ttt gca aaa gat caa cgg caa ata aag atg ttc ctt tat caa att ctc      336
Phe Ala Lys Asp Gln Arg Gln Ile Lys Met Phe Leu Tyr Gln Ile Leu
            100                 105                 110

tgt ggc att gct tac tgt cat tct cat aga gtt ctt cat aga gac ttg      384
Cys Gly Ile Ala Tyr Cys His Ser His Arg Val Leu His Arg Asp Leu
        115                 120                 125

aaa cca cag aat ctg ctg att gat cgc agc tct aat gcc gta aag ctt      432
Lys Pro Gln Asn Leu Leu Ile Asp Arg Ser Ser Asn Ala Val Lys Leu
    130                 135                 140

gca gat ttt gga ttg gcc agg gca ttt gga att cct gtc agg aca ttt      480
Ala Asp Phe Gly Leu Ala Arg Ala Phe Gly Ile Pro Val Arg Thr Phe
145                 150                 155                 160

aca cat gag gtg gtg aca ctc tgg tac aga gct cca gaa ata ttg ctt      528
Thr His Glu Val Val Thr Leu Trp Tyr Arg Ala Pro Glu Ile Leu Leu
                165                 170                 175

ggg tct cgt cat tat tct acc ccg gtt gat gtc tgg tca gtg gga tgc      576
Gly Ser Arg His Tyr Ser Thr Pro Val Asp Val Trp Ser Val Gly Cys
            180                 185                 190

ata ttt gca gag atg ata aac caa cgg cca ctt ttc cca ggg gac tct      624
Ile Phe Ala Glu Met Ile Asn Gln Arg Pro Leu Phe Pro Gly Asp Ser
        195                 200                 205
```

```
gag att gat gaa ttg ttt aaa ata ttc aga atc acg ggt aca ccg aat      672
Glu Ile Asp Glu Leu Phe Lys Ile Phe Arg Ile Thr Gly Thr Pro Asn
    210                 215                 220

gag gaa aca tgg cct gga gtg act tca ttg cct gat ttt aaa tca gcc      720
Glu Glu Thr Trp Pro Gly Val Thr Ser Leu Pro Asp Phe Lys Ser Ala
225                 230                 235                 240

ttt ccc aag tgg cca gct aag gac ctg gca act caa gtc cca aat ctg      768
Phe Pro Lys Trp Pro Ala Lys Asp Leu Ala Thr Gln Val Pro Asn Leu
                245                 250                 255

gag cca gct ggt ctt gat ctt cta tcc agt act tgt cgc ttg gat ccc      816
Glu Pro Ala Gly Leu Asp Leu Leu Ser Ser Thr Cys Arg Leu Asp Pro
            260                 265                 270

acc aga aga att act gcc agg gga gct ctt gag cat gaa tac ttc aaa      864
Thr Arg Arg Ile Thr Ala Arg Gly Ala Leu Glu His Glu Tyr Phe Lys
        275                 280                 285

gac att aag ttt gtc cca tga                                          885
Asp Ile Lys Phe Val Pro
    290


<210> SEQ ID NO 34
<211> LENGTH: 294
<212> TYPE: PRT
<213> ORGANISM: Medicago sativa

<400> SEQUENCE: 34

Met Glu Gln Tyr Glu Lys Val Glu Lys Ile Gly Glu Gly Thr Tyr Gly
1               5                   10                  15

Val Val Tyr Lys Ala Arg Asp Arg Ala Thr Asn Glu Thr Ile Ala Leu
            20                  25                  30

Lys Lys Ile Arg Leu Glu Gln Glu Asp Glu Gly Val Pro Ser Thr Ala
        35                  40                  45

Ile Arg Glu Ile Ser Leu Leu Lys Glu Met Gln His Arg Asn Ile Val
    50                  55                  60

Arg Leu Gln Asp Val Val His Ser Glu Lys Arg Leu Tyr Leu Val Phe
65                  70                  75                  80

Glu Tyr Leu Asp Leu Asp Leu Lys Lys Phe Met Asp Ser Ser Pro Glu
                85                  90                  95

Phe Ala Lys Asp Gln Arg Gln Ile Lys Met Phe Leu Tyr Gln Ile Leu
            100                 105                 110

Cys Gly Ile Ala Tyr Cys His Ser His Arg Val Leu His Arg Asp Leu
        115                 120                 125

Lys Pro Gln Asn Leu Leu Ile Asp Arg Ser Ser Asn Ala Val Lys Leu
    130                 135                 140

Ala Asp Phe Gly Leu Ala Arg Ala Phe Gly Ile Pro Val Arg Thr Phe
145                 150                 155                 160

Thr His Glu Val Val Thr Leu Trp Tyr Arg Ala Pro Glu Ile Leu Leu
                165                 170                 175

Gly Ser Arg His Tyr Ser Thr Pro Val Asp Val Trp Ser Val Gly Cys
            180                 185                 190

Ile Phe Ala Glu Met Ile Asn Gln Arg Pro Leu Phe Pro Gly Asp Ser
        195                 200                 205

Glu Ile Asp Glu Leu Phe Lys Ile Phe Arg Ile Thr Gly Thr Pro Asn
    210                 215                 220

Glu Glu Thr Trp Pro Gly Val Thr Ser Leu Pro Asp Phe Lys Ser Ala
225                 230                 235                 240

Phe Pro Lys Trp Pro Ala Lys Asp Leu Ala Thr Gln Val Pro Asn Leu
                245                 250                 255
```

```
Glu Pro Ala Gly Leu Asp Leu Leu Ser Ser Thr Cys Arg Leu Asp Pro
            260                 265                 270

Thr Arg Arg Ile Thr Ala Arg Gly Ala Leu Glu His Glu Tyr Phe Lys
        275                 280                 285

Asp Ile Lys Phe Val Pro
    290


<210> SEQ ID NO 35
<211> LENGTH: 1283
<212> TYPE: DNA
<213> ORGANISM: Antirrhinum majus
<220> FEATURE:
<221> NAME/KEY: CDS
<222> LOCATION: (29)..(913)
<223> OTHER INFORMATION: n means a or g or c or t/u, s means g or c

<400> SEQUENCE: 35

gtacatggtt tcatctcatc gatctctg atg gag cag tat gaa aag gtt gag        52
                               Met Glu Gln Tyr Glu Lys Val Glu
                               1               5

aag att ggg gag gga acg tat gga gtg gta tac aag gct cgt gat cgt      100
Lys Ile Gly Glu Gly Thr Tyr Gly Val Val Tyr Lys Ala Arg Asp Arg
    10                  15                  20

gta aca aat gag act ata gcc ttg aag aaa atc cgt cta gag cag gaa      148
Val Thr Asn Glu Thr Ile Ala Leu Lys Lys Ile Arg Leu Glu Gln Glu
25                  30                  35                  40

gat gag gga gtg ccc agc aca gct atc aga gag att tct ctc ttg aaa      196
Asp Glu Gly Val Pro Ser Thr Ala Ile Arg Glu Ile Ser Leu Leu Lys
                45                  50                  55

gag atg caa cat ggg aat atc gtg agg ttg cag gat gtg gtg cac agt      244
Glu Met Gln His Gly Asn Ile Val Arg Leu Gln Asp Val Val His Ser
            60                  65                  70

gag aag cgc ttg tac ctg gtg ttt gaa tat ctg gac ttg gat ttg aaa      292
Glu Lys Arg Leu Tyr Leu Val Phe Glu Tyr Leu Asp Leu Asp Leu Lys
        75                  80                  85

aaa cat atg gat tca tgc cca gaa ttc tcc cag gat cct cgt ttg gtt      340
Lys His Met Asp Ser Cys Pro Glu Phe Ser Gln Asp Pro Arg Leu Val
    90                  95                  100

aaa atg ttt ctg tat caa ata cta cgt ggt atc gcc tac tgt cat tct      388
Lys Met Phe Leu Tyr Gln Ile Leu Arg Gly Ile Ala Tyr Cys His Ser
105                 110                 115                 120

cat cgt gtc ctt cat cga gat ttg aag cct caa aac ttg ctg ata gac      436
His Arg Val Leu His Arg Asp Leu Lys Pro Gln Asn Leu Leu Ile Asp
                125                 130                 135

cgc cgt acc aat gca tta aag ctt gct gac ttt gga ttg gcc aga gca      484
Arg Arg Thr Asn Ala Leu Lys Leu Ala Asp Phe Gly Leu Ala Arg Ala
            140                 145                 150

ttt ggt att cca gtc agg act ttt aca cat gag gtt gtg aca ctg tgg      532
Phe Gly Ile Pro Val Arg Thr Phe Thr His Glu Val Val Thr Leu Trp
        155                 160                 165

tac agg gct cca gaa ata cta ctt gga tct cgc cat tat tct act cca      580
Tyr Arg Ala Pro Glu Ile Leu Leu Gly Ser Arg His Tyr Ser Thr Pro
    170                 175                 180

gtg gat gtc tgg tca gtt ggt tgt ata ttt gct gaa atg gtt aac caa      628
Val Asp Val Trp Ser Val Gly Cys Ile Phe Ala Glu Met Val Asn Gln
185                 190                 195                 200

cgg cct ttg ttt cct ggg gac tct gag att gat gaa cta ttc aaa att      676
Arg Pro Leu Phe Pro Gly Asp Ser Glu Ile Asp Glu Leu Phe Lys Ile
                205                 210                 215

ttt aga gtc atg ggt acc cca aat gaa gaa aca tgg cca gga gtg act      724
Phe Arg Val Met Gly Thr Pro Asn Glu Glu Thr Trp Pro Gly Val Thr
            220                 225                 230
```

```
tct ttg cct gat ttt aag tca gca ttt cca aaa tgg cca gct aag gag      772
Ser Leu Pro Asp Phe Lys Ser Ala Phe Pro Lys Trp Pro Ala Lys Glu
        235                 240                 245

ctg gct gct gta gtt ccg aat ctt gat gca tct ggc ctt gat ctc ctt      820
Leu Ala Ala Val Val Pro Asn Leu Asp Ala Ser Gly Leu Asp Leu Leu
    250                 255                 260

gat aaa atg ctt cgt ttg gac ccc agc aaa aga att acg gcc agg aat      868
Asp Lys Met Leu Arg Leu Asp Pro Ser Lys Arg Ile Thr Ala Arg Asn
265                 270                 275                 280

gct ctt cag cat gag tac ttc aag gat att ggt ttt gta ccc tgattggtgc   920
Ala Leu Gln His Glu Tyr Phe Lys Asp Ile Gly Phe Val Pro
                285                 290

ccctcattct ggtacgagta tatattgtta tatgacgtct ggggttttat tctgttccat    980

aggaattcgt gacagacgaa cgttatctct tgtttttgat tccttgggtg taattccatt   1040

tatattgaag ctgtgttggt tgaagcaagt taggantggc ctctgctggt gctttcactt   1100

gctttaaacc ccttgtgtga ttttgtcgat tttttgttcc ttttccattt ttaatttccc   1160

tgtaacatca tgctgatgta taacgtttga gtttttgtta tctggtttaa tatataaata   1220

tggtgtgcct tttagttgtt caaaaaaaaa aaaaaaaaaa aaaaaaccat ggtacccgga   1280

tcc                                                                  1283


<210> SEQ ID NO 36
<211> LENGTH: 294
<212> TYPE: PRT
<213> ORGANISM: Antirrhinum majus

<400> SEQUENCE: 36

Met Glu Gln Tyr Glu Lys Val Glu Lys Ile Gly Glu Gly Thr Tyr Gly
1               5                   10                  15

Val Val Tyr Lys Ala Arg Asp Arg Val Thr Asn Glu Thr Ile Ala Leu
            20                  25                  30

Lys Lys Ile Arg Leu Glu Gln Glu Asp Glu Gly Val Pro Ser Thr Ala
        35                  40                  45

Ile Arg Glu Ile Ser Leu Leu Lys Glu Met Gln His Gly Asn Ile Val
    50                  55                  60

Arg Leu Gln Asp Val Val His Ser Glu Lys Arg Leu Tyr Leu Val Phe
65                  70                  75                  80

Glu Tyr Leu Asp Leu Asp Leu Lys Lys His Met Asp Ser Cys Pro Glu
                85                  90                  95

Phe Ser Gln Asp Pro Arg Leu Val Lys Met Phe Leu Tyr Gln Ile Leu
            100                 105                 110

Arg Gly Ile Ala Tyr Cys His Ser His Arg Val Leu His Arg Asp Leu
        115                 120                 125

Lys Pro Gln Asn Leu Leu Ile Asp Arg Arg Thr Asn Ala Leu Lys Leu
    130                 135                 140

Ala Asp Phe Gly Leu Ala Arg Ala Phe Gly Ile Pro Val Arg Thr Phe
145                 150                 155                 160

Thr His Glu Val Val Thr Leu Trp Tyr Arg Ala Pro Glu Ile Leu Leu
                165                 170                 175

Gly Ser Arg His Tyr Ser Thr Pro Val Asp Val Trp Ser Val Gly Cys
            180                 185                 190

Ile Phe Ala Glu Met Val Asn Gln Arg Pro Leu Phe Pro Gly Asp Ser
        195                 200                 205

Glu Ile Asp Glu Leu Phe Lys Ile Phe Arg Val Met Gly Thr Pro Asn
    210                 215                 220
```

```
Glu Glu Thr Trp Pro Gly Val Thr Ser Leu Pro Asp Phe Lys Ser Ala
225                 230                 235                 240

Phe Pro Lys Trp Pro Ala Lys Glu Leu Ala Ala Val Val Pro Asn Leu
                245                 250                 255

Asp Ala Ser Gly Leu Asp Leu Leu Asp Lys Met Leu Arg Leu Asp Pro
            260                 265                 270

Ser Lys Arg Ile Thr Ala Arg Asn Ala Leu Gln His Glu Tyr Phe Lys
        275                 280                 285

Asp Ile Gly Phe Val Pro
    290


<210> SEQ ID NO 37
<211> LENGTH: 885
<212> TYPE: DNA
<213> ORGANISM: Chenopodium rubrum
<220> FEATURE:
<221> NAME/KEY: CDS
<222> LOCATION: (1)..(885)

<400> SEQUENCE: 37

atg gat cag tat gaa aaa gtt gag aag ata ggg gaa gga acc tat gga       48
Met Asp Gln Tyr Glu Lys Val Glu Lys Ile Gly Glu Gly Thr Tyr Gly
1               5                   10                  15

gtg gtt tat aag gcg cgg gac aag gtt acg aac gag act ata gct ttg       96
Val Val Tyr Lys Ala Arg Asp Lys Val Thr Asn Glu Thr Ile Ala Leu
            20                  25                  30

aag aaa att cgg ttg gaa cag gag gat gag gga gtt ccg agc acg gcg      144
Lys Lys Ile Arg Leu Glu Gln Glu Asp Glu Gly Val Pro Ser Thr Ala
        35                  40                  45

atc aga gaa ata tca ctt ttg aag gag atg cag cat ggc aac att gtc      192
Ile Arg Glu Ile Ser Leu Leu Lys Glu Met Gln His Gly Asn Ile Val
    50                  55                  60

agg ttg cag gat gtg gtg cat agt gag aag cgc tta tat ctg gtt ttt      240
Arg Leu Gln Asp Val Val His Ser Glu Lys Arg Leu Tyr Leu Val Phe
65                  70                  75                  80

gag tat ttg gac ctt gat ttg aag aaa cac atg gat tca tgc cct gat      288
Glu Tyr Leu Asp Leu Asp Leu Lys Lys His Met Asp Ser Cys Pro Asp
                85                  90                  95

ttt gca aag gat cca cgt atg att aaa agg ttt ctt tat cag att ctt      336
Phe Ala Lys Asp Pro Arg Met Ile Lys Arg Phe Leu Tyr Gln Ile Leu
            100                 105                 110

cgt ggt atc gct tat tgt cac tct cat agg gtc ctg cac cga gat ctg      384
Arg Gly Ile Ala Tyr Cys His Ser His Arg Val Leu His Arg Asp Leu
        115                 120                 125

aag ccg cag aat ctg ttg ata gat cgc caa act aat gca cta aaa ctt      432
Lys Pro Gln Asn Leu Leu Ile Asp Arg Gln Thr Asn Ala Leu Lys Leu
    130                 135                 140

gca gat ttt gga ttg gca agg gca ttt ggt att cct gtg agg act ttt      480
Ala Asp Phe Gly Leu Ala Arg Ala Phe Gly Ile Pro Val Arg Thr Phe
145                 150                 155                 160

aca cat gag gtg gtg aca ttg tgg tac aga gct cca gaa ata ttg ctt      528
Thr His Glu Val Val Thr Leu Trp Tyr Arg Ala Pro Glu Ile Leu Leu
                165                 170                 175

gga tct cga cat tac tct act cct gtg gat gtg tgg tct gtg ggt tgt      576
Gly Ser Arg His Tyr Ser Thr Pro Val Asp Val Trp Ser Val Gly Cys
            180                 185                 190

atc ttt gct gag atg gtg aat cag aag cca tta ttt cct gga gat tcc      624
Ile Phe Ala Glu Met Val Asn Gln Lys Pro Leu Phe Pro Gly Asp Ser
        195                 200                 205

gag att gat gaa ctt ttc aag att ttc agg acc ttg ggt aca cca aat      672
```

-continued

```
Glu Ile Asp Glu Leu Phe Lys Ile Phe Arg Thr Leu Gly Thr Pro Asn
    210                 215                 220

gag gag aca tgg cct gga gtg acc tcc ctt ccc gat ttc aaa tct tca      720
Glu Glu Thr Trp Pro Gly Val Thr Ser Leu Pro Asp Phe Lys Ser Ser
225                 230                 235                 240

ttt cct aaa tgg atc tcc aag gat ttg tct gca gta gta cca aat ctt      768
Phe Pro Lys Trp Ile Ser Lys Asp Leu Ser Ala Val Val Pro Asn Leu
                245                 250                 255

gat cca gct ggt att gat ctt cta aat aaa atg ctt tgc ttg gat ccg      816
Asp Pro Ala Gly Ile Asp Leu Leu Asn Lys Met Leu Cys Leu Asp Pro
            260                 265                 270

agc aaa agg att aca gcc agg aat gct ctt gaa cat gaa tac ttc aag      864
Ser Lys Arg Ile Thr Ala Arg Asn Ala Leu Glu His Glu Tyr Phe Lys
        275                 280                 285

gac att ggt ttt gta ccc tga                                          885
Asp Ile Gly Phe Val Pro
    290


<210> SEQ ID NO 38
<211> LENGTH: 294
<212> TYPE: PRT
<213> ORGANISM: Chenopodium rubrum

<400> SEQUENCE: 38

Met Asp Gln Tyr Glu Lys Val Glu Lys Ile Gly Glu Gly Thr Tyr Gly
1               5                   10                  15

Val Val Tyr Lys Ala Arg Asp Lys Val Thr Asn Glu Thr Ile Ala Leu
            20                  25                  30

Lys Lys Ile Arg Leu Glu Gln Glu Asp Glu Gly Val Pro Ser Thr Ala
        35                  40                  45

Ile Arg Glu Ile Ser Leu Leu Lys Glu Met Gln His Gly Asn Ile Val
    50                  55                  60

Arg Leu Gln Asp Val Val His Ser Glu Lys Arg Leu Tyr Leu Val Phe
65                  70                  75                  80

Glu Tyr Leu Asp Leu Asp Leu Lys Lys His Met Asp Ser Cys Pro Asp
                85                  90                  95

Phe Ala Lys Asp Pro Arg Met Ile Lys Arg Phe Leu Tyr Gln Ile Leu
            100                 105                 110

Arg Gly Ile Ala Tyr Cys His Ser His Arg Val Leu His Arg Asp Leu
        115                 120                 125

Lys Pro Gln Asn Leu Leu Ile Asp Arg Gln Thr Asn Ala Leu Lys Leu
    130                 135                 140

Ala Asp Phe Gly Leu Ala Arg Ala Phe Gly Ile Pro Val Arg Thr Phe
145                 150                 155                 160

Thr His Glu Val Val Thr Leu Trp Tyr Arg Ala Pro Glu Ile Leu Leu
                165                 170                 175

Gly Ser Arg His Tyr Ser Thr Pro Val Asp Val Trp Ser Val Gly Cys
            180                 185                 190

Ile Phe Ala Glu Met Val Asn Gln Lys Pro Leu Phe Pro Gly Asp Ser
        195                 200                 205

Glu Ile Asp Glu Leu Phe Lys Ile Phe Arg Thr Leu Gly Thr Pro Asn
    210                 215                 220

Glu Glu Thr Trp Pro Gly Val Thr Ser Leu Pro Asp Phe Lys Ser Ser
225                 230                 235                 240

Phe Pro Lys Trp Ile Ser Lys Asp Leu Ser Ala Val Val Pro Asn Leu
                245                 250                 255

Asp Pro Ala Gly Ile Asp Leu Leu Asn Lys Met Leu Cys Leu Asp Pro
```

```
            260                 265                 270

Ser Lys Arg Ile Thr Ala Arg Asn Ala Leu Glu His Glu Tyr Phe Lys
        275                 280                 285

Asp Ile Gly Phe Val Pro
    290


<210> SEQ ID NO 39
<211> LENGTH: 885
<212> TYPE: DNA
<213> ORGANISM: Zea mays
<220> FEATURE:
<221> NAME/KEY: CDS
<222> LOCATION: (1)..(885)

<400> SEQUENCE: 39

atg gag cag tac gag aag gtg gag aag atc ggg gag ggc acg tac ggg       48
Met Glu Gln Tyr Glu Lys Val Glu Lys Ile Gly Glu Gly Thr Tyr Gly
1               5                   10                  15

gtg gtg tac aag gcg ctg gac aag gcc acc aac gag acg atc gcg ctc       96
Val Val Tyr Lys Ala Leu Asp Lys Ala Thr Asn Glu Thr Ile Ala Leu
            20                  25                  30

aag aag atc cgc ctc gag cag gag gac gag ggc gtc ccg tcc acc gcc      144
Lys Lys Ile Arg Leu Glu Gln Glu Asp Glu Gly Val Pro Ser Thr Ala
        35                  40                  45

atc cgc gag atc tct ctc ctc aag gag atg aac cac ggc aac atc gtc      192
Ile Arg Glu Ile Ser Leu Leu Lys Glu Met Asn His Gly Asn Ile Val
    50                  55                  60

aga tta cat gat gtt gtc cac agc gag aag cgc ata tac ctt gtc ttc      240
Arg Leu His Asp Val Val His Ser Glu Lys Arg Ile Tyr Leu Val Phe
65                  70                  75                  80

gag tac ctg gat ctg gac ctc aag aag ttc atg gac tcc tgc ccg gag      288
Glu Tyr Leu Asp Leu Asp Leu Lys Lys Phe Met Asp Ser Cys Pro Glu
                85                  90                  95

ttt gct aag aat ccc act ttg atc aag tca tac ctc tac cag ata ctc      336
Phe Ala Lys Asn Pro Thr Leu Ile Lys Ser Tyr Leu Tyr Gln Ile Leu
            100                 105                 110

cac ggt gtt gcg tac tgc cat tct cat aga gtt ctt cat cga gac ttg      384
His Gly Val Ala Tyr Cys His Ser His Arg Val Leu His Arg Asp Leu
        115                 120                 125

aaa cct caa aac tta ttg ata gat cgg cgc act aat gca ctg aag ctt      432
Lys Pro Gln Asn Leu Leu Ile Asp Arg Arg Thr Asn Ala Leu Lys Leu
    130                 135                 140

gca gac ttt ggt tta gcc agg gca ttt gga att cct gtc cgt aca ttt      480
Ala Asp Phe Gly Leu Ala Arg Ala Phe Gly Ile Pro Val Arg Thr Phe
145                 150                 155                 160

act cat gag gta gtg aca tta tgg tac aga gct cca gaa att ctg ctt      528
Thr His Glu Val Val Thr Leu Trp Tyr Arg Ala Pro Glu Ile Leu Leu
                165                 170                 175

gga gcg cgg cag tat tcc aca cca gtt gat gtg tgg tct gtg ggc tgt      576
Gly Ala Arg Gln Tyr Ser Thr Pro Val Asp Val Trp Ser Val Gly Cys
            180                 185                 190

atc ttt gcg gaa atg gtg aac caa aag cca cta ttc cct ggc gat tct      624
Ile Phe Ala Glu Met Val Asn Gln Lys Pro Leu Phe Pro Gly Asp Ser
        195                 200                 205

gag atc gac gaa ctt ttt aag ata ttc agg ata cta ggt aca ccg aat      672
Glu Ile Asp Glu Leu Phe Lys Ile Phe Arg Ile Leu Gly Thr Pro Asn
    210                 215                 220

gag cag agt tgg cca gga gtc agt tgt ttg cct gac ttc aag aca gct      720
Glu Gln Ser Trp Pro Gly Val Ser Cys Leu Pro Asp Phe Lys Thr Ala
225                 230                 235                 240

ttc ccc agg tgg caa gct cag gac ctg gca aca gta gtc cca aat ctt      768
```

```
Phe Pro Arg Trp Gln Ala Gln Asp Leu Ala Thr Val Val Pro Asn Leu
                245                 250                 255

gac cct gct ggg ttg gac ctt ctc tct aaa atg ctt cga tac gag cca      816
Asp Pro Ala Gly Leu Asp Leu Leu Ser Lys Met Leu Arg Tyr Glu Pro
            260                 265                 270

agc aaa aga atc aca gcg agg caa gca ctt gag cat gag tac ttc aag      864
Ser Lys Arg Ile Thr Ala Arg Gln Ala Leu Glu His Glu Tyr Phe Lys
        275                 280                 285

gac ctt gaa gtg gta cag tga                                          885
Asp Leu Glu Val Val Gln
    290


<210> SEQ ID NO 40
<211> LENGTH: 294
<212> TYPE: PRT
<213> ORGANISM: Zea mays

<400> SEQUENCE: 40

Met Glu Gln Tyr Glu Lys Val Glu Lys Ile Gly Glu Gly Thr Tyr Gly
1               5                   10                  15

Val Val Tyr Lys Ala Leu Asp Lys Ala Thr Asn Glu Thr Ile Ala Leu
            20                  25                  30

Lys Lys Ile Arg Leu Glu Gln Glu Asp Glu Gly Val Pro Ser Thr Ala
        35                  40                  45

Ile Arg Glu Ile Ser Leu Leu Lys Glu Met Asn His Gly Asn Ile Val
    50                  55                  60

Arg Leu His Asp Val Val His Ser Glu Lys Arg Ile Tyr Leu Val Phe
65                  70                  75                  80

Glu Tyr Leu Asp Leu Asp Leu Lys Lys Phe Met Asp Ser Cys Pro Glu
                85                  90                  95

Phe Ala Lys Asn Pro Thr Leu Ile Lys Ser Tyr Leu Tyr Gln Ile Leu
            100                 105                 110

His Gly Val Ala Tyr Cys His Ser His Arg Val Leu His Arg Asp Leu
        115                 120                 125

Lys Pro Gln Asn Leu Leu Ile Asp Arg Arg Thr Asn Ala Leu Lys Leu
    130                 135                 140

Ala Asp Phe Gly Leu Ala Arg Ala Phe Gly Ile Pro Val Arg Thr Phe
145                 150                 155                 160

Thr His Glu Val Val Thr Leu Trp Tyr Arg Ala Pro Glu Ile Leu Leu
                165                 170                 175

Gly Ala Arg Gln Tyr Ser Thr Pro Val Asp Val Trp Ser Val Gly Cys
            180                 185                 190

Ile Phe Ala Glu Met Val Asn Gln Lys Pro Leu Phe Pro Gly Asp Ser
        195                 200                 205

Glu Ile Asp Glu Leu Phe Lys Ile Phe Arg Ile Leu Gly Thr Pro Asn
    210                 215                 220

Glu Gln Ser Trp Pro Gly Val Ser Cys Leu Pro Asp Phe Lys Thr Ala
225                 230                 235                 240

Phe Pro Arg Trp Gln Ala Gln Asp Leu Ala Thr Val Val Pro Asn Leu
                245                 250                 255

Asp Pro Ala Gly Leu Asp Leu Leu Ser Lys Met Leu Arg Tyr Glu Pro
            260                 265                 270

Ser Lys Arg Ile Thr Ala Arg Gln Ala Leu Glu His Glu Tyr Phe Lys
        275                 280                 285

Asp Leu Glu Val Val Gln
    290
```

-continued

<210> SEQ ID NO 41
<211> LENGTH: 885
<212> TYPE: DNA
<213> ORGANISM: Vigna aconitifolia
<220> FEATURE:
<221> NAME/KEY: CDS
<222> LOCATION: (1)..(885)

<400> SEQUENCE: 41

```
atg gaa cag tac gag aag gtg gag aag ata ggg gag gga aca tac ggc       48
Met Glu Gln Tyr Glu Lys Val Glu Lys Ile Gly Glu Gly Thr Tyr Gly
1               5                   10                  15

gtc gtt tac aag gct cgc gac cgc gtc acc aat gag acc atc gct ctt       96
Val Val Tyr Lys Ala Arg Asp Arg Val Thr Asn Glu Thr Ile Ala Leu
            20                  25                  30

aag aag att cgc ctc gag cag gaa gac gag ggg gtt ccc agc acc gcc      144
Lys Lys Ile Arg Leu Glu Gln Glu Asp Glu Gly Val Pro Ser Thr Ala
        35                  40                  45

att cgt gag att tcg ctc ctc aaa gag atg cag cat agg aac att gtt      192
Ile Arg Glu Ile Ser Leu Leu Lys Glu Met Gln His Arg Asn Ile Val
    50                  55                  60

agg ttg cag gat gta gtg cac agt gag aag cga ttg tat ctg gtt ttc      240
Arg Leu Gln Asp Val Val His Ser Glu Lys Arg Leu Tyr Leu Val Phe
65                  70                  75                  80

gag tat ctg gac ttg gat cta aag aaa cac atg gat tca tct cca gag      288
Glu Tyr Leu Asp Leu Asp Leu Lys Lys His Met Asp Ser Ser Pro Glu
                85                  90                  95

ttt gtg aaa gat cca cgg caa gta aaa atg ttc ctc tat caa att ctc      336
Phe Val Lys Asp Pro Arg Gln Val Lys Met Phe Leu Tyr Gln Ile Leu
            100                 105                 110

tgt ggc att gct tac tgc cat tcg cac aga gtt ctt cat cga gac ttg      384
Cys Gly Ile Ala Tyr Cys His Ser His Arg Val Leu His Arg Asp Leu
        115                 120                 125

aaa cca cag aat ttg ttg ata gac cgt cgt aca aat tcc tta aaa ctt      432
Lys Pro Gln Asn Leu Leu Ile Asp Arg Arg Thr Asn Ser Leu Lys Leu
    130                 135                 140

gca gat ttt gga ttg gct agg gca ttt ggc att cct gtc agg aca ttt      480
Ala Asp Phe Gly Leu Ala Arg Ala Phe Gly Ile Pro Val Arg Thr Phe
145                 150                 155                 160

act cat gag gtg gtg aca tta tgg tac aga gct cca gaa ata ttg ctt      528
Thr His Glu Val Val Thr Leu Trp Tyr Arg Ala Pro Glu Ile Leu Leu
                165                 170                 175

ggg tct cgt cat tat tct acc cca gtt gat gtt tgg tca gtg gga tgt      576
Gly Ser Arg His Tyr Ser Thr Pro Val Asp Val Trp Ser Val Gly Cys
            180                 185                 190

ata ttt gca gag atg gta aac cga cga cct cta ttc cca ggg gac tct      624
Ile Phe Ala Glu Met Val Asn Arg Arg Pro Leu Phe Pro Gly Asp Ser
        195                 200                 205

gag att gat gaa tta ttt aaa ata ttc aga ata ttg ggt aca cct aat      672
Glu Ile Asp Glu Leu Phe Lys Ile Phe Arg Ile Leu Gly Thr Pro Asn
    210                 215                 220

gaa gaa aca tgg cct gga gtt act gca tta ccg gat ttt aaa tca aca      720
Glu Glu Thr Trp Pro Gly Val Thr Ala Leu Pro Asp Phe Lys Ser Thr
225                 230                 235                 240

ttt ccc aaa tgg cca cct aag gat tta gca act gtg gtt cca aat ctt      768
Phe Pro Lys Trp Pro Pro Lys Asp Leu Ala Thr Val Val Pro Asn Leu
                245                 250                 255

gat gca gcg ggt ctt aat ctt ctt tct agt atg cta tgc ttg gat ccc      816
Asp Ala Ala Gly Leu Asn Leu Leu Ser Ser Met Leu Cys Leu Asp Pro
            260                 265                 270

agc aaa aga att act gcc agg atc gct gtg gag cac gaa tac ttc aaa      864
```

```
Ser Lys Arg Ile Thr Ala Arg Ile Ala Val Glu His Glu Tyr Phe Lys
        275                 280                 285

gac att aaa ttt gta ccc taa                                       885
Asp Ile Lys Phe Val Pro
    290


<210> SEQ ID NO 42
<211> LENGTH: 294
<212> TYPE: PRT
<213> ORGANISM: Vigna aconitifolia

<400> SEQUENCE: 42

Met Glu Gln Tyr Glu Lys Val Glu Lys Ile Gly Glu Gly Thr Tyr Gly
1               5                   10                  15

Val Val Tyr Lys Ala Arg Asp Arg Val Thr Asn Glu Thr Ile Ala Leu
            20                  25                  30

Lys Lys Ile Arg Leu Glu Gln Glu Asp Glu Gly Val Pro Ser Thr Ala
        35                  40                  45

Ile Arg Glu Ile Ser Leu Leu Lys Glu Met Gln His Arg Asn Ile Val
    50                  55                  60

Arg Leu Gln Asp Val Val His Ser Glu Lys Arg Leu Tyr Leu Val Phe
65                  70                  75                  80

Glu Tyr Leu Asp Leu Asp Leu Lys Lys His Met Asp Ser Ser Pro Glu
                85                  90                  95

Phe Val Lys Asp Pro Arg Gln Val Lys Met Phe Leu Tyr Gln Ile Leu
            100                 105                 110

Cys Gly Ile Ala Tyr Cys His Ser His Arg Val Leu His Arg Asp Leu
        115                 120                 125

Lys Pro Gln Asn Leu Leu Ile Asp Arg Arg Thr Asn Ser Leu Lys Leu
    130                 135                 140

Ala Asp Phe Gly Leu Ala Arg Ala Phe Gly Ile Pro Val Arg Thr Phe
145                 150                 155                 160

Thr His Glu Val Val Thr Leu Trp Tyr Arg Ala Pro Glu Ile Leu Leu
                165                 170                 175

Gly Ser Arg His Tyr Ser Thr Pro Val Asp Val Trp Ser Val Gly Cys
            180                 185                 190

Ile Phe Ala Glu Met Val Asn Arg Arg Pro Leu Phe Pro Gly Asp Ser
        195                 200                 205

Glu Ile Asp Glu Leu Phe Lys Ile Phe Arg Ile Leu Gly Thr Pro Asn
    210                 215                 220

Glu Glu Thr Trp Pro Gly Val Thr Ala Leu Pro Asp Phe Lys Ser Thr
225                 230                 235                 240

Phe Pro Lys Trp Pro Pro Lys Asp Leu Ala Thr Val Val Pro Asn Leu
                245                 250                 255

Asp Ala Ala Gly Leu Asn Leu Leu Ser Ser Met Leu Cys Leu Asp Pro
            260                 265                 270

Ser Lys Arg Ile Thr Ala Arg Ile Ala Val Glu His Glu Tyr Phe Lys
        275                 280                 285

Asp Ile Lys Phe Val Pro
    290


<210> SEQ ID NO 43
<211> LENGTH: 885
<212> TYPE: DNA
<213> ORGANISM: Oryza sativa
<220> FEATURE:
<221> NAME/KEY: CDS
<222> LOCATION: (1)..(885)
```

```
<400> SEQUENCE: 43

atg gag cag tac gag aag gag gag aag att ggg gag ggc acg tac ggg       48
Met Glu Gln Tyr Glu Lys Glu Glu Lys Ile Gly Glu Gly Thr Tyr Gly
1               5                   10                  15

gtg gtg tac agg gcg cgg gac aag gtc acc aac gag acg atc gcg ctc       96
Val Val Tyr Arg Ala Arg Asp Lys Val Thr Asn Glu Thr Ile Ala Leu
            20                  25                  30

aag aag atc cgg ctt gag cag gag gat gag ggc gtc ccc tcc acc gca      144
Lys Lys Ile Arg Leu Glu Gln Glu Asp Glu Gly Val Pro Ser Thr Ala
        35                  40                  45

atc cgc gag atc tcg ctc ctc aag gag atg cat cac ggc aac atc gtc      192
Ile Arg Glu Ile Ser Leu Leu Lys Glu Met His His Gly Asn Ile Val
    50                  55                  60

agg tta cac gat gtt atc cac agt gag aag cgc ata tat ctt gtc ttt      240
Arg Leu His Asp Val Ile His Ser Glu Lys Arg Ile Tyr Leu Val Phe
65                  70                  75                  80

gag tat ctg gat ctg gac cta aag aag ttc atg gac tct tgt cca gag      288
Glu Tyr Leu Asp Leu Asp Leu Lys Lys Phe Met Asp Ser Cys Pro Glu
                85                  90                  95

ttt gcg aaa aac ccc act tta att aag tca tat ctc tat cag ata ctc      336
Phe Ala Lys Asn Pro Thr Leu Ile Lys Ser Tyr Leu Tyr Gln Ile Leu
            100                 105                 110

cgc ggc gtt gct tac tgt cat tct cat aga gtt ctt cat cga gat ttg      384
Arg Gly Val Ala Tyr Cys His Ser His Arg Val Leu His Arg Asp Leu
        115                 120                 125

aaa cct cag aat tta ttg ata gat cgg cgt act aat gca ctg aag ctt      432
Lys Pro Gln Asn Leu Leu Ile Asp Arg Arg Thr Asn Ala Leu Lys Leu
    130                 135                 140

gca gac ttt ggt tta gcc agg gca ttt gga att cct gtc cgc acg ttt      480
Ala Asp Phe Gly Leu Ala Arg Ala Phe Gly Ile Pro Val Arg Thr Phe
145                 150                 155                 160

act cac gag gtt gta acc ttg tgg tat aga gct cca gag atc ctt ctt      528
Thr His Glu Val Val Thr Leu Trp Tyr Arg Ala Pro Glu Ile Leu Leu
                165                 170                 175

gga tca agg cag tat tct aca cca gtt gat atg tgg tca gtt ggt tgt      576
Gly Ser Arg Gln Tyr Ser Thr Pro Val Asp Met Trp Ser Val Gly Cys
            180                 185                 190

atc ttt gca gaa atg gtg aac cag aaa cca ctg ttc cct ggt gat tct      624
Ile Phe Ala Glu Met Val Asn Gln Lys Pro Leu Phe Pro Gly Asp Ser
        195                 200                 205

gag att gat gaa tta ttt aag ata ttc agg gta cta gga act cca aat      672
Glu Ile Asp Glu Leu Phe Lys Ile Phe Arg Val Leu Gly Thr Pro Asn
    210                 215                 220

gaa caa agt tgg cca gga gtt agc tca tta cct gac tac aag tct gct      720
Glu Gln Ser Trp Pro Gly Val Ser Ser Leu Pro Asp Tyr Lys Ser Ala
225                 230                 235                 240

ttc ccc aag tgg caa gca cag gat ctt gca act att gtc cct act ctt      768
Phe Pro Lys Trp Gln Ala Gln Asp Leu Ala Thr Ile Val Pro Thr Leu
                245                 250                 255

gac cct gct ggt ttg gac ctt ctc tct aaa atg ctt cgg tac gag cca      816
Asp Pro Ala Gly Leu Asp Leu Leu Ser Lys Met Leu Arg Tyr Glu Pro
            260                 265                 270

aac aaa agg atc aca gct aga cag gct ctt gag cat gaa tac ttc aag      864
Asn Lys Arg Ile Thr Ala Arg Gln Ala Leu Glu His Glu Tyr Phe Lys
        275                 280                 285

gac ctt gag atg gta caa tga                                          885
Asp Leu Glu Met Val Gln
    290             294
```

<210> SEQ ID NO 44
<211> LENGTH: 294
<212> TYPE: PRT
<213> ORGANISM: Oryza sativa

<400> SEQUENCE: 44

```
Met Glu Gln Tyr Glu Lys Glu Glu Lys Ile Gly Glu Gly Thr Tyr Gly
1               5                   10                  15

Val Val Tyr Arg Ala Arg Asp Lys Val Thr Asn Glu Thr Ile Ala Leu
            20                  25                  30

Lys Lys Ile Arg Leu Glu Gln Glu Asp Glu Gly Val Pro Ser Thr Ala
        35                  40                  45

Ile Arg Glu Ile Ser Leu Leu Lys Glu Met His His Gly Asn Ile Val
    50                  55                  60

Arg Leu His Asp Val Ile His Ser Glu Lys Arg Ile Tyr Leu Val Phe
65                  70                  75                  80

Glu Tyr Leu Asp Leu Asp Leu Lys Lys Phe Met Asp Ser Cys Pro Glu
                85                  90                  95

Phe Ala Lys Asn Pro Thr Leu Ile Lys Ser Tyr Leu Tyr Gln Ile Leu
            100                 105                 110

Arg Gly Val Ala Tyr Cys His Ser His Arg Val Leu His Arg Asp Leu
        115                 120                 125

Lys Pro Gln Asn Leu Leu Ile Asp Arg Arg Thr Asn Ala Leu Lys Leu
    130                 135                 140

Ala Asp Phe Gly Leu Ala Arg Ala Phe Gly Ile Pro Val Arg Thr Phe
145                 150                 155                 160

Thr His Glu Val Val Thr Leu Trp Tyr Arg Ala Pro Glu Ile Leu Leu
                165                 170                 175

Gly Ser Arg Gln Tyr Ser Thr Pro Val Asp Met Trp Ser Val Gly Cys
            180                 185                 190

Ile Phe Ala Glu Met Val Asn Gln Lys Pro Leu Phe Pro Gly Asp Ser
        195                 200                 205

Glu Ile Asp Glu Leu Phe Lys Ile Phe Arg Val Leu Gly Thr Pro Asn
    210                 215                 220

Glu Gln Ser Trp Pro Gly Val Ser Ser Leu Pro Asp Tyr Lys Ser Ala
225                 230                 235                 240

Phe Pro Lys Trp Gln Ala Gln Asp Leu Ala Thr Ile Val Pro Thr Leu
                245                 250                 255

Asp Pro Ala Gly Leu Asp Leu Leu Ser Lys Met Leu Arg Tyr Glu Pro
            260                 265                 270

Asn Lys Arg Ile Thr Ala Arg Gln Ala Leu Glu His Glu Tyr Phe Lys
        275                 280                 285

Asp Leu Glu Met Val Gln
    290
```

<210> SEQ ID NO 45
<211> LENGTH: 1113
<212> TYPE: DNA
<213> ORGANISM: Oryza sativa
<220> FEATURE:
<221> NAME/KEY: CDS
<222> LOCATION: (1)..(1113)

<400> SEQUENCE: 45

```
atg gcg atc atg gtg gat cct cca aat ggg atg ggt aac caa ggg aag       48
Met Ala Ile Met Val Asp Pro Pro Asn Gly Met Gly Asn Gln Gly Lys
1               5                   10                  15

tat tac tac tcg atg tgg caa act ttg ttt gag ata gac act aag tat       96
```

-continued

```
Tyr Tyr Tyr Ser Met Trp Gln Thr Leu Phe Glu Ile Asp Thr Lys Tyr
            20                  25                  30

gtg cca atc aag ccc atc ggg cga gga gct tat ggg att gtt tgt tca      144
Val Pro Ile Lys Pro Ile Gly Arg Gly Ala Tyr Gly Ile Val Cys Ser
        35                  40                  45

tcc ata aat cgt gag acc aac gag aaa gta gca ata aag aag ata cac      192
Ser Ile Asn Arg Glu Thr Asn Glu Lys Val Ala Ile Lys Lys Ile His
    50                  55                  60

aat gtt ttt gac aac cgt gtt gat gca cta agg act ttg cgg gag ctg      240
Asn Val Phe Asp Asn Arg Val Asp Ala Leu Arg Thr Leu Arg Glu Leu
65                  70                  75                  80

aaa ctt ctc cgg cat ctc cgc cat gag aat gtt att gct ttg aag gat      288
Lys Leu Leu Arg His Leu Arg His Glu Asn Val Ile Ala Leu Lys Asp
                85                  90                  95

ata atg atg cca gta cac agg agg agt ttt aaa gat gtg tac tta gtt      336
Ile Met Met Pro Val His Arg Arg Ser Phe Lys Asp Val Tyr Leu Val
            100                 105                 110

tat gaa ctc atg gat act gac ctg cat cag ata atc aag tca cct cag      384
Tyr Glu Leu Met Asp Thr Asp Leu His Gln Ile Ile Lys Ser Pro Gln
        115                 120                 125

ggt ctt tcc aat gat cac tgc caa tat ttt ctt ttt cag ttg ctt cga      432
Gly Leu Ser Asn Asp His Cys Gln Tyr Phe Leu Phe Gln Leu Leu Arg
    130                 135                 140

gga ctg aaa tat ctc cat tca gca gag ata ctc cac aga gac ctg aaa      480
Gly Leu Lys Tyr Leu His Ser Ala Glu Ile Leu His Arg Asp Leu Lys
145                 150                 155                 160

cct gga aat cta ctg gtt aat gca aac tgt gat ctc aag ata tgt gat      528
Pro Gly Asn Leu Leu Val Asn Ala Asn Cys Asp Leu Lys Ile Cys Asp
                165                 170                 175

ttt ggt ctt gca cgc aca aac agt agt aaa ggt cag ttt atg act gag      576
Phe Gly Leu Ala Arg Thr Asn Ser Ser Lys Gly Gln Phe Met Thr Glu
            180                 185                 190

tat gtt gtc acc cgc tgg tat aga gct cct gag ttg ctc ctt tgc tgt      624
Tyr Val Val Thr Arg Trp Tyr Arg Ala Pro Glu Leu Leu Leu Cys Cys
        195                 200                 205

gac aac tat ggc act tcc att gat gtt tgg tct gtt ggt tgc atc ttc      672
Asp Asn Tyr Gly Thr Ser Ile Asp Val Trp Ser Val Gly Cys Ile Phe
    210                 215                 220

gct gag cta ctt ggt cgg aaa cct att ttc cca gga act gag tgc cta      720
Ala Glu Leu Leu Gly Arg Lys Pro Ile Phe Pro Gly Thr Glu Cys Leu
225                 230                 235                 240

aat cag ctc aag ctc att gtc aat gtt ctt ggc acc atg agc gag tct      768
Asn Gln Leu Lys Leu Ile Val Asn Val Leu Gly Thr Met Ser Glu Ser
                245                 250                 255

gac ttg gag ttc att gac aac cca aaa gct cgc aga tat atc aaa tcc      816
Asp Leu Glu Phe Ile Asp Asn Pro Lys Ala Arg Arg Tyr Ile Lys Ser
            260                 265                 270

ctc ccc tac act ccc ggt gtg ccc ctc gcg agt atg tat ccg cat gca      864
Leu Pro Tyr Thr Pro Gly Val Pro Leu Ala Ser Met Tyr Pro His Ala
        275                 280                 285

cac cct ctt gcc att gat ctt tta cag aag atg ctc ata ttt gat cct      912
His Pro Leu Ala Ile Asp Leu Leu Gln Lys Met Leu Ile Phe Asp Pro
    290                 295                 300

acc aaa aga atc agt gtc acc gag gct ctt gag cac cct tac atg tcc      960
Thr Lys Arg Ile Ser Val Thr Glu Ala Leu Glu His Pro Tyr Met Ser
305                 310                 315                 320

cct ctg tat gat cca agt gca aat cct ccc gcg caa gtg cct atc gat     1008
Pro Leu Tyr Asp Pro Ser Ala Asn Pro Pro Ala Gln Val Pro Ile Asp
                325                 330                 335

ctg gac ata gac gag aac atc agt gca gat atg atc agg gaa atg atg     1056
```

-continued

```
Leu Asp Ile Asp Glu Asn Ile Ser Ala Asp Met Ile Arg Glu Met Met
            340                 345                 350

tgg cac gag atg ctc cac tac cac cct gaa gtt gtt gca gca atg agt      1104
Trp His Glu Met Leu His Tyr His Pro Glu Val Val Ala Ala Met Ser
        355                 360                 365

gcc cga tga                                                          1113
Ala Arg
    370


<210> SEQ ID NO 46
<211> LENGTH: 370
<212> TYPE: PRT
<213> ORGANISM: Oryza sativa

<400> SEQUENCE: 46

Met Ala Ile Met Val Asp Pro Pro Asn Gly Met Gly Asn Gln Gly Lys
1               5                   10                  15

Tyr Tyr Tyr Ser Met Trp Gln Thr Leu Phe Glu Ile Asp Thr Lys Tyr
            20                  25                  30

Val Pro Ile Lys Pro Ile Gly Arg Gly Ala Tyr Gly Ile Val Cys Ser
        35                  40                  45

Ser Ile Asn Arg Glu Thr Asn Glu Lys Val Ala Ile Lys Lys Ile His
    50                  55                  60

Asn Val Phe Asp Asn Arg Val Asp Ala Leu Arg Thr Leu Arg Glu Leu
65                  70                  75                  80

Lys Leu Leu Arg His Leu Arg His Glu Asn Val Ile Ala Leu Lys Asp
                85                  90                  95

Ile Met Met Pro Val His Arg Arg Ser Phe Lys Asp Val Tyr Leu Val
            100                 105                 110

Tyr Glu Leu Met Asp Thr Asp Leu His Gln Ile Ile Lys Ser Pro Gln
        115                 120                 125

Gly Leu Ser Asn Asp His Cys Gln Tyr Phe Leu Phe Gln Leu Leu Arg
    130                 135                 140

Gly Leu Lys Tyr Leu His Ser Ala Glu Ile Leu His Arg Asp Leu Lys
145                 150                 155                 160

Pro Gly Asn Leu Leu Val Asn Ala Asn Cys Asp Leu Lys Ile Cys Asp
                165                 170                 175

Phe Gly Leu Ala Arg Thr Asn Ser Ser Lys Gly Gln Phe Met Thr Glu
            180                 185                 190

Tyr Val Val Thr Arg Trp Tyr Arg Ala Pro Glu Leu Leu Leu Cys Cys
        195                 200                 205

Asp Asn Tyr Gly Thr Ser Ile Asp Val Trp Ser Val Gly Cys Ile Phe
    210                 215                 220

Ala Glu Leu Leu Gly Arg Lys Pro Ile Phe Pro Gly Thr Glu Cys Leu
225                 230                 235                 240

Asn Gln Leu Lys Leu Ile Val Asn Val Leu Gly Thr Met Ser Glu Ser
                245                 250                 255

Asp Leu Glu Phe Ile Asp Asn Pro Lys Ala Arg Arg Tyr Ile Lys Ser
            260                 265                 270

Leu Pro Tyr Thr Pro Gly Val Pro Leu Ala Ser Met Tyr Pro His Ala
        275                 280                 285

His Pro Leu Ala Ile Asp Leu Leu Gln Lys Met Leu Ile Phe Asp Pro
    290                 295                 300

Thr Lys Arg Ile Ser Val Thr Glu Ala Leu Glu His Pro Tyr Met Ser
305                 310                 315                 320

Pro Leu Tyr Asp Pro Ser Ala Asn Pro Pro Ala Gln Val Pro Ile Asp
```

```
                325                 330                 335

Leu Asp Ile Asp Glu Asn Ile Ser Ala Asp Met Ile Arg Glu Met Met
            340                 345                 350

Trp His Glu Met Leu His Tyr His Pro Glu Val Val Ala Ala Met Ser
        355                 360                 365

Ala Arg
    370


<210> SEQ ID NO 47
<211> LENGTH: 1044
<212> TYPE: DNA
<213> ORGANISM: Brassica napus
<220> FEATURE:
<221> NAME/KEY: CDS
<222> LOCATION: (1)..(1044)

<400> SEQUENCE: 47

atg tcg aaa tcg ggc gga aac caa ccc gta gat cga tac cta aga cgc       48
Met Ser Lys Ser Gly Gly Asn Gln Pro Val Asp Arg Tyr Leu Arg Arg
1               5                   10                  15

caa gtg ctc gga gaa gga aca tac ggt gtc gtt tac aaa gcc acc gac       96
Gln Val Leu Gly Glu Gly Thr Tyr Gly Val Val Tyr Lys Ala Thr Asp
            20                  25                  30

acc aag aca ggt aag acc gta gca gtg aag aag atc agg tta gga aac      144
Thr Lys Thr Gly Lys Thr Val Ala Val Lys Lys Ile Arg Leu Gly Asn
        35                  40                  45

cag aaa gaa ggc gtc aat ttc acg gcc ctt agg gag atc aag ctc cta      192
Gln Lys Glu Gly Val Asn Phe Thr Ala Leu Arg Glu Ile Lys Leu Leu
    50                  55                  60

aaa gag ctg aac cat ccc cac atc gtc gag ctc atc gac gcg ttt cct      240
Lys Glu Leu Asn His Pro His Ile Val Glu Leu Ile Asp Ala Phe Pro
65                  70                  75                  80

cac gac ggg agc ttg cat ctg gtt ttc gag tat atg cag acg gat ttg      288
His Asp Gly Ser Leu His Leu Val Phe Glu Tyr Met Gln Thr Asp Leu
                85                  90                  95

gaa gct gtg att cgt gac cgt aac att ttt ctt tct cct ggt gat atc      336
Glu Ala Val Ile Arg Asp Arg Asn Ile Phe Leu Ser Pro Gly Asp Ile
            100                 105                 110

aag tct tat atg ttg atg act ctt aag ggt tta gct tat tgt cac aag      384
Lys Ser Tyr Met Leu Met Thr Leu Lys Gly Leu Ala Tyr Cys His Lys
        115                 120                 125

aaa tgg gtt ctt cat agg gat atg aag cct aat aat cta ctg att gga      432
Lys Trp Val Leu His Arg Asp Met Lys Pro Asn Asn Leu Leu Ile Gly
    130                 135                 140

gag aat ggt ctg ttg aag tta gct gat ttt ggt ttg gcg aga gtg ttt      480
Glu Asn Gly Leu Leu Lys Leu Ala Asp Phe Gly Leu Ala Arg Val Phe
145                 150                 155                 160

ggg agt ccg aat cgg agg ttt act cat cag gta ttt gcg acg tgg tac      528
Gly Ser Pro Asn Arg Arg Phe Thr His Gln Val Phe Ala Thr Trp Tyr
                165                 170                 175

aga gcc ccc gag ttg ctg ttt ggg agt aga cag tat ggt gca gga gtt      576
Arg Ala Pro Glu Leu Leu Phe Gly Ser Arg Gln Tyr Gly Ala Gly Val
            180                 185                 190

gat gtc tgg gct gca ggc tgt atc ttt gct gag cta tta ctt cgt cga      624
Asp Val Trp Ala Ala Gly Cys Ile Phe Ala Glu Leu Leu Leu Arg Arg
        195                 200                 205

ccc ttt cta cct ggt tcc act gag ata gat caa ctg gga aag atc ttt      672
Pro Phe Leu Pro Gly Ser Thr Glu Ile Asp Gln Leu Gly Lys Ile Phe
    210                 215                 220

caa gct ttt gga act cca aca caa tcc caa tgg tct gac atg atc tat      720
Gln Ala Phe Gly Thr Pro Thr Gln Ser Gln Trp Ser Asp Met Ile Tyr
```

-continued

```
225                 230                 235                 240

ctc cca gag tac atg gag ttc tcc tac aca cct gct cca cca cta cgt      768
Leu Pro Glu Tyr Met Glu Phe Ser Tyr Thr Pro Ala Pro Pro Leu Arg
                245                 250                 255

acc att ttc cct atg gca agc gac gac gct ttg gat ctt cta tcc aaa      816
Thr Ile Phe Pro Met Ala Ser Asp Asp Ala Leu Asp Leu Leu Ser Lys
            260                 265                 270

atg ttc atc tac gac cca cgc caa cgt atc acc ata cag caa gct ttg      864
Met Phe Ile Tyr Asp Pro Arg Gln Arg Ile Thr Ile Gln Gln Ala Leu
        275                 280                 285

gac cac agg tat ttc tcg tct tct cca tca cca act gag cca ggg aag      912
Asp His Arg Tyr Phe Ser Ser Ser Pro Ser Pro Thr Glu Pro Gly Lys
    290                 295                 300

ctt cag att cca gct tcg aaa gga gac gcc ctc gaa cca aag gca tct      960
Leu Gln Ile Pro Ala Ser Lys Gly Asp Ala Leu Glu Pro Lys Ala Ser
305                 310                 315                 320

gag caa aac aac caa cac gga aac agc ccc gcc gtg cta tca cct cct     1008
Glu Gln Asn Asn Gln His Gly Asn Ser Pro Ala Val Leu Ser Pro Pro
                325                 330                 335

gga aaa atg agg aga gtg atg ggt cct gag gga taa                     1044
Gly Lys Met Arg Arg Val Met Gly Pro Glu Gly
            340                 345
```

<210> SEQ ID NO 48
<211> LENGTH: 347
<212> TYPE: PRT
<213> ORGANISM: Brassica napus

<400> SEQUENCE: 48

```
Met Ser Lys Ser Gly Gly Asn Gln Pro Val Asp Arg Tyr Leu Arg Arg
1               5                   10                  15

Gln Val Leu Gly Glu Gly Thr Tyr Gly Val Val Tyr Lys Ala Thr Asp
            20                  25                  30

Thr Lys Thr Gly Lys Thr Val Ala Val Lys Lys Ile Arg Leu Gly Asn
        35                  40                  45

Gln Lys Glu Gly Val Asn Phe Thr Ala Leu Arg Glu Ile Lys Leu Leu
    50                  55                  60

Lys Glu Leu Asn His Pro His Ile Val Glu Leu Ile Asp Ala Phe Pro
65                  70                  75                  80

His Asp Gly Ser Leu His Leu Val Phe Glu Tyr Met Gln Thr Asp Leu
                85                  90                  95

Glu Ala Val Ile Arg Asp Arg Asn Ile Phe Leu Ser Pro Gly Asp Ile
            100                 105                 110

Lys Ser Tyr Met Leu Met Thr Leu Lys Gly Leu Ala Tyr Cys His Lys
        115                 120                 125

Lys Trp Val Leu His Arg Asp Met Lys Pro Asn Asn Leu Leu Ile Gly
    130                 135                 140

Glu Asn Gly Leu Leu Lys Leu Ala Asp Phe Gly Leu Ala Arg Val Phe
145                 150                 155                 160

Gly Ser Pro Asn Arg Arg Phe Thr His Gln Val Phe Ala Thr Trp Tyr
                165                 170                 175

Arg Ala Pro Glu Leu Leu Phe Gly Ser Arg Gln Tyr Gly Ala Gly Val
            180                 185                 190

Asp Val Trp Ala Ala Gly Cys Ile Phe Ala Glu Leu Leu Leu Arg Arg
        195                 200                 205

Pro Phe Leu Pro Gly Ser Thr Glu Ile Asp Gln Leu Gly Lys Ile Phe
    210                 215                 220
```

-continued

```
Gln Ala Phe Gly Thr Pro Thr Gln Ser Gln Trp Ser Asp Met Ile Tyr
225                 230                 235                 240

Leu Pro Glu Tyr Met Glu Phe Ser Tyr Thr Pro Ala Pro Pro Leu Arg
                245                 250                 255

Thr Ile Phe Pro Met Ala Ser Asp Asp Ala Leu Asp Leu Leu Ser Lys
            260                 265                 270

Met Phe Ile Tyr Asp Pro Arg Gln Arg Ile Thr Ile Gln Gln Ala Leu
        275                 280                 285

Asp His Arg Tyr Phe Ser Ser Ser Pro Ser Pro Thr Glu Pro Gly Lys
    290                 295                 300

Leu Gln Ile Pro Ala Ser Lys Gly Asp Ala Leu Glu Pro Lys Ala Ser
305                 310                 315                 320

Glu Gln Asn Asn Gln His Gly Asn Ser Pro Ala Val Leu Ser Pro Pro
                325                 330                 335

Gly Lys Met Arg Arg Val Met Gly Pro Glu Gly
            340                 345


<210> SEQ ID NO 49
<211> LENGTH: 1353
<212> TYPE: DNA
<213> ORGANISM: Glycine max
<220> FEATURE:
<221> NAME/KEY: CDS
<222> LOCATION: (1)..(1353)

<400> SEQUENCE: 49

atg gag gag cct ttg aca gat tcg gga agc tac cca cac gat ttg gag       48
Met Glu Glu Pro Leu Thr Asp Ser Gly Ser Tyr Pro His Asp Leu Glu
1               5                   10                  15

gaa gac aaa gat gtg caa gga tgg aca atc aca aag tca aga tgg gct       96
Glu Asp Lys Asp Val Gln Gly Trp Thr Ile Thr Lys Ser Arg Trp Ala
            20                  25                  30

tgt gat gtt cgt ccc tca cca aga ggt gct gat gat gaa cag aag cac      144
Cys Asp Val Arg Pro Ser Pro Arg Gly Ala Asp Asp Glu Gln Lys His
        35                  40                  45

ggc aaa gtg agc tcc agt cct gaa att ggt gaa ttc cat ggc ggt gga      192
Gly Lys Val Ser Ser Ser Pro Glu Ile Gly Glu Phe His Gly Gly Gly
    50                  55                  60

act tca gag agc aca atc act aga tca tca gga agt agt ggt aga gat      240
Thr Ser Glu Ser Thr Ile Thr Arg Ser Ser Gly Ser Ser Gly Arg Asp
65                  70                  75                  80

cat tat ttg ggt gct tct tct gat gac act gat tct gaa aag gac ttc      288
His Tyr Leu Gly Ala Ser Ser Asp Asp Thr Asp Ser Glu Lys Asp Phe
                85                  90                  95

ctt atg gac tcc atg gtc aat gtt gag gaa caa agt gat gat ggt gat      336
Leu Met Asp Ser Met Val Asn Val Glu Glu Gln Ser Asp Asp Gly Asp
            100                 105                 110

tct cca tca gat tct gat gag tgt ggt gga ttg atg cat gtg ctg aga      384
Ser Pro Ser Asp Ser Asp Glu Cys Gly Gly Leu Met His Val Leu Arg
        115                 120                 125

aac ata aac atg ctt cag agt tgc aga agt gtg tgt gag ttt gag atg      432
Asn Ile Asn Met Leu Gln Ser Cys Arg Ser Val Cys Glu Phe Glu Met
    130                 135                 140

att aag aaa ata aac gaa gga act tat ggt gtt gtc tac aag gct agg      480
Ile Lys Lys Ile Asn Glu Gly Thr Tyr Gly Val Val Tyr Lys Ala Arg
145                 150                 155                 160

gat aag aag act gga gaa cta gta gca ttg aag aag gtg aag atg aac      528
Asp Lys Lys Thr Gly Glu Leu Val Ala Leu Lys Lys Val Lys Met Asn
                165                 170                 175

ata gag agg gat gga ttt cca atg tca tcc ttg aga gaa ata aac att      576
```

```
Ile Glu Arg Asp Gly Phe Pro Met Ser Ser Leu Arg Glu Ile Asn Ile
            180                 185                 190

ctc ttg tct ttt aat cat ccc tcc att gtg aat gtt aaa gaa gta gtt      624
Leu Leu Ser Phe Asn His Pro Ser Ile Val Asn Val Lys Glu Val Val
        195                 200                 205

gtt gat gat ttt gat ggt act ttt atg gta atg gag cac atg gag tat      672
Val Asp Asp Phe Asp Gly Thr Phe Met Val Met Glu His Met Glu Tyr
    210                 215                 220

gac ctg aag ggg ctg atg gag gtt aag aag cat ccc ttt agc atg agt      720
Asp Leu Lys Gly Leu Met Glu Val Lys Lys His Pro Phe Ser Met Ser
225                 230                 235                 240

gaa att aaa tcc ttg gta cgg caa ctt ctt gaa ggt gtc aag tat ctc      768
Glu Ile Lys Ser Leu Val Arg Gln Leu Leu Glu Gly Val Lys Tyr Leu
                245                 250                 255

cat gat aat tgg gtt atc cat agg gac ttg aaa tca tca aac atc ctg      816
His Asp Asn Trp Val Ile His Arg Asp Leu Lys Ser Ser Asn Ile Leu
            260                 265                 270

ctg aac cat gat ggg gag ctt aaa ata tgc gac ttt ggg ttg tca agg      864
Leu Asn His Asp Gly Glu Leu Lys Ile Cys Asp Phe Gly Leu Ser Arg
        275                 280                 285

cag tat gga agc ccg ctg aag cca tat act cct gtt gtg gtt aca cta      912
Gln Tyr Gly Ser Pro Leu Lys Pro Tyr Thr Pro Val Val Val Thr Leu
    290                 295                 300

tgg tac aga gca cct gaa ctt ttg ctg ggt gct aaa gaa tac tca act      960
Trp Tyr Arg Ala Pro Glu Leu Leu Leu Gly Ala Lys Glu Tyr Ser Thr
305                 310                 315                 320

gca att gac atg tgg tca gtg ggt tgc ata atg gct gaa tta att gcc     1008
Ala Ile Asp Met Trp Ser Val Gly Cys Ile Met Ala Glu Leu Ile Ala
                325                 330                 335

aag gaa cct ctg ttc agg ggt aaa agt gaa ctt gaa caa ctt gat aag     1056
Lys Glu Pro Leu Phe Arg Gly Lys Ser Glu Leu Glu Gln Leu Asp Lys
            340                 345                 350

att ttt cga acc ctg ggt acg cct gat gag aaa att tgg cca gga tta     1104
Ile Phe Arg Thr Leu Gly Thr Pro Asp Glu Lys Ile Trp Pro Gly Leu
        355                 360                 365

tcc aaa tta cct ggg gct aaa gca aat ttt gtt aag caa ctg ttt aat     1152
Ser Lys Leu Pro Gly Ala Lys Ala Asn Phe Val Lys Gln Leu Phe Asn
    370                 375                 380

aca cta agg aag aag ttt cca gct gcg tcg ttt att ggt ttg cca gtt     1200
Thr Leu Arg Lys Lys Phe Pro Ala Ala Ser Phe Ile Gly Leu Pro Val
385                 390                 395                 400

tta tct gag ctt gga ttt gac ttg ttg cag cag ctg cta act tat gac     1248
Leu Ser Glu Leu Gly Phe Asp Leu Leu Gln Gln Leu Leu Thr Tyr Asp
                405                 410                 415

cct gaa aag agg ata aca gca gaa gat gct ctc ctt cat gat tgg ttc     1296
Pro Glu Lys Arg Ile Thr Ala Glu Asp Ala Leu Leu His Asp Trp Phe
            420                 425                 430

cat gaa gcc cct ctt ccc aaa tct gat ttc aag cca att ttt cct tct     1344
His Glu Ala Pro Leu Pro Lys Ser Asp Phe Lys Pro Ile Phe Pro Ser
        435                 440                 445

tgg cag tga                                                         1353
Trp Gln
    450
```

<210> SEQ ID NO 50
<211> LENGTH: 450
<212> TYPE: PRT
<213> ORGANISM: Glycine max

<400> SEQUENCE: 50

```
Met Glu Glu Pro Leu Thr Asp Ser Gly Ser Tyr Pro His Asp Leu Glu
```

-continued

```
1               5                   10                  15

Glu Asp Lys Asp Val Gln Gly Trp Thr Ile Thr Lys Ser Arg Trp Ala
            20                  25                  30

Cys Asp Val Arg Pro Ser Pro Arg Gly Ala Asp Asp Glu Gln Lys His
        35                  40                  45

Gly Lys Val Ser Ser Ser Pro Glu Ile Gly Glu Phe His Gly Gly Gly
    50                  55                  60

Thr Ser Glu Ser Thr Ile Thr Arg Ser Ser Gly Ser Ser Gly Arg Asp
65                  70                  75                  80

His Tyr Leu Gly Ala Ser Ser Asp Asp Thr Asp Ser Glu Lys Asp Phe
                85                  90                  95

Leu Met Asp Ser Met Val Asn Val Glu Glu Gln Ser Asp Asp Gly Asp
            100                 105                 110

Ser Pro Ser Asp Ser Asp Glu Cys Gly Gly Leu Met His Val Leu Arg
        115                 120                 125

Asn Ile Asn Met Leu Gln Ser Cys Arg Ser Val Cys Glu Phe Glu Met
    130                 135                 140

Ile Lys Lys Ile Asn Glu Gly Thr Tyr Gly Val Val Tyr Lys Ala Arg
145                 150                 155                 160

Asp Lys Lys Thr Gly Glu Leu Val Ala Leu Lys Lys Val Lys Met Asn
                165                 170                 175

Ile Glu Arg Asp Gly Phe Pro Met Ser Ser Leu Arg Glu Ile Asn Ile
            180                 185                 190

Leu Leu Ser Phe Asn His Pro Ser Ile Val Asn Val Lys Glu Val Val
        195                 200                 205

Val Asp Asp Phe Asp Gly Thr Phe Met Val Met Glu His Met Glu Tyr
    210                 215                 220

Asp Leu Lys Gly Leu Met Glu Val Lys Lys His Pro Phe Ser Met Ser
225                 230                 235                 240

Glu Ile Lys Ser Leu Val Arg Gln Leu Leu Glu Gly Val Lys Tyr Leu
                245                 250                 255

His Asp Asn Trp Val Ile His Arg Asp Leu Lys Ser Ser Asn Ile Leu
            260                 265                 270

Leu Asn His Asp Gly Glu Leu Lys Ile Cys Asp Phe Gly Leu Ser Arg
        275                 280                 285

Gln Tyr Gly Ser Pro Leu Lys Pro Tyr Thr Pro Val Val Val Thr Leu
    290                 295                 300

Trp Tyr Arg Ala Pro Glu Leu Leu Leu Gly Ala Lys Glu Tyr Ser Thr
305                 310                 315                 320

Ala Ile Asp Met Trp Ser Val Gly Cys Ile Met Ala Glu Leu Ile Ala
                325                 330                 335

Lys Glu Pro Leu Phe Arg Gly Lys Ser Glu Leu Glu Gln Leu Asp Lys
            340                 345                 350

Ile Phe Arg Thr Leu Gly Thr Pro Asp Glu Lys Ile Trp Pro Gly Leu
        355                 360                 365

Ser Lys Leu Pro Gly Ala Lys Ala Asn Phe Val Lys Gln Leu Phe Asn
    370                 375                 380

Thr Leu Arg Lys Lys Phe Pro Ala Ala Ser Phe Ile Gly Leu Pro Val
385                 390                 395                 400

Leu Ser Glu Leu Gly Phe Asp Leu Leu Gln Gln Leu Leu Thr Tyr Asp
                405                 410                 415

Pro Glu Lys Arg Ile Thr Ala Glu Asp Ala Leu Leu His Asp Trp Phe
            420                 425                 430
```

```
His Glu Ala Pro Leu Pro Lys Ser Asp Phe Lys Pro Ile Phe Pro Ser
        435                 440                 445

Trp Gln
    450


<210> SEQ ID NO 51
<211> LENGTH: 885
<212> TYPE: DNA
<213> ORGANISM: Linum usitatissimum
<220> FEATURE:
<221> NAME/KEY: CDS
<222> LOCATION: (1)..(885)

<400> SEQUENCE: 51

atg gag cag tac gag aaa gtg gag aag att ggg gag gga act tac gga       48
Met Glu Gln Tyr Glu Lys Val Glu Lys Ile Gly Glu Gly Thr Tyr Gly
1               5                   10                  15

gtg gta tat aag gcc cgt gat cga aac acc aat cag act att gct ttg       96
Val Val Tyr Lys Ala Arg Asp Arg Asn Thr Asn Gln Thr Ile Ala Leu
            20                  25                  30

aag aag att cgc ctt gaa cag gaa gat gag ggc gtg cca agc acc gcc      144
Lys Lys Ile Arg Leu Glu Gln Glu Asp Glu Gly Val Pro Ser Thr Ala
        35                  40                  45

att aga gaa att tcg ctt ctg aaa gaa atg cag cat ggt aac att gtg      192
Ile Arg Glu Ile Ser Leu Leu Lys Glu Met Gln His Gly Asn Ile Val
    50                  55                  60

agg ttg cag gat gtg gtg cac agt gag aaa cgg cta tat ttg gtt ttt      240
Arg Leu Gln Asp Val Val His Ser Glu Lys Arg Leu Tyr Leu Val Phe
65                  70                  75                  80

gag tac ctg gac tta gat ttg aaa aag cac atg gac tca agt ccg gag      288
Glu Tyr Leu Asp Leu Asp Leu Lys Lys His Met Asp Ser Ser Pro Glu
                85                  90                  95

ttt gct aag gat ccg cgt ata gtc aaa act ttc cta tac caa atc ctc      336
Phe Ala Lys Asp Pro Arg Ile Val Lys Thr Phe Leu Tyr Gln Ile Leu
            100                 105                 110

cgt ggc att tct tat tgc cac tct cac agg gtt ctt cat cga gat cta      384
Arg Gly Ile Ser Tyr Cys His Ser His Arg Val Leu His Arg Asp Leu
        115                 120                 125

aag cca cag aat ctg ctt att gat cgt cgt acc aat gca ctc aag ctt      432
Lys Pro Gln Asn Leu Leu Ile Asp Arg Arg Thr Asn Ala Leu Lys Leu
    130                 135                 140

gca gat ttt ggt ctg gcc aga gct ttt ggt ata cct gtc agg aca ttc      480
Ala Asp Phe Gly Leu Ala Arg Ala Phe Gly Ile Pro Val Arg Thr Phe
145                 150                 155                 160

acc cat gag gtg gtg act ctc tgg tat aga gcc cca gag att ctt ctc      528
Thr His Glu Val Val Thr Leu Trp Tyr Arg Ala Pro Glu Ile Leu Leu
                165                 170                 175

gga tct cac cac tac tct act cca gtt gat gtg tgg tct ata gga tgt      576
Gly Ser His His Tyr Ser Thr Pro Val Asp Val Trp Ser Ile Gly Cys
            180                 185                 190

att ttc gcc gaa atg gtg aac cag cgc ccc tta ttc ccc ggg gac tct      624
Ile Phe Ala Glu Met Val Asn Gln Arg Pro Leu Phe Pro Gly Asp Ser
        195                 200                 205

gag att gat gag cta ttt aag att ttc aga atc atg ggg acg ccc aat      672
Glu Ile Asp Glu Leu Phe Lys Ile Phe Arg Ile Met Gly Thr Pro Asn
    210                 215                 220

gaa gac acc tgg gcc gga gta aca tct tta ccc gat ttc aag tcc acc      720
Glu Asp Thr Trp Ala Gly Val Thr Ser Leu Pro Asp Phe Lys Ser Thr
225                 230                 235                 240

ttc cca aag tgg cct tca aag gac ctg gca acc atg gtt caa act ctc      768
Phe Pro Lys Trp Pro Ser Lys Asp Leu Ala Thr Met Val Gln Thr Leu
                245                 250                 255
```

```
gag tca acc ggt gtt gac ctc tta cga aaa atg ctg tgc ttg gat cca      816
Glu Ser Thr Gly Val Asp Leu Leu Arg Lys Met Leu Cys Leu Asp Pro
            260                 265                 270

agc aaa aga att aca gcc agg act gcc cta gag cat gaa tac ttc aag      864
Ser Lys Arg Ile Thr Ala Arg Thr Ala Leu Glu His Glu Tyr Phe Lys
        275                 280                 285

gac att gga ttt gtg cca taa                                          885
Asp Ile Gly Phe Val Pro
    290             294


<210> SEQ ID NO 52
<211> LENGTH: 294
<212> TYPE: PRT
<213> ORGANISM: Linum usitatissimum

<400> SEQUENCE: 52

Met Glu Gln Tyr Glu Lys Val Glu Lys Ile Gly Glu Gly Thr Tyr Gly
1               5                   10                  15

Val Val Tyr Lys Ala Arg Asp Arg Asn Thr Asn Gln Thr Ile Ala Leu
            20                  25                  30

Lys Lys Ile Arg Leu Glu Gln Glu Asp Glu Gly Val Pro Ser Thr Ala
        35                  40                  45

Ile Arg Glu Ile Ser Leu Leu Lys Glu Met Gln His Gly Asn Ile Val
    50                  55                  60

Arg Leu Gln Asp Val Val His Ser Glu Lys Arg Leu Tyr Leu Val Phe
65                  70                  75                  80

Glu Tyr Leu Asp Leu Asp Leu Lys Lys His Met Asp Ser Ser Pro Glu
                85                  90                  95

Phe Ala Lys Asp Pro Arg Ile Val Lys Thr Phe Leu Tyr Gln Ile Leu
            100                 105                 110

Arg Gly Ile Ser Tyr Cys His Ser His Arg Val Leu His Arg Asp Leu
        115                 120                 125

Lys Pro Gln Asn Leu Leu Ile Asp Arg Arg Thr Asn Ala Leu Lys Leu
    130                 135                 140

Ala Asp Phe Gly Leu Ala Arg Ala Phe Gly Ile Pro Val Arg Thr Phe
145                 150                 155                 160

Thr His Glu Val Val Thr Leu Trp Tyr Arg Ala Pro Glu Ile Leu Leu
                165                 170                 175

Gly Ser His His Tyr Ser Thr Pro Val Asp Val Trp Ser Ile Gly Cys
            180                 185                 190

Ile Phe Ala Glu Met Val Asn Gln Arg Pro Leu Phe Pro Gly Asp Ser
        195                 200                 205

Glu Ile Asp Glu Leu Phe Lys Ile Phe Arg Ile Met Gly Thr Pro Asn
    210                 215                 220

Glu Asp Thr Trp Ala Gly Val Thr Ser Leu Pro Asp Phe Lys Ser Thr
225                 230                 235                 240

Phe Pro Lys Trp Pro Ser Lys Asp Leu Ala Thr Met Val Gln Thr Leu
                245                 250                 255

Glu Ser Thr Gly Val Asp Leu Leu Arg Lys Met Leu Cys Leu Asp Pro
            260                 265                 270

Ser Lys Arg Ile Thr Ala Arg Thr Ala Leu Glu His Glu Tyr Phe Lys
        275                 280                 285

Asp Ile Gly Phe Val Pro
    290


<210> SEQ ID NO 53
```

```
<211> LENGTH: 1152
<212> TYPE: DNA
<213> ORGANISM: Zea mays
<220> FEATURE:
<221> NAME/KEY: CDS
<222> LOCATION: (1)..(1152)

<400> SEQUENCE: 53

atg tca gat act gac tca gac aat gaa ata cac aga cct gaa acc cct       48
Met Ser Asp Thr Asp Ser Asp Asn Glu Ile His Arg Pro Glu Thr Pro
1               5                   10                  15

gaa aga gag aag gca cca cac agg tgt atc aat atg ctt caa gat tgc       96
Glu Arg Glu Lys Ala Pro His Arg Cys Ile Asn Met Leu Gln Asp Cys
            20                  25                  30

aga agt gtt gat gag ttt gag agg ctc aac aaa att aac gag ggc aca      144
Arg Ser Val Asp Glu Phe Glu Arg Leu Asn Lys Ile Asn Glu Gly Thr
        35                  40                  45

tat ggt gtt gta tac aga gca agg gat aag aag aca agt gag att gtt      192
Tyr Gly Val Val Tyr Arg Ala Arg Asp Lys Lys Thr Ser Glu Ile Val
    50                  55                  60

gca ttg aag aag gta aag atg gag aag gag cga gaa ggt ttc cca tta      240
Ala Leu Lys Lys Val Lys Met Glu Lys Glu Arg Glu Gly Phe Pro Leu
65                  70                  75                  80

acc tct ctt agg gaa ata aat atc ctc ttg tct ttc cac aat cct tca      288
Thr Ser Leu Arg Glu Ile Asn Ile Leu Leu Ser Phe His Asn Pro Ser
                85                  90                  95

att gtg gat gtt aag gaa gta gta gtt gga agt agt cta gat agt att      336
Ile Val Asp Val Lys Glu Val Val Val Gly Ser Ser Leu Asp Ser Ile
            100                 105                 110

ttt atg gtt atg gag tac atg gaa cat gat ctt aaa ggt gtc atg gag      384
Phe Met Val Met Glu Tyr Met Glu His Asp Leu Lys Gly Val Met Glu
        115                 120                 125

acc atg aaa caa cca tat acc caa agc gag gta aag tgt ttg atg ctt      432
Thr Met Lys Gln Pro Tyr Thr Gln Ser Glu Val Lys Cys Leu Met Leu
    130                 135                 140

cag ctg cta gaa ggt gta aaa tat cta cat gac aat tgg gtg ctt cat      480
Gln Leu Leu Glu Gly Val Lys Tyr Leu His Asp Asn Trp Val Leu His
145                 150                 155                 160

agg gat ctg aag acc tca aat ctt ttg ttg aat aac cgt ggt gag tta      528
Arg Asp Leu Lys Thr Ser Asn Leu Leu Leu Asn Asn Arg Gly Glu Leu
                165                 170                 175

aaa ata tgt gat ttt gga ctg tct cgt caa tat gga agc cca tta aaa      576
Lys Ile Cys Asp Phe Gly Leu Ser Arg Gln Tyr Gly Ser Pro Leu Lys
            180                 185                 190

cct tat act caa ctg gtt gtg act ttg tgg tac agg gcc cca gaa ttg      624
Pro Tyr Thr Gln Leu Val Val Thr Leu Trp Tyr Arg Ala Pro Glu Leu
        195                 200                 205

ttg tta gga aca aag gag tat tct act gct att gat atg tgg tct gtg      672
Leu Leu Gly Thr Lys Glu Tyr Ser Thr Ala Ile Asp Met Trp Ser Val
    210                 215                 220

ggc tgt ata atg gct gag ctt ctt gcc aaa gaa ccg tta ttc aat gga      720
Gly Cys Ile Met Ala Glu Leu Leu Ala Lys Glu Pro Leu Phe Asn Gly
225                 230                 235                 240

aaa aca gag ttt gaa cag cta gat aag att ttt aga aca ctc ggc aca      768
Lys Thr Glu Phe Glu Gln Leu Asp Lys Ile Phe Arg Thr Leu Gly Thr
                245                 250                 255

cct aat gag aag att tgg cct ggc tat gct aaa tta cca ggt gtg aaa      816
Pro Asn Glu Lys Ile Trp Pro Gly Tyr Ala Lys Leu Pro Gly Val Lys
            260                 265                 270

gta aat ttt gtt aaa caa ccg tat aat aga cta agg gat aag ttc cca      864
Val Asn Phe Val Lys Gln Pro Tyr Asn Arg Leu Arg Asp Lys Phe Pro
        275                 280                 285
```

```
gcc gct tct ttt tct ggg cga cca atc ctg tct gaa gct ggt ttt gat      912
Ala Ala Ser Phe Ser Gly Arg Pro Ile Leu Ser Glu Ala Gly Phe Asp
    290                 295                 300

cta ttg aac aga ctg ctg act tat gac cct gat aag cgc ata tca gca      960
Leu Leu Asn Arg Leu Leu Thr Tyr Asp Pro Asp Lys Arg Ile Ser Ala
305                 310                 315                 320

gac gat gct ctt aag cac aaa tgg ttc tct gaa gtt cct ctg cct aaa     1008
Asp Asp Ala Leu Lys His Lys Trp Phe Ser Glu Val Pro Leu Pro Lys
                325                 330                 335

tca aag gac ttc atg cca aca ttc cct gct ctt aat gaa ctt gac agg     1056
Ser Lys Asp Phe Met Pro Thr Phe Pro Ala Leu Asn Glu Leu Asp Arg
            340                 345                 350

cgt tcc aga agg tat ctg aag agt cct gat cct ctg gaa gag caa cgt     1104
Arg Ser Arg Arg Tyr Leu Lys Ser Pro Asp Pro Leu Glu Glu Gln Arg
        355                 360                 365

ttg aaa gaa ctg caa ggg aac ata ggc aac cat ggg ctt ttt ggg tga     1152
Leu Lys Glu Leu Gln Gly Asn Ile Gly Asn His Gly Leu Phe Gly
    370                 375                 380


<210> SEQ ID NO 54
<211> LENGTH: 383
<212> TYPE: PRT
<213> ORGANISM: Zea mays

<400> SEQUENCE: 54

Met Ser Asp Thr Asp Ser Asp Asn Glu Ile His Arg Pro Glu Thr Pro
1               5                   10                  15

Glu Arg Glu Lys Ala Pro His Arg Cys Ile Asn Met Leu Gln Asp Cys
            20                  25                  30

Arg Ser Val Asp Glu Phe Glu Arg Leu Asn Lys Ile Asn Glu Gly Thr
        35                  40                  45

Tyr Gly Val Val Tyr Arg Ala Arg Asp Lys Lys Thr Ser Glu Ile Val
    50                  55                  60

Ala Leu Lys Lys Val Lys Met Glu Lys Glu Arg Glu Gly Phe Pro Leu
65                  70                  75                  80

Thr Ser Leu Arg Glu Ile Asn Ile Leu Leu Ser Phe His Asn Pro Ser
                85                  90                  95

Ile Val Asp Val Lys Glu Val Val Val Gly Ser Ser Leu Asp Ser Ile
            100                 105                 110

Phe Met Val Met Glu Tyr Met Glu His Asp Leu Lys Gly Val Met Glu
        115                 120                 125

Thr Met Lys Gln Pro Tyr Thr Gln Ser Glu Val Lys Cys Leu Met Leu
    130                 135                 140

Gln Leu Leu Glu Gly Val Lys Tyr Leu His Asp Asn Trp Val Leu His
145                 150                 155                 160

Arg Asp Leu Lys Thr Ser Asn Leu Leu Leu Asn Asn Arg Gly Glu Leu
                165                 170                 175

Lys Ile Cys Asp Phe Gly Leu Ser Arg Gln Tyr Gly Ser Pro Leu Lys
            180                 185                 190

Pro Tyr Thr Gln Leu Val Val Thr Leu Trp Tyr Arg Ala Pro Glu Leu
        195                 200                 205

Leu Leu Gly Thr Lys Glu Tyr Ser Thr Ala Ile Asp Met Trp Ser Val
    210                 215                 220

Gly Cys Ile Met Ala Glu Leu Leu Ala Lys Glu Pro Leu Phe Asn Gly
225                 230                 235                 240

Lys Thr Glu Phe Glu Gln Leu Asp Lys Ile Phe Arg Thr Leu Gly Thr
                245                 250                 255
```

```
Pro Asn Glu Lys Ile Trp Pro Gly Tyr Ala Lys Leu Pro Gly Val Lys
            260                 265                 270

Val Asn Phe Val Lys Gln Pro Tyr Asn Arg Leu Arg Asp Lys Phe Pro
        275                 280                 285

Ala Ala Ser Phe Ser Gly Arg Pro Ile Leu Ser Glu Ala Gly Phe Asp
    290                 295                 300

Leu Leu Asn Arg Leu Leu Thr Tyr Asp Pro Asp Lys Arg Ile Ser Ala
305                 310                 315                 320

Asp Asp Ala Leu Lys His Lys Trp Phe Ser Glu Val Pro Leu Pro Lys
                325                 330                 335

Ser Lys Asp Phe Met Pro Thr Phe Pro Ala Leu Asn Glu Leu Asp Arg
            340                 345                 350

Arg Ser Arg Arg Tyr Leu Lys Ser Pro Asp Pro Leu Glu Glu Gln Arg
        355                 360                 365

Leu Lys Glu Leu Gln Gly Asn Ile Gly Asn His Gly Leu Phe Gly
    370                 375                 380


<210> SEQ ID NO 55
<211> LENGTH: 885
<212> TYPE: DNA
<213> ORGANISM: Helianthus annuus
<220> FEATURE:
<221> NAME/KEY: CDS
<222> LOCATION: (1)..(885)

<400> SEQUENCE: 55

atg gac cag tat gag aag gtt gag aag att ggt gaa gga aca tat ggt       48
Met Asp Gln Tyr Glu Lys Val Glu Lys Ile Gly Glu Gly Thr Tyr Gly
1               5                   10                  15

gtg gtc tac aag gct cgt gac aaa gtt acc aat gaa aca atc gct ttg       96
Val Val Tyr Lys Ala Arg Asp Lys Val Thr Asn Glu Thr Ile Ala Leu
            20                  25                  30

aag aag att cgt ctg gag caa gaa gac gag ggt gtc cca agc aca gct      144
Lys Lys Ile Arg Leu Glu Gln Glu Asp Glu Gly Val Pro Ser Thr Ala
        35                  40                  45

att aga gaa atc tcg tta ttg aaa gag atg caa cat gga aat att gtc      192
Ile Arg Glu Ile Ser Leu Leu Lys Glu Met Gln His Gly Asn Ile Val
    50                  55                  60

aag tta cag gat gtt gtg cac agt gac aaa cga ttg tat ctg gtt ttc      240
Lys Leu Gln Asp Val Val His Ser Asp Lys Arg Leu Tyr Leu Val Phe
65                  70                  75                  80

gag tat ctg gac ctg gat ttg aag aag cat atg gac tca tgt ccc gag      288
Glu Tyr Leu Asp Leu Asp Leu Lys Lys His Met Asp Ser Cys Pro Glu
                85                  90                  95

ttt tca aag gat cca cac att gta aaa atg ttt cta tat cag atc cta      336
Phe Ser Lys Asp Pro His Ile Val Lys Met Phe Leu Tyr Gln Ile Leu
            100                 105                 110

cgt ggc att gct tat tgc cat tcc cat aga gtt ctc cat aga gac tta      384
Arg Gly Ile Ala Tyr Cys His Ser His Arg Val Leu His Arg Asp Leu
        115                 120                 125

aaa cct caa aac ctt ttg att gat cgc cgt acc aat gca cta aag ctc      432
Lys Pro Gln Asn Leu Leu Ile Asp Arg Arg Thr Asn Ala Leu Lys Leu
    130                 135                 140

gca gat ttt gga ttg gcc agg gcc ttt ggc att cct gtc agg aca ttc      480
Ala Asp Phe Gly Leu Ala Arg Ala Phe Gly Ile Pro Val Arg Thr Phe
145                 150                 155                 160

aca cac gag gtg gtt aca ctg tgg tat aga gca cca gaa att ctt ctt      528
Thr His Glu Val Val Thr Leu Trp Tyr Arg Ala Pro Glu Ile Leu Leu
                165                 170                 175
```

```
gga tcg cgt cat tat tct act cct gtt gat gtg tgg tcg gtc ggt tgt      576
Gly Ser Arg His Tyr Ser Thr Pro Val Asp Val Trp Ser Val Gly Cys
            180                 185                 190

ata ttt gct gag atg gtg aac caa cgg cca ctc ttc cct ggt gaa tct      624
Ile Phe Ala Glu Met Val Asn Gln Arg Pro Leu Phe Pro Gly Glu Ser
        195                 200                 205

gag att gat gag ctg ttc aaa att ttc aga atc atg gga act cca aat      672
Glu Ile Asp Glu Leu Phe Lys Ile Phe Arg Ile Met Gly Thr Pro Asn
    210                 215                 220

gaa gat aca tgg cat ggt gtg aca tca ctg cct gac ttt aag tcc gcc      720
Glu Asp Thr Trp His Gly Val Thr Ser Leu Pro Asp Phe Lys Ser Ala
225                 230                 235                 240

ttt cca aaa tgg tca tca aag gac ctt gcg act atc gtc ccg aat ctt      768
Phe Pro Lys Trp Ser Ser Lys Asp Leu Ala Thr Ile Val Pro Asn Leu
                245                 250                 255

gaa aag ccc ggt ctt gat ctc cta cgt aaa atg ctg tgc ttg gat ccc      816
Glu Lys Pro Gly Leu Asp Leu Leu Arg Lys Met Leu Cys Leu Asp Pro
            260                 265                 270

agt aga aga att aca gcc cgg gcc gca ctg gaa cac gaa tac ttt aaa      864
Ser Arg Arg Ile Thr Ala Arg Ala Ala Leu Glu His Glu Tyr Phe Lys
        275                 280                 285

gat atc ggg ttt gtg cca taa                                          885
Asp Ile Gly Phe Val Pro
    290             294


<210> SEQ ID NO 56
<211> LENGTH: 294
<212> TYPE: PRT
<213> ORGANISM: Helianthus annuus

<400> SEQUENCE: 56

Met Asp Gln Tyr Glu Lys Val Glu Lys Ile Gly Glu Gly Thr Tyr Gly
1               5                   10                  15

Val Val Tyr Lys Ala Arg Asp Lys Val Thr Asn Glu Thr Ile Ala Leu
            20                  25                  30

Lys Lys Ile Arg Leu Glu Gln Glu Asp Glu Gly Val Pro Ser Thr Ala
        35                  40                  45

Ile Arg Glu Ile Ser Leu Leu Lys Glu Met Gln His Gly Asn Ile Val
    50                  55                  60

Lys Leu Gln Asp Val Val His Ser Asp Lys Arg Leu Tyr Leu Val Phe
65                  70                  75                  80

Glu Tyr Leu Asp Leu Asp Leu Lys Lys His Met Asp Ser Cys Pro Glu
                85                  90                  95

Phe Ser Lys Asp Pro His Ile Val Lys Met Phe Leu Tyr Gln Ile Leu
            100                 105                 110

Arg Gly Ile Ala Tyr Cys His Ser His Arg Val Leu His Arg Asp Leu
        115                 120                 125

Lys Pro Gln Asn Leu Leu Ile Asp Arg Arg Thr Asn Ala Leu Lys Leu
    130                 135                 140

Ala Asp Phe Gly Leu Ala Arg Ala Phe Gly Ile Pro Val Arg Thr Phe
145                 150                 155                 160

Thr His Glu Val Val Thr Leu Trp Tyr Arg Ala Pro Glu Ile Leu Leu
                165                 170                 175

Gly Ser Arg His Tyr Ser Thr Pro Val Asp Val Trp Ser Val Gly Cys
            180                 185                 190

Ile Phe Ala Glu Met Val Asn Gln Arg Pro Leu Phe Pro Gly Glu Ser
        195                 200                 205

Glu Ile Asp Glu Leu Phe Lys Ile Phe Arg Ile Met Gly Thr Pro Asn
```

-continued

```
    210                 215                 220

Glu Asp Thr Trp His Gly Val Thr Ser Leu Pro Asp Phe Lys Ser Ala
225                 230                 235                 240

Phe Pro Lys Trp Ser Ser Lys Asp Leu Ala Thr Ile Val Pro Asn Leu
                245                 250                 255

Glu Lys Pro Gly Leu Asp Leu Leu Arg Lys Met Leu Cys Leu Asp Pro
            260                 265                 270

Ser Arg Arg Ile Thr Ala Arg Ala Ala Leu Glu His Glu Tyr Phe Lys
        275                 280                 285

Asp Ile Gly Phe Val Pro
    290


<210> SEQ ID NO 57
<211> LENGTH: 11449
<212> TYPE: DNA
<213> ORGANISM: Unknown
<220> FEATURE:
<223> OTHER INFORMATION: vector

<400> SEQUENCE: 57

gtttacccgc caatatatcc tgtcaaacac tgatagtttg tggaattcga gctcggtacc     60

cggggatcct ctagagtcga cctgcaggca tgcaagcttt gcagtgcagc gtgacccggt    120

cgtgcccctc tctagagata atgagcattg catgtctaag ttataaaaaa ttaccacata    180

tttttttgt cacacttgtt tgaagtgcag tttatctatc tttatacata tatttaaact    240

ttactctacg aataatataa tctatagtac tacaataata tcagtgtttt agagaatcat    300

ataaatgaac agttagacat ggtctaaagg acaattgagt attttgacaa caggactcta    360

cagttttatc tttttagtgt gcatgtgttc tccttttttt ttgcaaatag cttcacctat    420

ataatacttc atccatttta ttagtacatc catttagggt ttagggttaa tggtttttat    480

agactaattt ttttagtaca tctattttat tctattttag cctctaaatt aagaaaacta    540

aaactctatt ttagtttttt tatttaatag tttagatata aaatagaata aaataaagtg    600

actaaaaatt aaacaaatac cctttaagaa attaaaaaaa ctaaggaaac atttttcttg    660

tttcgagtag ataatgccag cctgttaaac gccgtcgacg agtctaacgg acaccaacca    720

gcgaaccagc agcgtcgcgt cgggccaagc gaagcagacg gcacggcatc tctgtcgctg    780

cctctggacc cctctcgaga gttccgctcc accgttggac ttgctccgct gtcggcatcc    840

agaaattgcg tggcggagcg gcagacgtga gccggcacgg caggcggcct cctcctcctc    900

tcacggcacc ggcagctacg gggattcct ttcccaccgc tccttcgctt tcccttcctc    960

gcccgccgta ataaatagac accccctcca caccctcttt ccccaacctc gtgttgttcg   1020

gagcgcacac acacacaacc agatctcccc caaatccacc cgtcggcacc tccgcttcaa   1080

ggtacgccgc tcgtcctccc cccccccccc cctctctacc ttctctagat cggcgttccg   1140

gtccatggtt agggcccggt agttctactt ctgttcatgt ttgtgttaga tccgtgtttg   1200

tgttagatcc gtgctgctag cgttcgtaca cggatgcgac ctgtacgtca gacacgttct   1260

gattgctaac ttgccagtgt ttctctttgg ggaatcctgg gatggctcta gccgttccgc   1320

agacgggatc gatttcatga ttttttttgt ttcgttgcat agggtttggt ttgccctttt   1380

cctttatttc aatatatgcc gtgcacttgt ttgtcgggtc atcttttcat gcttttttt   1440

gtcttggttg tgatgatgtg gtctggttgg gcggtcgttc tagatcggag tagaattctg   1500

tttcaaacta cctggtggat ttattaattt tggatctgta tgtgtgtgcc atacatattc   1560

atagttacga attgaagatg atggatggaa atatcgatct aggataggta tacatgttga   1620
```

-continued

```
tgcgggtttt actgatgcat atacagagat gctttttgtt cgcttggttg tgatgatgtg   1680
gtgtggttgg gcggtcgttc attcgttcta gatcggagta gaatactgtt tcaaactacc   1740
tggtgtattt attaatttg gaactgtatg tgtgtgtcat acatcttcat agttacgagt    1800
ttaagatgga tggaaatatc gatctaggat aggtatacat gttgatgtgg gttttactga   1860
tgcatataca tgatggcata tgcagcatct attcatatgc tctaaccttg agtacctatc   1920
tattataata aacaagtatg ttttataatt atttcgatct tgatatactt ggatgatggc   1980
atatgcagca gctatatgtg gattttttta gccctgcctt catacgctat ttatttgctt   2040
ggtactgttt cttttgtcga tgctcaccct gttgtttggt gttacttctg cagggtaccc   2100
ccggggatcc actagttcta gaaaccatgg ccaccgccgc cgccgcgtct accgcgctca   2160
ctggcgccac taccgctgcg cccaaggcga ggcgccgggc gcacctcctg gccacccgcc   2220
gcgccctcgc cgcgcccatc aggtgctcag cggcgtcacc cgccatgccg atggctcccc   2280
cggccacccc gctccggccg tggggcccca ccgatccccg caagggcgcc gacatcctcg   2340
tcgagtccct cgagcgctgc ggcgtccgcg acgtcttcgc ctaccccggc ggcgcgtcca   2400
tggagatcca ccaggcactc acccgctccc ccgtcatcgc caaccacctc ttccgccacg   2460
agcaagggga ggcctttgcg gcctccggct acgcgcgctc ctcgggccgc gtcggcgtct   2520
gcatcgccac ctccggcccc ggcgccacca accttgtctc cgcgctcgcc gacgcgctgc   2580
tcgattccgt ccccatggtc gccatcacgg gacaggtgcc gcgacgcatg attggcaccg   2640
acgccttcca ggagacgccc atcgtcgagg tcacccgctc catcaccaag cacaactacc   2700
tggtcctcga cgtcgacgac atcccccgcg tcgtgcagga ggctttcttc ctcgcctcct   2760
ctggtcgacc ggggccggtg cttgtcgaca tccccaagga catccagcag cagatggcgg   2820
tgcctgtctg ggacaagccc atgagtctgc ctgggtacat tgcgcgcctt cccaagcccc   2880
ctgcgactga gttgcttgag caggtgctgc gtcttgttgg tgaatcccgg cgccctgttc   2940
tttatgttgg cggtggctgc gcagcatctg gtgaggagtt gcgacgcttt gtggagctga   3000
ctggaatccc ggtcacaact actcttatgg gcctcggcaa cttccccagc gacgacccac   3060
tgtctctgcg catgctaggt atgcatggca cggtgtatgc aaattatgca gtggataagg   3120
ccgatctgtt gcttgcactt ggtgtgcggt ttgatgatcg tgtgacaggg aagattgagg   3180
cttttgcaag cagggctaag attgtgcacg ttgatattga tccggctgag attggcaaga   3240
acaagcagcc acatgtgtcc atctgtgcag atgttaagct tgctttgcag ggcatgaatg   3300
ctcttcttga aggaagcaca tcaaagaaga gctttgactt tggctcatgg aacgatgagt   3360
tggatcagca gaagagggaa ttcccccttg ggtataaaac atctaatgag gagatccagc   3420
cacaatatgc tattcaggtt cttgatgagc tgacgaaagg cgaggccatc atcggcacag   3480
gtgttgggca gcaccagatg tgggcggcac agtactacac ttacaagcgg ccaaggcagt   3540
ggttgtcttc agctggtctt ggggctatgg gatttggttt gccggctgct gctggtgctt   3600
ctgtggccaa cccaggtgtt actgttgttg acatcgatgg agatggtagc tttctcatga   3660
acgttcagga gctagctatg atccgaattg agaacctccc ggtgaaggtc tttgtgctaa   3720
acaaccagca cctggggatg gtggtgcagt gggaggacag gttctataag gccaacagag   3780
cgcacacata cttgggaaac ccagagaatg aaagtgagat atatccagat ttcgtgacga   3840
tcgccaaagg gttcaacatt ccagcggtcc gtgtgacaaa gaagaacgaa gtccgcgcag   3900
cgataaagaa gatgctcgag actccagggc cgtacctctt ggatataatc gtcccacacc   3960
aggagcatgt gttgcctatg atccctaatg gtggggcttt caaggatatg atcctggatg   4020
```

-continued

```
gtgatggcag gactgtgtac tgatctaaaa tccagcaagc aactgatcta aaatccagca   4080
agcaccgcct ccctgctagt acaagggtga tatgttttta tctgtgtgat gttctcctgt   4140
attctatctt tttttgtagg ccgtcagcta tctgttatgg taatcctatg tagcttccga   4200
ccttgtaatt gtgtagtctg ttgttttcct tctggcatgt gtcataagag atcatttaag   4260
tgccttttgc tacatataaa taagataata agcactgcta tgcagtggtt ctgaattggc   4320
ttctgttgcc aaatttaagt gtccaactgg tccttgcttt tgttttcgct atttttttcc   4380
tttttagtt attattatat tggtaatttc aactcaacat atgatgtatg gaataatgct   4440
agggctgcaa tttcaaacta ttttacaaac cagaatggca ttttcgtggt ttgaggggag   4500
tgaaaaaaaa tgaggcattt gactgaatta gttacctgat ccattttcgt ggtttggatc   4560
attggaatta aattccattc taataatagt aattttggca tatatcaatt aagttaattc   4620
ggttttatgc aaaatatatt tgtatactat tattatcaag atgtcggaga tatttatatg   4680
ctacattttt actatacagg agtgagatga agagtgtcat gtaagttaca cagtagaaac   4740
aaattctatt aatgcataaa atcatttcca tcatccaccc tatgaatttg agatagacct   4800
atatctaaac tttgaaaagt ggttgaatat caaattccaa attaaataag ttattttatt   4860
gagtgaattc taatttctct aaaacgaagg gatctaaacg ccctctaaag ctaatttgga   4920
aactcaaact ttcttagcat tggaggggat tgagaaaaaa tattaattca ttttcatctc   4980
aatcattcaa tctccaaaga gatttgagtt ccttattagt ctgttccatg catcaaatcg   5040
gctcaatgtg tcattatttg ccatgacgat tgacgagttg ttctggggcc tagcgctttc   5100
cacgccgatg tgctggggcc tggtcctgga gaagacagct tgatatttaa agctatcaat   5160
tgtttcaatt gattcccact tcatttttct aaatgtagaa aacggtgacg tataagaaaa   5220
agaatgaatt aggactttta ttccgtacac taatctagag cggcccctta aggcgctgcg   5280
atcgcgttaa cagcttgctg aggaggcctc ggaccgttaa ttaacacgtg ggcgcgccac   5340
tagtcaattc agtacattaa aaacgtccgc aatgtgttat taagttgtct aagcgtcaat   5400
ttgtttacac cacaatatat cctgccacca gccagccaac agctccccga ccggcagctc   5460
ggcacaaaat caccactcga tacaggcagc ccatcagtcc gggacggcgt cagcgggaga   5520
gccgttgtaa ggcggcagac tttgctcatg ttaccgatgc tattcggaag aacggcaact   5580
aagctgccgg gtttgaaaca cggatgatct cgcggagggt agcatgttga ttgtaacgat   5640
gacagagcgt tgctgcctgt gatcaaatat catctccctc gcagagatcc gaattatcag   5700
ccttcttatt catttctcgc ttaaccgtga caggctgtcg atcttgagaa ctatgccgac   5760
ataataggaa atcgctggat aaagccgctg aggaagctga gtggcgctat ttctttagaa   5820
gtgaacgttg acgatcgtcg accgtacccc gatgaattaa ttcggacgta cgttctgaac   5880
acagctggat acttacttgg gcgattgtca tacatgacat caacaatgta cccgtttgtg   5940
taaccgtctc ttggaggttc gtatgacact agtggttccc ctcagcttgc gactagatgt   6000
tgaggcctaa cattttatta gagagcaggc tagttgctta gatacatgat cttcaggccg   6060
ttatctgtca gggcaagcga aaattggcca tttatgacga ccaatgcccc gcagaagctc   6120
ccatctttgc cgccatagac gccgcgcccc ccttttgggg tgtagaacat ccttttgcca   6180
gatgtggaaa agaagttcgt tgtcccattg ttggcaatga cgtagtagcc ggcgaaagtg   6240
cgagacccat ttgcgctata tataagccta cgatttccgt tgcgactatt gtcgtaattg   6300
gatgaactat tatcgtagtt gctctcagag ttgtcgtaat ttgatggact attgtcgtaa   6360
ttgcttatgg agttgtcgta gttgcttgga gaaatgtcgt agttggatgg ggagtagtca   6420
```

-continued

```
tagggaagac gagcttcatc cactaaaaca attggcaggt cagcaagtgc ctgccccgat   6480
gccatcgcaa gtacgaggct tagaaccacc ttcaacagat cgcgcatagt cttccccagc   6540
tctctaacgc ttgagttaag ccgcgccgcg aagcggcgtc ggcttgaacg aattgttaga   6600
cattatttgc cgactacctt ggtgatctcg cctttcacgt agtgaacaaa ttcttccaac   6660
tgatctgcgc gcgaggccaa gcgatcttct tgtccaagat aagcctgcct agcttcaagt   6720
atgacgggct gatactgggc cggcaggcgc tccattgccc agtcggcagc gacatccttc   6780
ggcgcgattt tgccggttac tgcgctgtac caaatgcggg acaacgtaag cactacattt   6840
cgctcatcgc cagcccagtc gggcggcgag ttccatagcg ttaaggtttc atttagcgcc   6900
tcaaatagat cctgttcagg aaccggatca aagagttcct ccgccgctgg acctaccaag   6960
gcaacgctat gttctcttgc ttttgtcagc aagatagcca gatcaatgtc gatcgtggct   7020
ggctcgaaga tacctgcaag aatgtcattg cgctgccatt ctccaaattg cagttcgcgc   7080
ttagctggat aacgccacgg aatgatgtcg tcgtgcacaa caatggtgac ttctacagcg   7140
cggagaatct cgctctctcc aggggaagcc gaagtttcca aaaggtcgtt gatcaaagct   7200
cgccgcgttg tttcatcaag ccttacggtc accgtaacca gcaaatcaat atcactgtgt   7260
ggcttcaggc cgccatccac tgcggagccg tacaaatgta cggccagcaa cgtcggttcg   7320
agatggcgct cgatgacgcc aactacctct gatagttgag tcgatacttc ggcgatcacc   7380
gcttccctca tgatgtttaa ctcctgaatt aagccgcgcc gcgaagcggt gtcggcttga   7440
atgaattgtt aggcgtcatc ctgtgctccc gagaaccagt accagtacat cgctgtttcg   7500
ttcgagactt gaggtctagt tttatacgtg aacaggtcaa tgccgccgag agtaaagcca   7560
cattttgcgt acaaattgca ggcaggtaca ttgttcgttt gtgtctctaa tcgtatgcca   7620
aggagctgtc tgcttagtgc ccactttttc gcaaattcga tgagactgtg cgcgactcct   7680
ttgcctcggt gcgtgtgcga cacaacaatg tgttcgatag aggctagatc gttccatgtt   7740
gagttgagtt caatcttccc gacaagctct tggtcgatga atgcgccata gcaagcagag   7800
tcttcatcag agtcatcatc cgagatgtaa tccttccggt aggggctcac acttctggta   7860
gatagttcaa agccttggtc ggataggtgc acatcgaaca cttcacgaac aatgaaatgg   7920
ttctcagcat ccaatgtttc cgccacctgc tcagggatca ccgaaatctt catatgacgc   7980
ctaacgcctg gcacagcgga tcgcaaacct ggcgcggctt ttggcacaaa aggcgtgaca   8040
ggtttgcgaa tccgttgctg ccacttgtta acccttttgc cagatttggt aactataatt   8100
tatgttagag gcgaagtctt gggtaaaaac tggcctaaaa ttgctgggga tttcaggaaa   8160
gtaaacatca ccttccggct cgatgtctat tgtagatata tgtagtgtat ctacttgatc   8220
gggggatctg ctgcctcgcg cgtttcggtg atgacggtga aaacctctga cacatgcagc   8280
tcccggagac ggtcacagct tgtctgtaag cggatgccgg gagcagacaa gcccgtcagg   8340
gcgcgtcagc gggtgttggc gggtgtcggg gcgcagccat gacccagtca cgtagcgata   8400
gcggagtgta tactggctta actatgcggc atcagagcag attgtactga gagtgcacca   8460
tatgcggtgt gaaataccgc acagatgcgt aaggagaaaa taccgcatca ggcgctcttc   8520
cgcttcctcg ctcactgact cgctgcgctc ggtcgttcgg ctgcggcgag cggtatcagc   8580
tcactcaaag gcggtaatac ggttatccac agaatcaggg gataacgcag gaaagaacat   8640
gtgagcaaaa ggccagcaaa aggccaggaa ccgtaaaaag gccgcgttgc tggcgttttt   8700
ccataggctc cgcccccctg acgagcatca caaaaatcga cgctcaagtc agaggtggcg   8760
aaacccgaca ggactataaa gataccaggc gtttccccct ggaagctccc tcgtgcgctc   8820
```

-continued

```
tcctgttccg accctgccgc ttaccggata cctgtccgcc tttctccctt cgggaagcgt   8880
ggcgctttct catagctcac gctgtaggta tctcagttcg gtgtaggtcg ttcgctccaa   8940
gctgggctgt gtgcacgaac cccccgttca gcccgaccgc tgcgccttat ccggtaacta   9000
tcgtcttgag tccaacccgg taagacacga cttatcgcca ctggcagcag ccactggtaa   9060
caggattagc agagcgaggt atgtaggcgg tgctacagag ttcttgaagt ggtggcctaa   9120
ctacggctac actagaagga cagtatttgg tatctgcgct ctgctgaagc cagttacctt   9180
cggaaaaaga gttggtagct cttgatccgg caaacaaacc accgctggta gcggtggttt   9240
ttttgtttgc aagcagcaga ttacgcgcag aaaaaaagga tctcaagaag atcctttgat   9300
cttttctacg gggtctgacg ctcagtggaa cgaaaactca cgttaaggga ttttggtcat   9360
gagattatca aaaaggatct tcacctagat ccttttaaat taaaaatgaa gttttaaatc   9420
aatctaaagt atatatgagt aaacttggtc tgacagttac caatgcttaa tcagtgaggc   9480
acctatctca gcgatctgtc tatttcgttc atccatagtt gcctgactcc ccgtcgtgta   9540
gataactacg atacgggagg gcttaccatc tggccccagt gctgcaatga taccgcgaga   9600
cccacgctca ccggctccag atttatcagc aataaaccag ccagccggaa gggccgagcg   9660
cagaagtggt cctgcaactt tatccgcctc catccagtct attaattgtt gccgggaagc   9720
tagagtaagt agttcgccag ttaatagttt gcgcaacgtt gttgccattg ctgcaggggg   9780
gggggggggg ggggacttcc attgttcatt ccacggacaa aaacagagaa aggaaacgac   9840
agaggccaaa aagcctcgct ttcagcacct gtcgtttcct ttcttttcag agggtatttt   9900
aaataaaaac attaagttat gacgaagaag aacggaaacg ccttaaaccg gaaaattttc   9960
ataaatagcg aaaacccgcg aggtcgccgc cccgtaacct gtcggatcac cggaaaggac  10020
ccgtaaagtg ataatgatta tcatctacat atcacaacgt gcgtggaggc catcaaacca  10080
cgtcaaataa tcaattatga cgcaggtatc gtattaattg atctgcatca acttaacgta  10140
aaaacaactt cagacaatac aaatcagcga cactgaatac ggggcaacct catgtccccc  10200
cccccccccc ccctgcaggc atcgtggtgt cacgctcgtc gtttggtatg gcttcattca  10260
gctccggttc ccaacgatca aggcgagtta catgatcccc catgttgtgc aaaaaagcgg  10320
ttagctcctt cggtcctccg atcgttgtca gaagtaagtt ggccgcagtg ttatcactca  10380
tggttatggc agcactgcat aattctctta ctgtcatgcc atccgtaaga tgcttttctg  10440
tgactggtga gtactcaacc aagtcattct gagaatagtg tatgcggcga ccgagttgct  10500
cttgcccggc gtcaacacgg gataataccg cgccacatag cagaacttta aaagtgctca  10560
tcattggaaa acgttcttcg gggcgaaaac tctcaaggat cttaccgctg ttgagatcca  10620
gttcgatgta acccactcgt gcacccaact gatcttcagc atcttttact ttcaccagcg  10680
tttctgggtg agcaaaaaca ggaaggcaaa atgccgcaaa aaagggaata agggcgacac  10740
ggaaatgttg aatactcata ctcttccttt ttcaatatta ttgaagcatt tatcagggtt  10800
attgtctcat gagcggatac atatttgaat gtatttagaa aaataaacaa ataggggttc  10860
cgcgcacatt tccccgaaaa gtgccacctg acgtctaaga aaccattatt atcatgacat  10920
taacctataa aaataggcgt atcacgaggc cctttcgtct tcaagaattg gtcgacgatc  10980
ttgctgcgtt cggatatttt cgtggagttc ccgccacaga cccggattga aggcgagatc  11040
cagcaactcg cgccagatca tcctgtgacg gaactttggc gcgtgatgac tggccaggac  11100
gtcggccgaa agagcgacaa gcagatcacg cttttcgaca gcgtcggatt tgcgatcgag  11160
gatttttcgg cgctgcgcta cgtccgcgac cgcgttgagg gatcaagcca cagcagccca  11220
```

-continued

```
ctcgaccttc tagccgaccc agacgagcca agggatcttt ttggaatgct gctccgtcgt  11280

caggctttcc gacgtttggg tggttgaaca gaagtcatta tcgtacggaa tgccaagcac  11340

tcccgagggg aaccctgtgg ttggcatgca catacaaatg gacgaacgga taaacctttt  11400

cacgcccttt taaatatccg ttattctaat aaacgctctt ttctcttag              11449
```

<210> SEQ ID NO 58
<211> LENGTH: 4510
<212> TYPE: DNA
<213> ORGANISM: Unknown
<220> FEATURE:
<223> OTHER INFORMATION: vector

<400> SEQUENCE: 58

```
acacaggaaa cagctatgac catgattacg ccaagctatc gtttaaacct taaggcgatc     60

gcgctgaggc ggaccgcacg tggaattagc ttggcgcgcc aattcccgat ctagtaacat    120

agatgacacc gcgcgcgata atttatccta gtttgcgcgc tatattttgt tttctatcgc    180

gtattaaatg tataattgcg ggactctaat cataaaaacc catctcataa ataacgtcat    240

gcattacatg ttaattatta catgcttaac gtaattcaac agaaattata tgataatcat    300

cgcaagaccg gcaacaggat tcaatcttaa gaaactttat tgccaaatgt ttgaacgatc    360

ggggaaattc gagctccacc gcggtggcgg ccgctctaga actagtggat cccccgggct    420

gcaggaattc gatatcaagc ttatcgatac cgtcgacctc gagggggggc ccggtacctt    480

ggtgaactac cgatgatcgt aagagcttac agacggtgcc ttatataggc agagcgtcgg    540

aagggggggtg gtgtcacaca cgcactgcga tccttgctta caagctaagc aaaggcatcg    600

tggcagacaa ggaataaagt ggcacaggtg ccaaaagaaa gtggacagca cacttgtccg    660

aaaagcacac aataatacaa ctcagtggag catccactga atgggcccag tactctccgc    720

tgcggtcatc cctgacgtca atgcctcctc aatcgtcatt gcttacgtct tggagatcta    780

gcacatcttc tgcggctact ggcgacatag cccttggtgt ggcctggtat tcctcgaact    840

cctgctcttc tatcttcagc ttggtgactt ccttcataag ttcctcctcc attgtttgca    900

cgccaccggt cttcagaact tcaagattct tgagaaattc atcaattctg tcttgaatgt    960

gttcttcaat gagatctgcc cagtaccagc aatggcattt gttcattgcg cacttgaaga   1020

atttccttcc tgggttggca gatgttctgg acactaactg aattgcaggc ttcctgcatg   1080

cacagagtag aactggttcc tctgttagca taaaagcttg ctctgttctt tcgaacatgt   1140

ccttcttgaa tgtggggaat ggatccagaa ttttgtttcc ccattctctg agttgctcag   1200

tgtatggatg atctggataa ggaattactt cccttatggc ttgtgtaagc aggatcatct   1260

cttccgttgg ttcattctga gctaatttgg ctttgagcct ggacaagatg tcagctaaac   1320

cattgctctt ccttttatg tgttcaatga ctatctctgg tcctgcacca gtgatgtagt   1380

ccatgaacct gatccatctg atctcagaag gcttgtgttc agcactcttg ttgtagaacc   1440

tttcgattgc actactgtca gttctgactg tgatctctct tttgtccaag tagaacaatc   1500

tcatcttttc taagccattc ataaccccat agatttctgc atcacaggtt ccttttggct   1560

tatcaaattt tccactggca tacctacaga tttgctctgt atttcttggg tctgccttgt   1620

ttttcttcca cttgcatact gctccccatc cagttgcaca tgcatctgtt tcaatgataa   1680

tgtatgcatc ttctggtgga atagtgagat ttggaagcgt tctcaccatt gtcttgatcc   1740

tattgatcag cttccaatct tctgaattga gccttcgctc acctttctct gaggtctttg   1800

gatataatgg gccaagaagc ttgcccatat ctttgatgtg gtttctggca tagttcagtg   1860
```

-continued

```
ttgctagcca ggattaatta aaggcctgtt aacagcgctg ggcccgataa ttcactggcc   1920
gtcgttttac aacgtcgtga ctgggaaaac cctggcgtta cccaacttaa tcgccttgca   1980
gcacatcccc ctttcgccag ctggcgtaat agcgaagagg cccgcaccga tcgcccttcc   2040
caacagttgc gcagcctgaa tggcgaatgg cgcctgatgc ggtattttct ccttacgcat   2100
ctgtgcggta tttcacaccg catatggtgc actctcagta caatctgctc tgatgccgca   2160
tagttaagcc agccccgaca cccgccaaca cccgctgacg cgccctgacg ggcttgtctg   2220
ctcccggcat ccgcttacag acaagctgtg accgtctccg ggagctgcat gtgtcagagg   2280
ttttcaccgt catcaccgaa acgcgcgaga cgaaagggcc tcgtgatacg cctattttta   2340
taggttaatg tcatgataat aatggtttct tagacgtcag gtggcacttt tcggggaaat   2400
gtgcgcggaa cccctatttg tttatttttc taaatacatt caaatatgta tccgctcatg   2460
agacaataac cctgataaat gcttcaataa tattgaaaaa ggaagagtat gagtattcaa   2520
catttccgtg tcgcccttat tccctttttt gcggcatttt gccttcctgt ttttgctcac   2580
ccagaaacgc tggtgaaagt aaaagatgct gaagatcagt tgggtgcacg agtgggttac   2640
atcgaactgg atctcaacag cggtaagatc cttgagagtt ttcgccccga agaacgtttt   2700
ccaatgatga gcacttttaa agttctgcta tgtggcgcgg tattatcccg tattgacgcc   2760
gggcaagagc aactcggtcg ccgcatacac tattctcaga atgacttggt tgagtactca   2820
ccagtcacag aaaagcatct tacggatggc atgacagtaa gagaattatg cagtgctgcc   2880
ataaccatga gtgataacac tgcggccaac ttacttctga caacgatcgg aggaccgaag   2940
gagctaaccg cttttttgca caacatgggg gatcatgtaa ctcgccttga tcgttgggaa   3000
ccggagctga atgaagccat accaaacgac gagcgtgaca ccacgatgcc tgtagcaatg   3060
gcaacaacgt tgcgcaaact attaactggc gaactactta ctctagcttc ccggcaacaa   3120
ttaatagact ggatggaggc ggataaagtt gcaggaccac ttctgcgctc ggcccttccg   3180
gctggctggt ttattgctga taaatctgga gccggtgagc gtgggtctcg cggtatcatt   3240
gcagcactgg ggccagatgg taagccctcc cgtatcgtag ttatctacac gacggggagt   3300
caggcaacta tggatgaacg aaatagacag atcgctgaga taggtgcctc actgattaag   3360
cattggtaac tgtcagacca agtttactca tatatacttt agattgattt aaaacttcat   3420
ttttaattta aaaggatcta ggtgaagatc ctttttgata atctcatgac caaaatccct   3480
taacgtgagt tttcgttcca ctgagcgtca gaccccgtag aaaagatcaa aggatcttct   3540
tgagatcctt tttttctgcg cgtaatctgc tgcttgcaaa caaaaaaacc accgctacca   3600
gcggtggttt gtttgccgga tcaagagcta ccaactcttt ttccgaaggt aactggcttc   3660
agcagagcgc agataccaaa tactgttctt ctagtgtagc cgtagttagg ccaccacttc   3720
aagaactctg tagcaccgcc tacatacctc gctctgctaa tcctgttacc agtggctgct   3780
gccagtggcg ataagtcgtg tcttaccggg ttggactcaa gacgatagtt accggataag   3840
gcgcagcggt cgggctgaac ggggggttcg tgcacacagc ccagcttgga gcgaacgacc   3900
tacaccgaac tgagatacct acagcgtgag ctatgagaaa gcgccacgct tcccgaaggg   3960
agaaaggcgg acaggtatcc ggtaagcggc agggtcggaa caggagagcg cacgagggag   4020
cttccagggg gaaacgcctg gtatctttat agtcctgtcg ggtttcgcca cctctgactt   4080
gagcgtcgat ttttgtgatg ctcgtcaggg gggcggagcc tatggaaaaa cgccagcaac   4140
gcggcctttt tacggttcct ggccttttgc tggccttttg ctcacatgtt ctttcctgcg   4200
ttatcccctg attctgtgga taaccgtatt accgcctttg agtgagctga taccgctcgc   4260
```

cgcagccgaa cgaccgagcg cagcgagtca gtgagcgagg aagcggaaga gcgcccaata 4320
cgcaaaccgc ctctccccgc gcgttggccg attcattaat gcagctggca cgacaggttt 4380
cccgactgga aagcgggcag tgagcgcaac gcaattaatg tgagttagct cactcattag 4440
gcaccccagg ctttacactt tatgcttccg gctcgtatgt tgtgtggaat tgtgagcgga 4500
taacaatttc 4510

<210> SEQ ID NO 59
<211> LENGTH: 13170
<212> TYPE: DNA
<213> ORGANISM: Unknown
<220> FEATURE:
<222> LOCATION: (1)..(13170)
<223> OTHER INFORMATION: vector

<400> SEQUENCE: 59
gtttacccgc caatatatcc tgtcaaacac tgatagtttg tggaattcga gctcggtacc 60
cggggatcct ctagagtcga cctgcaggca tgcaagcttc cggctgcagt gcagcgtgac 120
ccggtcgtgc ccctctctag agataatgag cattgcatgt ctaagttata aaaaattacc 180
acatattttt tttgtcacac ttgtttgaag tgcagtttat ctatctttat acatatattt 240
aaactttact ctacgaataa tataatctat agtactacaa taatatcagt gttttagaga 300
atcatataaa tgaacagtta gacatggtct aaaggacaat tgagtatttt gacaacagga 360
ctctacagtt ttatcttttt agtgtgcatg tgttctcctt ttttttgca aatagcttca 420 cctatataat acttcatcca ttttattagt acatccattt agggtttagg gttaatggtt 480
tttatagact aattttttta gtacatctat tttattctat tttagcctct aaattaagaa 540
aactaaaact ctattttagt ttttttattt aatagtttag atataaaata gaataaaata 600
aagtgactaa aaattaaaca aatacccttt aagaaattaa aaaaactaag gaaacatttt 660
tcttgtttcg agtagataat gccagcctgt taaacgccgt cgacgagtct aacggacacc 720
aaccagcgaa ccagcagcgt cgcgtcgggc caagcgaagc agacggcacg gcatctctgt 780
cgctgcctct ggacccctct cgagagttcc gctccaccgt tggacttgct ccgctgtcgg 840
catccagaaa ttgcgtggcg gagcggcaga cgtgagccgg cacggcaggc ggcctcctcc 900
tcctctcacg gcaccggcag ctacggggga ttcctttccc accgctcctt cgctttccct 960
tcctcgcccg ccgtaataaa tagacacccc ctccacaccc tctttcccca acctcgtgtt 1020
gttcggagcg cacacacaca caaccagatc tcccccaaat ccacccgtcg gcacctccgc 1080
ttcaaggtac gccgctcgtc ctcccccccc cccccctct ctaccttctc tagatcggcg 1140
ttccggtcca tggttagggc ccggtagttc tacttctgtt catgtttgtg ttagatccgt 1200
gtttgtgtta gatccgtgct gctagcgttc gtacacggat gcgacctgta cgtcagacac 1260
gttctgattg ctaacttgcc agtgtttctc tttggggaat cctgggatgg ctctagccgt 1320
tccgcagacg ggatcgattt catgattttt tttgtttcgt tgcatagggt ttggtttgcc 1380
cttttccttt atttcaatat atgccgtgca cttgtttgtc gggtcatctt ttcatgcttt 1440
tttttgtctt ggttgtgatg atgtggtctg gttgggcggt cgttctagat cggagtagaa 1500
ttctgtttca aactacctgg tggatttatt aattttggat ctgtatgtgt gtgccataca 1560
tattcatagt tacgaattga agatgatgga tggaaatatc gatctaggat aggtatacat 1620
gttgatgcgg gttttactga tgcatataca gagatgcttt ttgttcgctt ggttgtgatg 1680
atgtggtgtg gttgggcggt cgttcattcg ttctagatcg gagtagaata ctgtttcaaa 1740

-continued

```
ctacctggtg tatttattaa ttttggaact gtatgtgtgt gtcatacatc ttcatagtta   1800
cgagtttaag atggatggaa atatcgatct aggataggta tacatgttga tgtgggtttt   1860
actgatgcat atacatgatg gcatatgcag catctattca tatgctctaa ccttgagtac   1920
ctatctatta taataaacaa gtatgtttta taattatttc gatcttgata tacttggatg   1980
atggcatatg cagcagctat atgtggattt ttttagccct gccttcatac gctatttatt   2040
tgcttggtac tgtttctttt gtcgatgctc accctgttgt ttggtgttac ttctgcaggg   2100
tacccccggg gatccactag ttctagaaac catggccacc gccgccgccg cgtctaccgc   2160
gctcactggc gccactaccg ctgcgcccaa ggcgaggcgc cgggcgcacc tcctggccac   2220
ccgccgcgcc ctcgccgcgc ccatcaggtg ctcagcggcg tcacccgcca tgccgatggc   2280
tcccccggcc accccgctcc ggccgtgggg ccccaccgat ccccgcaagg gcgccgacat   2340
cctcgtcgag tccctcgagc gctgcggcgt ccgcgacgtc ttcgcctacc ccggcggcgc   2400
gtccatggag atccaccagg cactcacccg ctcccccgtc atcgccaacc acctcttccg   2460
ccacgagcaa ggggaggcct ttgcggcctc cggctacgcg cgctcctcgg gccgcgtcgg   2520
cgtctgcatc gccacctccg gccccggcgc caccaacctt gtctccgcgc tcgccgacgc   2580
gctgctcgat tccgtcccca tggtcgccat cacgggacag gtgccgcgac gcatgattgg   2640
caccgacgcc ttccaggaga cgcccatcgt cgaggtcacc cgctccatca ccaagcacaa   2700
ctacctggtc ctcgacgtcg acgacatccc ccgcgtcgtg caggaggctt tcttcctcgc   2760
ctcctctggt cgaccggggc cggtgcttgt cgacatcccc aaggacatcc agcagcagat   2820
ggcggtgcct gtctgggaca agcccatgag tctgcctggg tacattgcgc gccttcccaa   2880
gcccccctgcg actgagttgc ttgagcaggt gctgcgtctt gttggtgaat cccggcgccc   2940
tgttctttat gttggcggtg gctgcgcagc atctggtgag gagttgcgac gctttgtgga   3000
gctgactgga atcccggtca caactactct tatgggcctc ggcaacttcc ccagcgacga   3060
cccactgtct ctgcgcatgc taggtatgca tggcacggtg tatgcaaatt atgcagtgga   3120
taaggccgat ctgttgcttg cacttggtgt gcggtttgat gatcgtgtga cagggaagat   3180
tgaggctttt gcaagcaggg ctaagattgt gcacgttgat attgatccgg ctgagattgg   3240
caagaacaag cagccacatg tgtccatctg tgcagatgtt aagcttgctt tgcagggcat   3300
gaatgctctt cttgaaggaa gcacatcaaa gaagagcttt gactttggct catggaacga   3360
tgagttggat cagcagaaga gggaattccc ccttgggtat aaaacatcta atgaggagat   3420
ccagccacaa tatgctattc aggttcttga tgagctgacg aaaggcgagg ccatcatcgg   3480
cacaggtgtt gggcagcacc agatgtgggc ggcacagtac tacacttaca agcggccaag   3540
gcagtggttg tcttcagctg gtcttggggc tatgggattt ggtttgccgg ctgctgctgg   3600
tgcttctgtg gccaacccag gtgttactgt tgttgacatc gatggagatg gtagctttct   3660
catgaacgtt caggagctag ctatgatccg aattgagaac ctcccggtga aggtctttgt   3720
gctaaacaac cagcacctgg ggatggtggt gcagtgggag gacaggttct ataaggccaa   3780
cagagcgcac acatacttgg gaaacccaga gaatgaaagt gagatatatc cagatttcgt   3840
gacgatcgcc aaagggttca acattccagc ggtccgtgtg acaaagaaga acgaagtccg   3900
cgcagcgata aagaagatgc tcgagactcc agggccgtac ctcttggata taatcgtccc   3960
acaccaggag catgtgttgc ctatgatccc taatggtggg gctttcaagg atatgatcct   4020
ggatggtgat ggcaggactg tgtactgatc taaaatccag caagcaactg atctaaaatc   4080
cagcaagcac cgcctccctg ctagtacaag ggtgatatgt tttatctgt gtgatgttct   4140
```

-continued

```
cctgtattct atcttttttt gtaggccgtc agctatctgt tatggtaatc ctatgtagct   4200
tccgaccttg taattgtgta gtctgttgtt ttccttctgg catgtgtcat aagagatcat   4260
ttaagtgcct tttgctacat ataaataaga taataagcac tgctatgcag tggttctgaa   4320
ttggcttctg ttgccaaatt taagtgtcca actggtcctt gcttttgttt tcgctatttt   4380
tttccttttt tagttattat tatattggta atttcaactc aacatatgat gtatggaata   4440
atgctagggc tgcaatttca aactatttta caaaccagaa tggcattttc gtggtttgag   4500
gggagtgaaa aaaaatgagg catttgactg aattagttac ctgatccatt ttcgtggttt   4560
ggatcattgg aattaaattc cattctaata atagtaattt tggcatatat caattaagtt   4620
aattcggttt tatgcaaaat atatttgtat actattatta tcaagatgtc ggagatattt   4680
atatgctaca tttttactat acaggagtga gatgaagagt gtcatgtaag ttacacagta   4740
gaaacaaatt ctattaatgc ataaaatcat ttccatcatc caccctatga atttgagata   4800
gacctatatc taaactttga aaagtggttg aatatcaaat tccaaattaa ataagttatt   4860
ttattgagtg aattctaatt tctctaaaac gaagggatct aaacgccctc taaagctaat   4920
ttggaaactc aaactttctt agcattggag ggattgaga aaaaatatta attcattttc   4980
atctcaatca ttcaatctcc aaagagattt gagttcctta ttagtctgtt ccatgcatca   5040
aatcggctca atgtgtcatt atttgccatg acgattgacg agttgttctg gggcctagcg   5100
ctttccacgc cgatgtgctg gggcctggtc ctggagaaga cagcttgata tttaaagcta   5160
tcaattgttt caattgattc ccacttcatt tttctaaatg tagaaaacgg tgacgtataa   5220
gaaaaagaat gaattaggac ttttattccg tacactaatc tagagcggcc ccttaaggcg   5280
ctgcgatcgc gttaacagct tgctgaggag gcctcggacc gttaattaat cctggctagc   5340
aacactgaac tatgccagaa accacatcaa agatatgggc aagcttcttg gcccattata   5400
tccaaagacc tcagagaaag gtgagcgaag gctcaattca gaagattgga agctgatcaa   5460
taggatcaag acaatggtga gaacgcttcc aaatctcact attccaccag aagatgcata   5520
cattatcatt gaaacagatg catgtgcaac tggatgggga gcagtatgca agtggaagaa   5580
aaacaaggca gacccaagaa atacagagca aatctgtagg tatgccagtg gaaaatttga   5640
taagccaaaa ggaacctgtg atgcagaaat ctatggggtt atgaatggct tagaaaagat   5700
gagattgttc tacttggaca aaagagagat cacagtcaga actgacagta gtgcaatcga   5760
aaggttctac aacaagagtg ctgaacacaa gccttctgag atcagatgga tcaggttcat   5820
ggactacatc actggtgcag gaccagagat agtcattgaa cacataaaag ggaagagcaa   5880
tggtttagct gacatcttgt ccaggctcaa agccaaatta gctcagaatg aaccaacgga   5940
agagatgatc ctgcttacac aagccataag ggaagtaatt ccttatccag atcatccata   6000
cactgagcaa ctcagagaat ggggaaacaa aattctggat ccattcccca cattcaagaa   6060
ggacatgttc gaaagaacag agcaagcttt tatgctaaca gaggaaccag ttctactctg   6120
tgcatgcagg aagcctgcaa ttcagttagt gtccagaaca tctgccaacc caggaaggaa   6180
attcttcaag tgcgcaatga acaaatgcca ttgctggtac tgggcagatc tcattgaaga   6240
acacattcaa gacagaattg atgaatttct caagaatctt gaagttctga agaccggtgg   6300
cgtgcaaaca atggaggagg aacttatgaa ggaagtcacc aagctgaaga tagaagagca   6360
ggagttcgag gaataccagg ccacaccaag ggctatgtcg ccagtagccg cagaagatgt   6420
gctagatctc caagacgtaa gcaatgacga ttgaggaggc attgacgtca gggatgaccg   6480
cagcggagag tactgggccc attcagtgga tgctccactg agttgtatta ttgtgtgctt   6540
```

-continued

```
ttcggacaag tgtgctgtcc actttctttt ggcacctgtg ccactttatt ccttgtctgc   6600
cacgatgcct ttgcttagct tgtaagcaag gatcgcagtg cgtgtgtgac accacccccc   6660
ttccgacgct ctgcctatat aaggcaccgt ctgtaagctc ttacgatcat cggtagttca   6720
ccaaggtacg cccgggtcgc tcctacgcgt caatgatccg cggacgccga gcccgagctc   6780
gaatttcccc gatcgttcaa acatttggca ataaagtttc ttaagattga atcctgttgc   6840
cggtcttgcg atgattatca tataatttct gttgaattac gttaagcatg taataattaa   6900
catgtaatgc atgacgttat ttatgagatg ggtttttatg attagagtcc cgcaattata   6960
catttaatac gcgatagaaa acaaaatata gcgcgcaaac taggataaat tatcgcgcgc   7020
ggtgtcatct atgttactag atcgggaatt ggcgcgccac tagtcaattc agtacattaa   7080
aaacgtccgc aatgtgttat taagttgtct aagcgtcaat ttgtttacac cacaatatat   7140
cctgccacca gccagccaac agctccccga ccggcagctc ggcacaaaat caccactcga   7200
tacaggcagc ccatcagtcc gggacggcgt cagcgggaga gccgttgtaa ggcggcagac   7260
tttgctcatg ttaccgatgc tattcggaag aacggcaact aagctgccgg gtttgaaaca   7320
cggatgatct cgcggagggt agcatgttga ttgtaacgat gacagagcgt tgctgcctgt   7380
gatcaaatat catctccctc gcagagatcc gaattatcag ccttcttatt catttctcgc   7440
ttaaccgtga caggctgtcg atcttgagaa ctatgccgac ataataggaa atcgctggat   7500
aaagccgctg aggaagctga gtggcgctat ttctttagaa gtgaacgttg acgatcgtcg   7560
accgtacccc gatgaattaa ttcggacgta cgttctgaac acagctggat acttacttgg   7620
gcgattgtca tacatgacat caacaatgta cccgtttgtg taaccgtctc ttggaggttc   7680
gtatgacact agtggttccc ctcagcttgc gactagatgt tgaggcctaa cattttatta   7740
gagagcaggc tagttgctta gatacatgat cttcaggccg ttatctgtca gggcaagcga   7800
aaattggcca tttatgacga ccaatgcccc gcagaagctc ccatctttgc cgccatagac   7860
gccgcgcccc ccttttgggg tgtagaacat ccttttgcca gatgtggaaa agaagttcgt   7920
tgtcccattg ttggcaatga cgtagtagcc ggcgaaagtg cgagacccat ttgcgctata   7980
tataagccta cgatttccgt tgcgactatt gtcgtaattg gatgaactat tatcgtagtt   8040
gctctcagag ttgtcgtaat ttgatggact attgtcgtaa ttgcttatgg agttgtcgta   8100
gttgcttgga gaaatgtcgt agttggatgg ggagtagtca tagggaagac gagcttcatc   8160
cactaaaaca attggcaggt cagcaagtgc ctgccccgat gccatcgcaa gtacgaggct   8220
tagaaccacc ttcaacagat cgcgcatagt cttccccagc tctctaacgc ttgagttaag   8280
ccgcgccgcg aagcggcgtc ggcttgaacg aattgttaga cattatttgc cgactacctt   8340
ggtgatctcg cctttcacgt agtgaacaaa ttcttccaac tgatctgcgc gcgaggccaa   8400
gcgatcttct tgtccaagat aagcctgcct agcttcaagt atgacgggct gatactgggc   8460
cggcaggcgc tccattgccc agtcggcagc gacatccttc ggcgcgattt tgccggttac   8520
tgcgctgtac caaatgcggg acaacgtaag cactacattt cgctcatcgc cagcccagtc   8580
gggcggcgag ttccatagcg ttaaggtttc atttagcgcc tcaaatagat cctgttcagg   8640
aaccggatca aagagttcct ccgccgctgg acctaccaag gcaacgctat gttctcttgc   8700
ttttgtcagc aagatagcca gatcaatgtc gatcgtggct ggctcgaaga tacctgcaag   8760
aatgtcattg cgctgccatt ctccaaattg cagttcgcgc ttagctggat aacgccacgg   8820
aatgatgtcg tcgtgcacaa caatggtgac ttctacagcg cggagaatct cgctctctcc   8880
aggggaagcc gaagtttcca aaaggtcgtt gatcaaagct cgccgcgttg tttcatcaag   8940
```

-continued

```
ccttacggtc accgtaacca gcaaatcaat atcactgtgt ggcttcaggc cgccatccac   9000
tgcggagccg tacaaatgta cggccagcaa cgtcggttcg agatggcgct cgatgacgcc   9060
aactacctct gatagttgag tcgatacttc ggcgatcacc gcttccctca tgatgtttaa   9120
ctcctgaatt aagccgcgcc gcgaagcggt gtcggcttga atgaattgtt aggcgtcatc   9180
ctgtgctccc gagaaccagt accagtacat cgctgtttcg ttcgagactt gaggtctagt   9240
tttatacgtg aacaggtcaa tgccgccgag agtaaagcca cattttgcgt acaaattgca   9300
ggcaggtaca ttgttcgttt gtgtctctaa tcgtatgcca aggagctgtc tgcttagtgc   9360
ccactttttc gcaaattcga tgagactgtg cgcgactcct ttgcctcggt gcgtgtgcga   9420
cacaacaatg tgttcgatag aggctagatc gttccatgtt gagttgagtt caatcttccc   9480
gacaagctct tggtcgatga atgcgccata gcaagcagag tcttcatcag agtcatcatc   9540
cgagatgtaa tccttccggt aggggctcac acttctggta gatagttcaa agccttggtc   9600
ggataggtgc acatcgaaca cttcacgaac aatgaaatgg ttctcagcat ccaatgtttc   9660
cgccacctgc tcagggatca ccgaaatctt catatgacgc ctaacgcctg gcacagcgga   9720
tcgcaaacct ggcgcggctt ttggcacaaa aggcgtgaca ggtttgcgaa tccgttgctg   9780
ccacttgtta accctttgc cagatttggt aactataatt tatgttagag gcgaagtctt   9840
gggtaaaaac tggcctaaaa ttgctgggga tttcaggaaa gtaaacatca ccttccggct   9900
cgatgtctat tgtagatata tgtagtgtat ctacttgatc gggggatctg ctgcctcgcg   9960
cgtttcggtg atgacggtga aaacctctga cacatgcagc tcccggagac ggtcacagct  10020
tgtctgtaag cggatgccgg gagcagacaa gcccgtcagg gcgcgtcagc gggtgttggc  10080
gggtgtcggg gcgcagccat gacccagtca cgtagcgata gcggagtgta tactggctta  10140
actatgcggc atcagagcag attgtactga gagtgcacca tatgcggtgt gaaataccgc  10200
acagatgcgt aaggagaaaa taccgcatca ggcgctcttc cgcttcctcg ctcactgact  10260
cgctgcgctc ggtcgttcgg ctgcggcgag cggtatcagc tcactcaaag gcggtaatac  10320
ggttatccac agaatcaggg gataacgcag gaaagaacat gtgagcaaaa ggccagcaaa  10380
aggccaggaa ccgtaaaaag gccgcgttgc tggcgttttt ccataggctc cgcccccctg  10440
acgagcatca caaaaatcga cgctcaagtc agaggtggcg aaacccgaca ggactataaa  10500
gataccaggc gtttccccct ggaagctccc tcgtgcgctc tcctgttccg accctgccgc  10560
ttaccggata cctgtccgcc tttctccctt cgggaagcgt ggcgctttct catagctcac  10620
gctgtaggta tctcagttcg gtgtaggtcg ttcgctccaa gctgggctgt gtgcacgaac  10680
cccccgttca gcccgaccgc tgcgccttat ccggtaacta tcgtcttgag tccaacccgg  10740
taagacacga cttatcgcca ctggcagcag ccactggtaa caggattagc agagcgaggt  10800
atgtaggcgg tgctacagag ttcttgaagt ggtggcctaa ctacggctac actagaagga  10860
cagtatttgg tatctgcgct ctgctgaagc cagttacctt cggaaaaaga gttggtagct  10920
cttgatccgg caaacaaacc accgctggta gcggtggttt ttttgtttgc aagcagcaga  10980
ttacgcgcag aaaaaaagga tctcaagaag atcctttgat cttttctacg gggtctgacg  11040
ctcagtggaa cgaaaactca cgttaaggga ttttggtcat gagattatca aaaaggatct  11100
tcacctagat ccttttaaat taaaaatgaa gttttaaatc aatctaaagt atatatgagt  11160
aaacttggtc tgacagttac caatgcttaa tcagtgaggc acctatctca gcgatctgtc  11220
tatttcgttc atccatagtt gcctgactcc ccgtcgtgta gataactacg atacgggagg  11280
gcttaccatc tggccccagt gctgcaatga taccgcgaga cccacgctca ccggctccag  11340
```

```
atttatcagc aataaaccag ccagccggaa gggccgagcg cagaagtggt cctgcaactt  11400

tatccgcctc catccagtct attaattgtt gccgggaagc tagagtaagt agttcgccag  11460

ttaatagttt gcgcaacgtt gttgccattg ctgcaggggg gggggggggg ggggacttcc  11520

attgttcatt ccacggacaa aaacagagaa aggaaacgac agaggccaaa aagcctcgct  11580

ttcagcacct gtcgtttcct ttcttttcag agggtatttt aaataaaaac attaagttat  11640

gacgaagaag aacggaaacg ccttaaaccg gaaaattttc ataaatagcg aaaacccgcg  11700

aggtcgccgc cccgtaacct gtcggatcac cggaaaggac ccgtaaagtg ataatgatta  11760

tcatctacat atcacaacgt gcgtggaggc catcaaacca cgtcaaataa tcaattatga  11820

cgcaggtatc gtattaattg atctgcatca acttaacgta aaaacaactt cagacaatac  11880

aaatcagcga cactgaatac ggggcaacct catgtccccc cccccccccc ccctgcaggc  11940

atcgtggtgt cacgctcgtc gtttggtatg gcttcattca gctccggttc ccaacgatca  12000

aggcgagtta catgatcccc catgttgtgc aaaaaagcgg ttagctcctt cggtcctccg  12060

atcgttgtca gaagtaagtt ggccgcagtg ttatcactca tggttatggc agcactgcat  12120

aattctctta ctgtcatgcc atccgtaaga tgcttttctg tgactggtga gtactcaacc  12180

aagtcattct gagaatagtg tatgcggcga ccgagttgct cttgcccggc gtcaacacgg  12240

gataataccg cgccacatag cagaacttta aaagtgctca tcattggaaa acgttcttcg  12300

gggcgaaaac tctcaaggat cttaccgctg ttgagatcca gttcgatgta acccactcgt  12360

gcacccaact gatcttcagc atcttttact ttcaccagcg tttctgggtg agcaaaaaca  12420

ggaaggcaaa atgccgcaaa aaagggaata agggcgacac ggaaatgttg aatactcata  12480

ctcttccttt ttcaatatta ttgaagcatt tatcagggtt attgtctcat gagcggatac  12540

atatttgaat gtatttagaa aaataaacaa ataggggttc cgcgcacatt tccccgaaaa  12600

gtgccacctg acgtctaaga aaccattatt atcatgacat taacctataa aaataggcgt  12660

atcacgaggc cctttcgtct tcaagaattg gtcgacgatc ttgctgcgtt cggatatttt  12720

cgtggagttc ccgccacaga cccggattga aggcgagatc cagcaactcg cgccagatca  12780

tcctgtgacg gaactttggc gcgtgatgac tggccaggac gtcggccgaa agagcgacaa  12840

gcagatcacg cttttcgaca gcgtcggatt tgcgatcgag gatttttcgg cgctgcgcta  12900

cgtccgcgac cgcgttgagg gatcaagcca cagcagccca ctcgaccttc tagccgaccc  12960

agacgagcca agggatcttt ttggaatgct gctccgtcgt caggctttcc gacgtttggg  13020

tggttgaaca gaagtcatta tcgtacggaa tgccaagcac tcccgagggg aaccctgtgg  13080

ttggcatgca catacaaatg gacgaacgga taaacctttt cacgcccttt taaatatccg  13140

attattctaa taaacgctct tttctcttag                                13170
```

```
<210> SEQ ID NO 60
<211> LENGTH: 2709
<212> TYPE: DNA
<213> ORGANISM: unknown
<220> FEATURE:
<223> OTHER INFORMATION: artificial sequence
<220> FEATURE:
<222> LOCATION: (1)..(2709)
<223> OTHER INFORMATION: vector

<400> SEQUENCE: 60

cgtagtggct ggctgggcga cgtgggttta aaggaagagt gacctgctca agtgctcagt     60

agattaatta agggatttga attctggtcg tacgataaat taacttgagt tcaaaaatac    120

aagaaacatc agtttatatt tcatttcgtg taggacctat caatccaatt cgtacaagag    180
```

```
gaattgcata tttcaactca tagtcttaac taccattcaa attgatattt gcacgatgat    240
gattgtctgg tatagatttg actttttggg aactgaatca aatccagcat gattcatgca    300
agaaacttga attcaactca tacaagaaac atattcaatt tcaagctgtg caataatgca    360
cgtatcttaa gcaaagagta gtacgtctgc atcatatagt actcatgcaa gattgaaaca    420
gctaagaact tgatcaaatt caaagttttt ttgtgatcga agtttaaatc cagttcatac    480
aagaaacgca ttaaaaataa tcgatttaaa tatgagcaat aatgcatcta ctttaagcat    540
agggtttgac atcacggtat ggaagcaaat ttgaattaga cgcaaacttg gatctcattt    600
ttccagaaac tttgttcgat tggtaattaa aacagtgcaa cctttgcacg caaccaaata    660
tataaaaatc cctggttgct aggactgttg taatcctgac aaatttcctc taatcttaaa    720
acacttgggt cggctttctt tgccaacccg gcgaaaaaaa actatataaa aatcataatt    780
attactacct tcatttcagg ttataagact ttctaacatt gtccatattt atatatatgt    840
taatgaatct agacatatat ttgtgtctgg attcattaac atctatatga atgtggacaa    900
tgctagaaag ttttataacc tgaaacggag aagtatattt ttttgggtac ttgtgtcata    960
ttgtcatgtc atcaatgtgt atagtactaa ggttcaatga gaaatgatac aattgcaagc   1020
caaacaaatt gccgttacag aaatctgacg tcaacgacat tctggcaaga taatgcttga   1080
tacaatttgt gcagctatgc tactataaat aggggggggg ggggcgttat atctgcactg   1140
agttcatatc aagctttcaa tctctcattg catacaagtc cctgaagagt ttacaagaga   1200
cccagaagat catttttca ccagcaaagt tcatttaaat caactaggga tatcacaagt    1260
ttgtacaaaa aagcaggctt cacaatggag cagtacgaga aggaggagaa gattggggag   1320
ggcacgtacg gggtggtgta cagggcgcgg gacaaggtca ccaacgagac gatcgcgctc   1380
aagaagatcc ggcttgagca ggaggatgag ggcgtcccct ccaccgcaat ccgcgagatc   1440
tcgctcctca aggagatgca tcacggcaac atcgtcaggt tacacgatgt tatccacagt   1500
gagaagcgca tatatcttgt ctttgagtat ctggatctgg acctaaagaa gttcatggac   1560
tcttgtccag agtttgcgaa aaaccccact ttaattaagt catatctcta tcagatactc   1620
cgcggcgttg cttactgtca ttctcataga gttcttcatc gagatttgaa acctcagaat   1680
ttattgatag atcggcgtac taatgcactg aagcttgcag actttggttt agccagggca   1740
tttggaattc ctgtccgcac gtttgatcac gaggttgtaa ccttgtggta tagagctcca   1800
gagatccttc ttggatcaag gcagtattct acaccagttg atatgtggtc agttggttgt   1860
atctttgcag aaatggtgaa ccagaaacca ctgttccctg gtgattctga gattgatgaa   1920
ttatttaaga tattcagggt actaggaact ccaaatgaac aaagttggcc aggagttagc   1980
tcattacctg actacaagtc tgctttcccc aagtggcagg cacaggatct tgcaactatt   2040
gtccctactc ttgaccctgc tggtttggac cttctctcta aaatgcttcg gtacgagcca   2100
aacaaaagga tcacagctag acaggctctt gagcatgaat acttcaagga ccttgagatg   2160
gtacaatgaa cccagctttc ttgtacaaag tggtgatatc acaagcccgg gcggtcttct   2220
agggataaca gggtaattat atccctctag atcacaagcc cgggcggtct tctacgatga   2280
ttgagtaata atgtgtcacg catcaccatg ggtggcagtg tcagtgtgag caatgacctg   2340
aatgaacaat tgaaatgaaa agaaaaaaag tactccatct gttccaaatt aaaattcatt   2400
ttaacctttt aataggttta tacaataatt gatatatgtt ttctgtatat gtctaatttg   2460
ttatcatccg ggcggtcttc tagggataac agggtaatta tatccctcta gacaacacac   2520
aacaaataag agaaaaaaca aataatatta atttgagaat gaacaaaagg accatatcat   2580
```

tcattaactc ttctccatcc atttccattt cacagttcga tagcgaaaac cgaataaaaa 2640
acacagtaaa ttacaagcac aacaaatggt acaagaaaaa cagttttccc aatgccataa 2700
tactcgaac 2709

<210> SEQ ID NO 61
<211> LENGTH: 7
<212> TYPE: PRT
<213> ORGANISM: Artificial sequence
<220> FEATURE:
<223> OTHER INFORMATION: Description of artificial sequence: protein motif
<220> FEATURE:
<221> NAME/KEY: misc_feature
<222> LOCATION: (1)..(1)
<223> OTHER INFORMATION: Xaa at position 1 can be Pro, Asn, or Ala
<220> FEATURE:
<221> NAME/KEY: misc_feature
<222> LOCATION: (2)..(2)
<223> OTHER INFORMATION: Xaa at position 2 can be Ser, Leu, Met, or Phe
<220> FEATURE:
<221> NAME/KEY: misc_feature
<222> LOCATION: (3)..(3)
<223> OTHER INFORMATION: Xaa at position 3 can be Thr, Ser, or Arg
<220> FEATURE:
<221> NAME/KEY: misc_feature
<222> LOCATION: (4)..(4)
<223> OTHER INFORMATION: Xaa at position 4 can be Thr, Ser, or Ala
<220> FEATURE:
<221> NAME/KEY: misc_feature
<222> LOCATION: (5)..(5)
<223> OTHER INFORMATION: Xaa at position 5 can be Leu or Ile

<400> SEQUENCE: 61

Xaa Xaa Xaa Xaa Xaa Arg Glu
1               5

<210> SEQ ID NO 62
<211> LENGTH: 13
<212> TYPE: PRT
<213> ORGANISM: Artificial sequence
<220> FEATURE:
<223> OTHER INFORMATION: Description of artificial sequence: protein motif
<220> FEATURE:
<221> NAME/KEY: misc_feature
<222> LOCATION: (1)..(1)
<223> OTHER INFORMATION: Xaa at position 1 is Val, Phe, or Ile
<220> FEATURE:
<221> NAME/KEY: misc_feature
<222> LOCATION: (2)..(2)
<223> OTHER INFORMATION: Xaa at position 2 is Leu or Ile
<220> FEATURE:
<221> NAME/KEY: misc_feature
<222> LOCATION: (6)..(6)
<223> OTHER INFORMATION: Xaa at position 6 is Leu or Met
<220> FEATURE:
<221> NAME/KEY: misc_feature
<222> LOCATION: (8)..(8)
<223> OTHER INFORMATION: Xaa at position 8 is Pro, Ser, or Thr
<220> FEATURE:
<221> NAME/KEY: misc_feature
<222> LOCATION: (9)..(9)
<223> OTHER INFORMATION: Xaa at position 9 is Gln, Asp, Ser, or Gly
<220> FEATURE:
<221> NAME/KEY: misc_feature
<222> LOCATION: (11)..(11)
<223> OTHER INFORMATION: Xaa at position 11 is Leu or Ile
<220> FEATURE:
<221> NAME/KEY: misc_feature
<222> LOCATION: (13)..(13)
<223> OTHER INFORMATION: Xaa at positon 13 is Val, Leu, or Ile

<400> SEQUENCE: 62

```
Xaa Xaa His Arg Asp Xaa Lys Xaa Xaa Asn Xaa Leu Xaa
1               5                   10
```

```
<210> SEQ ID NO 63
<211> LENGTH: 25
<212> TYPE: PRT
<213> ORGANISM: Artificial sequence
<220> FEATURE:
<223> OTHER INFORMATION: Description of artificial sequence: protein
      motif
<220> FEATURE:
<221> NAME/KEY: misc_feature
<222> LOCATION: (1)..(1)
<223> OTHER INFORMATION: Xaa at position 1 is Ile or Leu
<220> FEATURE:
<221> NAME/KEY: misc_feature
<222> LOCATION: (2)..(2)
<223> OTHER INFORMATION: Xaa at position 2 is Gly or Asn
<220> FEATURE:
<221> NAME/KEY: misc_feature
<222> LOCATION: (3)..(3)
<223> OTHER INFORMATION: Xaa at position 3 is Glu or Arg
<220> FEATURE:
<221> NAME/KEY: misc_feature
<222> LOCATION: (5)..(5)
<223> OTHER INFORMATION: Xaa at position 5 is Thr or Ala
<220> FEATURE:
<221> NAME/KEY: misc_feature
<222> LOCATION: (8)..(8)
<223> OTHER INFORMATION: Xaa at position 8 is Val or Ile
<220> FEATURE:
<221> NAME/KEY: misc_feature
<222> LOCATION: (10)..(10)
<223> OTHER INFORMATION: Xaa at position 10 is Tyr or Cys
<220> FEATURE:
<221> NAME/KEY: misc_feature
<222> LOCATION: (11)..(11)
<223> OTHER INFORMATION: Xaa at position 11 is Arg, Lys, or Ser
<220> FEATURE:
<221> NAME/KEY: misc_feature
<222> LOCATION: (12)..(12)
<223> OTHER INFORMATION: Xaa at position 12 is Ala, Gly, or Ser
<220> FEATURE:
<221> NAME/KEY: misc_feature
<222> LOCATION: (13)..(13)
<223> OTHER INFORMATION: Xaa at position 13 is Arg, Leu, Thr, or Ile
<220> FEATURE:
<221> NAME/KEY: misc_feature
<222> LOCATION: (14)..(14)
<223> OTHER INFORMATION: Xaa at position 14 is Asp or Asn
<220> FEATURE:
<221> NAME/KEY: misc_feature
<222> LOCATION: (15)..(15)
<223> OTHER INFORMATION: Xaa at position 15 is Lys, Arg, or Glu
<220> FEATURE:
<221> NAME/KEY: misc_feature
<222> LOCATION: (16)..(16)
<223> OTHER INFORMATION: Xaa at position 16 is Val, Lys, Ala, Ser,
      Thr, or Asn
<220> FEATURE:
<221> NAME/KEY: misc_feature
<222> LOCATION: (18)..(18)
<223> OTHER INFORMATION: Xaa at position 18 is Asn, Ser, or Gly
<220> FEATURE:
<221> NAME/KEY: misc_feature
<222> LOCATION: (19)..(19)
<223> OTHER INFORMATION: Xaa at position 19 is Glu, Lys, or Gln
<220> FEATURE:
<221> NAME/KEY: misc_feature
<222> LOCATION: (20)..(20)
<223> OTHER INFORMATION: Xaa at position 20 is Thr, Leu, Ile, or Lys
<220> FEATURE:
<221> NAME/KEY: misc_feature
<222> LOCATION: (21)..(21)
<223> OTHER INFORMATION: Xaa at position 21 is Ile or Val
<220> FEATURE:
<221> NAME/KEY: misc_feature
<222> LOCATION: (23)..(23)
```

<223> OTHER INFORMATION: Xaa at position 23 is Leu, Val, or Ile

<400> SEQUENCE: 63

Xaa Xaa Xaa Gly Xaa Tyr Gly Xaa Val Xaa Xaa Xaa Xaa Xaa Xaa Xaa
1 5 10 15

Thr Xaa Xaa Xaa Xaa Ala Xaa Lys Lys
20 25

<210> SEQ ID NO 64
<211> LENGTH: 10
<212> TYPE: PRT
<213> ORGANISM: Artificial sequence
<220> FEATURE:
<223> OTHER INFORMATION: Description of artificial sequence: protein motif
<220> FEATURE:
<221> NAME/KEY: misc_feature
<222> LOCATION: (3)..(3)
<223> OTHER INFORMATION: Xaa at position 3 is Ile or Leu
<220> FEATURE:
<221> NAME/KEY: misc_feature
<222> LOCATION: (4)..(4)
<223> OTHER INFORMATION: Xaa at position 4 is Cys or Ala
<220> FEATURE:
<221> NAME/KEY: misc_feature
<222> LOCATION: (9)..(9)
<223> OTHER INFORMATION: Xaa at position 9 is Ala or Ser

<400> SEQUENCE: 64

Leu Lys Xaa Xaa Asp Phe Gly Leu Xaa Arg
1 5 10

<210> SEQ ID NO 65
<211> LENGTH: 10
<212> TYPE: PRT
<213> ORGANISM: Artificial sequence
<220> FEATURE:
<223> OTHER INFORMATION: Description of artificial sequence: protein motif
<220> FEATURE:
<221> NAME/KEY: misc_feature
<222> LOCATION: (7)..(7)
<223> OTHER INFORMATION: Xaa at position 7 is Leu or Ile
<220> FEATURE:
<221> NAME/KEY: misc_feature
<222> LOCATION: (9)..(9)
<223> OTHER INFORMATION: Xaa at position 9 is Leu or Phe
<220> FEATURE:
<221> NAME/KEY: misc_feature
<222> LOCATION: (10)..(10)
<223> OTHER INFORMATION: Xaa at position 10 is Cys or Gly

<400> SEQUENCE: 65

Trp Tyr Arg Ala Pro Glu Xaa Leu Xaa Xaa
1 5 10

<210> SEQ ID NO 66
<211> LENGTH: 7
<212> TYPE: PRT
<213> ORGANISM: Artificial sequence
<220> FEATURE:
<223> OTHER INFORMATION: Description of artificial sequence: protein motif
<220> FEATURE:
<221> NAME/KEY: misc_feature
<222> LOCATION: (4)..(4)
<223> OTHER INFORMATION: Xaa at position 4 is Phe or Met
<220> FEATURE:
<221> NAME/KEY: misc_feature
<222> LOCATION: (7)..(7)
<223> OTHER INFORMATION: Xaa at position 7 is Ile, Leu, or Met

<400> SEQUENCE: 66

Gly Cys Ile Xaa Ala Glu Xaa
1 5

<210> SEQ ID NO 67
<211> LENGTH: 15
<212> TYPE: PRT
<213> ORGANISM: Artificial sequence
<220> FEATURE:
<223> OTHER INFORMATION: Description of artificial sequence: protein motif
<220> FEATURE:
<221> NAME/KEY: misc_feature
<222> LOCATION: (4)..(4)
<223> OTHER INFORMATION: Xaa at position 4 is Gln, Asn, Ser, or Arg
<220> FEATURE:
<221> NAME/KEY: misc_feature
<222> LOCATION: (5)..(5)
<223> OTHER INFORMATION: Xaa at position 5 is Lys, Gln, or Arg
<220> FEATURE:
<221> NAME/KEY: misc_feature
<222> LOCATION: (6)..(6)
<223> OTHER INFORMATION: Xaa at position 6 is Leu or Met
<220> FEATURE:
<221> NAME/KEY: misc_feature
<222> LOCATION: (7)..(7)
<223> OTHER INFORMATION: Xaa at position 7 is Leu or Phe
<220> FEATURE:
<221> NAME/KEY: misc_feature
<222> LOCATION: (8)..(8)
<223> OTHER INFORMATION: Xaa at position 8 is Ile, Thr, or Cys
<220> FEATURE:
<221> NAME/KEY: misc_feature
<222> LOCATION: (9)..(9)
<223> OTHER INFORMATION: Xaa at position 9 is Phe, Tyr, or Leu
<220> FEATURE:
<221> NAME/KEY: misc_feature
<222> LOCATION: (12)..(12)
<223> OTHER INFORMATION: Xaa at position 12 is Thr, Glu, Asp, Arg, or Ser
<220> FEATURE:
<221> NAME/KEY: misc_feature
<222> LOCATION: (13)..(13)
<223> OTHER INFORMATION: Xaa at position 13 is Lys or Gln

<400> SEQUENCE: 67

Asp Leu Leu Xaa Xaa Xaa Xaa Xaa Xaa Asp Pro Xaa Xaa Arg Ile
1 5 10 15

<210> SEQ ID NO 68
<211> LENGTH: 21
<212> TYPE: PRT
<213> ORGANISM: Artificial sequence
<220> FEATURE:
<223> OTHER INFORMATION: Description of artificial sequence: peptide substrate for A-type CDK

<400> SEQUENCE: 68

Ala Asp Ala Gln His Ala Thr Pro Pro Lys Lys Lys Arg Lys Val Glu
1 5 10 15

Asp Pro Lys Asp Phe
20

PLANTS HAVING IMPROVED GROWTH CHARACTERISTICS AND METHOD FOR MAKING THE SAME

RELATED APPLICATIONS

This application is a national stage application (under 35 U.S.C. 371) of PCT/EP2007/055336, filed May 31, 2007, which claims benefit of European application 06115168.4, filed Jun. 8, 2006.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Sequence_List__13987 __00098$_{13}$ US. The size of the text file is 231 KB, and the text file was created on Dec. 4, 2008.

The present invention relates generally to the field of molecular biology and concerns a method for improving plant growth characteristics. More specifically, the present invention concerns a method for improving plant growth characteristics by modulating expression in a plant of a plant nucleic acid encoding a cyclin dependent kinase (CDK) and/or by modulating activity in a plant of a plant CDK protein, which CDK protein comprises different motifs or which CDK nucleic acid encodes such protein. The present invention also concerns plants having modulated expression of a plant CDK nucleic acid and/or modulated activity of a plant CDK protein, which CDK protein comprises different sequence motifs or which nucleic acid encodes such protein and which plants have improved growth characteristics relative to corresponding wild type plants.

The invention additionally relates to specific nucleic acid sequences encoding for the aforementioned proteins having the aforementioned plant growth improving activity, nucleic acid constructs, vectors and plants containing said nucleic acid sequences.

The ever-increasing world population and the dwindling supply of arable land available for agriculture fuel research towards improving the efficiency of agriculture. Conventional means for crop and horticultural improvements utilise selective breeding techniques to identify plants having desirable characteristics. However, such selective breeding techniques have several drawbacks, namely that these techniques are typically labour intensive and result in plants that often contain heterogeneous genetic components that may not always result in the desirable trait being passed on from parent plants. Advances in molecular biology have allowed mankind to modify the germplasm of animals and plants. Genetic engineering of plants entails the isolation and manipulation of genetic material (typically in the form of DNA or RNA) and the subsequent introduction of that genetic material into a plant. Such technology has the capacity to deliver crops or plants having various improved economic, agronomic or horticultural traits. A trait of particular economic interest is yield. Yield is normally defined as the measurable produce of economic value from a crop. This may be defined in terms of quantity and/or quality. Crop yield is influenced by the typical stresses to which plants or crops are subjected. Such stresses include environmental (abiotic) stresses (such as temperature stresses caused by atypical high or low temperatures; stresses caused by nutrient deficiency; stresses caused by lack of water (drought)) and biotic stresses (which can be imposed on plants by other plants (weeds), animal pests and pathogens). Crop yield may not only be increased by combating one or more of the stresses to which the crop or plant is subjected, but may also be increased by modifying the inherent growth mechanisms of a plant.

Plant biomass is yield for forage crops like alfalfa, silage corn and hay. Many proxies for yield have been used in grain crops. Chief amongst these are estimates of plant size. Plant size can be measured in many ways depending on species and developmental stage, but include total plant dry weight, above-ground dry weight, above-ground fresh weight, leaf area, stem volume, plant height, rosette diameter, leaf length, root length, root mass, tiller number and leaf number. Many species maintain a conservative ratio between the size of different parts of the plant at a given developmental stage. These allometric relationships are used to extrapolate from one of these measures of size to another (e.g. Tittonell et al 2005 Agric Ecosys & Environ 105: 213). Plant size at an early developmental stage will typically correlate with plant size later in development. A larger plant with a greater leaf area can typically absorb more light and carbon dioxide than a smaller plant and therefore will likely gain a greater weight during the same period (Fasoula & Tollenaar 2005 Maydica 50:39). This is in addition to the potential continuation of the micro-environmental or genetic advantage that the plant had to achieve the larger size initially. There is a strong genetic component to plant size and growth rate (e.g. ter Steege et al 2005 Plant Physiology 139:1078), and so for a range of diverse genotypes plant size under one environmental condition is likely to correlate with size under another (Hittalmani et al 2003 Theoretical Applied Genetics 107:679). In this way a standard environment is used as a proxy for the diverse and dynamic environments encountered at different locations and times by crops in the field.

Harvest index, the ratio of seed yield to above-ground dry weight, is relatively stable under many environmental conditions and so a robust correlation between plant size and grain yield can often be obtained (e.g. Rebetzke et al 2002 Crop Science 42:739). These processes are intrinsically linked because the majority of grain biomass is dependent on current or stored photosynthetic productivity by the leaves and stem of the plant (Gardener et al 1985 Physiology of Crop Plants. Iowa State University Press, pp 68-73) Therefore, selecting for plant size, even at early stages of development, has been used as an indicator for future potential yield (e.g. Tittonell et al 2005 Agric Ecosys & Environ 105: 213). When testing for the impact of genetic differences on stress tolerance, the ability to standardize soil properties, temperature, water and nutrient availability and light intensity is an intrinsic advantage of greenhouse or plant growth chamber environments compared to the field. However, artificial limitations on yield due to poor pollination due to the absence of wind or insects, or insufficient space for mature root or canopy growth, can restrict the use of these controlled environments for testing yield differences. Therefore, measurements of plant size in early development, under standardized conditions in a growth chamber or greenhouse, are standard practices to provide indication of potential genetic yield advantages.

The inherent growth mechanisms of a plant reside in a highly ordered sequence of events collectively known as the 'cell cycle'. The ability to influence the cell cycle in a plant (either using recombinant DNA technology or using non-recombinant means), and to thereby modify various growth characteristics of a plant, would have many applications in areas such as crop enhancement, plant breeding, production of ornamental plants, arboriculture, horticulture, forestry, the production of algae or plants (for example for use as bioreactors, for the production of substances such as pharmaceuticals, antibodies, or vaccines, or for the bioconversion of organic waste or for use as fuel in the case of high-yielding algae and plants).

Progression through the cell cycle is fundamental to the growth and development of all multicellular organisms and is crucial to cell proliferation. The major components of the cell cycle are highly conserved in yeast, mammals, and plants. The cell cycle is typically divided into the following sequential phases: G0-G1-S-G2-M. DNA replication or synthesis generally takes place during the S phase ("S" is for DNA synthesis) and mitotic segregation of the chromosomes occurs during the M phase (the "M" is for mitosis), with intervening gap phases, G1 (during which cells grow before DNA replication) and G2 (a period after DNA replication during which the cell prepares for division). Cell division is completed after cytokinesis, the last step of the M phase. Cells that have exited the cell cycle and that have become quiescent are said to be in the G0 phase. Cells in this phase may be stimulated to renter the cell cycle at the G1 phase. The "G" in G1, G2 and G0 stands for "gap". Completion of the cell cycle process allows each daughter cell during cell division to receive a full copy of the parental genome.

Cell division is controlled by two principal cell cycle events, namely initiation of DNA synthesis and initiation of mitosis. Each transition to each of these key events is controlled by a checkpoint represented by specific protein complexes (involved in DNA replication and division). The expression of genes necessary for DNA synthesis at the G1/S boundary is regulated by the E2F family of transcription factors in mammals and plant cells (WO 96/25494; Muller et al., Genes and Development 15, 267-285, 2001; De Veylder et al., EMBO J. 21, 13602-1368, 2002). Entry into the cell cycle is regulated/triggered by an E2F/Rb complex that integrates signals and allows activation of transcription of cell cycle genes. The transition between the different phases of the cell cycle, and therefore progression through the cell cycle, is driven by the formation and activation of different heterodimeric serine/threonine protein kinases, generally referred to as cyclin-dependent kinases (CDK). A prerequisite for activity of these kinases is the physical association with a specific cyclin, the timing of activation being largely dependent upon cyclin expression. Cyclin-binding induces conformational changes in the N-terminal lobe of the associating CDK and contributes to the localisation and substrate specificity of the complex. Monomeric CDKs are activated when they are associated with cyclins and thus have kinase activity. Cyclin protein levels fluctuate in the cell cycle and therefore represent a major factor in determining timing of CDK activation. The periodic activation of these complexes containing cyclins and CDK during cell cycle mediates the temporal regulation of cell-cycle transitions (checkpoints). Other factors regulating CDK activity include CDK inhibitors (CKIs or ICKs, KIPs, CIPs, INKs), CDK activating kinase (CAK), CDK phosphatase (Cdc25) and CDK subunit (CKS) (Mironov et al. Plant Cell 11, 509-522, 1999; Reed, S. I. Progress in Cell Cycle Research 2, 5-27, 1996).

In plants, two major classes of CDKs, known as A-type and B-type CDKs, have been studied to date. The A-type CDKs regulate both the G1-to-S and G2-to-M transitions, whereas the B-type CDKs seem to control the G2-to-M checkpoint only (Hemerly et al., 1995; Magyar et al., 1997; Porceddu et al., 2001). In addition, the presence of C-type CDKs and CDK-activating kinases (CAKs) has been reported (Magyar et al., 1997; Umeda et al., 1998; Joubès et al., 2001), as has the presence of D-type, E-type and F-type CDKs (Vandepoele et al. Plant Cell 14, 903-916, 2002).

A-type CDKs are known to have a conserved tertiary structure (Goldsmith and Cobb, Curr. Opin. Struct. Biol. 4, 833-840), including a highly conserved PSTAIRE motif that is involved in cyclin binding. The catalytic core of a CDK is composed of an N-terminal and a C-terminal lobe. The C-terminal lobe encompasses a catalytic cleft (responsible for ATP and substrate binding) and further comprises a so-called T-loop, named after a threonine residue that is conserved in several kinase families. In human CDK2, this threonine residue is on position 161, whereas in *Saccharomyces cerevisiae* cdc28 and in *Schizosaccharomyces pombe* cdc2 it is located on position 169 and 167 respectively. Phosphorylation of this threonine residue is reported to cause a structural conformation change in the T-loop that is necessary for switching the kinase into an active state (Gu et al., EMBO J. 11, 3995-4005). Several studies describe mutations of the conserved threonine in the T-loop (Ducommun et al. EMBO J. 10, 3311-3319, 1991; Gould et al. EMBO J. 10, 3297-3309; Marcote et al. Mol. Cell. Biol. 13, 5122-5131, 1993; Ducommun et al. Mol. Cell. Biol. 11, 6177-6184, 1991; Coleman et al. J. Biol. Chem. 272, 18869-18874, 1997; Martinez et al. EMBO J. 16, 343-354, 1997; Gould et al. Mol. Gen. Genet. 259, 437-448, 1998; Booher et al. Mol. Cell. Biol. 6, 3523-3530, 1986; Solomon et al. Mol. Biol. Cell 3, 13-27, 1992; Lim et al. Mol. Cell. Biol. 16, 4573-4583, 1996), all mutations tested were shown to have a serious impact on binding of ligands (such as cyclin or Suc1/ICK) and/or on kinase activity, resulting in defective or lethal phenotypes in yeast complementation experiments. Although the T169E mutation (according to the numbering for yeast cdc28), and by analogy also the T169D mutation, mimics a phosphorylation, it was demonstrated that none of the CDKs with such mutations were able to fully complement yeast.

Other residues that play an important role in A-type CDK protein activity are threonine at position 14 and tyrosine at position 15. Upon phosphorylation of at least one of these amino acids, the CDK becomes inactivated. WO 99/54489 describes the use of a CDK with threonine 14 and tyrosine 15 substituted by alanine and phenylalanine respectively to increase the tolerance of plants to salt stress. WO 00/52171 describes a method of modifying one or more plant cytokinin-mediated morphological, biochemical and physiological properties or characteristics comprising expressing a Cdc25 phosphoprotein phosphatase in a plant.

As mentioned above CDKs are cell cycle checkpoints, which are involved in signal transduction cascades that ensure genomic integrity during cell division. As checkpoints in mitosis CDKs are regulated by cyclin A or cyclin B. The CDKs are only active during the cell cycle in connection with their respective cyclin. Although their essential mitotic roles are clear, the molecular mechanisms by which these protein kinases act in the living cell must be clarified. In particular, the functions of the different CDK isoforms and CDK-subunits remain unclear. Genetic and biochemical analyses in various organisms have shown that the highly conserved CDKs are required for mitotic entry and exit. Structural and biochemical studies predict that CDKs coordinate specific substrate recognition, but at present the direct downstream effectors of CDKs are unknown. The situation is even more difficult as there most of the CDKs exist in different isoforms each having most likely a different function. That means further biochemical studies are needed to clarify the molecular pathways by which CDKs act.

Therefore there is still a great demand for new and more suitable genes, which encode CDKs, which participate in the differentiation of plants. Advantageously said new genes should have as many as possible of the following features:

participation in the cell cycle and/or cell division;
participation in the organogenesis;
participation in the morphogenesis;
influencing of the anatomy of the plants;
increasing metabolic activity;
increasing of the size of different organs of the plants, preferably of seeds or kernels; and/or
a broad activity in different organs and/or cell compartments.

BRIEF DESCRIPTION OF THE DRAWINGS

FIG. 4A-F show the vector sequences of EG073qcz, EG065qcz and pMME0607, which are also depicted in the sequence protocol as SEQ ID NO: 57 to 59.

DETAILED DESCRIPTION OF THE INVENTION

Figure 1:
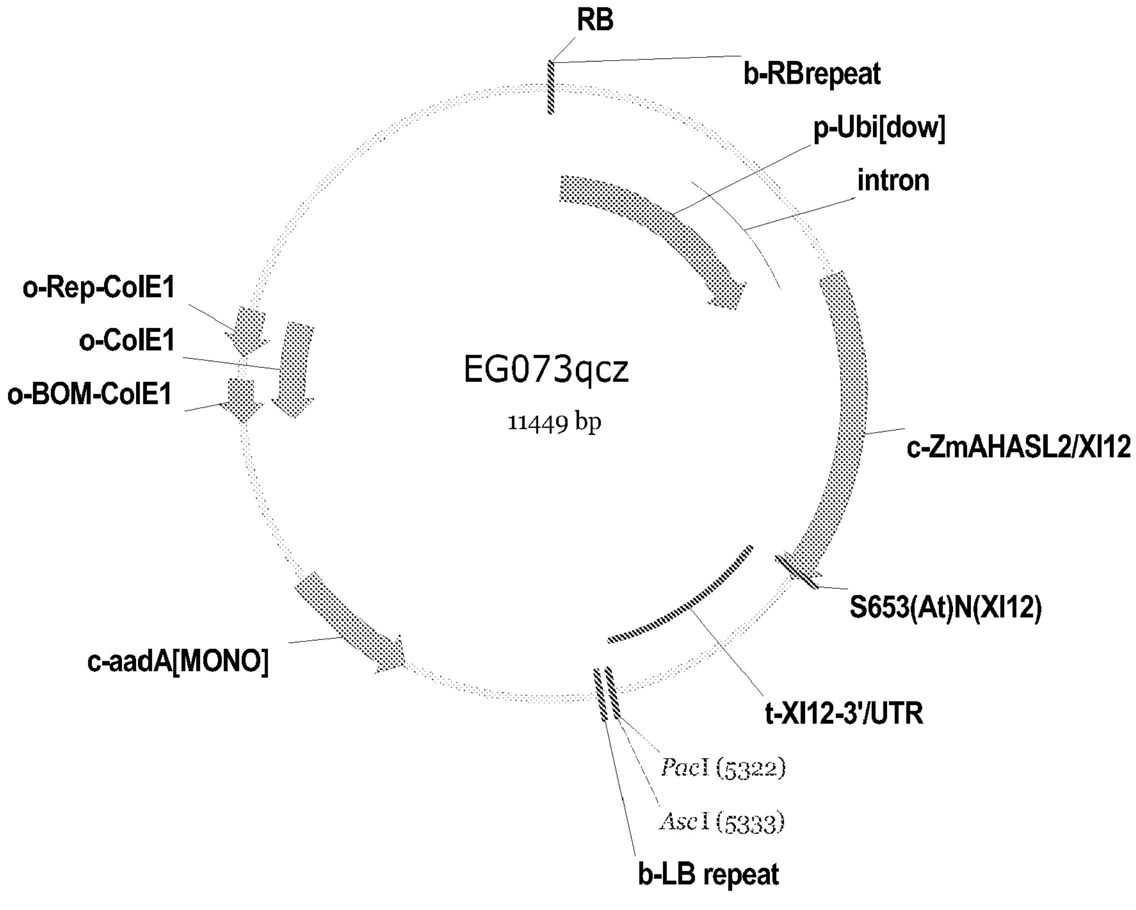
FIG. 1 shows the vector EG073qcz, which is also depicted in the sequence protocol as SEQ ID NO: 57.

It was therefore an object to provide further CDK genes, which are suitable for yield increase in plants. This object was achieved by the process according to the invention for the production of compounds of the formula I Therefore, according to one embodiment of the present invention there is provided a method for improving plant growth characteristics relative to corresponding wild type plants, comprising modulating activity in a plant of a CDK gene preferably of an A-type CDK and/or modulating expression of a nucleic acid encoding such CDK preferably A-type CDK, and optionally selecting plants having improved growth characteristics.

Advantageously, performance of the method according to the present invention results in plants having a variety of improved growth characteristics relative to corresponding wild type plants and which improved growth characteristics comprise at least increased yield relative to corresponding wild type plants.

The term "increased yield" as defined herein is taken to mean an increase in any one or more of the following, each relative to corresponding wild type plants:

(i) increased biomass (weight) of one or more parts of a plant, particularly above-ground (harvestable) parts, increased root biomass or increased biomass of any other harvestable part;
(ii) increased total seed yield, which includes an increase in seed biomass (seed weight) and which may be an increase in the seed weight per plant or on an individual seed basis;
(iii) increased number of flowers ("florets") per panicle
(iv) increased number of (filled) seeds;
(v) increased seed size, which may also influence the composition of seeds;
(vi) increased seed volume, which may also influence the composition of seeds (including oil, protein and carbohydrate total content and composition);
(vii) increased individual seed area;
(viii) increased individual seed length and/or width;
(ix) increased harvest index, which is expressed as a ratio of the yield of harvestable parts, such as seeds, over the total biomass; and
(x) increased thousand kernel weight (TKW), which is extrapolated from the number of filled seeds counted and their total weight. An increased TKW may result from an increased seed size and/or seed weight. An increased TKW may result from an increase in embryo size and/or endosperm size.

Taking corn as an example, a yield increase may be manifested as one or more of the following: increase in the number of plants per hectare or acre, an increase in the number of ears per plant, an increase in the number of rows, number of kernels per row, kernel weight, TKW, ear length/diameter, among others. Taking rice as an example, a yield increase may be manifested by an increase in one or more of the following: number of plants per hectare or acre, number of panicles per plant, number of spikelets per panicle, number of flowers per panicle, increase in the seed filling rate, expressed (in %) as the proportion of the number of filled seeds over the number of florets (total number of seeds), increase in TKW, among others. An increase in yield may also result in modified architecture, or may occur as a result of modified architecture.

According to a preferred feature, performance of the methods according to the present invention results in plants having increased yield and more particularly, increased biomass and/or increased seed yield. Preferably, the increased seed yield comprises an increase in one or more of the following: number of (filled) seeds, total seed weight, seed size, seed volume, thousand kernel weight and harvest index, each relative to control plants.

Therefore, according to the present invention, there is provided a method for increasing plant yield relative to corresponding control plants, which method comprises modulating activity of a CDK or a homologue thereof in a plant, which CDK or homologue has a one of the motifs mentioned herein, and/or modulating expression of a nucleic acid encoding such a CDKA or homologue thereof.

Since the plants according to the present invention have increased yield, it is likely that these plants exhibit an increased growth rate (during at least part of their life cycle), relative to the growth rate of corresponding wild type plants at a corresponding stage in their life cycle. The increased growth rate may be specific to one or more parts of a plant or cell types, including seeds, of a plant, or may be throughout substantially the whole plant. Plants having an increased growth rate may have a shorter life cycle. The life cycle of a plant may be taken to mean the time needed to grow from a dry mature seed up to the stage where the plant has produced dry mature seeds, similar to the starting material. This life cycle may be influenced by factors such as early vigour, growth rate, flowering time and speed of seed maturation. An increase in growth rate may take place at one or more stages in the life cycle of a plant or during substantially the whole plant life cycle. Increased growth rate during the early stages in the life cycle of a plant may reflect enhanced vigour. The increase in growth rate may alter the harvest cycle of a plant allowing plants to be sown later and/or harvested sooner than would otherwise be possible. If the growth rate is sufficiently increased, it may allow for the sowing of further seeds of the same plant species (for example sowing and harvesting of rice plants followed by sowing and harvesting of further rice plants all within one conventional growing period). Similarly, if the growth rate is sufficiently increased, it may allow for the further sowing of seeds of different plants species (for example the sowing and harvesting of rice plants followed by, for example, the sowing and optional harvesting of soy bean, potatoes or any other suitable plant). Harvesting additional times from the same rootstock in the case of some plants may also be possible. Altering the harvest cycle of a plant may lead to an increase in annual biomass production per acre (due to an increase in the number of times (say in a year) that any particular plant may be grown and harvested). An increase in growth rate may also allow for the cultivation of transgenic plants in a wider geographical area than their wild-type counterparts, since the territorial limitations for growing a crop are often determined by adverse environmental conditions either at the time of planting (early season) or at the time of harvesting (late season). Such adverse conditions may be avoided if the harvest cycle is shortened. The growth rate may be determined by deriving various parameters from growth curves plotting growth experiments, such parameters may be: T-Mid (the time taken for plants to reach 50% of their maximal size) and T-90 (time taken for plants to reach 90% of their maximal size), amongst others.

Performance of the methods of the invention gives plants having an increased growth rate. Therefore, according to the present invention, there is provided a method for increasing the growth rate of plants, which method comprises modulating activity of a CDK, its isoforms or a homologue thereof in a plant, which CDK or homologue has a (P/N/A)(S/L/M/F)(T/S/R)(T/S/A)(L/I)RE (SEQ ID NO: 61)motif or other motif mentioned herein, and/or modulating expression of a nucleic acid encoding such a CDKA or homologue thereof.

The term "isoform" as used herein shall mean different versions of a protein with some small differences, which also known as an isoenzyme if the protein is an enzyme. Isoforms can usually be separated by electrophoresis or some other separation technique. They exist by multiple mechanisms: different gene loci, multiple alleles (also called allelomorphs, allelozymes, or allozymes), different subunit interaction, different space forms, or different post-translational modification.

An increase in yield and/or growth rate occurs whether the plant is under non-stress conditions or whether the plant is exposed to various stresses compared to control plants. Plants typically respond to exposure to stress by growing more slowly. In conditions of severe stress, the plant may even stop growing altogether. Mild stress on the other hand is defined herein as being any stress to which a plant is exposed which does not result in the plant ceasing to grow altogether without the capacity to resume growth. Due to advances in agricultural practices (irrigation, fertilization, pesticide treatments) severe stresses are not often encountered in cultivated crop plants. As a consequence, the compromised growth induced by mild stress is often an undesirable feature for agriculture. Mild stresses are the typical stresses to which a plant may be exposed. These stresses may be the everyday biotic and/or abiotic (environmental) stresses to which a plant is exposed. Typical abiotic or environmental stresses include temperature stresses caused by atypical hot or cold/freezing temperatures; salt stress; water stress (drought or excess water). Abiotic stresses may also be caused by chemicals. Biotic stresses are typically those stresses caused by pathogens, such as bacteria, viruses, fungi and insects. The term "non-stress conditions" as used herein are those environmental conditions that do not significantly go beyond the everyday climatic and other abiotic conditions that plants may encounter. Persons skilled in the art are aware of normal soil conditions and climatic conditions for a given geographic location.

The terms "increase", "improving" or "improve" are interchangeable and shall mean in the sense of the application at least a 10%, 20%, 30%, 40% or 50%, preferably at least 60%, 70%, 80%, 90% or 100%, more preferably 150%, 200%, 300%, 400% or 500% more growth in comparison to the wild type plant as defined herein, e.g. that means in comparison to a plant without the introduction of the CDK encoding nucleic acid sequence according to the invention.

The increase referred to the activity of the polypeptide amounts in a cell, a tissue, a organelle, an organ or an organism or a part thereof preferably to at least 5%, preferably to at least 20% or at to least 50%, especially preferably to at least 70%, 80%, 90% or more, very especially preferably are to at least 200%, 300% or 400%, most preferably are to at least 500% or more in comparison to the control, reference or wild type.

The term "modulating the activity" shall mean any change of the expression of the inventive nucleic acid sequences or encoded proteins, which leads to an increase in growth of the plants.

The abovementioned growth characteristics may advantageously be modified in any plant.

The term "plant" as used herein encompasses whole plants, ancestors and progeny of the plants and plant parts, including seeds, shoots, stems, leaves, roots (including tubers), fruits, stalk, seedlings, tubers, flowers, and tissues and organs, wherein each of the aforementioned comprise the gene/nucleic acid of interest or the specific modification in the gene/nucleic acid of interest. The term "plant" also encompasses plant cells, suspension cultures, callus tissue, embryos, meristematic regions, gametophytes, sporophytes, pollen, and microspores, again wherein each of the aforementioned comprise the gene/nucleic acid of interest.

A "reference", "control" or "wild type" is in particular a cell, a tissue, an organ, an organism, or a part thereof, which was not produced according to the process of the invention. Accordingly, the terms "wild type", "control" or "reference" are exchangeable and can be a cell or a part of the plant such as an organelle or tissue, or a plant, which was not modified or treated according to the herein described process according to the invention. Accordingly, the cell or a part of the plant such as an organelle or a plant used as wild type, control or reference corresponds to the cell, plant or part thereof as much as possible and is in any other property but in the result of the process of the invention as identical to the subject matter of the invention as possible. Thus, the wild type, control or reference is treated identically or as identical as possible, saying that only conditions or properties might be different which do not influence the quality of the tested property. That means in other words that the wild type denotes (1) a plant, which carries the unaltered form of a gene or allele or (2) the starting material/plant from which the plants produced by the process or method of the invention are derived.

Preferably, any comparison between the wild type plants and the plants produced by the process of the invention is carried out under analogous conditions. The term "analogous conditions" means that all conditions such as, for example, culture or growing conditions, assay conditions (such as buffer composition, temperature, substrates, pathogen strain, concentrations and the like) are kept identical between the experiments to be compared.

The "reference", "control", or "wild type" is preferably a subject, e.g. an organelle, a cell, a tissue, a plant, which was not modified or treated according to the herein described process of the invention and is in any other property as similar to the subject matter of the invention as possible. The reference, control or wild type is in its genome, transcriptome, proteome or metabolome as similar as possible to the subject of the present invention. Preferably, the term "reference-" "control-" or "wild type-"-organelle, -cell, tissue or plant, relates to an organelle, cell, tissue or plant, which is nearly genetically identical to the organelle, cell, tissue or plant, of the present invention or a part thereof preferably 95%, more preferred are 98%, even more preferred are 99.00%, in particular 99.10%, 99.30%, 99.50%, 99.70%, 99.90%, 99.99%, 99. 999% or more. Most preferable the "reference", "control", or "wild type" is preferably a subject, e.g. an organelle, a cell, a tissue, a plant, which is genetically identical to the plant, cell organelle used according to the process of the invention except that nucleic acid molecules or the gene product encoded by them are changed or modified according to the inventive process. In case, a control, reference or wild type differing from the subject of the present invention only by not being subject of the process of the invention can not be provided, a control, reference or wild type can be an organism in which the cause for the modulation of the activity conferring the increase of the fine chemical as described herein has been switched back or off, e.g. by complementation of responsible reduced gene product, e.g. by stable or transient (over)expression, by activation of an activator or agonist, by inactivation of an inhibitor or antagonist, by adding active compounds as e.g. hormones, by introducing enhancers etc.

Plants that are particularly useful in the methods or processes of the invention include algae, ferns, and all plants which belong to the superfamily Viridiplantae, in particular monocotyledonous and dicotyledonous plants, including fodder or forage legumes, ornamental plants, food crops, trees, or shrubs selected from the list comprising *Abelmoschus* spp., *Acer* spp., *Actinidia* spp., *Agropyron* spp., *Allium* spp., *Amaranthus* spp., *Ananas comosus, Annona* spp., *Apium graveolens, Arabidopsis thaliana, Arachis* spp, *Artocarpus* spp., *Asparagus officinalis, Avena sativa, Averrhoa carambola, Benincasa hispida, Bertholletia excelsea, Beta vulgaris, Brassica* spp., *Cadaba farinosa, Camellia sinensis, Canna indica, Capsicum* spp., *Carica papaya, Carissa macrocarpa, Carthamus tinctorius, Carya* spp., *Castanea* spp., *Cichorium endivia, Cinnamomum* spp., *Citrullus lanatus, Citrus* spp., *Cocos* spp., *Coffea* spp., *Cola* spp., *Colocasia esculenta, Corylus* spp., *Crataegus* spp., *Cucumis* spp., *Cucurbita* spp., *Cynara* spp., *Daucus carota, Desmodium* spp., *Dimocarpus longan, Dioscorea* spp., *Diospyros* spp., *Echinochloa* spp., *Eleusine coracana, Eriobotrya japonica, Eugenia uniflora, Fagopyrum* spp., *Fagus* spp., *Ficus carica, Fortunella* spp., *Fragaria* spp., *Ginkgo biloba, Glycine* spp., *Gossypium hirsutum, Helianthus* spp., *Hibiscus* spp., *Hordeum* spp., *Ipomoea batatas, Juglans* spp., *Lactuca sativa, Lathyrus* spp., *Lemna* spp., *Lens culinaris, Linum usitatissimum, Litchi chinensis, Lotus* spp., *Luffa acutangula, Lupinus* spp., *Macrotyloma* spp., *Malpighia emarginata, Malus* spp., *Mammea americana, Mangifera indica, Manihot* spp., *Manilkara zapota, Medicago sativa, Melilotus* spp., *Mentha* spp., *Momordica* spp., *Morus nigra, Musa* spp., *Nicotiana* spp., *Olea* spp., *Opuntia* spp., *Ornithopus* spp., *Oryza* spp., *Panicum miliaceum, Passiflora edulis, Pastinaca sativa, Persea* spp., *Petroselinum crispum, Phaseolus* spp., *Phoenix* spp., *Physalis* spp., *Pinus* spp., *Pistacia vera, Pisum* spp., *Poa* spp., *Populus* spp., *Prosopis* spp., *Prunus* spp., *Psidium* spp., *Punica granatum, Pyrus communis, Quercus* spp., *Raphanus sativus, Rheum rhabarbarum, Ribes* spp., *Rubus* spp., *Saccharum* spp., *Sambucus* spp., *Secale cereale, Sesamum* spp., *Solanum* spp., *Sorghum bicolor, Spinacia* spp., *Syzygium* spp., *Tamarindus indica, Theobroma cacao, Trifolium* spp., *Triticosecale rimpaui, Triticum* spp., *Vaccinium* spp., *Vicia* spp., *Vigna* spp., *Vitis* spp., *Zea mays, Zizania palustris, Ziziphus* spp., amongst others.

According to a preferred feature of the present invention, the plant is a crop plant comprising soybean, sunflower, canola, alfalfa, rapeseed, cotton, tomato, potato or tobacco. Further preferably, the plant according to the present invention is a monocotyledonous plant such as sugar cane, most preferably a cereal, such as rice, maize, wheat, millet, barley, rye, oats or sorghum.

Particular preferred plants are plants selected from the group consisting of Asteraceae such as the genera *Helianthus*, Tagetes e.g. the species *Helianthus annus* [sunflower], *Tagetes lucida, Tagetes erecta* or *Tagetes tenuifolia* [Marigold], Brassicaceae such as the genera *Brassica, Arabadopsis* e.g. the species *Brassica napus, Brassica rapa* ssp. [canola, oilseed rape, turnip rape] or *Arabidopsis thaliana*. Fabaceae such as the genera *Glycine* e.g. the species *Glycine max, Soja hispida* or *Soja max* [soybean]. Linaceae such as the genera *Linum* e.g. the species *Linum usitatissimum*, [flax, linseed]; Poaceae such as the genera *Hordeum, Secale, Avena, Sorghum, Oryza, Zea, Triticum* e.g. the species *Hordeum vulgare* [barley]; *Secale cereale* [rye], *Avena sativa, Avena fatua, Avena byzantina, Avena fatua* var. *sativa, Avena hybrida* [oat], *Sorghum bicolor [Sorghum*, millet], *Oryza sativa, Oryza latifolia* [rice], *Zea mays* [corn, maize] *Triticum aestivum, Triticum durum, Triticum turgidum, Triticum hybernum, Triticum macha, Triticum sativum* or *Triticum vulgare* [wheat, bread wheat, common wheat]; Solanaceae such as the genera *Solanum, Lycopersicon* e.g. the species *Solanum tuberosum* [potato], *Lycopersicon esculentum, Lycopersicon lycopersicum, Lycopersicon pyriforme, Solanum integrifolium* or *Solanum lycopersicum* [tomato].

The activity of a CDKA protein may be modulated by modulating the levels of the CDKA protein. Alternatively, activity may also be modulated when there is no change in levels of a CDKA protein, this may occur when the intrinsic properties of the polypeptide are altered, for example by making a mutant. According to a preferred feature of the invention, modulated activity of the CDKA protein and/or modulated expression of a nucleic acid encoding this CDKA is introduced and/or increased activity of a CDKA protein and/or increased expression of a nucleic acid encoding this CDKA.

The terms "A-type CDK" or "CDKA" as defined herein may be used interchangeably and encompass any amino acid sequence having cyclin dependent kinase activity and which sequence when used in the construction of a CDK phylogenetic tree, such as the ones depicted in the sequence protocol preferably of SEQ ID NO: 45, 47, 49, 51, 53 and/or SEQ ID NO: 55, clusters around the A-type CDKs rather than any of the other CDK groups and which amino acid sequence comprises a (P/N/A)(S/L/M/F)(T/S/R)(T/S/A)(L/I)RE amino acid sequence (SEQ ID NO: 61) are preferred. A person skilled in the art could readily determine whether any amino acid sequence in question falls within the definition of an "A-type CDK" using known techniques and software for the making of such a phylogenetic tree, such as a GCG, EBI or CLUSTAL package, using default parameters (see for example Vandepoele et al. 2002). Upon construction of such a phylogenetic tree, sequences clustering in the A-type CDK group will be considered to fall within the definition of an "A-type CDK" or "CDKA", and will therefore be useful in performing the methods of the invention. Preferably the CDK further comprises in increasing order of preference at least 75%, 80%, 85%, 90%, 95%, 96%, 97%, 98%, 99% or more overall sequence identity to the amino acid depicted in SEQ ID NO: 2. Therefore programs based on said aforementioned algorithms are preferred. Advantageously the comparisons of sequences can be done with the program PileUp (J. Mol. Evolution., 25, 351-360, 1987, Higgins et al., CABIOS, 5 1989: 151-153) or preferably with the programs Gap and BestFit, which are respectively based on the algorithms of Needleman and Wunsch [J. Mol. Biol. 48; 443-453 (1970)] and Smith and Waterman [Adv. Appl. Math. 2; 482-489 (1981)]. Both programs are part of the GCG software-package [Genetics Computer Group, 575 Science Drive, Madison, Wis., USA 53711 (1991); Altschul et al. (1997) Nucleic Acids Res. 25:3389 et seq.]. Therefore preferably the calculations to determine the perentages of sequence homology are done with the program Gap over the whole range of the sequences. The following standard adjustments for the comparison of nucleic acid sequences were used: gap weight: 50, length weight: 3, average match: 10.000, average mismatch: 0.000.

Homology between two polypeptides is understood as meaning the identity of the amino acid sequence over in each case the entire sequence length which is calculated by comparison with the aid of the program algorithm GAP (Wisconsin Package Version 10.0, University of Wisconsin, Genetics Computer Group (GCG), Madison, USA), setting the following parameters:

| | | | |
|---|---|---|---|
| Gap weight: | 8 | Length weight: | 2 |
| Average match: | 2,912 | Average mismatch: | −2,003. |

In both cases (nucleic acid sequence or amino acid sequence comparison) of the mentioned parameters Average match and Average mismatch the numbers given above are the results of the calculation.

The various structural domains in a CDKA protein are well known (De Bondt et al., Nature 363, 595-602, 1993) and may be identified using specialised databases e.g. SMART (Schultz et al. (1998) Proc. Natl. Acad. Sci. USA 95, 5857-5864; Letunic et al. (2002) Nucleic Acids Res 30, 242-244; smart.embl-heidelberg.de/), InterPro (Mulder et al., (2003) Nucl. Acids. Res. 31, 315-318;www.ebi.ac.uk/interpro/), Prosite (Bucher and Bairoch (1994), A generalized profile syntax for biomolecular sequences motifs and its function in automatic sequence interpretation. (In) ISMB-94; Proceedings 2nd International Conference on Intelligent Systems for Molecular Biology. Altman R., Brutlag D., Karp P., Lathrop R., Searls D., Eds., pp 53-61, AAAIPress, Menlo Park; Hulo et al., Nucl. Acids. Res. 32:D134-D137, (2004), www.expasy.org/prosite/) or Pfam (Bateman et al., Nucleic Acids Research 30(1):276-280 (2002), (www.sanger.ac.uk/Software/Pfam/).

The kinase domain of CDK is of an S_TKc-type (SMART accession number SM00220, InterPro accession number IPR002290), and has Ser/Thr kinase activity. The predicted active site (VLHRDLKPQNLLI, wherein D is the predicted catalytic residue, SEQ ID NO: 62) corresponds to the PROSITE signature PS00108. In position 1 of the active site instead of a Valine a Phenylalanine may exist. In position 6 a Leucine Methionine exchange may occur and in position 9 Gln may be exchanged to Asn. The ATP binding site (IGEG-TYGVVYRARDKVTNETIALK, found within SEQ ID NO: 63) corresponds to the PROSITE signature PS00107. Also in the ATP binding site some mutations may occur. They are as follows: position 11 Arg→Lys; position 12 Ala→Gly, position 13 Arg→Leu, position 15 Lys→Arg and position 16 Val→Leu, Ala, Ser, Thr or Asn.

Methods for the search and identification of A-type CDK homologues would be well within the realm of persons skilled in the art. Such methods comprise comparison of the sequences represented by SEQ ID NO 1 or 2, or by GenBank accession CAA42922, in a computer readable format, with sequences that are available in public databases such as MIPS (mips.gsf.de/), GenBank (www.ncbi.nlm.nih.gov/Genbank/index.html) or EMBL Nucleotide Sequence Database (www.ebi.ac.uk/embl/index.html), using algorithms well known in the art for the alignment or comparison of sequences, such as GAP (Needleman and Wunsch, J. Mol. Biol. 48; 443-453 (1970)), BESTFIT (using the local homology algorithm of Smith and Waterman (Advances in Applied Mathematics 2; 482-489 (1981))), BLAST (Altschul, S. F., Gish, W., Miller, W., Myers, E. W. & Lipman, D. J., J. Mol. Biol. 215:403-410 (1990)), FASTA and TFASTA (W. R. Pearson and D. J. Lipman Proc. Natl. Acad. Sci. USA 85:2444-2448 (1988)). The software for performing BLAST analysis is publicly available through the National Centre for Biotechnology Information (NCBI). The homologues mentioned below were identified using BLAST default parameters (BLOSUM62 matrix, gap opening penalty 11 and gap extension penalty 1) and preferably the full-length sequences are used for analysis. These alignment methods also easily allow the identification of the conserved threonine that corresponds to threonine 161 in human CDC2 or rice CDKA;1 (SEQ ID NO: 8).

It is to be understood that the term "CDK or preferably A-type CDK or a homologue thereof" is not to be limited to the sequences as depicted in the sequence protocol, but that any polypeptide meeting the criteria of having cyclin dependent kinase activity, having a (P/N/A)(S/L/M/F)(T/S/R)(T/S/A)(L/I)RE (SEQ ID NO: 61) domain or other domain as disclosed herein, and having at least 80%, 85% or 90%, preferably 91%, 92%, 93%, 94% or 95%, most preferably 96%, 97%, 98%, 99% or 100% sequence identity to the sequences disclosed in the sequence protocol preferably to the sequences of SEQ ID NO: 45, 47, 49, 51, 53 and/or SEQ ID NO: 55, may be suitable for use in the methods of the invention, provided that the CDKs having the yield increasing property.

To determine the kinase activity of A-type CDKs, several assays are available and are well known in the art (for example Current Protocols in Molecular Biology, Volumes 1 and 2, Ausubel et al. (1994), Current Protocols; or online, such as www.protocol-online.org).

In brief, the kinase assay generally involves: (1) bringing the kinase protein into contact with a substrate polypeptide containing the target site to be phosphorylated; (2) allowing phosphorylation of the target site in an appropriate kinase buffer under appropriate conditions; (3) separating phosphorylated products from non-phosphorylated substrate after a suitable reaction period. The presence or absence of kinase activity is determined by the presence or absence of the phosphorylated target. In addition, quantitative measurements may be performed. Purified CDK protein, or cell extracts containing or enriched with the CDK protein may be used as a source of the kinase protein. Histone H1 or small peptides are particularly well suited as a substrate. The peptide must comprise one or more serine, threonine, or tyrosine residues in a phosphorylation site motif. A compilation of phosphorylation sites may be found in Biochimica et Biophysica Acta 1314, 191-225, (1996). In addition, the peptide substrates may advantageously have a net positive charge to facilitate binding to phosphocellulose filters, (allowing separation of the phosphorylated from non-phosphorylated peptides and detection of the phosphorylated peptides). If a phosphorylation site motif is not known, a general Ser/Thr kinase substrate may be used. For example, the peptide "ADAQHATPPKKKRKVEDPKDF"(Marshak et al. J. Cell. Biochem. 45, 391, 1991) is a specific substrate for A-type CDK. To determine the kinetic parameters for phosphorylation of the synthetic peptide, a range of peptide concentrations is required. For initial reactions, a peptide concentration of 0.7-1.5 mM may be used. For each kinase enzyme, it is important to determine the optimal buffer, ionic strength, and pH for activity. A standard 5× Kinase Buffer generally contains 5 mg/ml BSA (Bovine Serum Albumin preventing kinase adsorption to the assay tube), 150 mM Tris-Cl (pH 7.5), 100 mM $MgCl_2$. The optimal concentrations of divalent cations must be determined empirically for each protein kinase. Suitable buffers for CDK assays are known in the art (for example John et al., Protoplasma 161, 70-74, 1991). A commonly used donor of the phosphoryl group is radio-labelled [gamma-$^{32}$P]ATP (normally at 0.2 mM final concentration). The amount of $^{32}$P incorporated in the peptides may be determined by measuring activity on the nitrocellulose dry pads in a scintillation counter.

Furthermore, such "CDK or homologue or derivative thereof", when expressed under control of a shoot specific promoter in *Oryza sativa*, increases seed yield compared to corresponding wild type plants. This increase in seed yield may be measured in several ways, for example as an increase in the total weight of seeds, as an increase in the number of filled seeds harvested from a plant or as an increased Harvest Index.

The biological and/or functional activity of a CDK or a homologue thereof according to the present invention includes at least one of having cyclin dependent kinase activity or having yield-increasing activity in plants as described above.

"Active fragments" of a CDK preferably of an A-type CDK protein encompasses at least 100, 110, 120, 130, 140 or 150, preferably of 160, 170, 180, 190 or 200 amino acid residues of a CDK protein, which contiguous residues retain similar biological and/or functional activity to the naturally occurring protein.

A CDK or a homologue thereof as defined hereinabove is encoded by a CDK nucleic acid molecule. The nucleic acid encoding a CDK or a homologue thereof may be any natural or synthetic nucleic acid. Therefore the term "CDK nucleic acid molecule" or "CDK gene" as defined herein is any nucleic acid molecule (including those as a result of the degeneration of the genetic code) encoding a CDK polypeptide or a homologue thereof as defined hereinabove. Examples of CDK nucleic acid molecules include the ones represented in the sequence protocoll, and those encoding the above-mentioned homologues. CDK nucleic acids and functional variants thereof may be suitable in practising the methods of the invention. Such functional variant CDK nucleic acids include portions of a CDK nucleic acid molecule, allelic variants, splice variants and/or nucleic acids capable of hybridising with a CDK nucleic acid molecule. The term "functional" in the context of a functional variant refers to a variant (i.e. a portion or a hybridising sequence), which encodes a polypeptide having cyclin-dependent kinase activity.

A further embodiment of the invention is an isolated nucleic acid molecule comprising a nucleic acid molecule selected from the group consisting of:

a) an isolated nucleic acid molecule as depicted in SEQ ID NO: 45, 47, 49, 51, 53 or 55;

b) an isolated nucleic acid molecule encoding the amino acid sequence as depicted in SEQ ID NO: 46, 48, 50, 52, 54 or 56;

c) an isolated nucleic acid molecule whose sequence can be deduced from a polypeptide sequence as depicted in SEQ ID NO: 46, 48, 50, 52, 54 or 56 as a result of the degeneracy of the genetic code;

d) an isolated nucleic acid molecule which encodes a polypeptide which has at least 80% identity with the amino acid sequence of the polypeptide encoded by the nucleic acid molecule of (i) to (iii);

e) an isolated nucleic acid molecule encoding a homologue, derivative or active fragment of the amino acid molecule as depicted in SEQ ID NO: 46, 48, 50, 52, 54 or 56, which homologue, derivative or fragment is of plant origin and comprises advantageously a (P/N/A)(S/L/M/F)(T/S/R)(T/S/A)(L/I) (found within SEQ ID NO: 61) motif;

f) an isolated nucleic acid molecule encoding a protein comprising an amino acid sequence selected from the group consisting of:

```
                                            (SEQ ID: 61)
aa) (P/N/A)(S/L/M/F)(T/S/R)(T/S/A)(L/I)RE;

                                            (SEQ ID: 62)
ab) (V/F/I)(L/I)HRD(L/M)K(P/S/T)(Q/N/S/G)N(L/I)L
    (V/L/I);

                                            (SEQ ID: 63)
ac) (I/L)(G/N)(E/R)G(T/A)YG(V/I)V(Y/C)(R/K/S)
    (A/G/S)(R/L/T/I)(D/N)(K/R/E)(V/K/A/S/T/N)T
    (N/S/G)(E/K/Q)  (T/L/I/K)(I/V)A(L/V/I)KK;

                                            (SEQ ID: 64)
ad) LK(I/L)(C/A)DFGL(A/S)R;

                                            (SEQ ID: 65)
ae) WYRAPE(L/I)L(L/F)(C/G);

                                            (SEQ ID: 66)
af) GCI(F/M)AE(I/L/M);
and

                                            (SEQ ID: 67)
ag) DLL(Q/N/S/R)(K/Q/R)(L/M)(L/F)(I/T/I/C)(F/Y/L)DP
    (T/E/D/R/S)(K/Q)RI;
```

g) an isolated nucleic acid molecule capable of hybridising with a nucleic acid of (i) to (iii) above, or its complement, wherein the hybridising sequence or the complement thereof encodes a plant CDK protein that comprises advantageously a (P/N/A)(S/L/M/F)(T/S/R)(T/S/A)(L/I) (found within SEQ ID NO: 61 ) motif;

whereby the nucleic acid molecule has growth increasing activities in plants.

The present invention also provides an isolated nucleic acid molecule (=nucleic acid sequence) selected from the group consisting of:

a) an isolated nucleic acid molecule as depicted in SEQ ID NO: 45, 47, 49, 51, 53 or 55;

b) an isolated nucleic acid molecule encoding the amino acid sequence as depicted in SEQ ID NO: 46, 48, 50, 52, 54 or 56;

c) an isolated nucleic acid molecule whose sequence can be deduced from a polypeptide sequence as depicted in SEQ ID NO: 46, 48, 50, 52, 54 or 56 as a result of the degeneracy of the genetic code;

d) an isolated nucleic acid molecule which encodes a polypeptide which has at least 80% identity with the amino acid sequence of the polypeptide encoded by the nucleic acid molecule of (a) to (c);

e) an isolated nucleic acid molecule encoding a homologue, derivative or active fragment of the amino acid molecule as depicted in SEQ ID NO: 46, 48, 50, 52, 54 or 56, which homologue, derivative or fragment is of plant origin and comprises advantageously a (P/N/A)(S/L/M/F)(T/S/R)(T/S/A)(L/I)RE (SEQ ID NO: 61) motif;

f) an isolated nucleic acid molecule encoding a protein comprising an amino acid sequence selected from the group consisting of:

```
                                            (SEQ ID: 61)
i)    (P/N/A)(S/L/M/F)(T/S/R)(T/S/A)(L/I)RE,
      preferably PSTAIRE (found within SEQ ID
       NO: 61);
```

-continued

```
                                        (SEQ ID: 62)
ii)  (V/F/I)(L/I)HRD(L/M)K(P/S/T)(Q/N/S/G)N(L/I)L
     (V/L/I); preferably HRDXKXXXNXL (found within
     SEQ ID NO: 62);

                                     (SEQ ID NO: 63)
iii) (I/L)(G/N)(E/R)G(T/A)YG(V/I)V(Y/C)(R/K/S)

     (A/G/S)(R/L/T/I)(D/N)(K/R/E)(V/K/A/S/T/N)T

     (N/S/G)(E/K/Q)(T/L/I/K)(I/V)A(L/V/I)KK;

     preferably GXVXXXXXXXTXXXXAXKK (found within
     SEQ ID NO: 63);

                                     (SEQ ID NO: 64)
iv)  LK(I/L)(C/A)DFGL(A/S)R, peferably LKXXDFGLXR
     (SEQ ID NO: 64;

                                     (SEQ ID NO: 65)
v)   WYRAPE(L/I)L(L/F)(C/G), preferably WYRAPE
     (found within SEQ ID NO: 65);

                                     (SEQ ID NO: 66)
vi)  GCI(F/M)AE(I/L/M), preferably GCIXAEX;
     (SEQ ID NO: 66)
     and

                                     (SEQ ID NO: 67)
vii) DLL(Q/N/S/R)(K/Q/R)(L/M)(L/F)(I/T/I/C)(F/Y/L)

     DP(T/E/D/R/S)(K/Q)RI, preferably

     DLLXXXXXXDPXXRI (SEQ ID NO: 67).
```

g) an isolated nucleic acid molecule capable of hybridising with a nucleic acid of (a) to (c) above, or its complement, wherein the hybridising sequence or the complement thereof encodes a plant CDK protein that comprises advantageously a (P/N/A)(S/L/M/F)(T/S/R)(T/S/A)(L/I)RE (SEQ ID NO: 61) motif;

h) allelic variants of a nucleic acid according to any of (a) to (d) above, which allelic variants encode a plant CDK; and i) alternative splice variants of a nucleic acid according to any of (a) to (d), which alternative splice variants encode a plant CDK protain comprising advantageously a (P/N/A)(S/L/M/F)(T/S/R)(T/S/A)(L/I)RE (SEQ ID NO: 61) motif;

whereby the variant X means any amino acid and whereby the encoded protein conferrin an increase in yield.

With regard to the nucleic acid sequence as depicted a nucleic acid construct which contains a nucleic acid sequence mentioned herein or an organism (=transgenic organism) which is transformed with said nucleic acid sequence or said nucleic acid construct, “transgene” means all those constructs which have been brought about by genetic manipulation methods, preferably in which either a) the nucleic acid sequence as shown in table I A and/or I B, application no. 1, columns 5 and 7 or a derivative thereof, or b) a genetic regulatory element, for example a promoter, which is functionally linked to the nucleic acid sequence as shown table I A and/or I B, application no. 1, columns 5 and 7 or a derivative thereof, or c) (a) and (b)

is/are not present in its/their natural genetic environment or has/have been modified by means of genetic manipulation methods, it being possible for the modification to be, by way of example, a substitution, addition, deletion, inversion or insertion of one or more nucleotide. “Natural genetic environment” means the natural chromosomal locus in the organism of origin or the presence in a genomic library. In the case of a genomic library, the natural, genetic environment of the nucleic acid sequence is preferably at least partially still preserved. The environment flanks the nucleic acid sequence at least on one side and has a sequence length of at least 50 bp, preferably at least 500 bp, particularly preferably at least 1000 bp, very particularly preferably at least 5000 bp.

Unless otherwise specified, the terms “polynucleotides”, “nucleic acid” and “nucleic acid molecule” as used herein are interchangeably. Unless otherwise specified, the terms “peptide”, “polypeptide” and “protein” are interchangeably in the present context. The term “sequence” may relate to polynucleotides, nucleic acids, nucleic acid molecules, peptides, polypeptides and proteins, depending on the context in which the term “sequence” is used. The terms “gene(s)”, “polynucleotide”, “nucleic acid sequence”, “nucleotide sequence”, or “nucleic acid molecule(s)” as used herein refers to a polymeric form of nucleotides of any length, either ribonucleotides or deoxyribonucleotides. The terms refer only to the primary structure of the molecule.

Thus, the terms “gene(s)”, “polynucleotide”, “nucleic acid sequence”, “nucleotide sequence”, or “nucleic acid molecule(s)” as used herein include double- and single-stranded DNA and RNA. They also include known types of modifications, for example, methylation, “caps”, substitutions of one or more of the naturally occurring nucleotides with an analog. Preferably, the DNA or RNA sequence of the invention comprises a coding sequence encoding the herein defined polypeptide.

A “coding sequence” is a nucleotide sequence, which is transcribed into mRNA and/or translated into a polypeptide when placed under the control of appropriate regulatory sequences. The boundaries of the coding sequence are determined by a translation start codon at the 5'-terminus and a translation stop codon at the 3'-terminus. A coding sequence can include, but is not limited to mRNA, cDNA, recombinant nucleotide sequences or genomic DNA, while introns may be present as well under certain circumstances.

An “isolated” polynucleotide or nucleic acid molecule is separated from other polynucleotides or nucleic acid molecules, which are present in the natural source of the nucleic acid molecule. An isolated nucleic acid molecule may be a chromosomal fragment of several kb, or preferably, a molecule only comprising the coding region of the gene. Accordingly, an isolated nucleic acid molecule of the invention may comprise chromosomal regions, which are adjacent 5' and 3' or further adjacent chromosomal regions, but preferably comprises no such sequences which naturally flank the nucleic acid molecule sequence in the genomic or chromosomal context in the organism from which the nucleic acid molecule originates (for example sequences which are adjacent to the regions encoding the 5'- and 3'-UTRs of the nucleic acid molecule). In various embodiments, the isolated nucleic acid molecule used in the process according to the invention may, for example comprise less than approximately 5 kb, 4 kb, 3 kb, 2 kb, 1 kb, 0.5 kb or 0.1 kb nucleotide sequences which naturally flank the nucleic acid molecule in the genomic DNA of the cell from which the nucleic acid molecule originates.

A nucleic acid molecule encompassing a complete sequence of the nucleic acid molecules used in the process, for example the polynucleotide of the invention, or a part thereof may additionally be isolated by polymerase chain reaction, oligonucleotide primers based on this sequence or on parts thereof being used. For example, a nucleic acid molecule comprising the complete sequence or part thereof can be isolated by polymerase chain reaction using oligonucleotide primers which have been generated on the basis of this very sequence. For example, mRNA can be isolated from cells (for example by means of the guanidinium thiocyanate extraction method of Chirgwin et al. (1979) Biochemistry 18:5294-5299) and cDNA can be generated by means of reverse transcriptase (for example Moloney MLV reverse transcriptase, available from Gibco/BRL, Bethesda, Md., or AMV reverse transcriptase, obtainable from Seikagaku America, Inc., St. Petersburg, Fla.).

Nucleic acid molecules which are advantageously for the process according to the invention can be isolated based on their homology to the nucleic acid molecules disclosed herein using the sequences or part thereof as hybridization probe and following standard hybridization techniques under stringent hybridization conditions. In this context, it is possible to use, for example, isolated nucleic acid molecules of at least 15, 20, 25, 30, 35, 40, 50, 60 or more nucleotides, preferably of at least 15, 20 or 25 nucleotides in length which hybridize under stringent conditions with the above-described nucleic acid molecules, in particular with those which encompass a nucleotide sequence of the nucleic acid molecule used in the process of the invention or encoding a protein used in the invention or of the nucleic acid molecule of the invention. Nucleic acid molecules with 30, 50, 100, 250 or more nucleotides may also be used.

The nucleic acid sequences used in the process of the invention, which are depicted in the sequence protocol in particular SEQ ID NO: 45, 47, 49, 51, 53 or 55 are advantageously introduced in a nucleic acid construct, preferably an expression cassette, which makes the expression of the nucleic acid molecules in a plant possible.

Accordingly, the invention also relates to a nucleic acid construct, preferably to an expression construct, comprising the nucleic acid molecule of the present invention functionally linked to one or more regulatory elements or signals.

As described herein, the nucleic acid construct can also comprise further genes, which are to be introduced into the organisms or cells. It is possible and advantageous to introduce into, and express in, the host organisms regulatory genes such as genes for inductors, repressors or enzymes, which, owing to their enzymatic activity, engage in the regulation of one or more genes of a biosynthetic pathway. These genes can be of heterologous or homologous origin. Moreover, further biosynthesis genes may advantageously be present, or else these genes may be located on one or more further nucleic acid constructs. Genes, which are advantageously employed are genes, which influence the growth of the plants such as regulator sequences or factors. An enhancement of the regulator elements may advantageously take place at the transcriptional level by using strong transcription signals such as promoters and/or enhancers. In addition, however, an enhancement of translation is also possible, for example by increasing mRNA stability or by inserting a translation enhancer sequence.

In principle, the nucleic acid construct can comprise the herein described regulator sequences and further sequences relevant for the expression of the comprised genes. Thus, the nucleic acid construct of the invention can be used as expression cassette and thus can be used directly for introduction into the plant, or else they may be introduced into a vector. Accordingly in one embodiment the nucleic acid construct is an expression cassette comprising a microorganism promoter or a microorganism terminator or both. In another embodiment the expression cassette encompasses a plant promoter or a plant terminator or both.

To introduce a nucleic acid molecule into a nucleic acid construct, e.g. as part of an expression cassette, the codogenic gene segment is advantageously subjected to an amplification and ligation reaction in the manner known by a skilled person. It is preferred to follow a procedure similar to the protocol for the Pfu DNA polymerase or a Pfu/Taq DNA polymerase mixture. The primers are selected according to the sequence to be amplified. The primers should expediently be chosen in such a way that the amplificate comprise the codogenic sequence from the start to the stop codon. After the amplification, the amplificate is expediently analyzed. For example, the analysis may consider quality and quantity and be carried out following separation by gel electrophoresis. Thereafter, the amplificate can be purified following a standard protocol (for example Qiagen). An aliquot of the purified amplificate is then available for the subsequent cloning step. The skilled worker generally knows suitable cloning vectors.

They include, in particular, vectors which are capable of replication in easy to handle cloning systems like as bacterial yeast or insect cell based (e.g. baculovirus expression) systems, that is to say especially vectors which ensure efficient cloning in *E. coli*, and which make possible the stable transformation of plants. Vectors, which must be mentioned, in particular are various binary and cointegrated vector systems, which are suitable for the T-DNA-mediated transformation. Such vector systems are generally characterized in that they contain at least the vir genes, which are required for the *Agrobacterium*-mediated transformation, and the T-DNA border sequences.

In general, vector systems preferably also comprise further cis-regulatory regions such as promoters and terminators and/or selection markers by means of which suitably transformed organisms can be identified. While vir genes and T-DNA sequences are located on the same vector in the case of cointegrated vector systems, binary systems are based on at least two vectors, one of which bears vir genes, but no T-DNA, while a second one bears T-DNA, but no vir gene. Owing to this fact, the last-mentioned vectors are relatively small, easy to manipulate and capable of replication in *E. coli* and in *Agrobacterium*. These binary vectors include vectors from the series pBIB-HYG, pPZP, pBecks, pGreen. Those which are preferably used in accordance with the invention are Bin19, pBI101, pBinAR, pGPTV and pCAMBIA. An overview of binary vectors and their use is given by Hellens et al, Trends in Plant Science (2000) 5, 446-451. The vectors are preferably modified in such a manner, that they already contain the nucleic acid coding for the transitpeptide and that the nucleic acids of the invention, preferentially the nucleic acid sequences encoding the polypeptides shown in table II, application no. 1, columns 5 and 7 can be cloned 3' prime to the transitpeptide encoding sequence, leading to a functional preprotein, which is directed to the plastids and which means that the mature protein fulfills its biological activity.

In a recombinant expression vector, "operable linkage" means that the nucleic acid molecule of interest is linked to the regulatory signals in such a way that expression of the nucleic acid molecule is possible: they are linked to one another in such a way that the two sequences fulfill the predicted function assigned to the sequence (for example in an in-vitro transcription/translation system, or in a host cell if the vector is introduced into the host cell).

The term portion as defined herein refers to a piece of a DNA encoding a CDK, comprising at least 300, 350, 400, 450 or 500, preferably 550, 600, 650 or 700 nucleotides and which portion encodes a polypeptide having cyclin-dependent kinase activity, having a (P/N/A)(S/L/M/F)(T/S/R)(T/S/A)(L/I)RE (SEQ ID NO: 61) motif and having an active site of the following sequence VLHRDLKPQNLLI (SEQ ID NO: 62), wherein D is the predicted catalytic residue and wherein the following modifications of said sequence may occur: position 1: Val→Phe; position 6: Leu→Met; position 9: Gln→Asn. Furthermore said CDK sequence may advantageously have an ATP binding site of the following IGEGTYGVVYRARDKVTNETIALK (found within SEQ ID NO: 63). Also in the ATP binding site some mutations may occur. They are as follows: position 11 Arg→Lys; position 12 Ala→Gly, position 13 Arg→Leu, position 15 Lys→Arg and position 16 Val→Leu, Ala, Ser, Thr or Asn. A portion may be prepared, for example, by making one or more deletions to a CDK nucleic acid. The portions may be used in isolated form or they may be fused to other coding (or non coding) sequences in order to, for example, produce a protein that combines several activities, one of them being cyclin-dependent kinase activity. When fused to other coding sequences, the resulting polypeptide produced upon translation may be bigger than that predicted for the CDK fragment. Preferably, the functional portion is a portion of a CDK nucleic acid, more preferably a portion of the nucleic acid molecule as represented by SEQ ID NO: 45, 47, 49, 51, 53 or 55.

The terms "fragment", "fragment of a sequence" or "part of a sequence" "portion" or "portion thereof" mean a truncated sequence of the original sequence referred to. The truncated sequence (nucleic acid or protein sequence) can vary widely in length; the minimum size being a sequence of sufficient size to provide a sequence with at least a comparable function and/or activity of the original sequence referred to or hybridizing with the nucleic acid molecule of the invention or used in the process of the invention under stringend conditions, while the maximum size is not critical. In some applications, the maximum size usually is not substantially greater than that required to provide the desired activity and/or function(s) of the original sequence.

Typically, the truncated amino acid sequence will range from about 5 to about 310 amino acids in length. More typically, however, the sequence will be a maximum of about 250 amino acids in length, preferably a maximum of about 200 or 100 amino acids. It is usually desirable to select sequences of at least about 10, 12 or 15 amino acids, up to a maximum of about 20 or 25 amino acids.

Another variant of a CDK nucleic acid molecule is a nucleic acid molecule capable of hybridising under reduced stringency conditions, preferably under stringent conditions, with a CDK nucleic acid molecule as hereinbefore defined, which hybridising sequence encodes a CDK polypeptide comprising the abovementioned motifs. Preferably, the hybridising sequence is one that is capable of hybridising to the nucleic acid molecule of SEQ ID NO: 45, 47, 49, 51, 53 or 55, or to a nucleic acid encoding one of the above mentioned homologues, or to a portion of any of the aforementioned sequences. Most preferably, the hybridising sequence is capable of hybridising to the nucleic acid molecule of SEQ ID NO: 45, 47, 49, 51, 53 or 55.

The term "hybridisation" as defined herein is a process wherein substantially homologous complementary nucleotide sequences anneal to each other. The hybridisation process may occur entirely in solution, i.e. both complementary nucleic acids are in solution. The hybridisation process may also occur with one of the complementary nucleic acids immobilised to a matrix such as magnetic beads, Sepharose beads or any other resin. The hybridisation process can furthermore occur with one of the complementary nucleic acids immobilised to a solid support such as a nitro-cellulose or nylon membrane or immobilised by e.g. photolithography to, for example, a siliceous glass support (the latter known as nucleic acid arrays or microarrays or as nucleic acid chips). In order to allow hybridisation to occur, the nucleic acid molecules are generally thermally or chemically denatured to melt a double strand into two single strands and/or to remove hairpins or other secondary structures from single stranded nucleic acids. The stringency of hybridisation is influenced by conditions such as temperature, salt concentration, ionic strength and hybridisation buffer composition.

"Stringent hybridisation conditions" and "stringent hybridisation wash conditions" in the context of nucleic acid hybridisation experiments such as Southern and Northern hybridisations are sequence dependent and are different under different environmental parameters. The skilled artisan is aware of various parameters which may be altered during hybridisation and washing and which will either maintain or change the stringency conditions.

The $T_m$ is the temperature under defined ionic strength and pH, at which 50% of the target sequence hybridises to a perfectly matched probe. The $T_m$ is dependent upon the solution conditions and the base composition and length of the probe. For example, longer sequences hybridise specifically at higher temperatures. The maximum rate of hybridisation is obtained from about 16° C. up to 32° C. below $T_m$. The presence of monovalent cations in the hybridisation solution reduce the electrostatic repulsion between the two nucleic acid strands thereby promoting hybrid formation; this effect is visible for sodium concentrations of up to 0.4M. Formamide reduces the melting temperature of DNA-DNA and DNA-RNA duplexes with 0.6 to 0.7° C. for each percent formamide, and addition of 50% formamide allows hybridisation to be performed at 30 to 45° C., though the rate of hybridisation will be lowered. Base pair mismatches reduce the hybridisation rate and the thermal stability of the duplexes. On average and for large probes, the $T_m$ decreases about 1° C. per % base mismatch. The $T_m$ may be calculated using the following equations, depending on the types of hybrids:

DNA-DNA hybrids (Meinkoth and Wahl, Anal. Biochem., 138: 267-284, 1984):

$$T_m=81.5° C.+16.6\times\log [Na^+]^a+0.41\times\%[G/C^b]-500\times[L^c]^{-1}-0.61\times\% \text{ formamide}$$

DNA-RNA or RNA-RNA hybrids:

$$T_m=79.8+18.5(\log_{10}[Na^+]^a)+0.58 (\%G/C^b)+11.8(\%G/C^b)^2-820/L^c$$

oligo-DNA or oligo-RNA[d] hybrids:

For <20 nucleotides: $T_m=2\ (I_n)$

For 20-35 nucleotides: $T_m=22+1.46\ (I_n)$

[a] or for other monovalent cation, but only accurate in the 0.01-0.4M range.

[b] only accurate for % GC in the 30% to 75% range.

[c] L =length of duplex in base pairs.

[d] Oligo, oligonucleotide; $I_n$, effective length of primer =(no. of A/T).

Note: for each 1% formamide, the $T_m$ is reduced by about 0.6 to 0.7° C., while the presence of 6M urea reduces the $T_m$ by about 30° C.

Specificity of hybridisation is typically the function of post-hybridisation washes. To remove background resulting from non-specific hybridisation, samples are washed with dilute salt solutions. Critical factors of such washes include the ionic strength and temperature of the final wash solution: the lower the salt concentration and the higher the wash temperature, the higher the stringency of the wash. Wash conditions are typically performed at or below hybridisation stringency. Generally, suitable stringent conditions for nucleic acid hybridisation assays or gene amplification detection procedures are as set forth above. More or less stringent conditions may also be selected. Generally, low stringency conditions are selected to be about 50° C. lower than the thermal melting point ($T_m$) for the specific sequence at a defined ionic strength and pH. Medium stringency conditions are when the temperature is 20° C. below $T_m$, and high stringency conditions are when the temperature is 10° C. below $T_m$. For example, stringent conditions are those that are at least as stringent as, for example, conditions A-L; and reduced stringency conditions are at least as stringent as, for example, conditions M-R. Non-specific binding may be controlled using any one of a number of known techniques such as, for example, blocking the membrane with protein containing solutions, additions of heterologous RNA, DNA, and SDS to the hybridisation buffer, and treatment with Rnase.

Examples of hybridisation and wash conditions are listed in Table 1:

cies. The nucleic acid may be isolated from a monocotyledonous species, preferably from the family Poaceae, further preferably from *Oryza sativa* or *Zea mays*. More preferably, the CDK isolated from *Oryza sativa* is SEQ ID NO: 45 or from *Zea mays* and is SEQ ID NO: 53. In another embodiment of the invention the nucleic acid may be isolated from a dicotyledonous species, preferably from the family Brassicaceae, Aceraceae, Linaceae or Asteraceae further preferably from *Brassica napus, Glycine max, Linum usitatissimum* or *Helianthus annuus*. More preferably, the CDK isolated from *Brassica napus* is SEQ ID NO: 47, *Glycine max* is SEQ ID NO: 49, *Linum usitatissimum* is SEQ ID NO: 51 or *Helianthus annuus* is SEQ ID NO: 55.

TABLE 1

| Stringency Condition | Polynucleotide Hybrid± | Hybrid Length (bp)‡ | Hybridization Temperature and Buffer† | Wash Temperature and Buffer† |
|---|---|---|---|---|
| A | DNA:DNA | >or equal to 50 | 65° C. 1 × SSC; or 42° C., 1 × SSC and 50% formamide | 65° C.; 0.3 × SSC |
| B | DNA:DNA | <50 | Tb*; 1 × SSC | Tb*; 1 × SSC |
| C | DNA:RNA | >or equal to 50 | 67° C. 1 × SSC; or 45° C., 1 × SSC and 50% formamide | 67° C.; 0.3 × SSC |
| D | DNA:RNA | <50 | Td*; 1 × SSC | Td*; 1 × SSC |
| E | RNA:RNA | >or equal to 50 | 70° C. 1 × SSC; or 50° C., 1 × SSC and 50% formamide | 70° C.; 0.3 × SSC |
| F | RNA:RNA | <50 | Tf*; 1 × SSC | Tf*; 1 × SSC |
| G | DNA:DNA | >or equal to 50 | 65° C. 4 × SSC; or 45° C., 4 × SSC and 50% formamide | 65° C.; 1 × SSC |
| H | DNA:DNA | <50 | Th*; 4 × SSC | Th*; 4 × SSC |
| I | DNA:RNA | >or equal to 50 | 67° C. 4 × SSC; or 45° C., 4 × SSC and 50% formamide | 67° C.; 1 × SSC |
| J | DNA:RNA | <50 | Tj*; 4 × SSC | Tj*; 4 × SSC |
| K | RNA:RNA | >or equal to 50 | 70° C. 4 × SSC; or 40° C., 6 × SSC and 50% formamide | 67° C.; 1 × SSC |
| L | RNA:RNA | <50 | Tl*; 2 × SSC | Tl*; 2 × SSC |
| M | DNA:DNA | >or equal to 50 | 50° C. 4 × SSC; or 40° C., 6 × SSC and 50% formamide | 50° C.; 2 × SSC |
| N | DNA:DNA | <50 | Tn*; 6 × SSC | Tn*; 6 × SSC |
| O | DNA:RNA | >or equal to 50 | 55° C. 4 × SSC; or 42° C., 6 × SSC and 50% formamide | 55° C.; 2 × SSC |
| P | DNA:RNA | <50 | Tp*; 6 × SSC | Tp*; 6 × SSC |
| Q | RNA:RNA | >or equal to 50 | 60° C. 4 × SSC; or 45° C., 6 × SSC and 50% formamide | 60° C.; 2 × SSC |
| R | RNA:RNA | <50 | Tr*; 4 × SSC | Tr*; 4 × SSC |

‡The "hybrid length" is the anticipated length for the hybridising nucleic acid. When nucleic acids of known sequence are hybridised, the hybrid length may be determined by aligning the sequences and identifying the conserved regions described herein.
†SSPE (1 × SSPE is 0.15M NaCl, 10 mM $NaH_2PO_4$, and 1.25 mM EDTA, pH 7.4) may be substituted for SSC (1 × SSC is 0.15M NaCl and 15 mM sodium citrate) in the hybridisation and wash buffers; washes are performed for 15 minutes after hybridisation is complete. The hybridisations and washes may additionally include 5x Denhardt's reagent, 0.5-1.0% SDS, 100 μg/ml denatured, fragmented salmon sperm DNA, 0.5% sodium pyrophosphate, and up to 50% formamide.
*Tb-Tr: The hybridisation temperature for hybrids anticipated to be less than 50 base pairs in length should be 5-10° C. less than the melting temperature $T_m$ of the hybrids; the $T_m$ is determined according to the above-mentioned equations.
±The present invention also encompasses the substitution of any one, or more DNA or RNA hybrid partners with either a PNA, or a modified nucleic acid.

For the purposes of defining the level of stringency, reference may conveniently be made to Sambrook et al. (2001) Molecular Cloning: a laboratory manual, $3^{rd}$ Edition Cold Spring Harbor Laboratory Press, CSH, New York or to Current Protocols in Molecular Biology, John Wiley & Sons, N.Y. (1989).

After hybridisation and washing, the duplexes may be detected by autoradiography (when radiolabeled probes were used) or by chemiluminescence, immunodetection, by fluorescent or chromogenic detection, depending on the type of probe labelling. Alternatively, a ribonuclease protection assay may be performed for detection of RNA:RNA hybrids.

The CDK nucleic acid molecule or variant thereof may be derived from any plant or artificial source. This nucleic acid may be modified from its native form in composition and/or genomic environment through deliberate human manipulation. The nucleic acid is preferably of plant origin, whether from the same plant species (for example to the one in which it is to be introduced) or whether from a different plant spe- The activity of a CDK polypeptide or a homologue thereof and/or expression of a nucleic acid encoding such a CDK may be modulated by introducing a genetic modification (preferably in the locus of a CDK gene). The locus of a gene as defined herein is taken to mean a genomic region, which includes the gene of interest and 10 kb up- or downstream of the coding region.

The genetic modification may be introduced, for example, by any one (or more) of the following methods: TILLING, site-directed mutagenesis, directed evolution and homologous recombination or by introducing and expressing in a plant a nucleic acid encoding a CDK polypeptide or a homologue thereof, which CDK or homologue comprises a motif as mentioned above. Following introduction of the genetic modification there follows a step of selecting for increased expression of a nucleic acid encoding a CDK polypeptide with a motif as mentioned above and/or selecting for increased activity of said CDK polypeptide, which increase in expression and/or activity gives plants having improved growth characteristics.

A genetic modification may also be introduced in the locus of a CDK gene using the technique of TILLING (Targeted Induced Local Lesions In Genomes). This is a mutagenesis technology useful to generate and/or identify, and to eventually isolate mutagenised variants of a nucleic acid molecule encoding a CDK with sequences as mentioned herein capable of exhibiting cyclin-dependent kinase activity. TILLING also allows selection of plants carrying such mutant variants. TILLING combines high-density mutagenesis with high-throughput screening methods. The steps typically followed in TILLING are: (a) EMS mutagenesis (Redei and Koncz (1992), In: C Koncz, N-H Chua, J Schell, eds, Methods in *Arabidopsis* Research. World Scientific, Singapore, pp 16-82; Feldmann et al., (1994) In: E M Meyerowitz, C R Somerville, eds, *Arabidopsis*. Cold Spring Harbor Laboratory Press, Cold Spring Harbor, N.Y., pp 137-172; Lightner and Caspar (1998), In: J Martinez-Zapater, J Salinas, eds, Methods on Molecular Biology, Vol. 82. Humana Press, Totowa, N.J., pp 91-104); (b) DNA preparation and pooling of individuals; (c) PCR amplification of a region of interest; (d) denaturation and annealing to allow formation of heteroduplexes; (e) DHPLC, where the presence of a heteroduplex in a pool is detected as an extra peak in the chromatogram; (f) identification of the mutant individual; and (g) sequencing of the mutant PCR product. Methods for TILLING are well known in the art (McCallum Nature Biotechnol. 18, 455-457, 2000, Stemple Nature Rev. Genet. 5, 145-150, 2004).

Site-directed mutagenesis may be used to generate variants of CDK nucleic acids or portions thereof that retain activity (such as cyclin-dependent kinase activity). Several methods are available to achieve site-directed mutagenesis, the most common being PCR based methods (See for example Ausubel et al., Current Protocols in Molecular Biology. Wiley Eds. www.4ulr.com/products/currentprotocols/index.html).

Directed evolution may also be used to generate variants of CDK nucleic acids. This consists of iterations of DNA shuffling followed by appropriate screening and/or selection to generate variants of CDK nucleic acids or portions thereof encoding CDK polypeptides or homologues or portions thereof having a modified biological activity (Castle et al., (2004) Science 304 (5674): 1151-4; U.S. Pat. No. 5,811,238 and U.S. Pat. No. 6,395,547).

TILLING, site-directed mutagenesis and directed evolution are examples of technologies that enable the generation novel alleles and variants of CDK that retain CDK function and which are therefore useful in the methods of the invention.

Homologous recombination allows introduction in a genome of a selected nucleic acid at a defined selected position. Homologous recombination is a standard technology used routinely in biological sciences for lower organism such as yeast or the moss *Physcomitrella*. Methods for performing homologous recombination in plants have been described not only for model plants (Offring a et al. (1990) EMBO J. 9, 3077-3084) but also for crop plants, for example rice (Terada et al., (2002) Nature Biotechnol. 20, 1030-1034; or Iida and Terada (2004) Curr. Opin. Biotechnol. 15, 132-138). The nucleic acid to be targeted (which may be a CDK nucleic acid molecule or variant thereof as hereinbefore defined) need not be targeted to the locus of a CDK gene, but may be introduced in, for example, regions of high expression. The nucleic acid to be targeted may be an improved allele used to replace the endogenous gene or may be introduced in addition to the endogenous gene.

A preferred method for introducing a genetic modification (which in this case need not be in the locus of a CDK gene) is to introduce and express in a plant a nucleic acid encoding a CDK polypeptide, or a homologue thereof. A CDK polypeptide or a homologue thereof as mentioned above, and suitable for practising the present invention, is one having cyclin-dependent kinase activity and, in increasing order of preference, having at least 75%, 80%, 85%, 90%, 95%, 96%, 97%, 98%, 99% or more sequence identity to the amino acid sequence represented by 46, 48, 50, 52, 54 or 56, and which CDK polypeptide comprises a motif as described herein. The nucleic acid to be introduced into a plant may be a portion or a hybridising sequence as hereinbefore defined.

"Homologues" of a protein encompass peptides, oligopeptides, polypeptides, proteins and enzymes having amino acid substitutions, deletions and/or insertions relative to the unmodified protein in question and having similar biological and functional activity as the unmodified protein from which they are derived. That means they have a common ancestor.

Encompassed by the term "homologues" are orthologous and paralogous sequences, two special forms of homology, which encompass evolutionary concepts used to describe ancestral relationships of genes. Preferably the orthologues and paralogues useful in the present invention have the same structure and activity as a CDK and have the highest similarity to SEQ ID NO: 46, 48, 50, 52, 54 or 56 in a reciprocal BLAST search.

The term "paralogues" relates to homologous genes that result from one or more gene duplications within the genome of a species. Paralogues of a CDK may easily be identified by performing a BLAST analysis against a set of sequences from the same species as the query sequence.

The term "orthologues" relates to homologous genes in different organisms due to ancestral relationship of these genes. Orthologues in, for example, monocot or dicot plant species may easily be found by performing a so-called reciprocal blast search. This may be done by a first blast involving blasting the sequence in question (for example, SEQ ID NO 45, 47, 49, 51, 53 or 55, being from the monocotyledonous species *Oryza sativa* or *Zea mays* or the dicotyledonous species *Brassica napus, Glycine max, Linum usitatissimum* or *Helianthus annuus*) against any sequence database, such as the publicly available NCBI database which may be found at: www.ncbi.nlm.nih.gov. BLASTn or tBLASTX may be used when starting from nucleotides or BLASTP or TBLASTN when starting from the protein, with standard default values. The blast results may be filtered. The full-length sequences of either the filtered results or the non-filtered results are then blasted back (second blast) against the sequences of the organism from which the sequence in question is derived, in casu *Oryza sativa, Zea mays, Brassica napus, Glycine max, Linum usitatissimum* or *Helianthus annuus*. The results of the first and second blasts are then compared. A paralogue is identified if a high-ranking hit from the second blast is from the same species as from which the query sequence is derived; an orthologue is identified if a highest ranking hit is not from the same species as from which the query sequence is derived. Such paralogue or orthologue is also considered a homologue of CDK, provided that this homologue comprises a serine/threonine kinase domain and comprises a (P/N/A)(S/L/M/F)(T/S/R)(T/S/A)(L/I)RE (SEQ ID NO: 61) motif. In the case of large families, ClustalW may be used, followed by the construction of a neighbour joining tree, to help visualize the clustering of related genes and identify orthologues and paralogues.

A homologue may be in the form of a "substitutional variant" of a protein, i.e. where at least one residue in an amino acid sequence has been removed and a different residue inserted in its place. Amino acid substitutions are typically of single residues, but may be clustered depending upon functional constraints placed upon the polypeptide; insertions will usually be of the order of about 1, 2, 3, 4 or 5, preferably 6, 7, 8, 9 or 10 amino acid residues. Preferably, amino acid substitutions comprise conservative amino acid substitutions (Table 2). To produce such homologues, amino acids of the protein may be replaced by other amino acids having similar properties (such as similar hydrophobicity, hydrophilicity, antigenicity, propensity to form or break α-helical structures or β-sheet structures). Conservative substitution tables are well known in the art (see for example Creighton (1984) Proteins. W.H. Freeman and Company). The substitutional variant useful in the methods of the present invention is a substitutional variant of a CDK polypeptide and comprises a (P/N/A)(S/L/M/F)(T/S/R)(T/S/A)(L/I)RE (SEQ ID NO: 61) motif and the other motifs mentioned above.

TABLE 2

Examples of conserved amino acid substitutions:

| Residue | Conservative Substitutions |
|---|---|
| Ala | Ser |
| Arg | Lys |
| Asn | Gln; His |
| Asp | Glu |
| Gln | Asn |
| Cys | Ser |
| Glu | Asp |
| Gly | Pro |
| His | Asn; Gln |
| Ile | Leu, Val |
| Leu | Ile; Val |
| Lys | Arg; Gln |
| Met | Leu; Ile |
| Phe | Met; Leu; Tyr |
| Ser | Thr; Gly |
| Thr | Ser; Val |
| Trp | Tyr |
| Tyr | Trp; Phe |
| Val | Ile; Leu |

Less conserved substitutions may be made in case the above-mentioned amino acid properties are not so critical.

A homologue may also be in the form of an "insertional variant" of a protein, i.e. where one or more amino acid residues are introduced into a predetermined site in a protein. Insertions may comprise amino-terminal and/or carboxy-terminal fusions as well as intra-sequence insertions of single or multiple amino acids. Generally, insertions within the amino acid sequence will be smaller than amino- or carboxy-terminal fusions, of the order of about 1 to 10 residues. Examples of amino- or carboxy-terminal fusion proteins or peptides include the binding domain or activation domain of a transcriptional activator as used in the yeast two-hybrid system, phage coat proteins, (histidine)6-tag, glutathione S-transferase-tag, protein A, maltose-binding protein, dihydrofolate reductase, Tag 100 epitope, c-myc epitope, FLAG®-epitope, lacZ, CMP (calmodulin-binding peptide), HA epitope, protein C epitope and VSV epitope. The insertional variant useful in the methods of the present invention is an insertional variant of a CDK polypeptide and comprises the motifs mentioned herein.

Homologues in the form of "deletion variants" of a protein are characterised by the removal of one or more amino acids from a protein, and encompass active fragments.

Amino acid variants of a protein may readily be made using peptide synthetic techniques well known in the art, such as solid phase peptide synthesis and the like, or by recombinant DNA manipulations. Methods for the manipulation of DNA sequences to produce substitution, insertion or deletion variants of a protein are well known in the art. For example, techniques for making mutations at predetermined sites in DNA are well known to those skilled in the art and include M13 mutagenesis, T7-Gen in vitro mutagenesis (USB, Cleveland, Ohio), QuickChange Site Directed mutagenesis (Stratagene, San Diego, Calif.), PCR-mediated site-directed mutagenesis or other site-directed mutagenesis protocols.

The CDK polypeptide or homologue thereof with a (P/N/A)(S/L/M/F)(T/S/R)(T/S/A)(L/I)RE (SEQ ID NO: 61) motif, may also be a derivative. "Derivatives" include peptides, oligopeptides, polypeptides, proteins and enzymes which may comprise substitutions, deletions or additions of naturally and non-naturally occurring amino acid residues compared to the amino acid sequence of a naturally-occurring form of the protein, for example, as presented in in sequences 46, 48, 50, 52, 54 or 56. "Derivatives" of a protein encompass peptides, oligopeptides, polypeptides, proteins and enzymes which may comprise naturally occurring altered, glycosylated, acylated or non-naturally occurring amino acid residues compared to the amino acid sequence of a naturally-occurring form of the polypeptide. A derivative may also comprise one or more non-amino acid substituents compared to the amino acid sequence from which it is derived, for example a reporter molecule or other ligand, covalently or non-covalently bound to the amino acid sequence, such as a reporter molecule which is bound to facilitate its detection, and non-naturally occurring amino acid residues relative to the amino acid sequence of a naturally-occurring protein. The derivative useful in the methods of the present invention is a derivative of a CDK polypeptide, having the biological activity of the CDKs and the motifs mentioned herein.

The CDK type kinases in plants have a modular structure, consisting of an N-lobe and a C-lobe comprising a catalytic cleft and a T-loop (De Bondt et al. 1993). Therefore, it is envisaged that engineering of the domains of the kinase in such a way that the activity of the CDK protein is retained or modified, may result in the creation of a CDKA mutant that is useful for performing the methods of the invention. A preferred type of variant includes those generated by domain deletion, stacking or shuffling (see for example He et al., Science 288, 2360-2363, 2000; or U.S. Pat. Nos. 5,811,238 and 6,395,547), provided that the resulting CDK comprises a (P/N/A)(S/L/M/F)(T/S/R)(T/S/A)(L/I)RE (SEQ ID NO: 61), ATP binding and active center motif.

The CDK polypeptide or homologue thereof may be encoded by an alternative splice variant of a CDK nucleic acid molecule or gene. The term "alternative splice variant" as used herein encompasses variants of a nucleic acid sequence in which selected introns and/or exons have been excised, replaced or added. Such variants will be ones that encode polypeptides that comprise mutations and in which the biological activity of the protein is retained, which may be achieved by selectively retaining functional segments of the protein. Such splice variants may be found in nature or may be manmade. Methods for making such splice variants are well known in the art. Preferred splice variants are splice variants derived from the nucleic acid represented by SEQ ID NO 45, 47, 49, 51, 53 or 55. Further preferred are splice variants encoding a polypeptide retaining cyclin-dependent kinase activity and having the motifs as mentioned herein.

The homologue may also be encoded by an allelic variant of a nucleic acid encoding a CDK polypeptide or a homologue thereof, preferably an allelic variant of the nucleic acid represented by SEQ ID NO 45, 47, 49, 51, 53 or 55, provided that the polypeptide encoded by the allelic variant has cyclin-dependent kinase activity and comprises the motifs as mentioned above. Allelic variants exist in nature and encompassed within the methods of the present invention is the use of these natural alleles. Allelic variants encompass Single Nucleotide Polymorphisms (SNPs), as well as Small Insertion/Deletion Polymorphisms (INDELs). The size of INDELs is usually less than 100 bp. SNPs and INDELs form the largest set of sequence variants in naturally occurring polymorphic strains of most organisms.

According to a preferred aspect of the present invention, enhanced or increased expression of the CDK nucleic acid molecule or variant thereof according to the invention is envisaged. Methods for obtaining enhanced or increased expression (overexpression) of genes or gene products are well documented in the art and include, for example, overexpression driven by appropriate promoters, the use of transcription enhancers or translation enhancers. Isolated nucleic acids which serve as promoter or enhancer elements may be introduced in an appropriate position (typically upstream) of a non-heterologous form of a polynucleotide so as to upregulate expression of a CDK nucleic acid or variant thereof according to the invention. For example, endogenous promoters may be altered in vivo by mutation, deletion, and/or substitution (see, Kmiec, U.S. Pat. No. 5,565,350; Zarling et al., PCT/US93/03868), or isolated promoters may be introduced into a plant cell in the proper orientation and distance from a gene modified according to the present invention so as to control the expression of the gene.

If polypeptide expression is desired, it is generally desirable to include a polyadenylation region at the 3'-end of a polynucleotide coding region. The polyadenylation region may be derived from the natural gene, from a variety of other plant genes, or from T-DNA. The 3' end sequence to be added may be derived from, for example, the nopaline synthase or octopine synthase genes, or alternatively from another plant gene, or less preferably from any other eukaryotic gene.

An intron sequence may also be added to the 5' untranslated region or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg, Mol. Cell Biol. 8, 4395-4405 (1988); Callis et al., Genes Dev. 1, 1183-1200 (1987)). Such intron enhancement of gene expression is typically greatest when placed near the 5' end of the transcription unit. Use of the maize introns Adh1-S intron 1, 2, and 6, the Bronze-1 intron are known in the art. See generally, The Maize Handbook, Chapter 116, Freeling and Walbot, Eds., Springer, N.Y. (1994).

The invention also provides genetic constructs and vectors to facilitate introduction and/or expression of the nucleotide sequences useful in the methods according to the invention.

Therefore, there is provided a gene construct comprising:

(i) a CDK nucleic acid molecule or functional variant thereof, which nucleic acid or variant encodes a CDK comprising a (P/N/A)(S/L/M/F)(T/S/R)(T/S/A)(L/I)RE (SEQ ID NO: 61), ATP binding and active site motif;

(ii) one or more control sequence(s) capable of driving expression in a plant of the nucleic acid sequence of (i); and optionally (iii) a transcription termination sequence.

Constructs useful in the methods according to the present invention may be constructed using recombinant DNA technology well known to persons skilled in the art. The gene constructs may be inserted into vectors, which may be commercially available, suitable for transforming into plants and suitable for expression of the gene of interest in the transformed cells.

Plants are transformed with a vector comprising the sequence of interest (i.e., a CDK nucleic acid or variant thereof according to the present invention). The sequence of interest is operably linked to one or more control sequences (at least to a promoter). The terms "regulatory element", "regulatory sequence(s)", "control sequence" and "promoter" are all used interchangeably herein and are to be taken in a broad context to refer to regulatory nucleic acid sequences capable of effecting expression of the sequences to which they are ligated. Encompassed by the aforementioned terms are transcriptional regulatory sequences derived from a classical eukaryotic genomic gene (including the TATA box which is required for accurate transcription initiation, with or without a CCAAT box sequence) and additional regulatory elements (i.e. upstream activating sequences, enhancers and silencers) which modulate gene expression in response to developmental and/or external stimuli, or in a tissue-specific manner. Also included within the term is a transcriptional regulatory sequence of a classical prokaryotic gene, in which case it may include a −35 box sequence and/or −10 box transcriptional regulatory sequences. The term "regulatory element" also encompasses a synthetic fusion molecule or derivative, which confers, activates or enhances expression of a nucleic acid molecule in a cell, tissue or organ. The term "operably linked" as used herein refers to a functional linkage between the promoter sequence and the gene of interest, such that the promoter sequence is able to initiate transcription of the gene of interest.

Regulatory sequences can be operatively linked to the coding sequence of an endogenous or transgenic protein and control its transcription and/or translation or the stability or decay of the encoding mRNA or the expressed protein. In order to modify and control the expression of a coding sequence its regulatory elements such as promoters, UTRs, splicing sites, processing signals, polyadenylation sites, terminators, enhancers, inductors, repressors, post transcriptional or posttranslational modification sites can be changed, added or amended. The regulatory sequences include, in particular, plant sequences like the herein-described promoters and terminators. For example, the activation of plant genes by random integrations of enhancer elements has been described by Hayashi et al., 1992 (Science 258:1350-1353) or Weigel et al., 2000 (Plant Physiol. 122, 1003-1013) and others cited therein. For example, the expression level of the endogenous protein can be modulated by replacing the endogenous promoter with a stronger transgenic promoter or by replacing the endogenous 3'UTR with a 3'UTR, which provides more stability without amending the coding region. Further, the transcriptional regulation can be modulated by introduction of an artificial transcription factor as described in the examples. Alternative promoters, terminators and UTR are described below.

Regulatory sequences are intended to enable the specific expression of the genes and the expression of protein. Depending on the host plant, this may mean, for example, that the gene is expressed and/or overexpressed after induction only, or that it is expressed and/or overexpressed constitutively. These regulatory sequences are, for example, sequences to which the inductors or repressors bind and which thus regulate the expression of the nucleic acid. In addition to these novel regulatory sequences, or instead of these sequences, the natural regulation of these sequences may still be present before the actual structural genes and, if appropriate, may have been genetically modified so that the natural regulation has been switched off and gene expression has been increased. As a rule, said regulatory sequences are located upstream (5'), within, and/or downstream (3') relative to the coding sequence of the nucleic acid sequence, which shall be expressed. However, the nucleic acid construct (=expression cassette, expression construct or gene construct) used in the inventive process and described herein can also be simpler in construction, that is to say no additional regulatory signals have been inserted before the nucleic acid sequence or its derivatives, and the natural promoter together with its regulation has not been removed. Instead, the natural regulatory sequence has been mutated in such a way that regulation no longer takes place and/or gene expression is increased. These modified promoters can also be introduced on their own before the natural gene in the form of part sequences (=promoter with parts of the nucleic acid sequences according to the invention) in order to increase the activity. Moreover, the gene construct can advantageously also comprise one or more of what are known as enhancer sequences in operable linkage with the promoter, and these enable an increased expression of the nucleic acid sequence. Also, it is possible to insert additional advantageous sequences at the 3' end of the DNA sequences, such as, for example, further regulatory elements or terminators.

Regulatory sequences include transcription and translation regulating sequences or signals, e.g. sequences located upstream (5'), which concern in particular the regulation of transcription or translation initiation, such as promoters or start codons, and sequences located downstream (3'), which concern in particular the regulation of transcription or translation termination and transcript stability, such as polyadenylation signals or stop codons. Regulatory sequences can also be present in transcribed coding regions as well in transcribed non-coding regions, e.g. in introns, as for example splicing sites, promoters for the regulation of expression of the nucleic acid molecule according to the invention in a cell and which can be employed are, in principle, all those which are capable of stimulating the transcription of genes in the plants in question. A “coding sequence” is a nucleotide sequence, which is transcribed into mRNA and/or translated into a polypeptide when placed under the control of appropriate regulatory sequences. The boundaries of the coding sequence are determined by a translation start codon at the 5'-terminus and a translation stop codon at the 3'-terminus. A coding sequence can include, but is not limited to mRNA, cDNA, recombinant nucleotide sequences or genomic DNA, while introns may be present as well under certain circumstances.

The regulatory sequences or factors can, as described above, have a positive effect on, the expression of the genes introduced, thus increasing their expression. Thus, an enhancement of the expression can advantageously take place at the transcriptional level by using strong transcription signals such as strong promoters and/or strong enhancers. In addition, enhancement of expression on the translational level is also possible, for example by introducing translation enhancer sequences, e.g., the Ω enhancer e.g. improving the ribosomal binding to the transcript, or by increasing the stability of the mRNA, e.g. by replacing the 3'UTR coding region by a region encoding a 3'UTR known as conferring an high stability of the transcript or by stabilization of the transcript through the elimination of transcript instability, so that the mRNA molecule is translated more often than the wild type. For example in plants AU-rich elements (AREs) and DST (downstream) elements destabilized transcripts. Mutagenesis studies have demonstrated that residues within two of the conserved domains, the ATAGAT and the GTA regions, are necessary for instability function. Therefore removal or mutation of such elements would obviously lead to more stable transcripts, higher transcript rates and higher protein activity. Translation enhancers are also the “overdrive sequence”, which comprises the tobacco mosaic virus 5'-untranslated leader sequence and which increases the protein/RNA ratio (Gallie et al., 1987, Nucl. Acids Research 15:8693-8711).

Enhancers are generally defined as cis active elements, which can stimulate gene transcription independent of position and orientation. Different enhancers have been identified in plants, which can either stimulate transcription constitutively, or tissue or stimuli specific. Well known examples for constitutive enhancers are the enhancer from the 35S promoter (Odell et al., 1985, Nature 313:810-812) or the ocs enhancer (Fromm et al., 1989, Plant Cell 1: 977:984). Another examples are the G-Box motif tetramer which confers high-level constitutive expression in dicot and monocot plants (Ishige et al., 1999, Plant Journal, 18, 443-448) or the petE, a A/T-rich sequence which act as quantitative enhancers of gene expression in transgenic tobacco and potato plants (Sandhu et al., 1998; Plant Mol. Biol. 37 (5):885-96). Beside that, a large variety of cis-active elements have been described which contribute to specific expression pattern, like organ specific expression or induced expression in response to biotic or abiotic stress. Examples are elements, which provide pathogen or wound-induced expression (Rushton, 2002, Plant Cell, 14, 749-762) or guard cell-specific expression (Plesch, 2001, Plant Journal 28, 455-464).

Advantageously, any type of promoter may be used to drive expression of the nucleic acid sequence. The promoter may be an inducible promoter, i.e. having induced or increased transcription initiation in response to a developmental, chemical, environmental or physical stimulus. Additionally or alternatively, the promoter may be a constitutive promoter, i.e. a promoter that is expressed predominantly in at least one tissue or organ and predominantly at any life stage of the plant. Additionally or alternatively, the promoter may be a tissue-preferred or cell-preferred promoter, i.e. one that is capable of preferentially initiating transcription in certain tissues, such as the leaves, roots, seed tissue etc, or even in specific cells. Promoters able to initiate transcription only in certain tissues or cells are respectively referred to herein as “tissue-specific”, and “cell-specific”.

Suitable promoters, which are functional in these plants, are generally known. They may take the form of constitutive or inducible promoters. Suitable promoters can enable the development- and/or tissue-specific expression in multi-celled eukaryotes; thus, leaf-, root-, flower-, seed-, stomata-, tuber- or fruit-specific promoters may advantageously be used in plants.

Different plant promoters usable in plants are promoters such as, for example, the USP, the LegB4-, the DC3 promoter or the ubiquitin promoter from parsley.

A “plant” promoter comprises regulatory elements, which mediate the expression of a coding sequence segment in plant cells. Accordingly, a plant promoter need not be of plant origin, but may originate from viruses or microorganisms, in particular for example from viruses which attack plant cells.

The “plant” promoter can also originates from a plant cell, e.g. from the plant, which is transformed with the nucleic acid sequence to be expressed in the inventive process and described herein.

This also applies to other “plant” regulatory signals, for example in “plant” terminators.

For expression in plants, the nucleic acid molecule must, as described above, be linked operably to or comprise a suitable promoter which expresses the gene at the right point in time and in a cell- or tissue-specific manner. Usable promoters are constitutive promoters (Benfey et al., EMBO J. 8 (1989) 2195-2202), such as those which originate from plant viruses, such as 35S CAMV (Franck et al., Cell 21 (1980) 285-294), 19S CaMV (see also U.S. Pat. No. 5,352,605 and WO 84/02913), 34S FMV (Sanger et al., Plant. Mol. Biol., 14, 1990: 433-443), the parsley ubiquitin promoter, or plant promoters such as the Rubisco small subunit promoter described in U.S. Pat. No. 4,962,028 or the plant promoters PRP1 [Ward et al., Plant. Mol. Biol. 22 (1993)], SSU, PGEL1, OCS [Leisner (1988) Proc Natl Acad Sci USA 85 (5): 2553-2557], lib4, usp, mas [Comai (1990) Plant Mol Biol 15 (3):373-381], STLS1, ScBV (Schenk (1999) Plant Mol Biol 39(6):1221-1230), B33, SAD1 or SAD2 (flax promoters, Jain et al., Crop Science, 39 (6), 1999: 1696-1701) or nos [Shaw et al. (1984) Nucleic Acids Res. 12 (20):7831-7846]. Further examples of constitutive plant promoters are the sugarbeet V-ATPase promoters (WO 01/14572). Examples of synthetic constitutive promoters are the Super promoter (WO 95/14098) and promoters derived from G-boxes (WO 94/12015). If appropriate, chemical inducible promoters may furthermore also be used, compare EP-A 388186, EP-A 335528, WO 97/06268. Stable, constitutive expression of the proteins according to the invention a plant can be advantageous. However, inducible expression of the polypeptide of the invention is advantageous, if a late expression before the harvest is of advantage, as metabolic manipulation may lead to plant growth retardation.

The expression of plant genes can also be facilitated via a chemical inducible promoter (for a review, see Gatz 1997, Annu. Rev. Plant Physiol. Plant Mol. Biol., 48:89-108). Chemically inducible promoters are particularly suitable when it is desired to express the gene in a time-specific manner. Examples of such promoters are a salicylic acid inducible promoter (WO 95/19443), and abscisic acid-inducible promoter (EP 335 528), a tetracyclin-inducible promoter (Gatz et al. (1992) Plant J. 2, 397-404), a cyclohexanol- or ethanol-inducible promoter (WO 93/21334) or others as described herein.

Other suitable promoters are those which react to biotic or abiotic stress conditions, for example the pathogen-induced PRP1 gene promoter (Ward et al., Plant. Mol. Biol. 22 (1993) 361-366), the tomato heat-inducible hsp80 promoter (U.S. Pat. No. 5,187,267), the potato chill-inducible alpha-amylase promoter (WO 96/12814) or the wound-inducible pinII promoter (EP-A-0 375 091) or others as described herein.

Preferred promoters are in particular those which bring gene expression in tissues and organs, in seed cells, such as endosperm cells and cells of the developing embryo. Suitable promoters are the oilseed rape napin gene promoter (U.S. Pat. No. 5,608,152), the *Vicia faba* USP promoter (Baeumlein et al., Mol Gen Genet, 1991, 225 (3): 459-67), the *Arabidopsis* oleosin promoter (WO 98/45461), the *Phaseolus vulgaris* phaseolin promoter (U.S. Pat. No. 5,504,200), the *Brassica* Bce4 promoter (WO 91/13980), the bean arc5 promoter, the carrot DcG3 promoter, or the Legumin B4 promoter (LeB4; Baeumlein et al., 1992, Plant Journal, 2 (2): 233-9), and promoters which bring about the seed-specific expression in monocotyledonous plants such as maize, barley, wheat, rye, rice and the like. Advantageous seed-specific promoters are the sucrose binding protein promoter (WO 00/26388), the phaseolin promoter and the napin promoter. Suitable promoters which must be considered are the barley Ipt2 or Ipt1 gene promoter (WO 95/15389 and WO 95/23230), and the promoters described in WO 99/16890 (promoters from the barley hordein gene, the rice glutelin gene, the rice oryzin gene, the rice prolamin gene, the wheat gliadin gene, the wheat glutelin gene, the maize zein gene, the oat glutelin gene, the sorghum kasirin gene and the rye secalin gene). Further suitable promoters are Amy32b, Amy 6-6 and Aleurain [U.S. Pat. No. 5,677,474], Bce4 (oilseed rape) [U.S. Pat. No. 5,530,149], glycinin (soya) [EP 571 741], phosphoenolpyruvate carboxylase (soya) [JP 06/62870], ADR12-2 (soya) [WO 98/08962], isocitrate lyase (oilseed rape) [U.S. Pat. No. 5,689,040] or α-amylase (barley) [EP 781 849]. Other promoters which are available for the expression of genes in plants are leaf-specific promoters such as those described in DE-A 19644478 or light-regulated promoters such as, for example, the pea petE promoter.

Further suitable plant promoters are the cytosolic FBPase promoter or the potato ST-LSI promoter (Stockhaus et al., EMBO J. 8, 1989, 2445), the *Glycine max* phospho-ribosylpyrophosphate amidotransferase promoter (GenBank Accession No. U87999) or the node-specific promoter described in EP-A-0 249 676.

Preferably, the CDK nucleic acid or variant thereof according to the invention is operably linked to a shoot-specific promoter. The term "shoot-specific" as defined herein refers to a promoter that is expressed predominantly in the shoot and at any stage in the life of the plant. The term "shoot" as used in herein encompasses all aerial parts of the plant, including stems and branches, leaves, buds, reproductive organs, including shoot-derived structures such as stolons, corms, rhizomes or tubers. Preferably, the shoot-specific promoter capable of preferentially expressing the nucleic acid throughout the shoot is a weak promoter. Promoter strength and/or expression pattern may be analysed for example by coupling the promoter to a reporter gene and assaying the expression of the reporter gene in various tissues of the plant. One suitable reporter gene well known to persons skilled in the art is beta-glucuronidase. Promoter strength and/or expression pattern can then be compared to that of a well-characterised shoot-specific reference promoter, such as the Cab27 promoter (weak expression, GenBank AP004700), or the putative protochlorophyllid reductase promoter (strong expression, GenBank AL606456). Reference to a "weak promoter" indicates a promoter that drives expression of a coding sequence at a low level, namely at levels of about 1/10,000 transcripts to about 1/100,000 transcripts, to about 1/500, 0000 transcripts per cell. Conversely, a "strong promoter" drives expression of a coding sequence at a high level, or at about 1/10 transcripts to about 1/100 transcripts to about 1/1,000 transcripts per cell. Most preferably, the promoter capable of preferentially expressing the nucleic acid throughout the plant is a metallothionein promoter from rice. It should be clear that the applicability of the present invention is not restricted to the CDK nucleic acids as depicted in the sequence protocol, preferably as depicted in SEQ ID NO: 45, 47, 49, 51, 53 or 55.

Optionally, one or more terminator sequences may also be used in the construct introduced into a plant. The term "terminator" encompasses a control sequence which is a DNA sequence at the end of a transcriptional unit which signals 3' processing (behind the stop codon) and polyadenylation of a primary transcript and termination of transcription. A terminator, which may be used in the inventive process is, for example, the OCS1 terminator, the nos3 terminator or the 35S terminator. As is the case with the promoters, different terminator sequences should be used for each gene. Terminators, which are useful in microorganisms are for example the fimA terminator, txn terminator or trp terminator. Such terminators can be rho-dependent or rho-independent. Additional regulatory elements may include transcriptional as well as translational enhancers. Those skilled in the art will be aware of terminator and enhancer sequences, which may be suitable for use in performing the invention. Such sequences would be known or may readily be obtained by a person skilled in the art.

The genetic constructs of the invention may further include an origin of replication sequence, which is required for maintenance and/or replication in a specific cell type. One example is when a genetic construct is required to be maintained in a bacterial cell as an episomal genetic element (e.g. plasmid or cosmid molecule). Preferred origins of replication include, but are not limited to, the f1-ori and colE1.

For the detection and/or selection of the successful transfer of the nucleic acid sequences as depicted in the sequence protocol and used in the process of the invention, it is advantageous to use marker genes (=reporter genes). These marker genes enable the identification of a successful transfer of the nucleic acid molecules via a series of different principles, for example via visual identification with the aid of fluorescence, luminescence or in the wavelength range of light which is discernible for the human eye, by a resistance to herbicides or antibiotics, via what are known as nutritive markers (auxotrophism markers) or antinutritive markers, via enzyme assays or via phytohormones. Examples of such markers which may be mentioned are GFP (=green fluorescent protein); the luciferin/luceferase system, the β-galactosidase with its colored substrates, for example X-Gal, the herbicide resistances to, for example, imidazolinone, glyphosate, phosphinothricin or sulfonylurea, the antibiotic resistances to, for example, bleomycin, hygromycin, streptomycin, kanamycin, tetracyclin, chloramphenicol, ampicillin, gentamycin, geneticin (G418), spectinomycin or blasticidin, to mention only a few, nutritive markers such as the utilization of mannose or xylose, or antinutritive markers such as the resistance to 2-deoxyglucose. This list is a small number of possible markers. The skilled worker is very familiar with such markers. Different markers are preferred, depending on the organism and the selection method.

Therefore the genetic construct may optionally comprise a selectable marker gene. As used herein, the term "selectable marker or selectable marker gene" includes any gene, which confers a phenotype on a cell in which it is expressed to facilitate the identification and/or selection of cells which are transfected or transformed with a nucleic acid construct of the invention. Examples of selectable marker genes include genes encoding proteins that confer resistance to antibiotics (such as nptII that phosphorylates neomycin and kanamycin, or hpt, phosphorylating hygromycin), to herbicides (for example bar which provides resistance to Basta; aroA or gox providing resistance against glyphosate), or genes that provide a metabolic trait (such as manA that allows plants to use mannose as sole carbon source). Genes encoding visual marker proteins result in the formation of colour (for example β-glucuronidase, GUS), luminescence (such as luciferase) or fluorescence (Green Fluorescent Protein, GFP, and derivatives thereof).

It is known of the stable or transient integration of nucleic acids into plant cells that only a minority of the cells takes up the foreign DNA and, if desired, integrates it into its genome, depending on the expression vector used and the transfection technique used. To identify and select these integrants, a gene encoding for a selectable marker (as described above, for example resistance to antibiotics) is usually introduced into the host cells together with the gene of interest. Preferred selectable markers in plants comprise those, which confer resistance to an herbicide such as glyphosate or gluphosinate. Other suitable markers are, for example, markers, which encode genes involved in biosynthetic pathways of, for example, sugars or amino acids, such as β-galactosidase, ura3 or ilv2. Markers, which encode genes such as luciferase, gfp or other fluorescence genes, are likewise suitable. These markers and the aforementioned markers can be used in mutants in whom these genes are not functional since, for example, they have been deleted by conventional methods. Furthermore, nucleic acid molecules, which encode a selectable marker, can be introduced into a host cell on the same vector as those, which encode the polypeptides of the invention or used in the process or else in a separate vector. Cells which have been transfected stably with the nucleic acid introduced can be identified for example by selection (for example, cells which have integrated the selectable marker survive whereas the other cells die).

Since the marker genes, as a rule specifically the gene for resistance to antibiotics and herbicides, are no longer required or are undesired in the transgenic host cell once the nucleic acids have been introduced successfully, the process according to the invention for introducing the nucleic acids advantageously employs techniques which enable the removal, or excision, of these marker genes. One such a method is what is known as cotransformation. The cotransformation method employs two vectors simultaneously for the transformation, one vector bearing the nucleic acid according to the invention and a second bearing the marker gene(s). A large proportion of transformants receives or, in the case of plants, comprises (up to 40% of the transformants and above), both vectors. In case of transformation with Agrobacteria, the transformants usually receive only a part of the vector, the sequence flanked by the T-DNA, which usually represents the expression cassette. The marker genes can subsequently be removed from the transformed plant by performing crosses. In another method, marker genes integrated into a transposon are used for the transformation together with desired nucleic acid (known as the Ac/Ds technology). The transformants can be crossed with a transposase resource or the transformants are transformed with a nucleic acid construct conferring expression of a transposase, transiently or stable. In some cases (approx. 10%), the transposon jumps out of the genome of the host cell once transformation has taken place successfully and is lost. In a further number of cases, the transposon jumps to a different location. In these cases, the marker gene must be eliminated by performing crosses. In microbiology, techniques were developed which make possible, or facilitate, the detection of such events. A further advantageous method relies on what are known as recombination systems; whose advantage is that elimination by crossing can be dispensed with. The best-known system of this type is what is known as the Cre/lox system. Cre1 is a recombinase, which removes the sequences located between the loxP sequences. If the marker gene is integrated between the loxP sequences, it is removed, once transformation has taken place successfully, by expression of the recombinase. Further recombination systems are the HIN/HIX, FLP/FRT and REP/STB system (Tribble et al., J. Biol. Chem., 275, 2000: 22255-22267; Velmurugan et al., J. Cell Biol., 149, 2000: 553-566). A site-specific integration into the plant genome of the nucleic acid sequences according to the invention is possible. Naturally, these methods can also be applied to microorganisms such as yeast, fungi or bacteria.

The present invention also encompasses plants or plant cells obtainable by the methods according to the present invention. The present invention therefore provides plants or plant cells obtainable by the method according to the present invention, which plants or plant cells have introduced therein a CDK nucleic acid or variant thereof, encoding a CDK comprising a (P/N/A)(S/L/M/F)(T/S/R)(T/S/A)(L/I)RE (SEQ ID NO: 61), ATP binding and active site motif as disclosed herein.

The invention also provides a method for the production of transgenic plant cells or transgenic plants having improved growth characteristics, comprising introduction and expression in a plant of a CDK nucleic acid or a variant thereof, encoding a CDK that comprises a (P/N/A)(S/L/M/F)(T/S/R)(T/S/A)(L/I)RE (SEQ ID NO: 61), ATP binding and active site motif as disclosed herein.

More specifically, the present invention provides a method for the production of trans-genic plants having improved growth characteristics, which method comprises:

(i) introducing into a plant or plant cell a nucleic acid encoding an CDK or a homologue thereof; and (ii) cultivating the plant cell under conditions promoting plant growth and development.

The nucleic acid may be introduced directly into a plant cell or into the plant itself (including introduction into a tissue, organ or any other part of a plant). According to a preferred feature of the present invention, the nucleic acid is preferably introduced into a plant by transformation.

The terms "transformation" or "introduction" as referred to herein encompasses the transfer of an exogenous polynucleotide into a host cell, irrespective of the method used for transfer. Plant tissue capable of subsequent clonal propagation, whether by organogenesis or embryogenesis, may be transformed with a genetic construct of the present invention and a whole plant regenerated therefrom. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem). The polynucleotide may be transiently or stably introduced into a host cell and may be maintained non-integrated, for example, as a plasmid. Alternatively, it may be integrated into the host genome. The resulting transformed plant cell may then be used to regenerate a transformed plant in a manner known to persons skilled in the art.

The transfer of foreign genes into the genome of a plant is called transformation. In doing this the methods described for the transformation and regeneration of plants from plant tissues or plant cells are utilized for transient or stable transformation. An advantageous transformation method is the transformation in planta. To this end, it is possible, for example, to allow the agrobacteria to act on plant seeds or to inoculate the plant meristem with agrobacteria. It has proved particularly expedient in accordance with the invention to allow a suspension of transformed agrobacteria to act on the intact plant or at least the flower primordia. The plant is subsequently grown on until the seeds of the treated plant are obtained (Clough and Bent, Plant J. (1998) 16, 735-743). To select transformed plants, the plant material obtained in the transformation is, as a rule, subjected to selective conditions so that transformed plants can be distinguished from untransformed plants. For example, the seeds obtained in the above-described manner can be planted and, after an initial growing period, subjected to a suitable selection by spraying. A further possibility consists in growing the seeds, if appropriate after sterilization, on agar plates using a suitable selection agent so that only the trans-formed seeds can grow into plants. Further advantageous transformation methods, in particular for plants, are known to the skilled worker and are described hereinbelow.

Transformation of plant species is now a fairly routine technique. Advantageously, any of several transformation methods may be used to introduce the gene of interest into a suitable ancestor cell. Transformation methods include the use of liposomes, electroporation, chemicals that increase free DNA uptake, injection of the DNA directly into the plant, particle gun bombardment, transformation using viruses or pollen and micro-projection. Methods may be selected from the calcium/polyethylene glycol method for protoplasts (Krens et al. (1982) Nature 296, 72-74; Negrutiu et al. (1987) Plant Mol. Biol. 8, 363-373); electroporation of protoplasts (Shillito et al. (1985) Bio/Technol 3, 1099-1102); microinjection into plant material (Crossway et al. (1986) Mol. Gen. Genet. 202, 179-185); DNA or RNA-coated particle bombardment (Klein et al. (1987) Nature 327, 70) infection with (non-integrative) viruses and the like. Transgenic plants expressing a CDK according to the present invention are preferably produced via *Agrobacterium*-mediated transformation using any of the well known methods for example for *Brassica*, soybean, corn or rice transformation, such as described in any of the following: published European patent application EP 1198985 A1, Aldemita and Hodges (Planta 199, 612-617, 1996); Chan et al. (Plant Mol. Biol. 22, 491-506, 1993), Hiei et al. (Plant J. 6, 271-282, 1994), which disclosures are incorporated by reference herein as if fully set forth. In the case of corn transformation, the preferred method is as described in either Ishida et al. (Nature Biotechnol. 14, 745-50, 1996) or Frame et al. (Plant Physiol. 129, 13-22, 2002), which disclosures are incorporated by reference herein as if fully set forth. Said methods are further described by way of example in B. Jenes et al., Techniques for Gene Transfer, in: Transgenic Plants, Vol. 1, Engineering and Utilization, eds. S. D. Kung and R. Wu, Academic Press (1993) 128-143 and in Potrykus Annu. Rev. Plant Physiol. Plant Molec. Biol. 42 (1991) 205-225). The nucleic acids or the construct to be expressed is preferably cloned into a vector, which is suitable for transforming *Agrobacterium tumefaciens*, for example pBin19 (Bevan et al., Nucl. Acids Res. 12 (1984) 8711). Agrobacteria transformed by such a vector can then be used in known manner for the transformation of plants, in particular of crop plants such as by way of example tobacco plants, for example by bathing bruised leaves or chopped leaves in an agrobacterial solution and then culturing them in suitable media. The transformation of plants by means of *Agrobacterium tumefaciens* is described, for example, by Höfgen and Willmitzer in Nucl. Acid Res. (1988) 16, 9877 or is known inter alia from F. F. White, Vectors for Gene Transfer in Higher Plants; in Transgenic Plants, Vol. 1, Engineering and Utilization, eds. S. D. Kung and R. Wu, Academic Press, 1993, pp. 15-38.

Generally after transformation, plant cells or cell groupings are selected for the presence of one or more markers which are encoded by plant-expressible genes co-transferred with the gene of interest, following which the transformed material is regenerated into a whole plant.

As mentioned Agrobacteria transformed with an expression vector according to the invention may also be used in the manner known per se for the transformation of plants such as experimental plants like *Arabidopsis* or crop plants, such as, for example, cereals, maize, oats, rye, barley, wheat, soya, rice, cotton, sugarbeet, canola, sunflower, flax, hemp, potato, tobacco, tomato, carrot, bell peppers, oilseed rape, tapioca, cassava, arrow root, tagetes, alfalfa, lettuce and the various tree, nut, and grapevine species, in particular oil-containing crop plants such as soya, peanut, castor-oil plant, sunflower, maize, cotton, flax, oilseed rape, coconut, oil palm, safflower (*Carthamus tinctorius*) or cocoa beans, for example by bathing scarified leaves or leaf segments in an agrobacterial solution and subsequently growing them in suitable media.

In addition to the transformation of somatic cells, which then has to be regenerated into intact plants, it is also possible to transform the cells of plant meristems and in particular those cells which develop into gametes. In this case, the transformed gametes follow the natural plant development, giving rise to transgenic plants. Thus, for example, seeds of *Arabidopsis* are treated with agrobacteria and seeds are obtained from the developing plants of which a certain proportion is transformed and thus transgenic (Feldman, K A and Marks M D (1987). Mol Gen Genet. 208:274-289; Feldmann K (1992). In: C Koncz, N-H Chua and J Shell, eds, Methods in *Arabidopsis* Research. Word Scientific, Singapore, pp. 274-289). Alternative methods are based on the repeated removal of the influorescences and incubation of the excision site in the center of the rosette with transformed agrobacteria, whereby transformed seeds can likewise be obtained at a later point in time (Chang (1994). Plant J. 5: 551-558; Katavic (1994). Mol Gen Genet, 245: 363-370). However, an especially effective method is the vacuum infiltration method with its modifications such as the "floral dip" method. In the case of vacuum infiltration of *Arabidopsis*, intact plants under reduced pressure are treated with an agrobacterial suspension (Bechthold, N (1993). C R Acad Sci Paris Life Sci, 316: 1194-1199), while in the case of the"floral dip" method the developing floral tissue is incubated briefly with a surfactant-treated agrobacterial suspension (Clough, S J and Bent, A F (1998). The Plant J. 16, 735-743). A certain proportion of transgenic seeds are harvested in both cases, and these seeds can be distinguished from nontransgenic seeds by growing under the above-described selective conditions. In addition the stable transformation of plastids is of advantages because plastids are inherited maternally is most crops reducing or eliminating the risk of transgene flow through pollen. The transformation of the chloroplast genome is generally achieved by a process, which has been schematically displayed in Klaus et al., 2004 (Nature Biotechnology 22 (2), 225-229). Briefly the sequences to be transformed are cloned together with a selectable marker gene between flanking sequences homologous to the chloroplast genome. These homologous flanking sequences direct site specific integration into the plastome. Plastidal transformation has been described for many different plant species and an overview can be taken from Bock (2001) Transgenic plastids in basic research and plant biotechnology. J Mol. Biol. 2001 Sep. 21; 312 (3):425-38 or Maliga, P (2003) Progress towards commercialization of plastid transformation technology. Trends Biotechnol. 21, 20-28. Further biotechnological progress has recently been reported in form of marker free plastid transformants, which can be produced by a transient cointegrated maker gene (Klaus et al., 2004, Nature Biotechnology 22 (2), 225-229).

The genetically modified plant cells can be regenerated via all methods with which the skilled worker is familiar. Suitable methods can be found in the abovementioned publications by S. D. Kung and R. Wu, Potrykus or Höfgen and Willmitzer.

Following DNA transfer and regeneration, putatively transformed plants may be evaluated, for instance using Southern analysis, for the presence of the gene of interest, copy number and/or genomic organisation. Alternatively or additionally, expression levels of the newly introduced DNA may be monitored using Northern and/or Western analysis, both techniques being well known to persons having ordinary skill in the art.

The generated transformed plants may be propagated by a variety of means, such as by clonal propagation or classical breeding techniques. For example, a first generation (or T1) transformed plant may be selfed to give homozygous second generation (or T2) transformants, and the T2 plants further propagated through classical breeding techniques.

The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

The present invention clearly extends to any plant cell or plant produced or obtainable by any of the methods described herein, and to all plant parts and propagules thereof. The present invention extends further to encompass the progeny of a primary trans-formed or transfected cell, tissue, organ or whole plant that has been produced by any of the aforementioned methods, the only requirement being that progeny exhibit the same genotypic and/or phenotypic characteristic(s) as those produced in the parent by the methods according to the invention.

The invention also includes host cells containing an isolated plant CDK nucleic acid or variant thereof, encoding an CDK comprising the features as disclosed herein. Preferred host cells according to the invention are plant cells.

The invention also extends to harvestable parts of a plant according to the invention such as but not limited to seeds, leaves, fruits, flowers, stems, rhizomes, tubers and bulbs. The invention furthermore relates to products derived, preferably directly derived, from a harvestable part of such a plant, such as dry pellets or powders, oil, fat and fatty acids, starch and proteins.

The present invention furthermore encompasses the use of a CDK gene and the encoded protein for improving the growth characteristics of plants; such improved growth characteristics are as defined herein above.

The present invention also encompasses use of CDK nucleic acids or variants thereof, and to use of CDK polypeptides or homologues thereof, which CDK or homologue comprises a (P/N/A)(S/L/M/F)(T/S/R)(T/S/A)(L/I)RE(SEQ ID NO: 61), ATP binding and active site motif as disclosed herein, or which CDK nucleic acid or variant encodes such a protein. On such use relates to improving the growth characteristics of plants, in particular in improving yield, especially seed yield. The seed yield may include any one or more of the following: increased total number of seeds, increased number of filled seeds, increased seed weight, increased harvest index, among others.

CDK nucleic acids or variants thereof, or CDK polypeptides or homologues thereof, may find use in breeding programmes in which a DNA marker is identified which may be genetically linked to a CDK gene or variant thereof. The CDK or variants thereof, or CDKA or homologues thereof, may be used to define a molecular marker. This DNA or protein marker may then be used in breeding programs to select plants having improved growth characteristics. The CDK gene or variant thereof may, for example, be a nucleic acid as depicted in the sequence protocol preferably as depicted in SEQ ID NO: 45, 47, 49, 51, 53 or 55, or a nucleic acid encoding any of the homologues as defined herein.

Allelic variants of a CDK may also find use in marker-assisted breeding programmes. Such breeding programmes sometimes require introduction of allelic variation by mutagenic treatment of the plants, using for example EMS mutagenesis; alternatively, the programme may start with a collection of allelic variants of so called "natural" origin caused unintentionally. Identification of allelic variants then takes place by, for example, PCR. This is followed by a selection step for selection of superior allelic variants of the sequence in question and which give improved growth characteristics in a plant. Selection is typically carried out by monitoring growth performance of plants containing different allelic variants of the sequence in question, for example, different allelic variants of SEQ ID NO: 45, 47, 49, 51, 53 or 55, or of nucleic acids encoding any of the above mentioned homologues. Growth performance may be monitored in a greenhouse or in the field. Further optional steps include crossing plants, in which the superior allelic variant was identified, with another plant. This could be used, for example, to make a combination of interesting phenotypic features.

CDK nucleic acids or variants thereof according to the invention may also be used as probes for genetically and physically mapping the genes that they are a part of, and as markers for traits linked to those genes. Such information may be useful in plant breeding in order to develop lines with desired phenotypes. Such use of CDK nucleic acids or variants thereof requires only a nucleic acid sequence of at least 15 nucleotides in length. The CDK nucleic acids or variants thereof may be used as restriction fragment length polymorphism (RFLP) markers. Southern blots of restriction-digested plant genomic DNA may be probed with the CDK nucleic acids or variants thereof. The resulting banding patterns may then be subjected to genetic analyses using computer programs such as MapMaker (Lander et al. (1987) Genomics 1, 174-181) in order to construct a genetic map. In addition, the nucleic acids may be used to probe Southern blots containing restriction endonuclease-treated genomic DNAs of a set of individuals representing parent and progeny of a defined genetic cross. Segregation of the DNA polymorphisms is noted and used to calculate the position of the CDK nucleic acid or variant thereof in the genetic map previously obtained using this population (Botstein et al. (1980) Am. J. Hum. Genet. 32, 314-331).

The production and use of plant gene-derived probes for use in genetic mapping is described in Bernatzky and Tanksley (Genetics 112, 887-898, 1986). Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

The nucleic acid probes may also be used for physical mapping (i.e., placement of sequences on physical maps; see Hoheisel et al. In: Nonmammalian Genomic Analysis: A Practical Guide, Academic press 1996, pp. 319-346, and references cited therein).

In another embodiment, the nucleic acid probes may be used in direct fluorescence in situ hybridization (FISH) mapping (Trask (1991) Trends Genet. 7, 149-154). Although current methods of FISH mapping favour use of large clones (several to several hundred kb; see Laan et al. (1995) Genome Res. 5, 13-20), improvements in sensitivity may allow performance of FISH mapping using shorter probes.

A variety of nucleic acid amplification-based methods of genetic and physical mapping may be carried out using the nucleic acids. Examples include allele-specific amplification (Kazazian (1989) J. Lab. Clin. Med. 11, 95-96), polymorphism of PCR-amplified fragments (CAPS; Sheffield et al. (1993) Genomics 16, 325-332), allele-specific ligation (Landegren et al. (1988) Science 241, 1077-1080), nucleotide extension reactions (Sokolov (1990) Nucleic Acid Res. 18, 3671), Radiation Hybrid Mapping (Walter et al. (1997) Nat. Genet. 7, 22-28) and Happy Mapping (Dear and Cook (1989) Nucleic Acid Res. 17, 6795-6807). For these methods, the sequence of a nucleic acid is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

In this way, generation, identification and/or isolation of improved plants with modulated cyclin-dependent kinase activity displaying improved growth characteristics may be performed.

CDK nucleic acids or variants thereof or CDK polypeptides or homologues thereof according to the present invention may also find use as growth regulators. Since these molecules have been shown to be useful in improving the growth characteristics of plants, they would also be useful growth regulators, such as herbicides or growth stimulators. The present invention therefore provides a composition comprising a CDK or variant thereof or a CDK polypeptide or homologue thereof, together with a suitable carrier, diluent or excipient, for use as a growth regulator, which CDK or homologue comprises a (P/N/A)(S/L/M/F)(T/S/R)(T/S/A)(L/I)RE (SEQ ID NO: 61), ATP binding and active site motif as disclosed herein, or which CDK or variant encodes such protein.

The methods according to the present invention result in plants having improved growth characteristics, as described hereinbefore. These advantageous growth characteristics may also be combined with other economically advantageous traits, such as further yield-enhancing traits, tolerance to various stresses, traits modifying various architectural features and/or biochemical and/or physiological features.

DESCRIPTION OF FIGURES

The present invention will now be described with reference to the following figures in which:

FIG. 1 shows the vector EG073qcz, which is also depicted in the sequence protocol as SEQ ID NO: 57.

Figure 2:
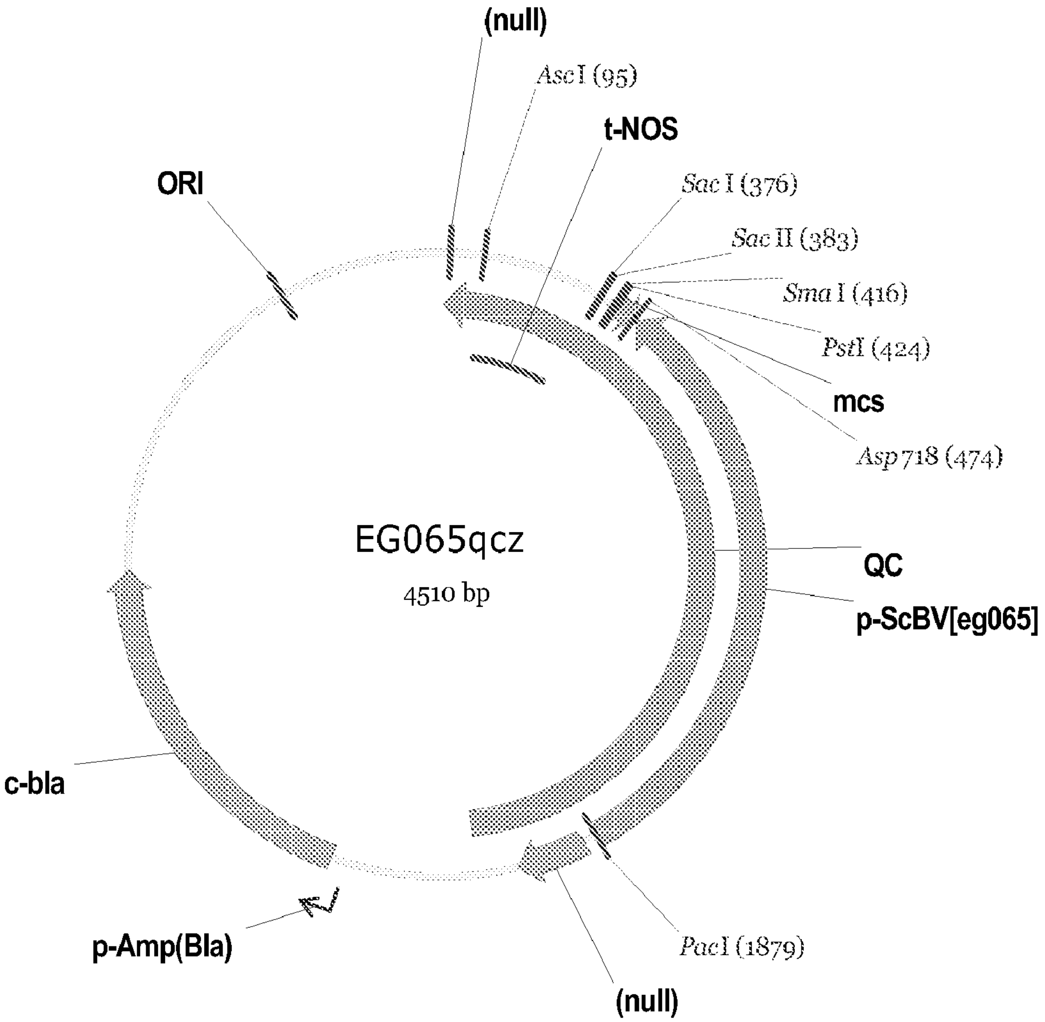
FIG. 2 shows the vector EG065qcz, which is also depicted in the sequence protocol as SEQ ID NO: 58.

FIG. 2 shows the vector EG065qcz, which is also depicted in the sequence protocol as SEQ ID NO: 58.

Figure 3:
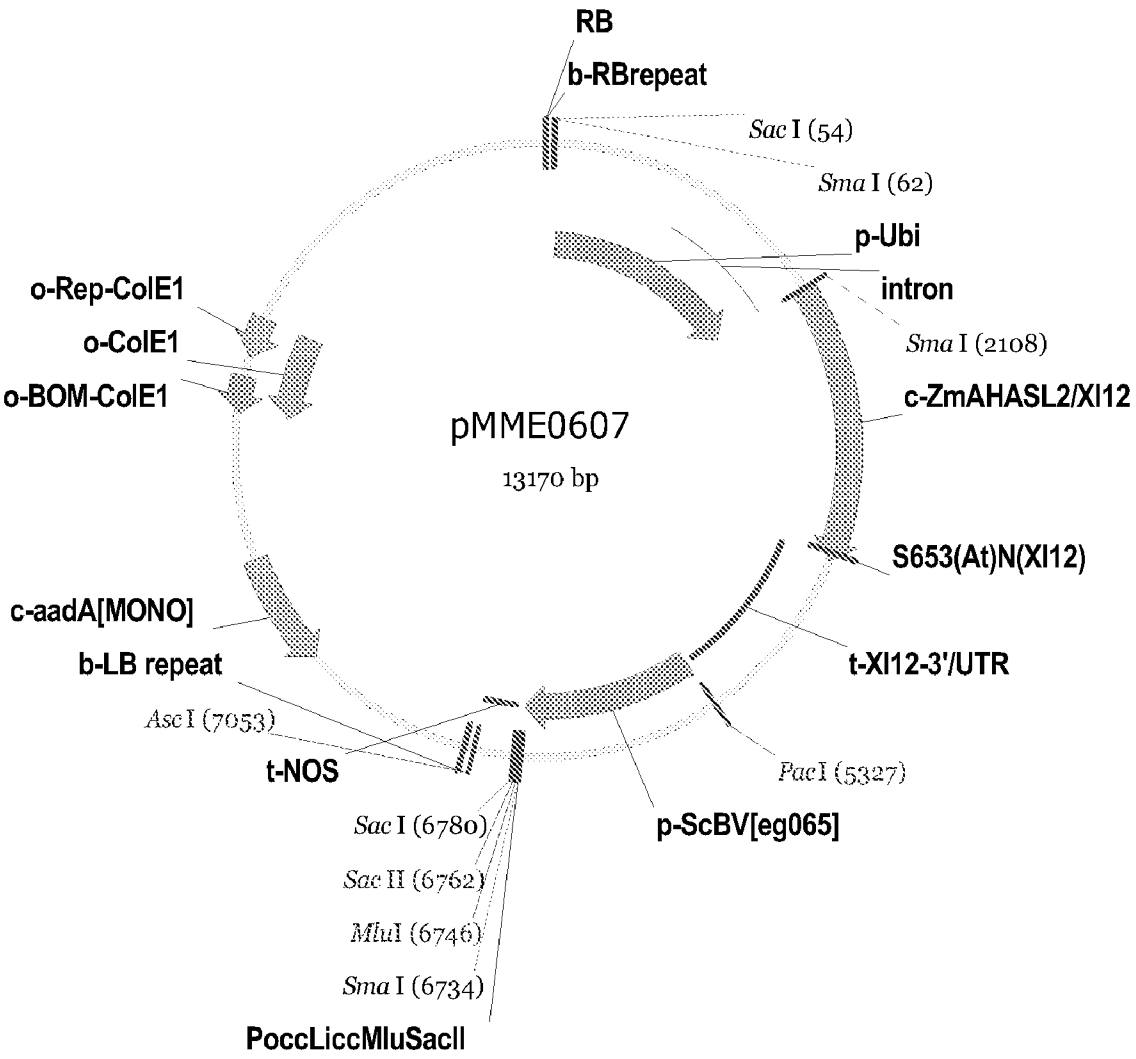
FIG. 3 shows the vector pMME0607, which is also depicted in the sequence protocol as SEQ ID NO: 59.

FIG. 3 shows the vector pMME0607, which is also depicted in the sequence protocol as SEQ ID NO: 59.

FIG. 4 shows the vector sequences of EG073qcz, EG065qcz and pMME0607, which are also depicted in the sequence protocol as SEQ ID NO: 57 to 59.

Further embodiments of the invention are:

The use of the nucleic acid sequence according to the invention or of the nucleic acid construct according to the invention for the generation of transgenic plants.

EXAMPLES

The present invention will now be described with reference to the following examples, which are by way of illustration alone.

DNA manipulation: unless otherwise stated, recombinant DNA techniques are performed according to standard protocols described in (Sambrook (2001) Molecular Cloning: a laboratory manual, 3rd Edition Cold Spring Harbor Laboratory Press, CSH, New York) or in Volumes 1 and 2 of Ausubel et al. (1994), Current Protocols in Molecular Biology, Current Protocols (www.4ulr.com/products/currentprotocols/index.html). Standard materials and methods for plant molecular work are described in Plant Molecular Biology Labfax (1993) by R. D. D. Croy, published by BIOS Scientific Publications Ltd (UK) and Blackwell Scientific Publications (UK).

Example 1

Gene Cloning

SEQ ID NO: 45 can be cloned into the plasmids pBR322 (Sutcliffe, J. G. (1979) Proc. Natl. Acad. Sci. USA, 75: 3737-3741); pACYC177 (Change & Cohen (1978) J. Bacteriol. 134: 1141-1156); plasmids of the pBS series (pBSSK+, pBSSK− and others; Stratagene, LaJolla, USA) or cosmids such as SuperCosi (Stratagene, LaJolla, USA) or Lorist6 (Gibson, T. J. Rosenthal, A., and Waterson, R. H. (1987) Gene 53: 283-286) for expression in *E. coli* using known, well-established procedures (see, for example, Sambrook, J. et al. (1989) "Molecular Cloning: A Laboratory Manual". Cold Spring Harbor Laboratory Press or Ausubel, F. M. et al. (1994) "Current Protocols in Molecular Biology", John Wiley & Sons).

Example 2

DNA Sequencing and Computerized Functional Analysis

The DNA was sequenced by standard procedures, in particular the chain determination method, using ABI377 sequencers (see, for example, Fleischman, R. D. et al. (1995) "Whole-genome Random Sequencing and Assembly of *Haemophilus Influenzae* Rd., Science 269; 496-512)".

Example 3

DNA Transfer Between Different Microorganisms Such as *Escherichia coli* and *Agrobacterium tumefaciens*

Shuttle vectors such as pYE22m, pPAC-ResQ, pClasper, pAUR224, pAMH10, pAML10, pAMT10, pAMU10, pGMH10, pGML10, pGMT10, pGMU10, pPGAL1, pPADH1, pTADH1, pTAex3, pNGA142, pHT3101 and derivatives thereof which allow the transfer of nucleic acid sequences between different microorganisms are available to the skilled worker. An easy method to isolate such shuttle vectors is disclosed by Soni R. and Murray J. A. H. [Nucleic Acid Research, vol. 20 no. 21, 1992: 5852]: If necessary such shuttle vectors can be constructed easily using standard vectors for *E. coli* (Sambrook, J. et al., (1989), "Molecular Cloning: A Laboratory Manual", Cold Spring Harbor Laboratory Press or Ausubel, F. M. et al. (1994) "Current Protocols in Molecular Biology", John Wiley & Sons) and/or the aforementioned vectors, which have a replication origin for, and suitable marker from, *Escherichia coli* or *Agrobacterium tumefaciens* added. Such replication origins are preferably taken from endogenous plasmids, which have been isolated from species used for the production of plants used in the inventive process. Genes, which are used in particular as transformation markers for these species are genes for kanamycin resistance (such as those which originate from the Tn5 or Tn-903 transposon) or for chloramphenicol resistance (Winnacker, E. L. (1987) "From Genes to Clones—Introduction to Gene Technology, VCH, Weinheim) or for other antibiotic resistance genes such as for G418, gentamycin, neomycin, hygromycin or tetracycline resistance.

Using standard methods, it is possible to clone a gene of interest into one of the above-described shuttle vectors and to introduce such hybrid vectors into the microorganism strains used in the inventive process.

Example 4

Determining the Expression of the Mutant/Transgenic Protein

The observations of the activity of a mutated, or transgenic, protein in a transformed host cell are based on the fact that the protein is expressed in a similar manner and in a similar quantity as the wild-type protein. A suitable method for determining the transcription quantity of the mutant, or transgenic, gene (a sign for the amount of mRNA which is available for the translation of the gene product) is to carry out a Northern blot (see, for example, Ausubel et al., (1988) Current Protocols in Molecular Biology, Wiley: New York), where a primer which is designed in such a way that it binds to the gene of interest is provided with a detectable marker (usually a radioactive or chemiluminescent marker) so that, when the total RNA of a culture of the organism is extracted, separated on a gel, applied to a stable matrix and incubated with this probe, the binding and quantity of the binding of the probe indicates the presence and also the amount of mRNA for this gene. Another method is a quantitative PCR. This information detects the extent to which the gene has been transcribed. Total cell RNA can be isolated for example from yeasts or *E. coli* by a variety of methods, which are known in the art, for example with the Ambion kit according to the instructions of the manufacturer or as described in Edgington et al., Promega Notes Magazine Number 41, 1993, p. 14.

Standard techniques, such as Western blot, may be employed to determine the presence or relative amount of protein translated from this mRNA (see, for example, Ausubel et al. (1988) "Current Protocols in Molecular Biology", Wiley, New York). In this method, total cell proteins are extracted, separated by gel electrophoresis, transferred to a matrix such as nitrocellulose and incubated with a probe, such as an antibody, which binds specifically to the desired protein. This probe is usually provided directly or indirectly with a chemiluminescent or colorimetric marker, which can be detected readily. The presence and the observed amount of marker indicate the presence and the amount of the sought mutant protein in the cell. However, other methods are also known.

Example 5

Growth of Genetically Modified Microorganism: Media and Culture Conditions

Genetically modified microorganisms such as *Escherichia coli* can be grown in synthetic or natural growth media known by the skilled worker. A number of different growth media for microorganisms such as *Escherichia coli* are well known and widely available.

Example 6

Transformation of *Agrobacteria*

Plasmids can be transformed into *Agrobacterium tumefaciens* (GV3101 pMP90; Koncz and Schell, 1986, Mol. Gen. Genet. 204: 383-396) using heat shock or electroporation protocols. Transformed colonies can be grown on YEP media and selected by respective antibiotics (Rif/Gent/Km) for 2 d at 28° C. These *Agrobacterium* cultures were used for the plant transformation.

*Arabidopsis thaliana* can be grown and transformed according to standard conditions Bechtold 1993 (Bechtold, N., Ellis, J., Pelletier, G. 1993. In planta *Agrobacterium* mediated gene transfer by infiltration of *Arabidopsis thaliana* plants C. R. Acad. Sci. Paris. 316:1194-1199); Bent et al. 1994 (Bent, A., Kunkel, B. N., Dahlbeck, D., Brown, K. L., Schmidt, R., Giraudat, J., Leung, J., and Staskawicz, B. J. 1994; PPCS2 of *Arabidopsis thaliana*: A leucin-rich repeat class of plant disease resistant genes; Science 265: 1856-1860).

Transgenic *A. thaliana* plants can be grown individually in pots containing a 4:1 (v/v) mixture of soil and quartz sand in a York growth chamber. Standard growth conditions are: photoperiod of 16 h light and 8 h dark, 20° C., 60% relative humidity, and a photon flux density of 150 µE. To induce germination, sown seeds are kept at 4° C., in the dark, for 3 days. Plants are watered daily until they are approximately 3 weeks old at which time drought are imposed by withholding water. Parallely, the relative humidity was reduced in 10% increments every second day to 20%. The plants can be assayed for improved growth under said conditions.

In general it is useful to conduct said experiments in three successive independent experiments. In the first experiment, 10 independent T2 lines should be sown for each gene being tested. The percentage of plants not showing visual symptoms of injury are determined. In the second experiment positive lines should be then confirmed in an identical experimental procedure. In a third experiment, at least 7 replicates of the best lines showing improved growth should be then again confirmed.

In a further experiment, for individual major lines, other lines containing the same gene construct, but resulting from a different transformation event should be tested again. All results are summmarised and analysed.

Example 6

Vector Construction and Rice Transformation

For the expression in rice the a vector such as the ones shown in FIGS. 1 to 4 containing the expression cassette SEQ ID NO: 60 is useful. Into said vector SEQ ID NO: 1 as shown in the sequence protocol can be introduced. Said vector can be trans-formed into the *Agrobacterium* strain LBA4404 and subsequently to *Oryza sativa* plants. Transformed rice plants are allowed to grow and are then examined for the parameters described in Example 7.

Example 7

Evaluation of Transformants: Growth Measurements

Approximately 15 to 20 independent T0 transformants are generated commenly. The primary transformants are transferred from tissue culture chambers to a greenhouse for growing and harvest of T1 seed. Four events of which the T1 progeny segregated 3:1 for presence/absence of the transgene are retained. For each of these events, 10 T1 seedlings containing the transgene (hetero- and homo-zygotes), and 10 T1 seedlings lacking the transgene (nullizygotes), are selected by visual marker screening. The selected T1 plants are transferred to a greenhouse. Each plant received a unique barcode label to unambiguously link the phenotyping data to the corresponding plant. The selected T1 plants are grown on soil in 10 cm diameter pots under the following environmental settings: photoperiod=11.5 h, daylight intensity=30,000 lux or more, daytime temperature=28° C. or higher, night time temperature=22° C., relative humidity=60-70%. Transgenic plants and the corresponding nullizygotes are grown side-by-side at random positions. From the stage of sowing until the stage of maturity the plants are passed several times through a digital imaging cabinet. At each time point digital images (2048×1536 pixels, 16 million colours) are taken of each plant from at least 6 different angles.

The mature primary panicles are harvested, bagged, barcode-labelled and then dried for three days in the oven at 37° C. The panicles are then threshed and all the seeds collected. The filled husks are separated from the empty ones using an air-blowing device. After separation, both seed lots are then counted using a commercially available counting machine. The empty husks are discarded. The filled husks are weighed on an analytical balance and the cross-sectional area of the seeds was measured using digital imaging. This procedure results in the set of seed-related parameters described below.

These parameters are derived in an automated way from the digital images using image analysis software and are analysed statistically. A two factor ANOVA (analyses of variance) is corrected for the unbalanced design and is used as statistical model for the overall evaluation of plant phenotypic characteristics. An F-test is carried out on all the parameters measured of all the plants of all the events transformed with that gene. The F-test is carried out to check for an effect of the gene over all the transformation events and to verify for an overall effect of the gene, also refers to herein as a "global gene effect". If the value of the F test shows that the data are significant, than it is concluded that there is a "gene" effect, meaning that not only presence or the position of the gene that causes the effect. The threshold for significance for a true global gene effect is set at 5% probability level for the F test.

To check for an effect of the genes within an event, i.e., for a line-specific effect, a t-test is performed within each event using data sets from the transgenic plants and the corresponding null plants. "Null plants" or "null segregants" or "nullizygotes" refer to the plants treated in the same way as the transgenic plant, but from which the transgene has segregated. Null plants can also be described as the homozygous negative trans-formed plants. The threshold for significance for the t-test is set at a 10% probability level. The results for some events can be above or below this threshold. This is based on the hypothesis that a gene might only have an effect in certain positions in the genome, and that the occurrence of this position-dependent effect is not uncommon. This kind of gene effect is also referred to herein as a "line effect of the gene". The p-value is obtained by comparing the t-value to the t-distribution or alternatively, by comparing the F-value to the F-distribution. The p-value then gives the probability that the null hypothesis (i.e., that there is no effect of the transgene) is correct.

The data obtained in the first experiment are confirmed in a second experiment with T2 plants. Three lines are selected for further analysis. Seed batches from the positive plants (both hetero- and homozygotes) in T1, are screened by monitoring marker expression. For each chosen event, the heterozygote seed batches are then retained for T2 evaluation. Within each seed batch an equal number of positive and negative plants are grown in the greenhouse for evaluation.

A total number of 120 transformed plants are evaluated in the T2 generation, that is 40 plants per event of which 20 are positive for the transgene and 20 negative.

Because two experiments with overlapping events are carried out, a combined analysis was performed. This is useful to check consistency of the effects over the two experiments, and if this is the case, to accumulate evidence from both experiments in order to increase confidence in the conclusion. The method used is a mixed-model approach that takes into account the multilevel structure of the data (i.e. experiment— event—segregants). P-values are obtained by comparing likelihood ratio test to chi square distributions.

Example 8

Evaluation of Transformants: Measurement of Yield-Related Parameters

Upon analysis of the seeds as described above, the inventors are able to find that plants transformed with the CDK gene construct encoding a CDK with the motifs mentioned herein has an increased number of filled seeds, an increased total weight of seeds and an increased harvest index compared to plants lacking the CDK transgene.

Positive results are obtained for plants in the T1 generation and are again obtained in the T2 generation. These T2 data are re-evaluated in a combined analysis with the results for the T1 generation, and the obtained p-values show that the observed effects are significant.

Number of Filled Seeds

The number of filled seeds is determined by counting the number of filled husks that remain after the separation step. Typically 3 out of the 4 tested lines are showing an significant increase in filled seed numbers.

Total Seed Yield

The total seed yield (total weight of seeds) per plant is measured by weighing all filled husks harvested from a plant. Typically 3 of the 4 transgenic T1 lines are showing an increase in total seed weight.

Harvest Index

The harvest index in the present invention is defined herein as the ratio between the total seed yield and the above ground area ($mm^2$), multiplied by a factor $10^6$. All tested lines are showing an increased harvest index.

Furthermore, there is in general a tendency for an increased total number of seeds.

Example 9

Plant Culture for Bioanalytical Analyses

For the bioanalytical analyses of the transgenic plants, the latter are grown as described above.

Example 10

Metabolic Analysis of Transformed Plants

The modifications identified in accordance with the invention are identified by the following procedure:

a) Homogenization of the Samples

Homogenization of the samples is performed using a ball-mill (Retsch). Ten to thirty rice kernels are transferred into plastic tubes (Eppendorf, Safe-Lock, 2 mL) and homogenized with a stainless steel ball under cooling with liquid nitrogen.

b) Lyophilization

During the experiment, care is taken that the samples either remain in the deep-frozen state (temperatures <−40° C.) or are freed from water by lyophilization of the homogenized material until the first contact with solvents.

The samples are transferred in the pre-cooled (−40° C.) freeze dryer. The initial temperature during the main drying phase is −35° C. and the pressure is 0.120 mbar. During the drying phase, the parameters are altered following a pressure and temperature program. The final temperature after 12 hours is +30° C. and the final pressure is 0.001 to 0.004 mbar. After the vacuum pump and the refrigerating machine has been switched off, the system is flushed with air (dried via a drying tube) or argon.

c) Extraction

Immediately after the lyophilization apparatus has been flushed, the tubes with the lyophilized plant material are tightly sealed to prevent the material from air humidity. For the extraction a portion of 50 mg of the dried homogenized plant material is weighed in glass fibre extraction thimbles and transferred into 5 ml extraction cartridges of the ASE device (Accelerated Solvent Extractor ASE 200 with Solvent Controller and AutoASE software (DIONEX)).

The 24 sample positions of an ASE device (Accelerated Solvent Extractor ASE 200 with Solvent Controller and AutoASE software (DIONEX)) are filled with plant samples, including some samples for testing quality control.

The polar substances are extracted with approximately 10 ml of methanol/water (80/20, v/v) at T=70° C. and p=140 bar, 5 minutes heating-up phase, 1 minute static extraction. The more lipophilic substances are extracted with approximately 10 ml of methanol/dichloromethane (40/60, v/v) at T=70° C. and p=140 bar, 5 minute heating-up phase, 1 minute static extraction. The two solvent mixtures are extracted into the same glass tubes (centrifuge tubes, 50 ml, equipped with screw cap and pierceable septum for the ASE (DIONEX)).

The solution is treated with commercial available internal standards, such as ribitol, L-glycine-2,2-$d_2$, L-alanine-2,3,3,3-$d_4$, methionine-$d_3$, Arginine_($^{13}C$), Tryptophan-$d_5$, and α-methylglucopyranoside and methyl nonadecanoate, methyl undecanoate, methyl tridecanoate, methyl pentadecanoate, methyl nonacosanoate.

The total extract is treated with 8 ml of water. The solid residue of the plant sample and the extraction sleeve are discarded.

The extract is shaken and then centrifuged for 5 to 10 minutes at least 1 400 g in order to accelerate phase separation. 1 ml of the supernatant methanol/water phase ("polar phase", colorless) is removed for the further GC analysis, and 1 ml is removed for the LC analysis. The remainder of the methanol/water phase is discarded. 0.75 ml of the organic phase ("lipid phase", dark green) is removed for the further GC analysis and 0.75 ml is removed for the LC analysis. All the portions removed are evaporated to dryness using the IR Dancer infrared vacuum evaporator (Hettich). The maximum temperature during the evaporation process does not exceed 40° C. Pressure in the apparatus is not less than 10 mbar.

d) Processing the Lipid and Polar Phase for the LC/MS or LC/MS/MS Analysis

The lipid extract, which has been evaporated to dryness is taken up in mobile phase. The polar extract, which has been evaporated to dryness is taken up in mobile phase.

e) LC-MS Analysis

The LC part is carried out on a commercially available LCMS system from Agilent Technologies, USA. For polar extracts 10 μl are injected into the system at a flow rate of 200 μl/min. The separation column (Reversed Phase C18) is maintained at 15° C. during chromatography. For lipid extracts 5 μl are injected into the system at a flow rate of 200 μl/min. The separation column (Reversed Phase C18) is maintained at 30° C. HPLC is performed with gradient elution.

The mass spectrometric analysis is performed on a Applied Biosystems API 4000 triple quadrupole instrument with turbo ion spray source. For polar extracts the instrument measures in negative ion mode in fullscan mode from 100-1000 amu. For lipid extracts the instrument measures in positive ion mode in fullscan mode from 100-1000 amu f) Derivatization of the Lipid Phase for the GC/MS Analysis For the transmethanolysis, a mixture of 140 μl of chloroform, 37 μl of hydrochloric acid (37% by weight HCl in water), 320 μl of methanol and 20 μl of toluene is added to the evaporated extract. The vessel is sealed tightly and heated for 2 hours at 100° C., with shaking. The solution is subsequently evaporated to dryness. The residue is dried completely.

The methoximation of the carbonyl groups is carried out by reaction with methoxyamine hydrochloride (5 mg/ml in pyridine, 100 μl for 1.5 hours at 60° C.) in a tightly sealed vessel. 20 μl of a solution of odd-numbered, straight-chain fatty acids (solution of each 0.3 mg/mL of fatty acids from 7 to 25 carbon atoms and each 0.6 mg/mL of fatty acids with 27, 29 and 31 carbon atoms in 3/7 (v/v) pyridine/toluene) are added as time standards. Finally, the derivatization with 100 μl of N-methyl-N-(trimethylsilyl)-2,2,2-trifluoroacetamide (MSTFA) is carried out for 30 minutes at 60° C., again in the tightly sealed vessel. The final volume before injection into the GC was 220 μl.

g) Derivatization of the Polar Phase for the GC/MS Analysis

The methoximation of the carbonyl groups is carried out by reaction with methoxyamine hydrochloride (5 mg/ml in pyridine, 50 μl for 1.5 hours at 60° C.) in a tightly sealed vessel. 10 μl of a solution of odd-numbered, straight-chain fatty acids (solution of each 0.3 mg/mL of fatty acids from 7 to 25 carbon atoms and each 0.6 mg/mL of fatty acids with 27, 29 and 31 carbon atoms in 3/7 (v/v) pyridine/toluene) are added as time standards. Finally, the derivatization with 50 μl of N-methyl-N-(trimethylsilyl)-2,2,2-trifluoroacetamide (MSTFA) is carried out for 30 minutes at 60° C., again in the tightly sealed vessel. The final volume before injection into the GC was 110 μl.

h) GC-MS Analysis

The GC-MS systems consist of an Agilent 6890 GC coupled to an Agilent 5973 MSD. The autosamplers are CompiPal or GCPal from CTC. For the analysis usual commercial capillary separation columns (30 m×0.25 mm×0.25 μm) with different polymethyl-siloxane stationary phases containing 0% up to 35% of aromatic moieties, depending on the analysed sample materials and fractions from the phase separation step, are used (for example: DB-1 ms, HP-5 ms, DB-XLB, DB-35 ms, Agilent Technologies). Up to 1 μL of the final volume is injected splitless and the oven temperature program is started at 70° C. and ended at 340° C. with different heating rates depending on the sample material and fraction from the phase separation step in order to achieve a sufficient chromatographic separation and number of scans within each analyte peak. Usual GC-MS standard conditions, for example constant flow with nominal 1 to 1.7 ml/min. and helium as the mobile phase gas are used. Ionisation is done by electron impact with 70 eV, scanning within a m/z range from 15 to 600 with scan rates from 2.5 to 3 scans/sec and standard tune conditions.

i) Analysis of the Various Plant Samples

The samples are measured in individual series of 20 plant samples each (also referred to as sequences). In the experiments each sequence contained at least 3 replicates per transgenic line plus at least 3 plants of the respective null-segregant line as controls. The peak areas for each analyte are adjusted for the dry weight established for the plant (normalized area). Ratio values are calculated by further normalization to the control. In the experiments ratio values are calculated by dividing the normalized area by the mean of the corresponding data of the control group of the same sequence. The values obtained are referred to as ratio_by_control. They are comparable between sequences and indicate how much the analyte concentration in the mutant differs from the control group, which are the plants of the respective null-segregant lines in a given sequence. Appropriate controls are done before to proof that the vector and transformation procedure itself has no significant influence on the metabolic composition of the plants. Therefore the described changes in comparison with the control group are undoubtedly caused by the mutation.

The results of the different plant analyses can be seen from the following table 3:

Analyzed are seeds of rice plants containing genes encoding CDK proteins as disclosed herein.

TABLE 3

Results of the metabolic analysis of CDK proteins in rice plants

| Metabolite | min_ratio | max_ratio | Method |
|---|---|---|---|
| Methionine | 1.254 | 1.456 | GC |
| Proline | 0.627 | 0.628 | GC |
| Asparagine | 1.845 | 2.255 | GC |
| Cysteine | 1.526 | 2.029 | GC |
| Lutein | 1.793 | 2.593 | LC |
| Zeaxanthin | 2.165 | 4.267 | LC |
| Coenzyme Q9 | 1.368 | 1.391 | LC |

Column 1 shows the analyzed metabolite Column 2 and 3 are showing the range of increase of the analyzed metabolite as found between the transgenic plants in comparison to the control lines. Column 4 indicates the analytical method.

The invention claimed is:

1. A method for improving a plant growth characteristic relative to a corresponding control plant comprising:

(a) introducing into a plant at least one nucleic acid sequence which encodes a cyclin dependent kinase (CDK), wherein the at least one nucleic acid sequence comprises a nucleic acid sequence selected from the group consisting of:

i) the isolated nucleic acid molecule of SEQ ID NO: 45;

ii) an isolated nucleic acid molecule encoding the amino acid sequence of SEQ ID NO: 46;

iii) an isolated nucleic acid molecule which encodes a polypeptide which has at least 80% identity with the amino acid sequence of the polypeptide encoded by the nucleic acid molecule of (i) or (ii) and which comprises the DLL(Q/N/S/R)(K/Q/R)(L/M)(L/F)(I/T/I/C)(F/Y/L)DP (T/E/D/R/S)(K/Q)RI motif of SEQ ID NO: 67; and iv) an isolated nucleic acid molecule encoding a homologue of the amino acid molecule of SEQ ID NO: 46, which homologue is of plant origin and comprises the DLL(Q/N/S/R)(K/Q/R)(L/M)(L/F)(I/T/I/C)(F/Y/L) DP(T/E/D/R/S)(K/Q)RI motif of SEQ ID NO: 67; and (b) selecting for a plant having an improved growth characteristic relative to a corresponding control plant.

2. The method of claim 1, wherein the improved growth characteristic is effected by introducing a nucleic acid sequence encoding a CDK derived from a plant.

3. The method of claim 1, wherein said nucleic acid sequence encoding a CDK is derived from a monocotyledonous or dicotyledonous plant.

4. The method of claim 1, wherein the nucleic acid sequence encoding the cyclin dependent kinase is derived from the species *Oryza sativa, Brassica napus, Glycine max, Linum usitatissimum, Zea mays* or *Helianthus annuus.*

5. The method of claim 1, wherein said nucleic acid encoding a CDK is operably linked to a regulatory sequence.

6. The method of claim 1, wherein said improved plant growth characteristic is increased yield relative to a corresponding control plant.

7. The method of claim 6, wherein said increased yield is increased seed yield.

8. The method of claim 7, wherein said increased seed yield is selected from any one or more of: (i) increased seed weight; (ii) increased total number of seeds;

(iii) increased number of filled seeds; (iv) increased harvest index.

9. A plant, plant part or plant cell obtained by the method of claim 1, or progeny thereof, wherein the plant, plant part or plant cell or progeny thereof comprises the nucleic acid and has an improved growth characteristic relative to a corresponding control plant, plant part or plant cell.

10. A process for improving a plant growth characteristic relative to a corresponding control plant, which comprises:

(a) introducing into a plant at least one nucleic acid sequence which encodes a cyclin dependent kinase (CDK), wherein the at least one nucleic acid sequence comprises a nucleic acid sequence selected from the group consisting of:

i) the isolated nucleic acid molecule of SEQ ID NO: 45;

ii) an isolated nucleic acid molecule encoding the amino acid sequence of SEQ ID NO: 46;

iii) an isolated nucleic acid molecule which encodes a polypeptide which has at least 80% identity with the amino acid sequence of the polypeptide encoded by the nucleic acid molecule of (i) or (ii) and which comprises the DLL(Q/N/S/R)(K/Q/R)(L/M)(L/F)(I/T/I/C)(F/Y/L)DP (T/E/D/R/S)(K/Q)RI motif of SEQ ID NO: 67; and iv) an isolated nucleic acid molecule encoding a homologue of the amino acid molecule of SEQ ID NO: 46, which homologue is of plant origin and comprises the DLL(Q/N/S/R)(K/Q/R)(L/M)(L/F)(I/T/I/C)(F/Y/L) DP(T/E/D/R/S)(K/Q)RI motif of SEQ ID NO: 67;

(b) selecting for a plant having an improved growth characteristic relative to a corresponding control plant; and (c) cultivating the plant under conditions enabling plant growth and development.

11. The process as claimed in claim 10, wherein the nucleic acid sequence encoding the cyclin dependent kinase is derived from a plant.

12. The process of claim 10, wherein said nucleic acid sequence encoding a CDK is derived from a monocotyledonous or dicotyledonous plant.

13. The process of claim 10, wherein said nucleic acid sequence encoding the cyclin dependent kinase is derived from the species *Oryza sativa, Brassica napus, Glycine max, Linum usitatissimum, Zea mays* or *Helianthus annuus.*

14. The process of claim 10, wherein said nucleic acid sequence encoding the CDK is operably linked to a regulatory sequence.

15. The process of claim 10, wherein said improved plant growth characteristic is increased yield relative to a corresponding control plant.

16. The process of claim 15, wherein said increased yield is increased seed yield.

17. The process of claim 16, wherein said increased seed yield is selected from any one or more of: (i) increased seed weight; (ii) increased total number of seeds;

(iii) increased number of filled seeds; (iv) increased harvest index.

18. A plant, plant part or plant cell obtained by the process of claim 10, or progeny thereof, wherein the plant, plant part, or plant cell, or progeny thereof comprises the nucleic acid and has an improved growth relative to a corresponding control plant plant part or plant cell.

19. An expression cassette comprising:

(i) an isolated nucleic acid molecule comprising a nucleic acid molecule selected from the group consisting of:

a) the isolated nucleic acid molecule of SEQ ID NO: 45;

b) an isolated nucleic acid molecule encoding the amino acid sequence of SEQ ID NO: 46;

c) an isolated nucleic acid molecule which encodes a polypeptide which has at least 80% identity with the amino acid sequence of the polypeptide encoded by the nucleic acid molecule of (i) or (ii) and which comprises the DLL(Q/N/S/R)(K/Q/R)(L/M)(L/F)(I/T/I/C)(F/Y/L)DP (T/E/D/R/S)(K/Q)RI motif of SEQ ID NO: 67; and d) an isolated nucleic acid molecule encoding a homologue of the amino acid molecule of SEQ ID NO: 46, which homologue is of plant origin and comprises the-DLL(Q/N/S/R)(K/Q/R)(L/M)(L/F)(I/T/I/C)(F/Y/L)DP (T/E/D/R/S)(K/Q)RI motif of SEQ ID NO: 67; and ii) a plant regulatory signal, wherein expression of the expression cassette in a plant increases yield.

20. A vector comprising the expression cassette of claim 19.

21. A transgenic plant comprising (a) the expression cassette of claim 19, or (b) a vector comprising said expression cassette.

22. The transgenic plant as claimed in claim 21, wherein said plant is a dicotyledonous or monocotyledonous plant.

23. The transgenic plant as claimed in claim 21, wherein said plant is selected from the group consisting of sugar cane, canola, oilseed rape, soybean, rice, cotton, potato, maize, wheat, barley, millet, rye oats, oil palm, sugarbeet, sunflower, and sorghum.

24. A method for producing a transgenic plant having increased seed yield relative to a corresponding control plant comprising a) introducing into a plant cell the expression cassette of claim 19, or a vector comprising said expression cassette;

b) generating a plant from the plant cell; and c) selecting for a plant with increased seed yield relative to a corresponding control plant.

25. The method of claim 1, wherein the at least one nucleic acid sequence encodes a protein further comprising one or more amino acid sequences selected from the group consisting of:

i) (V/F/I)(L/I)HRD(L/M)K(P/S/T)(Q/N/S/G)N(L/I)L(V/L/I); (SEQ ID NO: 62)

ii) (I/L)(G/N)(E/R)G(T/A)YG(V/I)V(Y/C)(R/K/S)(A/G/S)(R/L/T/I)(D/N)(K/R/E)(V/K/A/S/T/N)T(N/S/G)(E/K/Q)(T/L/I/K)(I/V)A(L/V/I)KK; (SEQ ID NO: 63)

iii) LK(I/L)(C/A)DFGL(A/S)R; (SEQ ID NO: 64)

iv) WYRAPE(L/I)L(L/F)(C/G); and (SEQ ID NO: 65)

v) GCI(F/M)AE(I/L/M). (SEQ ID NO: 66)

26. The method of claim 1, wherein the at least one nucleic acid sequence hybridizes with i) the isolated nucleic acid molecule of SEQ ID NO: 45, or its complement; or ii) an isolated nucleic acid molecule encoding the amino acid sequence of SEQ ID NO: 46, or its complement, under stringent hybridization conditions of 1×SSC at 65° C. followed by one or more washes in 0.3×SSC at 65° C., wherein the hybridizing sequence or the complement thereof encodes a plant CDK protein that comprises the DLL(Q/N/S/R)(K/Q/R)(L/M)(L/F)(I/T/I/C)(F/Y/L)DP (T/E/D/R/S)(K/Q)RI motif of SEQ ID NO: 67.

27. The method of claim 1, wherein the at least one nucleic acid sequence encodes a polypeptide which has at least 90% identity with the amino acid sequence of SEQ ID NO: 46 and comprises the DLL(Q/N/S/R)(K/Q/R)(L/M)(L/F)(I/T/I/C)(F/Y/L)DP (T/E/D/R/S)(K/Q)RI motif of SEQ ID NO: 67.

28. The method of claim 1, wherein the at least one nucleic acid sequence encodes a polypeptide which has at least 95% identity with the amino acid sequence of SEQ ID NO: 46.

29. The method of claim 1, wherein the at least one nucleic acid sequence encodes a polypeptide which comprises the amino acid sequence of SEQ ID NO: 46.

30. The method of claim 1, wherein the at least one nucleic acid sequence encodes a polypeptide which comprises the amino acid sequence of SEQ ID NO: 48, 50, 52 or 54.

31. The expression cassette of claim 19, wherein the at least one nucleic acid sequence encodes a polypeptide which has at least 95% identity with the amino acid sequence of SEQ ID NO: 46.

32. The expression cassette of claim 19, wherein the isolated nucleic acid molecule comprises the nucleic acid sequence of SEQ ID NO: 45.

33. A transgenic plant, plant cell, or part thereof comprising the expression cassette of claim 31.

34. A transgenic plant, plant cell, or part thereof comprising the expression cassette of claim 32.

* * * * *